(12) United States Patent
Kim et al.

(10) Patent No.: US 10,505,124 B2
(45) Date of Patent: Dec. 10, 2019

(54) CARBAZOLE-BASED COMPOUND AND ORGANIC LIGHT-EMITTING DEVICE INCLUDING THE SAME

(71) Applicants: Samsung Electronics Co., Ltd., Suwon-si, Gyeonggi-do (KR); Samsung SDI Co., Ltd., Yongin-si, Gyeonggi-do (KR)

(72) Inventors: Hyunjung Kim, Suwon-si (KR); Miyoung Chae, Suwon-si (KR); Dalho Huh, Suwon-si (KR); Sangmo Kim, Hwaseong-si (KR); Jhunmo Son, Yongin-si (KR); Soonok Jeon, Seoul (KR); Yeonsook Chung, Seoul (KR); Yongsik Jung, Yongin-si (KR); Namheon Lee, Suwon-si (KR)

(73) Assignees: SAMSUNG ELECTRONICS CO., LTD., Gyeonggi-Do (KR); SAMSUNG SDI CO., LTD., Gyeonggi-Do (KR)

(*) Notice: Subject to any disclaimer, the term of this patent is extended or adjusted under 35 U.S.C. 154(b) by 317 days.

(21) Appl. No.: 14/669,102

(22) Filed: Mar. 26, 2015

(65) Prior Publication Data

US 2016/0126474 A1    May 5, 2016

(30) Foreign Application Priority Data

Oct. 31, 2014 (KR) .................. 10-2014-0150627

(51) Int. Cl.
*H01L 51/00* (2006.01)
*C07D 401/14* (2006.01)
(Continued)

(52) U.S. Cl.
CPC ........ *H01L 51/0072* (2013.01); *C07D 209/86* (2013.01); *C07D 401/14* (2013.01);
(Continued)

(58) Field of Classification Search
CPC .. C07D 209/86; C07D 401/14; C07D 471/04; C09K 11/06; C09K 2211/1007;
(Continued)

(56) References Cited

U.S. PATENT DOCUMENTS 8,168,308 B2 * 5/2012 Yokoyama ........... C07D 471/04
                                                    313/504
2009/0030202 A1   1/2009 Iwakuma et al.
(Continued)

FOREIGN PATENT DOCUMENTS

JP    2011166104 A      8/2011
JP    2011256143 A   * 12/2011
(Continued)

OTHER PUBLICATIONS

JP 2011256143 A, Dec. 2011, Machine translation.*
JP-2011256143-A, Dec. 2011, Partial Machine translation.*

*Primary Examiner* — Satya B Sastri
(74) *Attorney, Agent, or Firm* — Cantor Colburn LLP

(57) ABSTRACT

A carbazole compound represented by Formula 1:

(Continued)

wherein in Formula 1, groups $X_1$ to $X_8$, $X_{11}$ to $X_{19}$, and $R_{41}$ to $R_{43}$ are the same as in the specification.

20 Claims, 1 Drawing Sheet

(51) Int. Cl.
*C09K 11/06* (2006.01)
*C07D 471/04* (2006.01)
*H01L 51/50* (2006.01)
*C07D 209/86* (2006.01)

(52) U.S. Cl.
CPC ............ *C07D 471/04* (2013.01); *C09K 11/06* (2013.01); *H01L 51/006* (2013.01); *H01L 51/0051* (2013.01); *H01L 51/0058* (2013.01); *H01L 51/0067* (2013.01); *H01L 51/0073* (2013.01); *H01L 51/0085* (2013.01); *C09K 2211/1007* (2013.01); *C09K 2211/1029* (2013.01); *C09K 2211/1044* (2013.01); *H01L 51/5016* (2013.01)

(58) Field of Classification Search
CPC .... C09K 2211/1029; C09K 2211/1044; H01L 51/0067; H01L 51/0072
See application file for complete search history.

(56) References Cited

U.S. PATENT DOCUMENTS

2012/0298977 A1* 11/2012 Kitamura ................ C07C 15/28
257/40
2016/0013423 A1   1/2016 Huh et al.
2016/0301015 A1* 10/2016 Zheng .................... C09K 11/06

FOREIGN PATENT DOCUMENTS

| JP | 2011256143 A | * | 12/2011 |
|---|---|---|---|
| KR | 1020050100694 A | | 10/2005 |
| KR | 101233375 B1 | | 2/2013 |
| KR | 101233378 B1 | | 2/2013 |
| KR | 101233380 B1 | | 2/2013 |
| KR | 101317511 B1 | | 10/2013 |

* cited by examiner

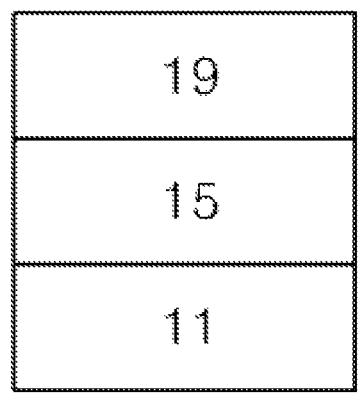

CARBAZOLE-BASED COMPOUND AND ORGANIC LIGHT-EMITTING DEVICE INCLUDING THE SAME

CROSS-REFERENCE TO RELATED APPLICATION

This application claims priority to Korean Patent Application No. 10-2014-0150627, filed on Oct. 31, 2014, in the Korean Intellectual Property Office, and all the benefits accruing therefrom under 35 U.S.C. § 119, the content of which is incorporated herein in its entirety by reference.

BACKGROUND

1. Field

One or more embodiments relate to a carbazole compound and an organic light-emitting device including the same.

2. Description of the Related Art

Organic light-emitting devices (OLEDs) are self-emission devices that have wide viewing angles, high contrast ratios, and short response times. In addition, OLEDs display excellent brightness, driving voltage, and response speed characteristics, and produce full-color images.

In an example, an organic light-emitting device includes an anode, a cathode, and an organic layer that is disposed between the anode and the cathode and includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, are recombined in the emission layer to produce excitons. These excitons change from an excited state to a ground state, thereby generating light.

Various types of organic light emitting devices are known. However, there still remains a need in OLEDs having low driving voltage, high efficiency, high brightness, and long lifespan.

SUMMARY

One or more embodiments relate to a novel carbazole compound and an organic light-emitting device including the same.

Additional aspects will be set forth in part in the description which follows and, in part, will be apparent from the description, or may be learned by practice of the presented exemplary embodiments.

An aspect provides a carbazole compound represented by Formula 1:

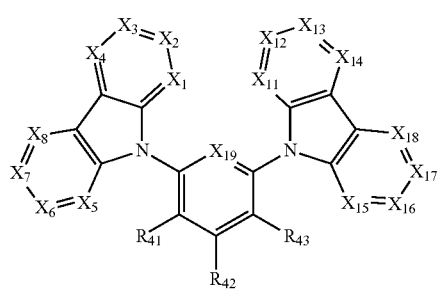

Formula 1

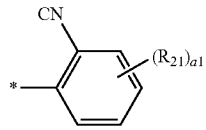

Formula 2A(1)

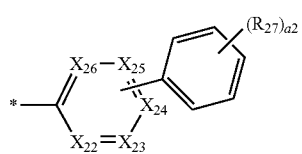

Formula 2A(2)

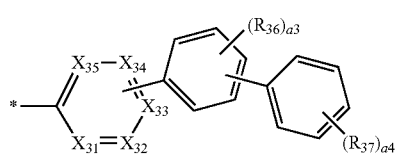

Formula 2B

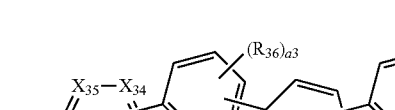

Formula 2C

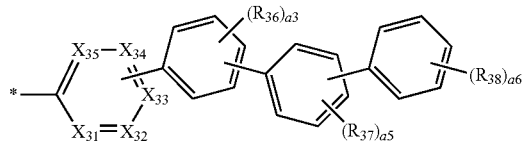

Formula 2D wherein in the formulae 1, 2A(1), 2A(2), 2B, 2C, and 2D,
$X_1$ is N or $C(R_1)$, $X_2$ is N or $C(R_2)$, $X_3$ is N or $C(R_3)$, $X_4$ is N or $C(R_4)$, $X_5$ is N or $C(R_5)$, $X_6$ is N or $C(R_6)$, $X_7$ is N or $C(R_7)$, $X_8$ is N or $C(R_8)$, $X_{11}$ is N or $C(R_{11})$, $X_{12}$ is N or $C(R_{12})$, $X_{13}$ is N or $C(R_{13})$, $X_{14}$ is N or $C(R_{14})$, $X_{15}$ is N or $C(R_{15})$, $X_{16}$ is N or $C(R_{16})$, $X_{17}$ is N or $C(R_{17})$, $X_{18}$ is N or $C(R_{18})$, $X_{19}$ is N or $C(R_{19})$, $X_{22}$ is N, C or $C(R_{22})$, $X_{23}$ is N, C or $C(R_{23})$, $X_{24}$ is N, C or $C(R_{24})$, $X_{25}$ is N, C or $C(R_{25})$, $X_{26}$ is N, C or $C(R_{26})$, $X_{31}$ is N, C or $C(R_{31})$, $X_{32}$ is N, C or $C(R_{32})$, $X_{33}$ is N, C or $C(R_{33})$, $X_{34}$ is N, C or $C(R_{34})$, and $X_{35}$ is N, C or $C(R_{35})$, provided that when $X_{22}$ is C, $X_{22}$ is connected to a carbon of a phenyl group of Formula 2B, when $X_{23}$ is C, $X_{23}$ is connected to a carbon of a phenyl group of Formula 2B, when $X_{24}$ is C, $X_{24}$ is connected to a carbon of a phenyl group of Formula 2B, when $X_{25}$ is C, $X_{25}$ is connected to a carbon of a phenyl group of Formula 2B, when $X_{26}$ is C, $X_{26}$ is connected to a carbon of a phenyl group of Formula 2B, when $X_{31}$ is C, $X_{31}$ is connected to a carbon of a phenyl group of Formulae 2C and 2D, when $X_{32}$ is C, $X_{32}$ is connected to a carbon of a phenyl group of Formulae 2C and 2D, when $X_{33}$ is C, $X_{33}$ is connected to a carbon of a phenyl group of Formulae 2C and 2D, when $X_{34}$ is C, $X_{34}$ is connected to a carbon of a phenyl group of Formulae 2C and 2D, when $X_{35}$ is C, $X_{35}$ is connected to a carbon of a phenyl group of Formulae 2C and 2D, one selected from $X_{22}$ to $X_{26}$ in Formula 2B is C, and one selected from $X_{31}$ to $X_{35}$ in Formulae 2C and 2D is C, $R_1$ to $R_8$, $R_{11}$ to $R_{19}$, $R_{21}$ to $R_{27}$, and $R_{31}$ to $R_{38}$ may be each independently selected from a hydrogen, a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof and a phosphoric acid group or a salt thereof;

a phenyl group, a pyridinyl group, a fluorenyl group, a dibenzofuranyl group, and a dibenzothiophenyl group;

a phenyl group, a pyridinyl group, a fluorenyl group, a dibenzofuranyl group and a dibenzothiophenyl group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group, and —Si($Q_1$)($Q_2$)($Q_3$); and —Si($Q_{11}$)($Q_{12}$)($Q_{13}$), a1, a3, and a5 may be each independently an integer selected from 1 to 4, and a2, a4 and a6 may be each independently an integer selected from 1 to 5, each of $R_{22}$ to $R_{26}$ is not a cyano group, at least one of groups $R_{27}$ in the number of a2 in Formula 2B is a cyano group, at least one selected from $R_{31}$ to $R_{35}$, groups $R_{36}$ in the number of a3 and groups $R_{37}$ in the number of a4 in Formula 2C is a cyano group, and at least one selected from $R_{31}$ to $R_{35}$, groups $R_{36}$ in the number of a3, groups $R_{37}$ in the number of a5, and groups $R_{38}$ in the number of a6 in Formula 2D is a cyano group, i) when each of $X_1$ to $X_8$ and $X_{11}$ to $X_{19}$ is not N, $R_{41}$ to $R_{43}$ are each independently selected from groups represented by Formulae 2A(1), 2B, 2C, and 2D;

a hydrogen, a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof and a phosphoric acid group or a salt thereof;

a phenyl group, a pyridinyl group, a fluorenyl group, a dibenzofuranyl group, and a dibenzothiophenyl group;

a phenyl group, a pyridinyl group, a fluorenyl group, a dibenzofuranyl group and a dibenzothiophenyl group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group, and —Si($Q_{21}$)($Q_{22}$)($Q_{23}$); and —Si($Q_{31}$)($Q_{32}$)($Q_{33}$), at least one selected from $R_{41}$ to $R_{43}$ is a group represented by one of Formulae 2A(1), 2B, 2C, and 2D, ii) when at least one selected from $X_1$ to $X_8$ and $X_{11}$ to $X_{19}$ is N, $R_{41}$ to $R_{43}$ are each independently selected from groups represented by Formulae 2A(2), 2B, 2C, and 2D;

a hydrogen, a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof and a phosphoric acid group or a salt thereof;

a phenyl group, a pyridinyl group, a fluorenyl group, a dibenzofuranyl group, and a dibenzothiophenyl group;

a phenyl group, a pyridinyl group, a fluorenyl group, a dibenzofuranyl group and a dibenzothiophenyl group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group, and —Si($Q_{21}$)($Q_{22}$)($Q_{23}$); and —Si($Q_{31}$)($Q_{32}$)($Q_{33}$), at least one selected from $R_{41}$ to $R_{43}$ is a group represented by one of Formulae 2A(2), 2B, 2C, and 2D, $Q_1$ to $Q_3$, $Q_{11}$ to $Q_{13}$, $Q_{21}$ to $Q_{23}$ and $Q_{31}$ to $Q_{33}$ are each independently selected from a hydrogen, a $C_1$-$C_{20}$ alkyl group, a $C_1$-$C_{20}$ alkoxy group, a phenyl group, a naphthyl group, a pyridinyl group, a fluorenyl group, a dibenzofuranyl group, and a dibenzothiophenyl group.

Another aspect provides an organic light-emitting device that includes:

a first electrode;

a second electrode; and an organic layer that is disposed between the first electrode and the second electrode, wherein the organic layer includes an emission layer and at least one carbazole compound represented by Formula 1 described above.

BRIEF DESCRIPTION OF THE DRAWINGS

These and/or other aspects will become apparent and more readily appreciated from the following description of the exemplary embodiments, taken in conjunction with FIG. 1 which is a schematic view of an organic light-emitting device according to an embodiment.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the FIGURES, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the FIGURES. It will be understood that the spatially relative terms are intended to encompass different orientations of the device in use or operation in addition to the orientation depicted in the FIGURES. For example, if the device in the FIGURES is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

An aspect provides a carbazole compound represented by Formula 1 below:

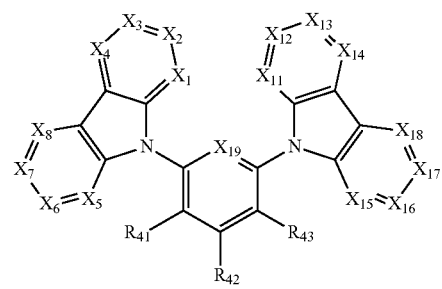

Formula 1 i) when each of $X_1$ to $X_8$ and $X_{11}$ to $X_{19}$ is not N, at least one selected from $R_{41}$ to $R_{43}$ in Formula 1 may be represented by one selected from groups represented by Formulae 2A(1), 2B, 2C and 2D, and ii) when at least one selected from $X_1$ to $X_8$ and $X_{11}$ to $X_{19}$ is N, at least one selected from $R_{41}$ to $R_{43}$ of Formula 1 may be represented by one selected from groups represented by Formulae 2A(2), 2B, 2C, and 2D.

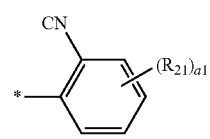

Formula 2A(1)

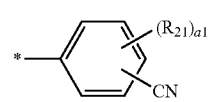

Formula 2A(2)

Formula 2B

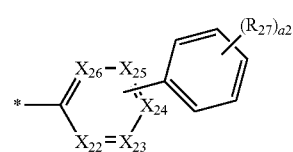

Formula 2C

Formula 2D

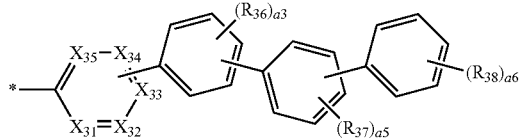

In Formulae 1, 2A(1), 2A(2), 2B, 2C, and 2D, $X_1$ is N or $C(R_1)$, $X_2$ is N or $C(R_2)$, $X_3$ is N or $C(R_3)$, $X_4$ is N or $C(R_4)$, $X_5$ is N or $C(R_5)$, $X_6$ is N or $C(R_6)$, $X_7$ is N or $C(R_7)$, $X_8$ is N or $C(R_8)$, $X_{11}$ is N or $C(R_{11})$, $X_{12}$ is N or $C(R_{12})$, $X_{13}$ is N or $C(R_{13})$, $X_{14}$ is N or $C(R_{14})$, $X_{15}$ is N or $C(R_{15})$, $X_{16}$ is N or $C(R_{16})$, $X_{17}$ is N or $C(R_{17})$, $X_{18}$ is N or $C(R_{18})$, $X_{19}$ is N or $C(R_{19})$, $X_{22}$ is N, C or $C(R_{22})$, $X_{23}$ is N, C or $C(R_{23})$, $X_{24}$ is N, C or $C(R_{24})$, $X_{25}$ is N, C or $C(R_{25})$, $X_{26}$ is N, C or $C(R_{26})$, $X_{31}$ is N, C or $C(R_{31})$, $X_{32}$ is N, C or $C(R_{32})$, $X_{33}$ is N, C or $C(R_{33})$, $X_{34}$ is N, C or $C(R_{34})$, and $X_{35}$ is N, C or $C(R_{35})$, when $X_{22}$ is C, $X_{22}$ is connected to a carbon of a phenyl group of Formula 2B, when $X_{23}$ is C, $X_{23}$ is connected to a carbon of a phenyl group of Formula 2B, when $X_{24}$ is C, $X_{24}$ is connected to a carbon of a phenyl group of Formula 2B, when $X_{25}$ is C, $X_{25}$ is connected to a carbon of a phenyl group of Formula 2B, when $X_{26}$ is C, $X_{26}$ is connected to a carbon of a phenyl group of Formula 2B, when $X_{31}$ is C, $X_{31}$ is connected to a carbon of a phenyl group of Formulae 2C and 2D, when $X_{32}$ is C, $X_{32}$ is connected to a carbon of a phenyl group of Formulae 2C and 2D, when $X_{33}$ is C, $X_{33}$ is connected to a carbon of a phenyl group of Formulae 2C and 2D, when $X_{34}$ is C, $X_{34}$ is connected to a carbon of a phenyl group of Formulae 2C and 2D, when $X_{35}$ is C, $X_{35}$ is connected to a carbon of a phenyl group of Formulae 2C and 2D, one selected from $X_{22}$ to $X_{26}$ in Formula 2B is C, and one selected from $X_{31}$ to $X_{35}$ in Formulae 2C and 2D is C.

In some embodiments, in Formula 1, $X_1$ may be $C(R_1)$, $X_2$ may be $C(R_2)$, $X_3$ may be $C(R_3)$, $X_4$ may be $C(R_4)$, $X_5$ may be $C(R_5)$, $X_6$ may be $C(R_6)$, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but embodiments are not limited thereto.

In some embodiments, in Formula 2B, $X_{22}$ may be C or $C(R_{22})$, $X_{23}$ may be C or $C(R_{23})$, $X_{24}$ may be C or $C(R_{24})$, $X_{25}$ may be C or $C(R_{25})$, $X_{26}$ may be C or $C(R_{26})$; or one selected from $X_{22}$ to $X_{26}$ may be N, but embodiments are not limited thereto.

In some embodiments, in Formulae 2C and 2D, $X_{31}$ may be C or $C(R_{31})$, $X_{32}$ may be C or $C(R_{32})$, $X_{33}$ may be C or $C(R_{33})$, $X_{34}$ may be C or $C(R_{34})$, $X_{35}$ may be C or $C(R_{35})$; or one selected from $X_{31}$ to $X_{35}$ may be N, but embodiments are not limited thereto.

$R_1$ to $R_8$, $R_{11}$ to $R_{19}$, $R_{21}$ to $R_{27}$, and $R_{31}$ to $R_{38}$ in Formulae 1, 2A(1), 2A(2), 2B, 2C, and 2D may be each independently selected from a hydrogen, a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof and a phosphoric acid group or a salt thereof;

a phenyl group, a pyridinyl group, a fluorenyl group, a dibenzofuranyl group, and a dibenzothiophenyl group;

a phenyl group, a pyridinyl group, a fluorenyl group, a dibenzofuranyl group and a dibenzothiophenyl group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group, and —$Si(Q_1)(Q_2)(Q_3)$; and —$Si(Q_{11})(Q_{12})(Q_{13})$.

$Q_1$ to $Q_3$ and $Q_{11}$ to $Q_{13}$ may be each independently selected from a hydrogen, a $C_1$-$C_{20}$ alkyl group, a $C_1$-$C_{20}$ alkoxy group, a phenyl group, a naphthyl group, a pyridinyl group, a fluorenyl group, a dibenzofuranyl group, and a dibenzothiophenyl group.

In Formulae 2A(1), 2A(2), 2B, 2C, and 2D, a1, a3, and a5 may be each independently an integer selected from 1 to 4, and a2, a4, and a6 may be each independently an integer selected from 1 to 5.

a1 indicates the number of groups $R_{21}$, and when a1 is 2 or more, two or more groups $R_{21}$ may be identical or different. a2 indicates the number of groups $R_{27}$, and when a2 is 2 or more, two or more groups $R_{27}$ may be identical or different. a3 indicates the number of groups $R_{36}$, and when a3 is 2 or more, two or more groups $R_{36}$ may be identical or different. a4 indicates the number of groups $R_{37}$ in Formula 2C, and when a4 is 2 or more, two or more groups $R_{37}$ may be identical or different. a5 indicates the number of groups $R_{37}$ in Formula 2D, and when a5 is 2 or more, two or more groups $R_{37}$ may be identical or different. a6 indicates the number of groups $R_{38}$, and when a6 is 2 or more, two or more groups $R_{38}$ may be identical or different.

According to an embodiment, a1 to a6 may be each independently an integer selected from 1 to 3. In some embodiments, a1 to a6 may be each independently 1 or 2. In some embodiments, a1 to a6 may be each independently 1, but embodiments are not limited thereto.

$R_{22}$ to $R_{26}$ in Formula 2B may not be a cyano group.

At least one of groups $R_{27}$ in the number of a2 in Formula 2B is a cyano group, at least one selected from $R_{31}$ to $R_{35}$, groups $R_{36}$ in the number of a3 and groups $R_{37}$ in the number of a4 in Formula 2C is a cyano group, and at least one selected from $R_{31}$ to $R_{35}$, groups $R_{36}$ in the number of a3, groups $R_{37}$ in the number of a5, and groups $R_{38}$ in the number of a6 in Formula 2D is a cyano group.

In some embodiments, one or two of groups $R_{27}$ in the number of a2 in Formula 2B is a cyano group, one or two selected from $R_{31}$ to $R_{35}$, groups in the number of a3 and groups $R_{37}$ in the number of a4 in Formula 2C is a cyano group, and one or two selected from $R_{31}$ to $R_{35}$, groups $R_{36}$ in the number of a3, groups $R_{37}$ in the number of a5, and groups $R_{38}$ in the number of a6 in Formula 2D is a cyano group, but embodiments are not limited thereto.

In some embodiments, $R_1$ to $R_8$, $R_{11}$ to $R_{19}$, $R_{21}$ to $R_{27}$, and $R_{31}$ to $R_{38}$ in Formulae 1, 2A(1), 2A(2), 2B, 2C, and 2D may be each independently selected from a hydrogen, a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a $C_1$-$C_{10}$ alkyl group and a $C_1$-$C_{10}$ alkoxy group, each substituted with at least one selected from a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof and a phosphoric acid group or a salt thereof;

a phenyl group and a pyridinyl group;

a phenyl group and a pyridinyl group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a pyridinyl group, and —Si($Q_1$)($Q_2$)($Q_3$); and —Si($Q_{11}$)($Q_{12}$)($Q_{13}$), a1 to a6 may be each independently an integer selected from 1 to 3, $Q_1$ to $Q_3$ and $Q_{11}$ to $Q_{13}$ may be each independently selected from a $C_1$-$C_{10}$ alkyl group, a $C_1$-$C_{10}$ alkoxy group, a phenyl group, a naphthyl group and a pyridinyl group.

In Formula 1, i) when each of $X_1$ to $X_8$ and $X_{11}$ to $X_{19}$ is not N, $R_{41}$ to $R_{43}$ are each independently selected from groups represented by Formulae 2A(1), 2B, 2C, and 2D;

a hydrogen, a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof and a phosphoric acid group or a salt thereof;

a phenyl group, a pyridinyl group, a fluorenyl group, a dibenzofuranyl group, and a dibenzothiophenyl group;

a phenyl group, a pyridinyl group, a fluorenyl group, a dibenzofuranyl group and a dibenzothiophenyl group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group, and —Si($Q_{21}$)($Q_{22}$)($Q_{23}$); and —Si($Q_{31}$)($Q_{32}$)($Q_{33}$), at least one selected from $R_{41}$ to $R_{43}$ is a group represented by one of Formulae 2A(2), 2B, 2C, and 2D, $Q_{21}$ to $Q_{23}$ and $Q_{31}$ to $Q_{33}$ may be each independently selected from a hydrogen, a $C_1$-$C_{20}$ alkyl group, a $C_1$-$C_{20}$ alkoxy group, a phenyl group, a naphthyl group, a pyridinyl group, a fluorenyl group, a dibenzofuranyl group, and a dibenzothiophenyl group.

In Formula 1, i) when each of $X_1$ to $X_8$ and $X_{11}$ to $X_{19}$ is not N, $R_{41}$ to $R_{43}$ are each independently selected from groups represented by Formulae 2A(1), 2B, 2C, and 2D;

a hydrogen, a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a $C_1$-$C_{10}$ alkyl group and a $C_1$-$C_{10}$ alkoxy group, each substituted with at least one selected from a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof and a phosphoric acid group or a salt thereof;

a phenyl group and a pyridinyl group;

a phenyl group and a pyridinyl group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a pyridinyl group, and —Si($Q_{21}$)($Q_{22}$)($Q_{23}$); and —Si($Q_{31}$)($Q_{32}$)($Q_{33}$), at least one selected from $R_{41}$ to $R_{43}$ is a group represented by one of Formulae 2A(1), 2B, 2C, and 2D, ii) when at least one selected from $X_1$ to $X_8$ and $X_{11}$ to $X_{19}$ is N, $R_{41}$ to $R_{43}$ are each independently selected from groups represented by Formulae 2A(2), 2B, 2C, and 2D;

a hydrogen, a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a $C_1$-$C_{10}$ alkyl group and a $C_1$-$C_{10}$ alkoxy group, each substituted with at least one selected from a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof and a phosphoric acid group or a salt thereof;

a phenyl group and a pyridinyl group;

a phenyl group and a pyridinyl group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a pyridinyl group, and —Si($Q_{21}$)($Q_{22}$)($Q_{23}$); and —Si($Q_{31}$)($Q_{32}$)($Q_{33}$), at least one selected from $R_{41}$ to $R_{43}$ is a group represented by one of Formulae 2A(2), 2B, 2C, and 2D, $Q_{21}$ to $Q_{23}$ and $Q_{31}$ to $Q_{33}$ may be each independently selected from a $C_1$-$C_{10}$alkyl group, a $C_1$-$C_{10}$ alkoxy group, a phenyl group, a naphthyl group, and a pyridinyl group. However, embodiments are not limited thereto.

For example, i) when each of $X_1$ to $X_8$ and $X_{11}$ to $X_{19}$ is not N, $R_{42}$ in Formula 1 is represented by one of Formulae 2A(1), 2B, 2C and 2D, ii) when at least one selected from $X_1$ to $X_8$ and $X_{11}$ to $X_{19}$ is N, $R_{42}$ in Formula 1 may be represented by Formulae 2A(2), 2B, 2C, and 2D.

In Formula 1, i) when each of $X_1$ to $X_8$ and $X_{11}$ to $X_{19}$ is not N, $R_{42}$ may be represented by one of Formulae 2A(1), 2B, 2C, and 2D, $R_{19}$, $R_{41}$, and $R_{43}$ may be each independently selected from a hydrogen, a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a $C_1$-$C_{10}$ alkyl group and a $C_1$-$C_{10}$ alkoxy group, each substituted with at least one selected from a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, and a phosphoric acid group or a salt thereof; and —Si($Q_{31}$)($Q_{32}$)($Q_{33}$), ii) when at least one selected from $X_1$ to $X_8$ and $X_{11}$ to $X_{19}$ is N, $R_{42}$ may be represented by one of Formulae 2A(2), 2B, 2C, and 2D, $R_{19}$, $R_{41}$, and $R_{43}$ may be each independently selected from a hydrogen, a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a $C_1$-$C_{10}$ alkyl group and a $C_1$-$C_{10}$ alkoxy group, each substituted with at least one selected from a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, and a phosphoric acid group or a salt thereof; and —Si($Q_{31}$)($Q_{32}$)($Q_{33}$), $Q_{21}$ to $Q_{23}$ and $Q_{31}$ to $Q_{33}$ may be each independently selected from a $C_1$-$C_{10}$ alkyl group, a $C_1$-$C_{10}$ alkoxy group, a phenyl group, a naphthyl group and a pyridinyl group.

In some embodiments, in Formula 1, i) when each of $X_1$ to $X_8$ and $X_{11}$ to $X_{19}$ is not N, $R_{42}$ may be represented by one of Formulae 2A(1), 2B, 2C, and 2D, and each of $R_{19}$, $R_{41}$ and $R_{43}$ may be a hydrogen, ii) when at least one selected from $X_1$ to $X_8$ and $X_{11}$ to $X_{19}$ is N, $R_{42}$ may be represented by one of Formulae 2A(2), 2B, 2C, and 2D, and each of $R_{19}$, $R_{41}$ and $R_{43}$ may be a hydrogen, but embodiments are not limited thereto.

According to an embodiment, the carbazole compound represented by Formula 1 may be represented by Formula 1A to 1F below:

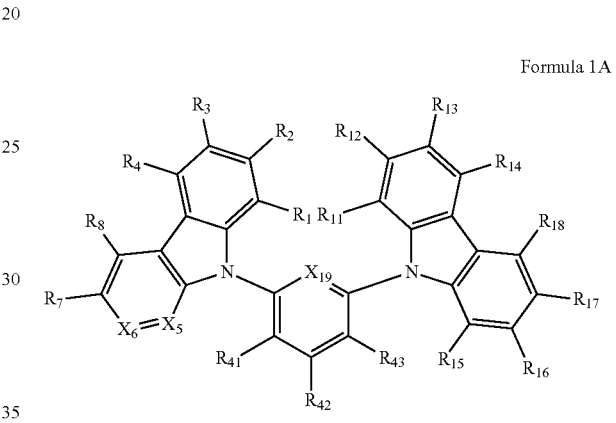

Formula 1A

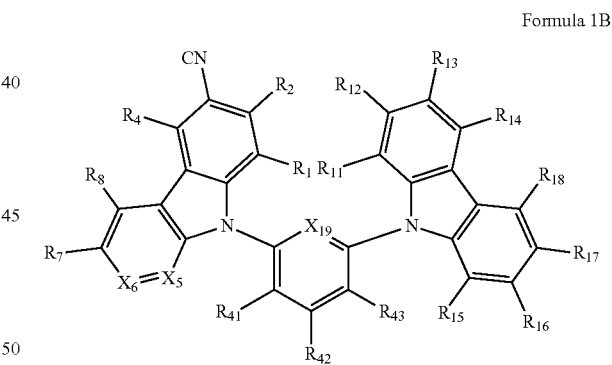

Formula 1B

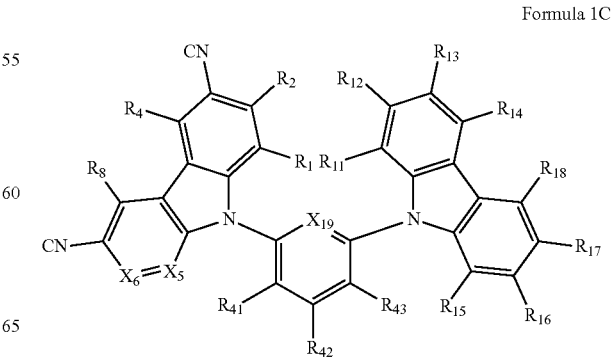

Formula 1C

-continued

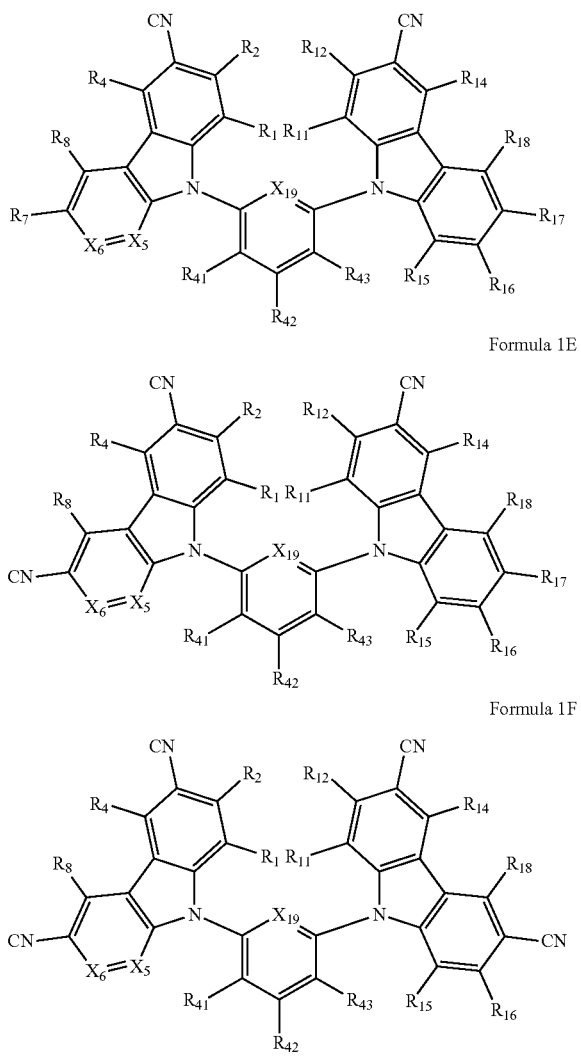

Formula 1D

Formula 1E

Formula 1F

Descriptions of $X_5$, $X_6$, $R_1$ to $R_8$, $R_{11}$ to $R_{18}$, $X_{19}$ and $R_{41}$ to $R_{43}$ in Formulae 1A to 1F are the same as provided above.

For example, in Formulae 1A to 1F, $X_5$ may be N, and $X_6$ may be $C(R_6)$.

In some embodiments, in Formulae 1A to 1F, $X_5$ may be $C(R_5)$, and $X_6$ may be N.

In some embodiments, in Formulae 1A to 1F, $X_5$ may be $C(R_5)$, and $X_6$ may be $C(R_6)$.

For example, $R_1$ to $R_8$ and $R_{11}$ to $R_{18}$ in Formulae 1A to 1F may not be a cyano group.

According to an embodiment, $R_1$ to $R_8$ and $R_{11}$ to $R_{18}$ in Formulae 1A to 1F may be each independently selected from a hydrogen, a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a $C_1$-$C_{10}$ alkyl group and a $C_1$-$C_{10}$ alkoxy group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof and a phosphoric acid group or a salt thereof; a phenyl group and a pyridinyl group;

a phenyl group and a pyridinyl group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a pyridinyl group, and —Si$(Q_1)(Q_2)(Q_3)$; and —Si$(Q_{11})(Q_{12})(Q_{13})$, wherein $Q_1$ to $Q_3$ and $Q_{11}$ to $Q_{13}$ may be each independently selected from a $C_1$-$C_{10}$ alkyl group, a $C_1$-$C_{10}$ alkoxy group, a phenyl group, a naphthyl group, a pyridinyl group, a fluorenyl group, a dibenzofuranyl group, and a dibenzothiophenyl group, but they are not limited thereto.

$R_{21}$ to $R_{27}$ and $R_{31}$ to $R_{38}$ in Formulae 2A(1), 2A(2), 2B, 2C, and 2D may be each independently selected from a hydrogen, a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, and a phosphoric acid group or a salt thereof; and —Si$(Q_{11})(Q_{12})(Q_{13})$, a1 to a6 may be 1 or 2, but are not limited thereto.

According to an embodiment, the group represented by Formula 2A(1) may include groups represented by Formulae 2A-1 to 2A-4, and the group represented by Formula 2A(2) may include groups represented by Formulae 2A-1 to 2A-7, but embodiments are not limited thereto:

Formula 2A-1

Formula 2A-2

Formula 2A-3

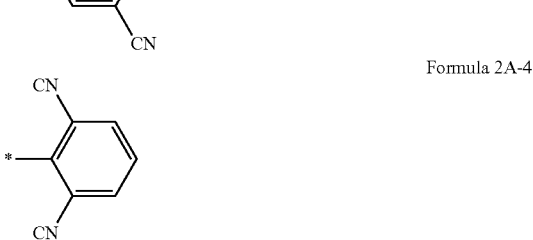

Formula 2A-4

-continued

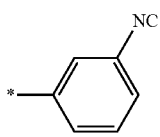
Formula 2A-5

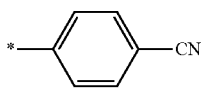
Formula 2A-6

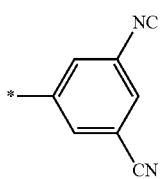
Formula 2A-7

In some embodiments, the group represented by Formula 2B may include groups represented by Formulae 2B-1 to 2B-7:

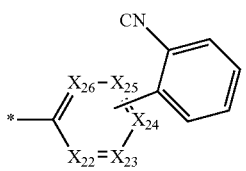
Formula 2B-1

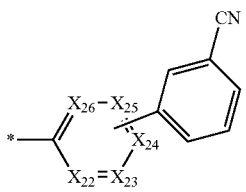
Formula 2B-2

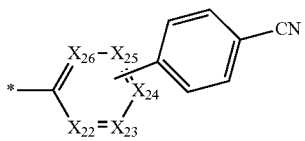
Formula 2B-3

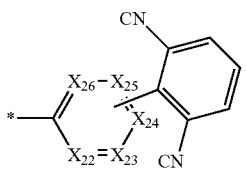
Formula 2B-4

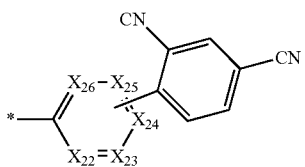
Formula 2B-5

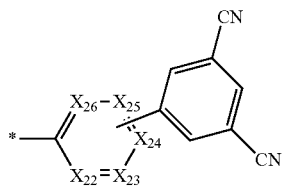
Formula 2B-6

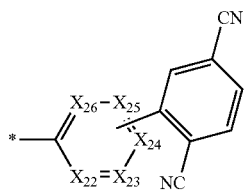
Formula 2B-7

Descriptions of $X_{22}$ to $X_{26}$ in Formulae 2B-1 to 2B-7 are the same as provided above.

In some embodiments, the group represented by Formula 2B may include groups represented by Formulae 2B(1) to 2B(13), but embodiments are not limited thereto:

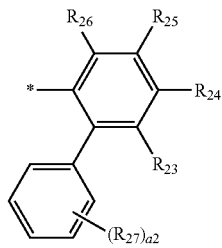
Formula 2B(1)

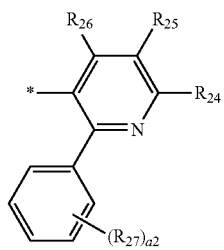
Formula 2B(2)

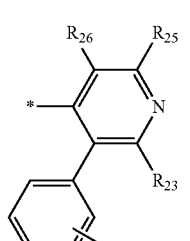
Formula 2B(3)

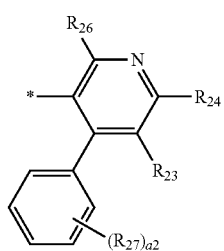
Formula 2B(4)

Formula 2B(5) 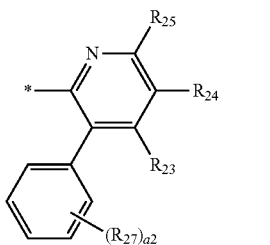

Formula 2B(6) 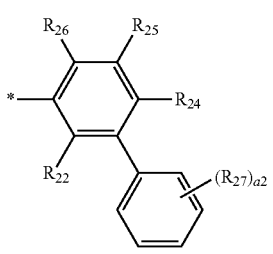

Formula 2B(7) 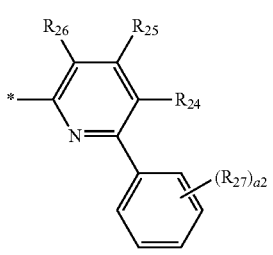

Formula 2B(8) 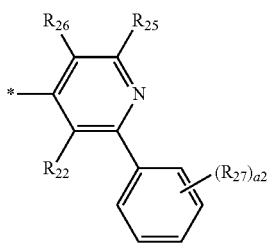

Formula 2B(9) 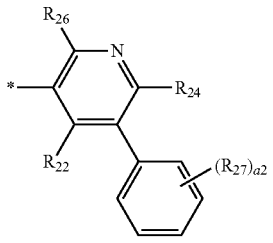

Formula 2B(10) 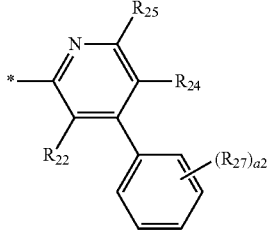

Formula 2B(11) 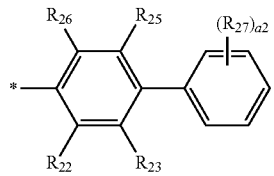

Formula 2B(12) 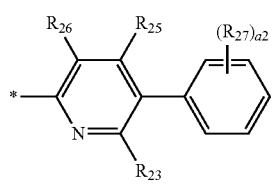

Formula 2B(13) 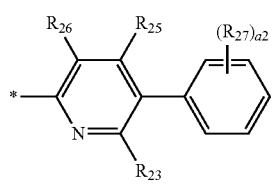

Descriptions of $R_{22}$ to $R_{27}$ and a2 in Formulae 2B(1) to 2B(13) are the same as provided above.

For example, in Formulae 2B(1) and 2B(13), $R_{22}$ to $R_{26}$ are each independently selected from a hydrogen, a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof and a phosphoric acid group or a salt thereof; and —Si($Q_{11}$)($Q_{12}$)($Q_{13}$), $R_{27}$ may be selected from a hydrogen, a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, and a phosphoric acid group or a salt thereof; and —Si($Q_{11}$)($Q_{12}$)($Q_{13}$), a2 is 1 or 2, at least one of groups $R_{27}$ in the number of a2 is a cyano group.

In some embodiments, the group represented by Formula 2B may include a group represented by one of Formulae 2B(1)-1 to 2B(13)-1, 2B(1)-2 to 2B(13)-2, 2B(1)-3 to 2B(13)-3, 2B(1)-4 to 2B(13)-4, 2B(1)-5 to 2B(13)-5, 2B(1)-6 to 2B(13)-6, and 2B(1)-7 to 2B(13)-7:

Formula 2B(1)-1
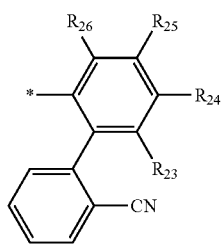
Formula 2B(2)-1
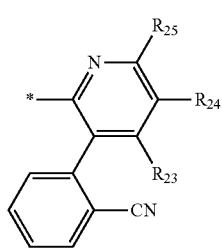
Formula 2B(3)-1
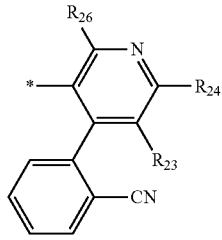
Formula 2B(4)-1
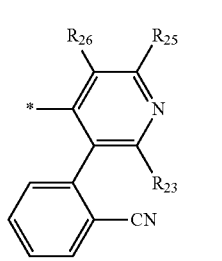
Formula 2B(5)-1
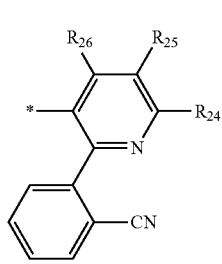
Formula 2B(6)-1
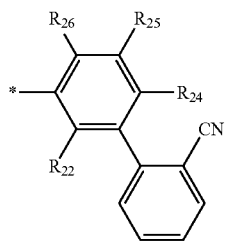
Formula 2B(7)-1
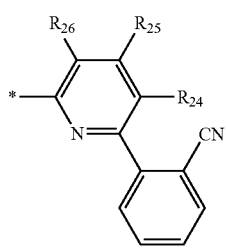
Formula 2B(8)-1
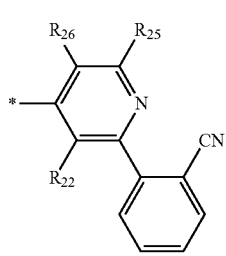
Formula 2B(9)-1
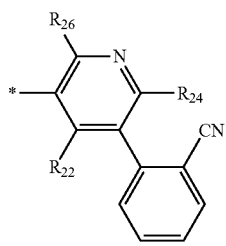
Formula 2B(10)-1
Formula 2B(11)-1
Formula 2B(12)-1
Formula 2B(13)-1

Formula 2B(1)-2
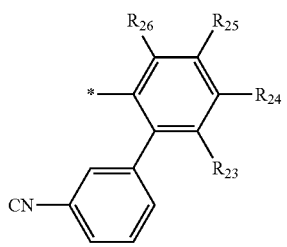
Formula 2B(2)-2
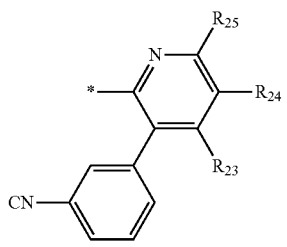
Formula 2B(3)-2
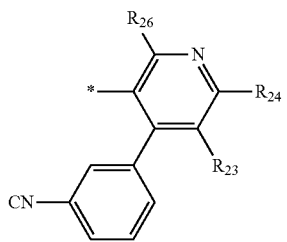
Formula 2B(4)-2
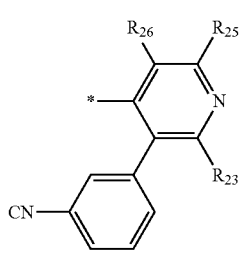
Formula 2B(5)-2
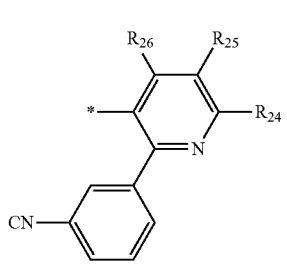
Formula 2B(6)-2
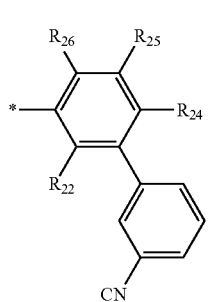
Formula 2B(7)-2
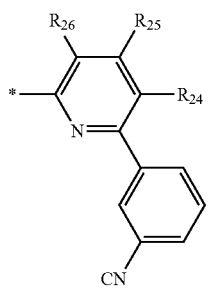
Formula 2B(8)-2
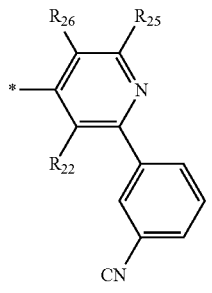
Formula 2B(9)-2
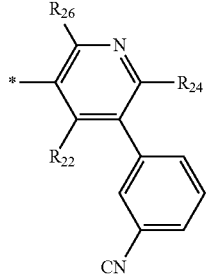
Formula 2B(10)-2
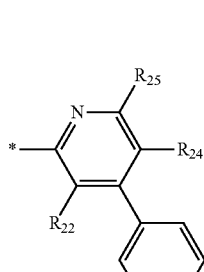
Formula 2B(11)-2
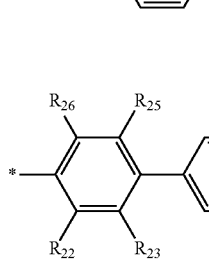
Formula 2B(12)-2
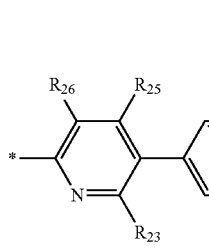

Formula 2B(13)-2
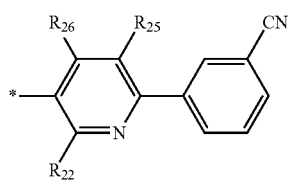
Formula 2B(1)-3
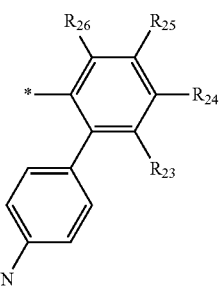
Formula 2B(2)-3
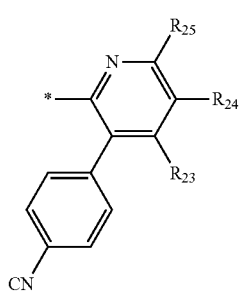
Formula 2B(3)-3
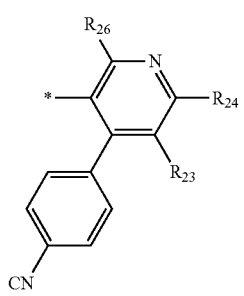
Formula 2B(4)-3
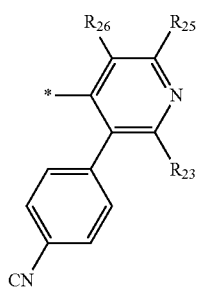
Formula 2B(5)-3
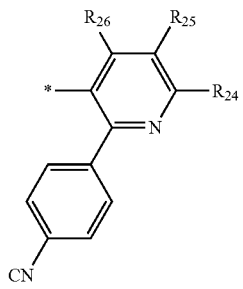
Formula 2B(6)-3
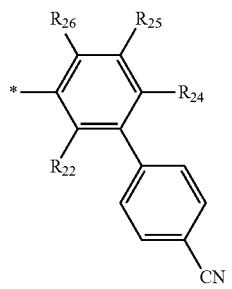
Formula 2B(7)-3
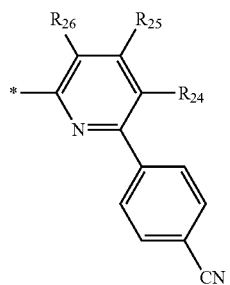
Formula 2B(8)-3
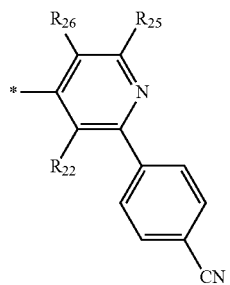
Formula 2B(9)-3
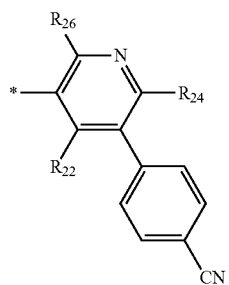
Formula 2B(10)-3
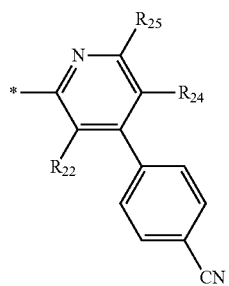
Formula 2B(11)-3
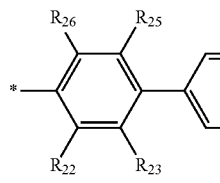

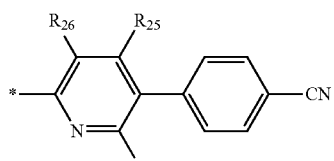
Formula 2B(12)-3
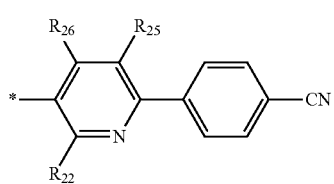
Formula 2B(13)-3
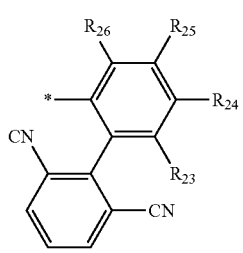
Formula 2B(1)-4
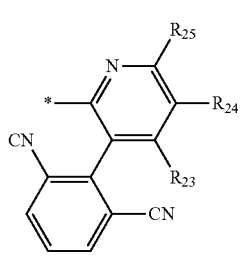
Formula 2B(2)-4
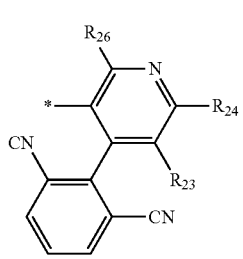
Formula 2B(3)-4
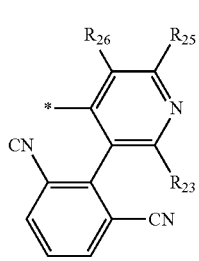
Formula 2B(4)-4
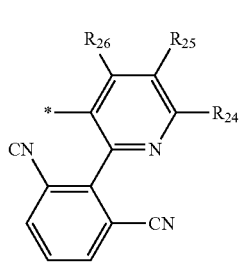
Formula 2B(5)-4
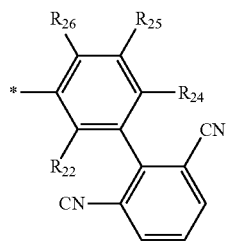
Formula 2B(6)-4
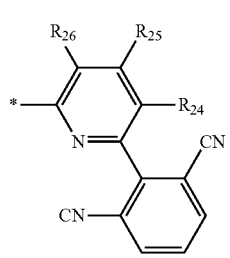
Formula 2B(7)-4
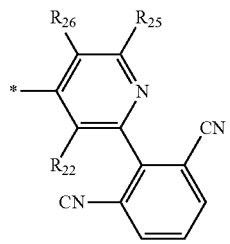
Formula 2B(8)-4
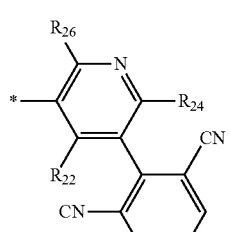
Formula 2B(9)-4
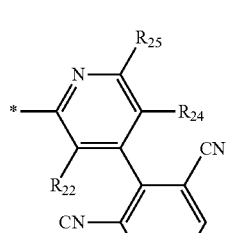
Formula 2B(10)-4
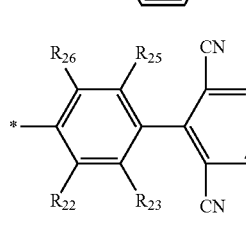
Formula 2B(11)-4
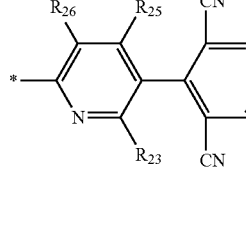
Formula 2B(12)-4

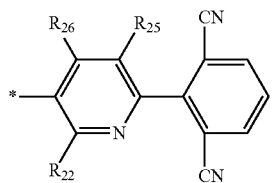
Formula 2B(13)-4
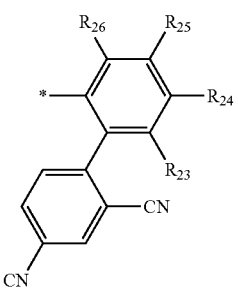
Formula 2B(1)-5
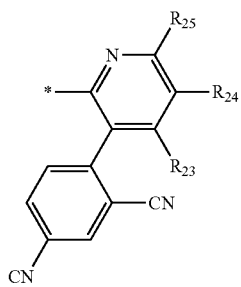
Formula 2B(2)-5
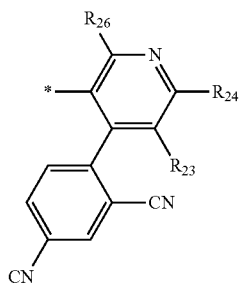
Formula 2B(3)-5
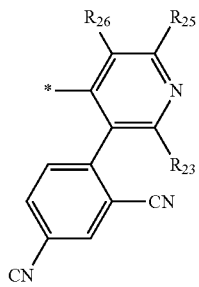
Formula 2B(4)-5
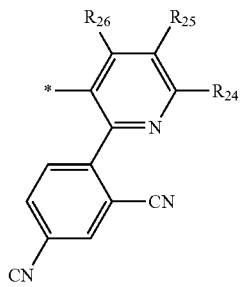
Formula 2B(5)-5
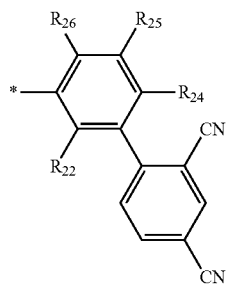
Formula 2B(6)-5
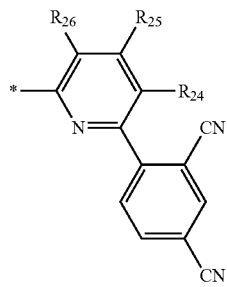
Formula 2B(7)-5
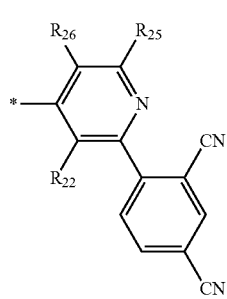
Formula 2B(8)-5
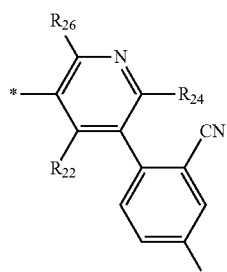
Formula 2B(9)-5
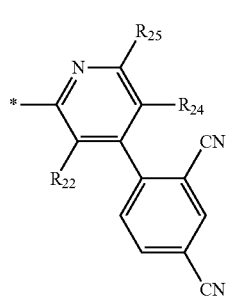
Formula 2B(10)-5
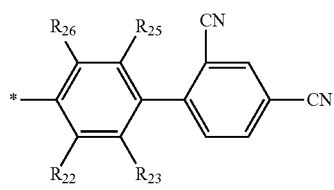
Formula 2B(11)-5

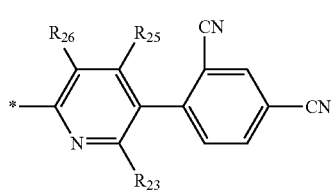
Formula 2B(12)-5
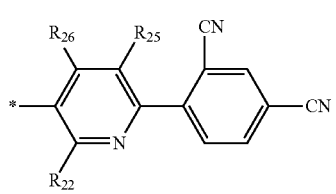
Formula 2B(13)-5
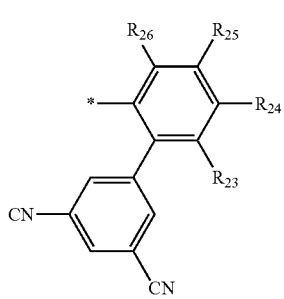
Formula 2B(1)-6
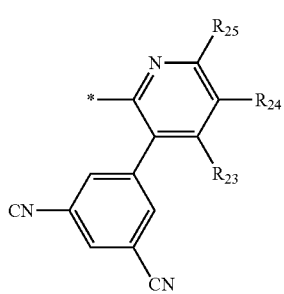
Formula 2B(2)-6
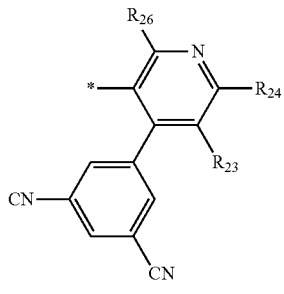
Formula 2B(3)-6
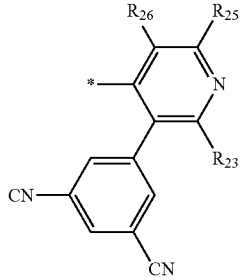
Formula 2B(4)-6
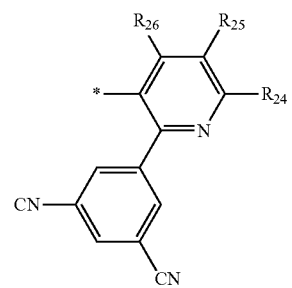
Formula 2B(5)-6
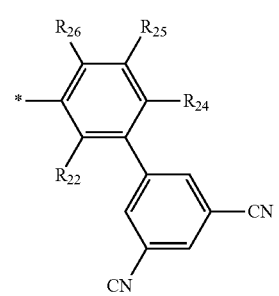
Formula 2B(6)-6
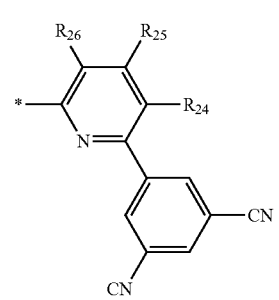
Formula 2B(7)-6
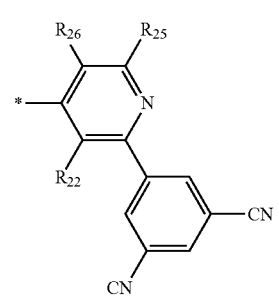
Formula 2B(8)-6
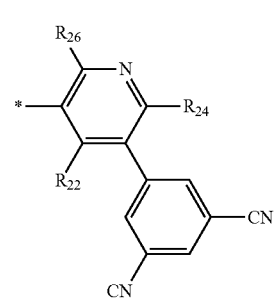
Formula 2B(9)-6

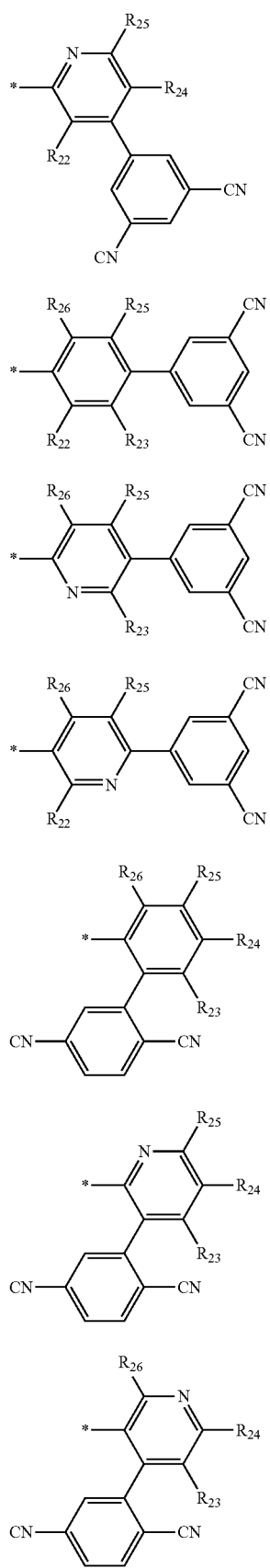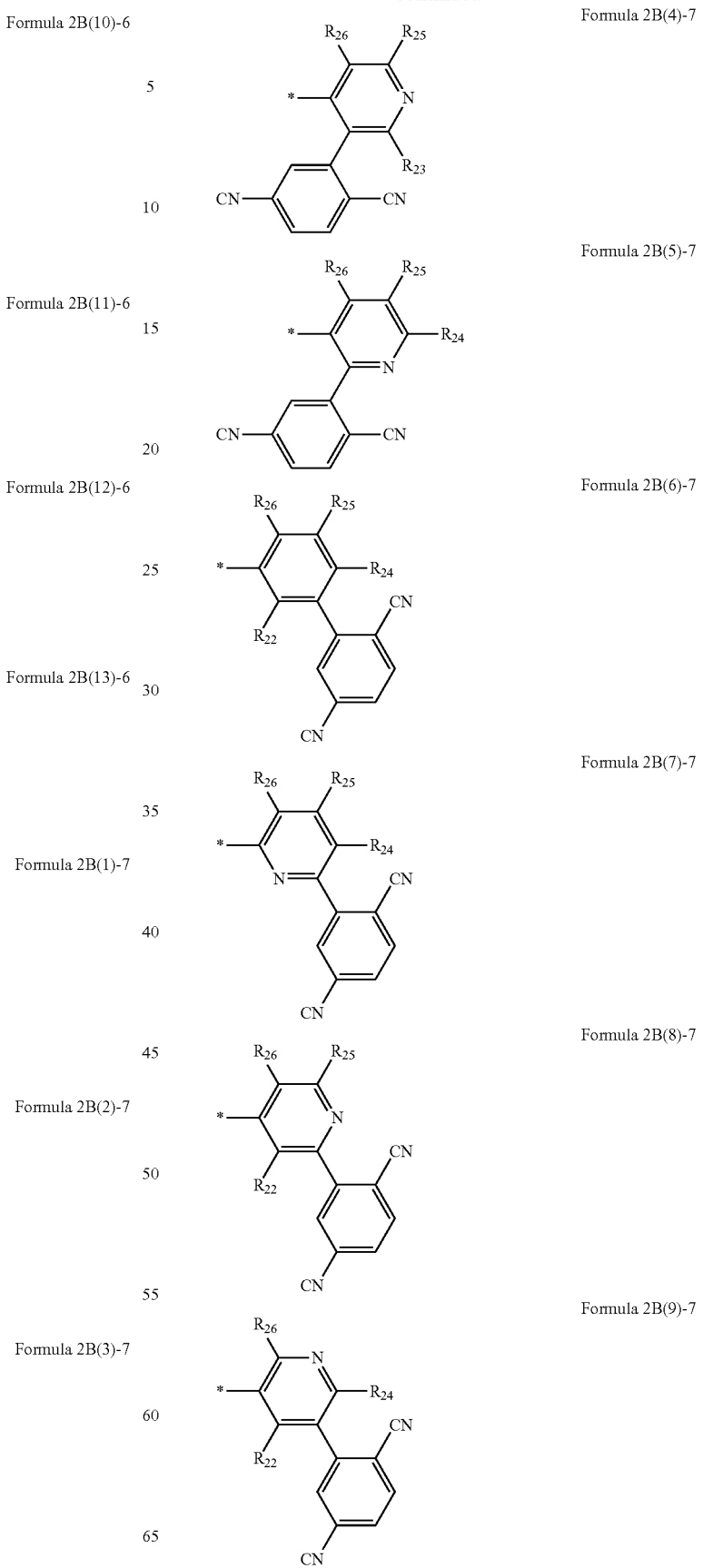

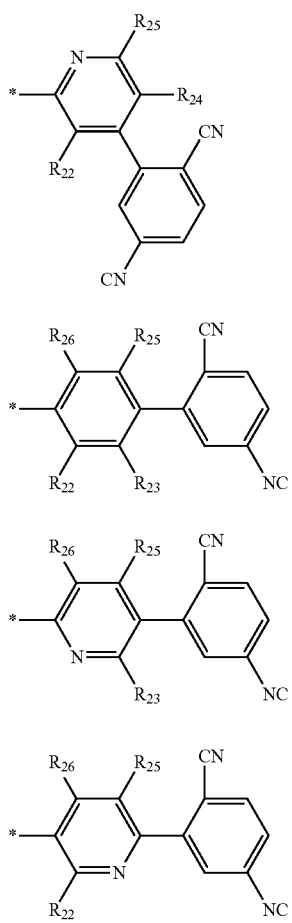

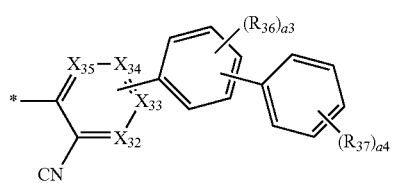

Formula 2C-1

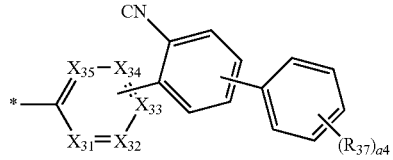

Formula 2C-2


Formula 2C-3


Formula 2C-4

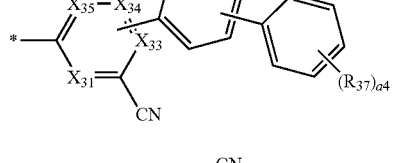

Formula 2C-5

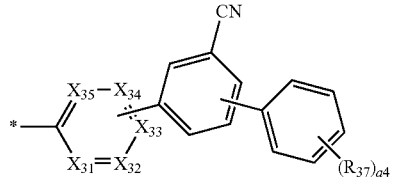

Formula 2C-6

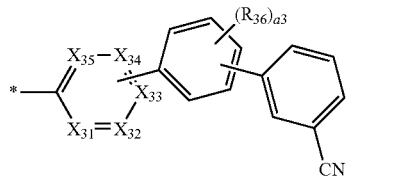

Formula 2C-7

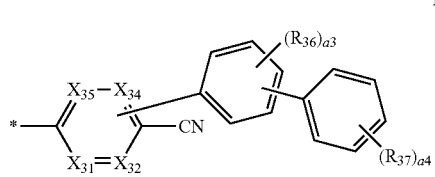

Formula 2C-8

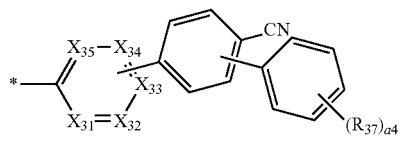

Formula 2C-9

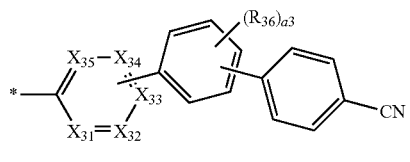

Descriptions of $R_{22}$ to $R_{26}$ in Formulae 2B(1)-1 to 2B(13)-1, 2B(1)-2 to 2B(13)-2, 2B(1)-3 to 2B(13)-3, 2B(1)-4 to 2B(13)-4, 2B(1)-5 to 2B(13)-5, 2B(1)-6 to 2B(13)-6, and 2B(1)-7 to 2B(13)-7 are the same as provided above.

In some embodiments, $R_{22}$ to $R_{26}$ in Formulae 2B(1)-1 to 2B(13)-1, 2B(1)-2 to 2B(13)-2, 2B(1)-3 to 2B(13)-3, 2B(1)-4 to 2B(13)-4, 2B(1)-5 to 2B(13)-5, 2B(1)-6 to 2B(13)-6, and 2B(1)-7 to 2B(13)-7 may be each independently selected from a hydrogen, a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof and a phosphoric acid group or a salt thereof; and —Si($Q_{11}$)($Q_{12}$)($Q_{13}$), but embodiments are not limited thereto.

The group represented by Formula 2C may include groups represented by Formulae 2C-1 to 2C-9, and 2C-1(1) to 2C-9(1):

Descriptions of $X_{31}$ to $X_{35}$, $R_{36}$, $R_{37}$, a3, and a4 in Formulae 2C-1 to 2C-9, and 2C-1(1) to 2C-9(1) are the same as provided above.

For example, each of $X_{31}$ to $X_{35}$ in Formulae 2C-1 to 2C-9 may not be N.

In some embodiments, $X_{31}$, $X_{32}$, $X_{33}$, and $X_{35}$ in Formulae 2C-1(1) to 2C-9(1) may not be N.

In some embodiments, the group represented by Formula 2C may include a group represented by one of Formulae 2C(1) to 2C(9):

-continued
Formula 2C(4)
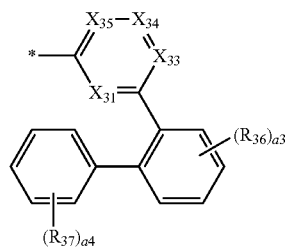
Formula 2C(5)
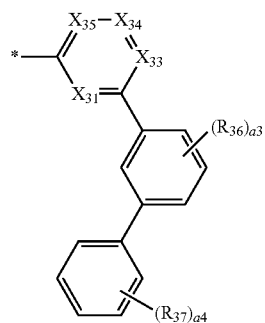
Formula 2C(6)
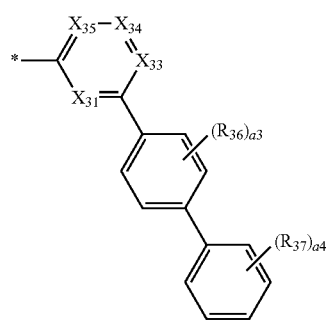
Formula 2C(7)
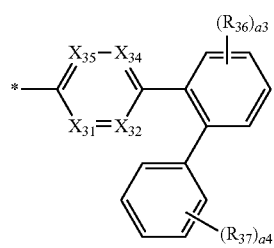
Formula 2C(8)
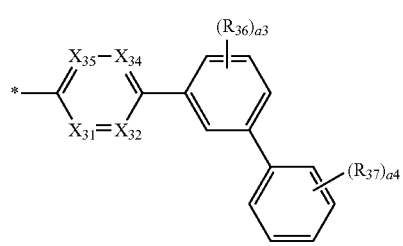
Formula 2C(9)
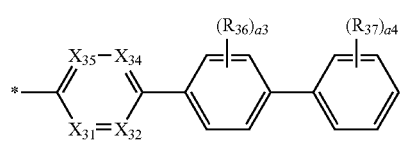
Descriptions of $X_{31}$ to $X_{35}$, $R_{36}$, $R_{37}$, a3, and a4 in Formulae 20(1) to 20(9) are the same as provided above.
The group represented by Formula 2D may include a group represented by one of Formulae 2D-1 to 2D-12 and 2D-1(1) to 2D-12(1):
Formula 2D-1
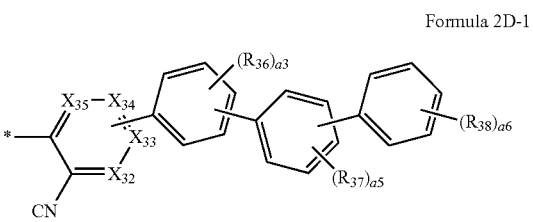
Formula 2D-2
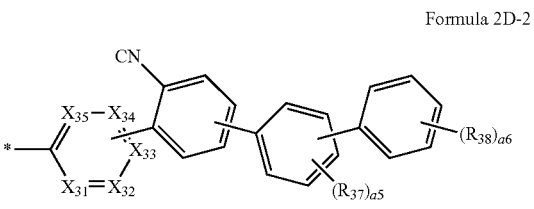
Formula 2D-3
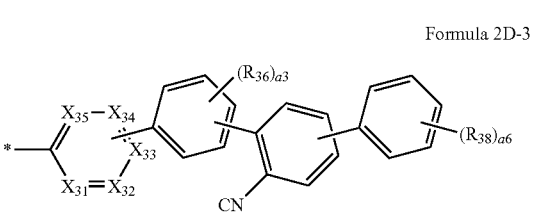
Formula 2D-4
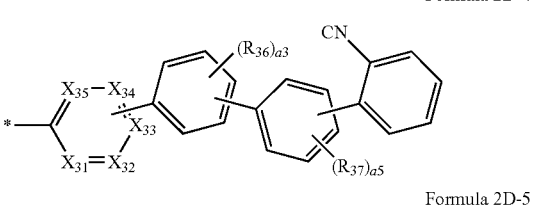
Formula 2D-5
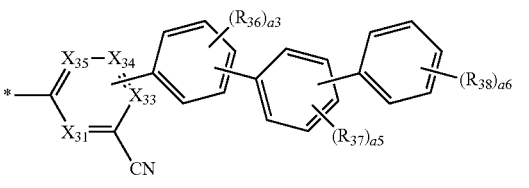
Formula 2D-6
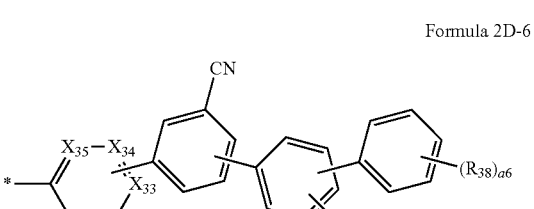
Formula 2D-7
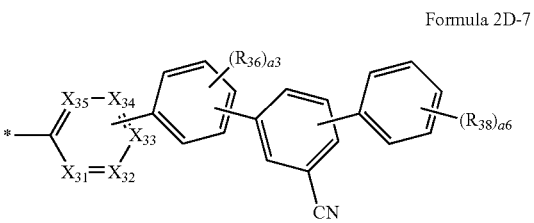

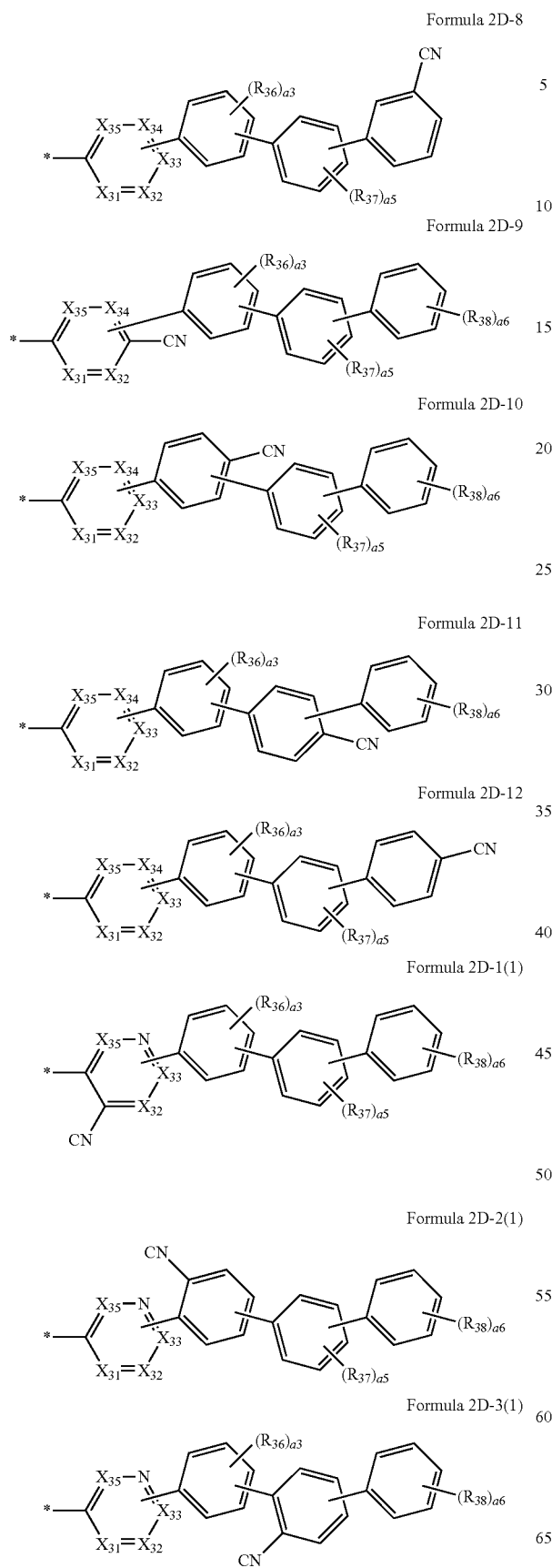
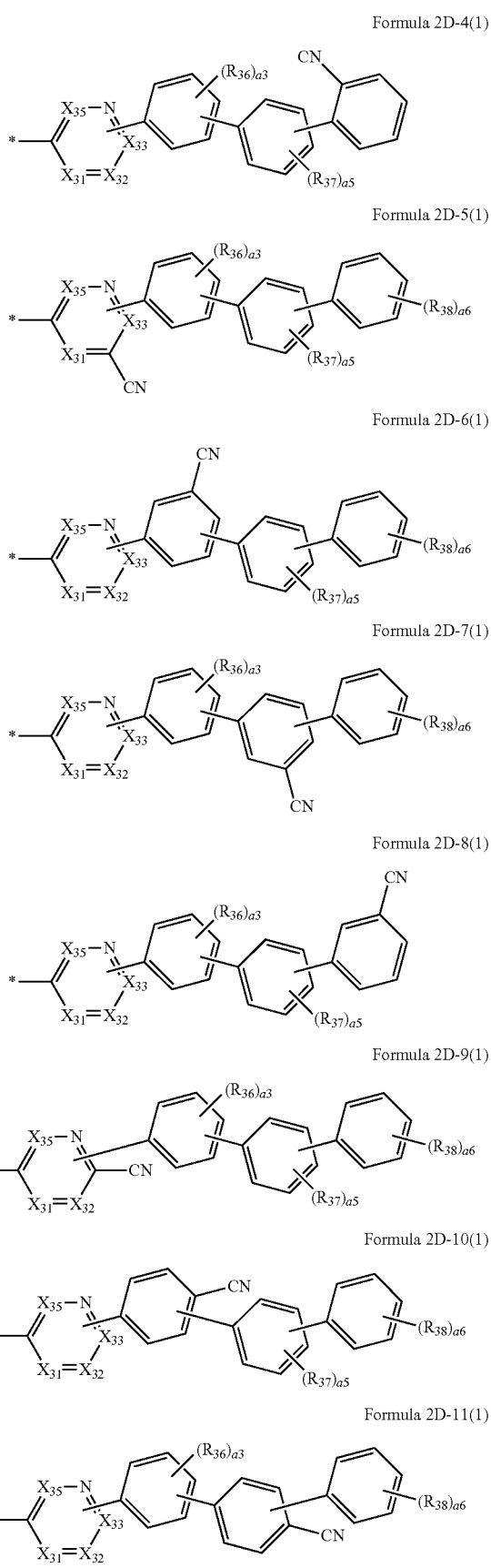

Formula 2D-12(1)

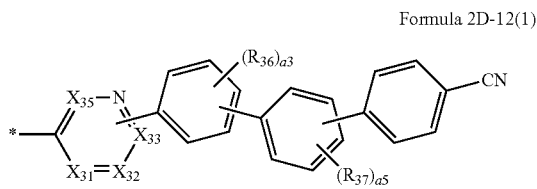

Descriptions of $X_{31}$ to $X_{35}$, $R_{36}$, $R_{37}$, $R_{38}$, a3, a5 and a6 in Formulae 2D-1 to 2D-12 and 2D-1(1) to 2D-12(1) are the same as provided above.

For example, each of $X_{31}$ to $X_{35}$ in Formulae 2D-1 to 2D-12 may not be N.

In some embodiments, $X_{31}$, $X_{32}$, $X_{33}$, and $X_{35}$ in Formulae 2D-1(1) to 2D-12(1) may not be N.

In some embodiments, the group represented by Formula 2D may include groups represented by Formulae 2D(1) to 2D(27):

Formula 2D(1)

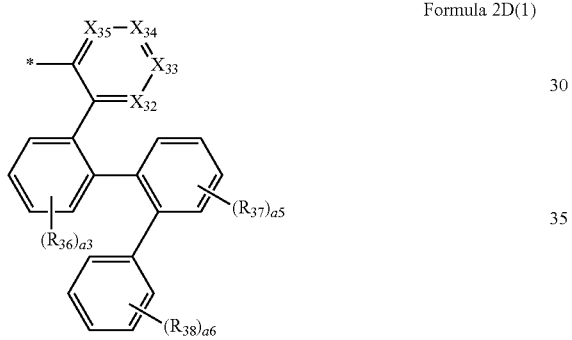

Formula 2D(2)

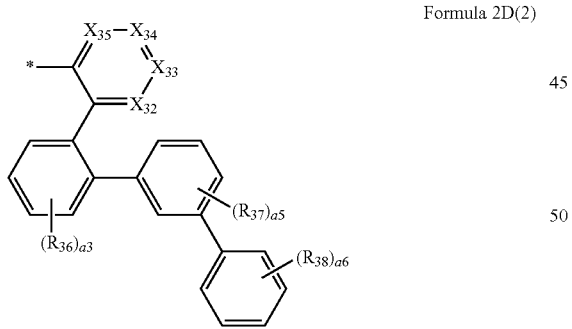

Formula 2D(3)

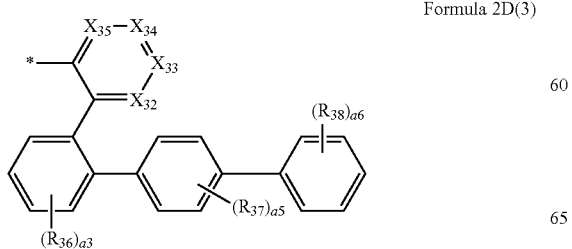

Formula 2D(4)

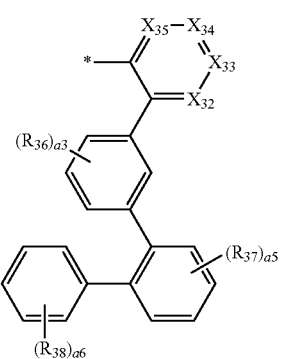

Formula 2D(5)

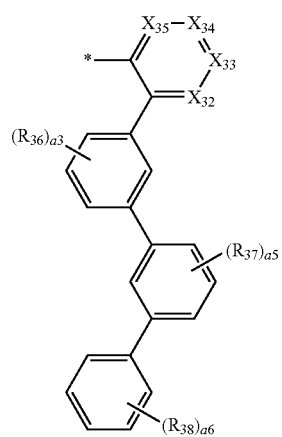

Formula 2D(6)

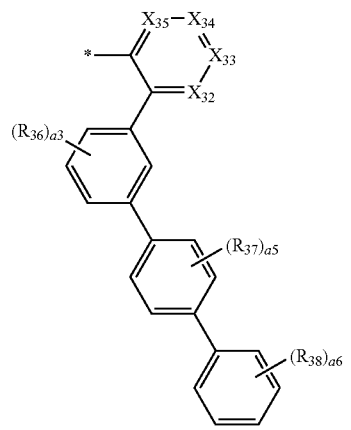

Formula 2D(7)

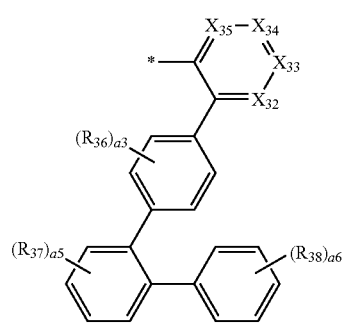

-continued
Formula 2D(8)
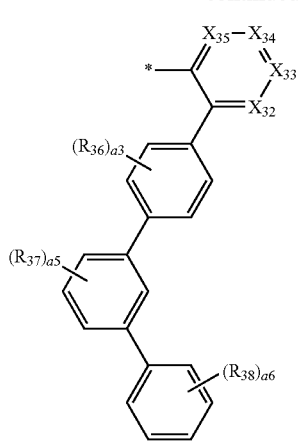
Formula 2D(9)
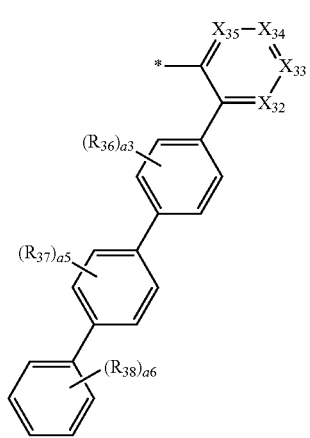
Formula 2D(10)
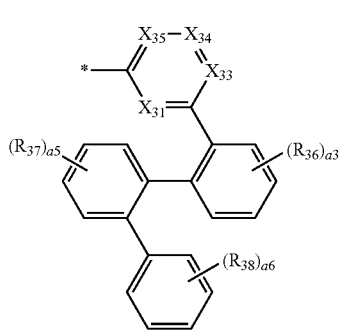
Formula 2D(11)
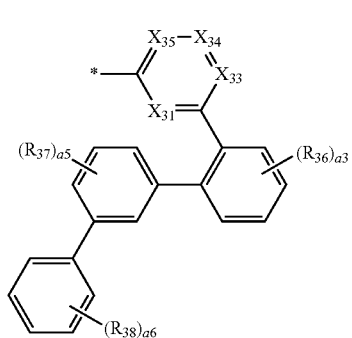
-continued
Formula 2D(12)
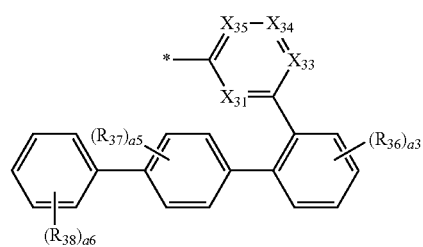
Formula 2D(13)
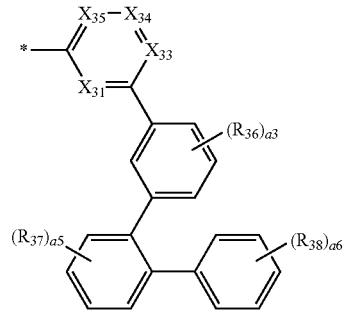
Formula 2D(14)
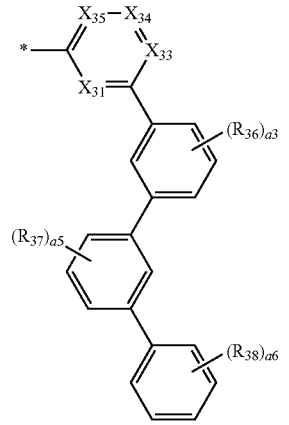
Formula 2D(15)
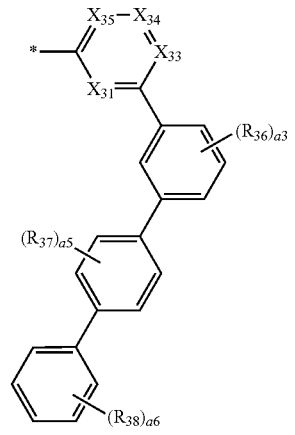

Formula 2D(16)
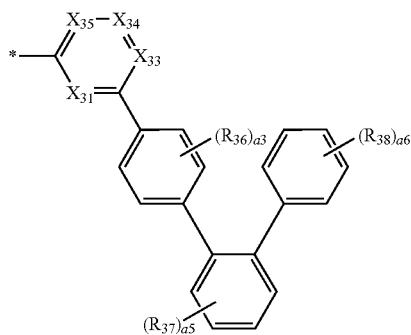
Formula 2D(17)
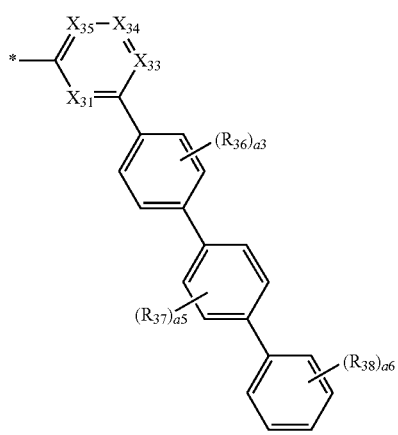
Formula 2D(18)
Formula 2D(19)
Formula 2D(20)
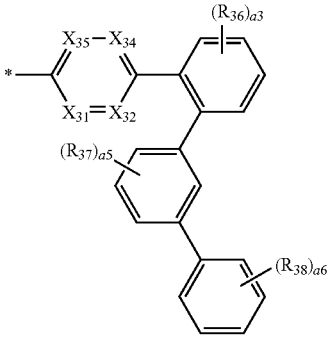
Formula 2D(21)
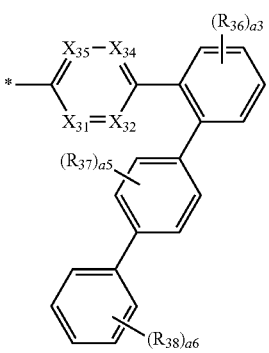
Formula 2D(22)
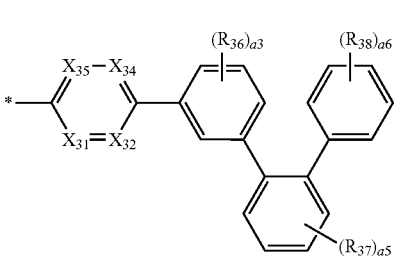
Formula 2D(23)
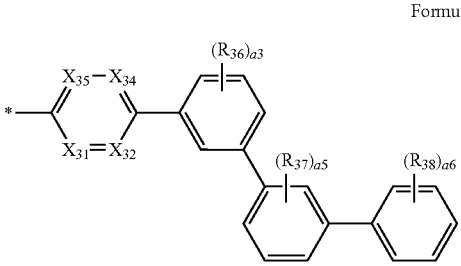
Formula 2D(24)
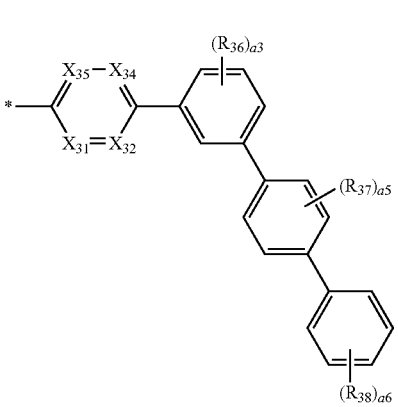

-continued

Formula 2D(25)

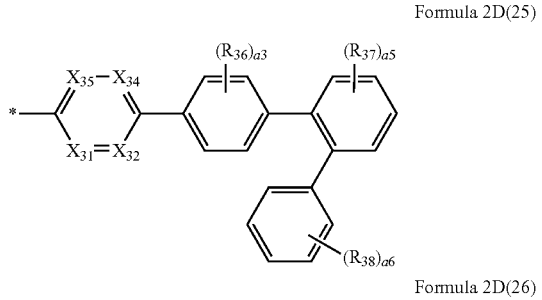

Formula 2D(26)

Formula 2D(27)

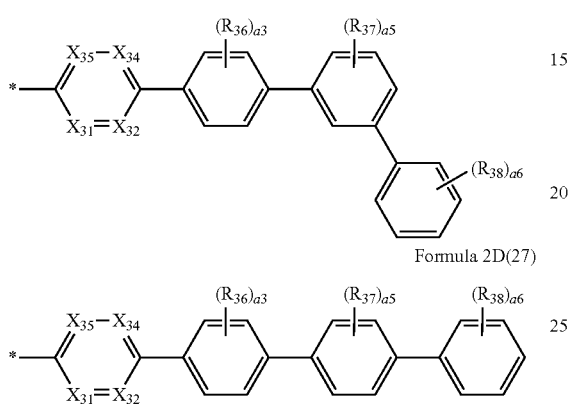

Descriptions of $X_{31}$ to $X_{35}$, $R_{36}$, $R_{37}$, $R_{38}$, a3, a5 and a6 in Formulae 2D(1) to 2D(27) are the same as provided above.

In some embodiments, the carbazole compound represented by Formula 1 is represented by one of Formulae 1A to 1F, and in Formulae 1A to 1F, i) when each of $R_5$, $R_6$ and $R_{19}$ are not N, at least one selected from $R_{41}$ to $R_{43}$ is a group represented by one of Formulae 2A-1 to 2A-4, 2B-1 to 2B-7, 2C-1 to 2C-9, 2C-1(1) to 2C-9(1), 2D-1 to 2D-12, and 2D-1(1) to 2D-12 (1), and ii) when at least one selected from $R_5$, $R_6$ and $R_{19}$ is N, at least one selected from $R_{41}$ to $R_{43}$ may be a group represented by one of Formulae 2A-1 to 2A-7, 2B-1 to 2B-7, 2C-1 to 2C-9, 2C-1(1) to 2C-9(1), 2D-1 to 2D-12 and 2D-1 (1) to 2D-12(1).

In some embodiments, the carbazole compound represented by Formula 1 is represented by one of Formulae 1A to 1F, and at least one selected from $R_{41}$ to $R_{43}$ in Formulae 1A to 1F may be a group represented by one of Formulae 2B(1) to 2B(13), 2C(1) to 2C(9) and 2D(1) to 2D(27).

In some embodiments, the carbazole compound represented by Formula 1 is represented by one of Formulae 1A to 1F, and in Formulae 1A to 1F, when i) each of $R_5$, $R_6$ and $R_{19}$ is not N, at least one selected from $R_{41}$ to $R_{43}$ may be a group represented by one of Formulae 2A-1 to 2A-4, 2B(1)-1 to 2B(13)-1, 2B(1)-2 to 2B(13)-2, 2B(1)-3 to 2B(13)-3, 2B(1)-4 to 2B(13)-4, 2B(1)-5 to 2B(13)-5, 2B(1)-6 to 2B(13)-6 and 2B(1)-7 to 2B(13)-7, and ii) when at least one selected from $R_5$, $R_6$ and $R_{19}$ is N, at least one selected from $R_{41}$ to $R_{43}$ may be a group represented by one of Formulae 2A-1 to 2A-7, 2B(1)-1 to 2B(13)-1, 2B(1)-2 to 2B(13)-2, 2B(1)-3 to 2B(13)-3, 2B(1)-4 to 2B(13)-4, 2B(1)-5 to 2B(13)-5, 2B(1)-6 to 2B(13)-6 and 2B(1)-7 to 2B(13)-7.

In some embodiments, regarding Formula 1, i) when each of $X_1$ to $X_8$ and $X_{11}$ to $X_{19}$ is not N, one selected from $R_{41}$ to $R_{43}$ in Formula 1 may be represented by one of Formulae 2A-1 to 2A-4, 3B-1 to 3B-12, 3C-1 to 3C-6, and 3D-1 to 3D-6, ii) when at least one selected from $X_1$ to $X_8$ and $X_{11}$ to $X_{19}$ is N, one selected from $R_{41}$ to $R_{43}$ in Formula 1 may be represented by one of Formulae 2A-1 to 2A-7, 3B-1 to 3B-12, 3C-1 to 3C-6, and 3D-1 to 3D-6:

Formula 3B-2
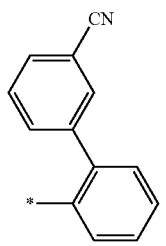
Formula 3B-3
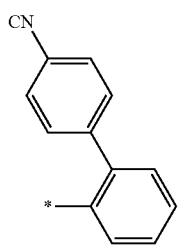
Formula 3B-4
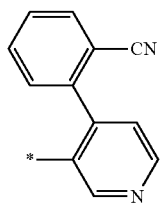
Formula 3B-5
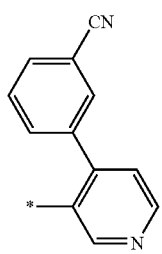
Formula 3B-6
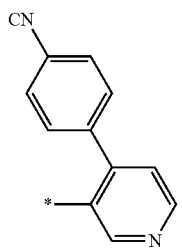
Formula 3B-7
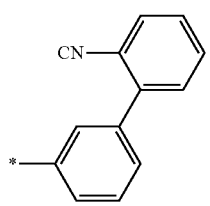
Formula 3B-8
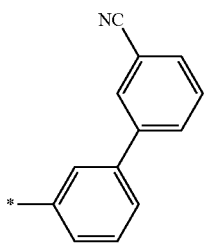
Formula 3B-9
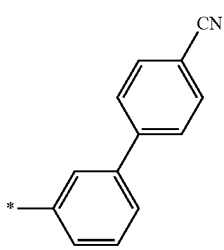
Formula 3B-10
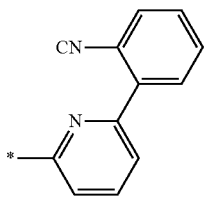
Formula 3B-11
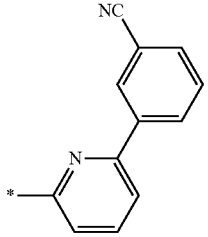
Formula 3B-12
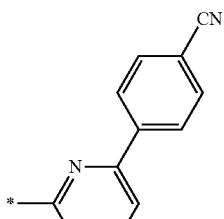
Formula 3C-1
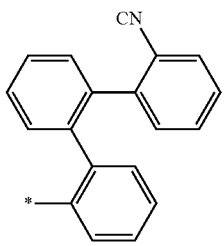

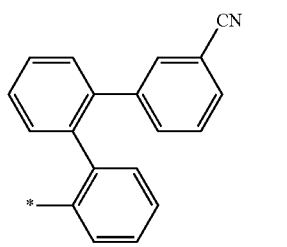
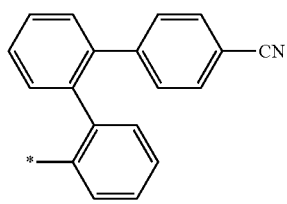
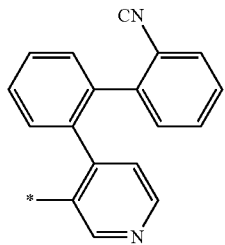
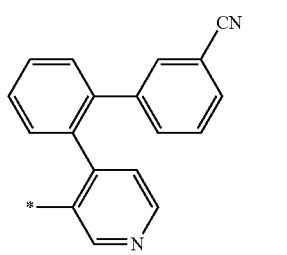
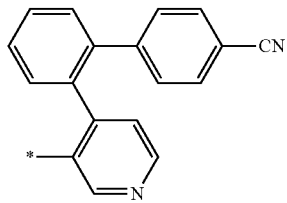
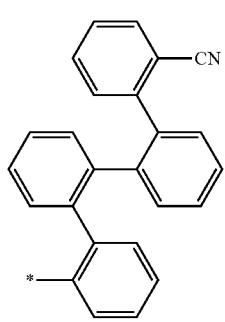
Formula 3C-2
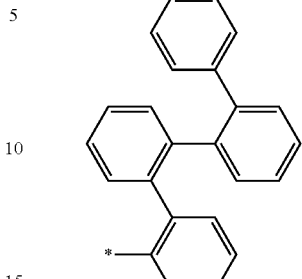
Formula 3C-3
Formula 3C-4
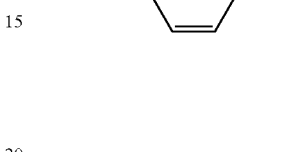
Formula 3C-5
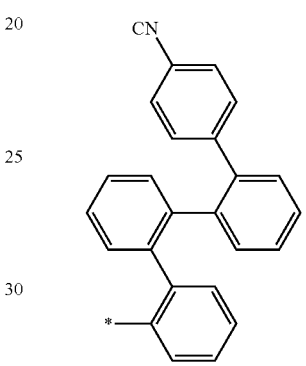
Formula 3C-6
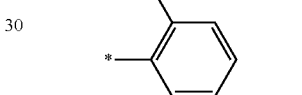
Formula 3D-1
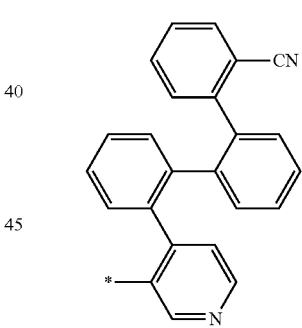
Formula 3D-2
Formula 3D-3
Formula 3D-4
Formula 3D-5
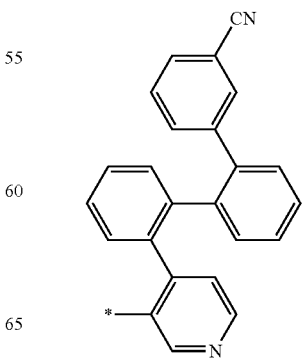

Formula 3D-6

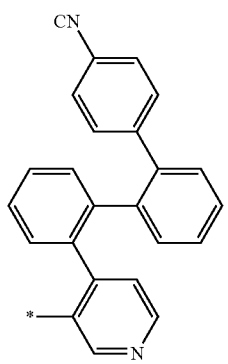

In some embodiments, regarding Formula 1, i) when each of $X_1$ to $X_8$ and $X_{11}$ to $X_{19}$ is not N, $R_{42}$ in Formula 1 may be represented by one of Formulae 2A-1 to 2A-4, 3B-1 to 3B-12, 3C-1 to 3C-6, and 3D-1 to 3D-6, ii) when at least one selected from $X_1$ to $X_8$ and $X_{11}$ to $X_{19}$ is N, $R_{42}$ in Formula 1 may be represented by one of Formulae 2A-1 to 2A-7, 3B-1 to 3B-12, 3C-1 to 3C-6, and 3D-1 to 3D-6:

In some embodiments, the carbazole compound represented by Formula 1 may be represented by one of Formulae 1A to 1F, i) when each of $X_1$ to $X_8$ and $X_{11}$ to $X_{19}$ is not N, $R_{42}$ in Formulae 1A to 1F may be represented by one of Formulae 2A-1 to 2A-4, 3B-1 to 3B-12, 3C-1 to 3C-6, and 3D-1 to 3D-6, ii) when at least one selected from $X_1$ to $X_8$ and $X_{11}$ to $X_{19}$ is N, $R_{42}$ in Formulae 1A to 1F may be represented by one of Formulae 2A-1 to 2A-7, 3B-1 to 3B-12, 3C-1 to 3C-6, and 3D-1 to 3D-6.

For example, the carbazole compound represented by Formula 1 may be one selected from Compounds 1 to 202 below, but embodiments are not limited thereto.

1

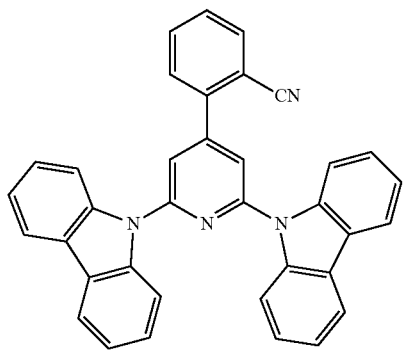

2

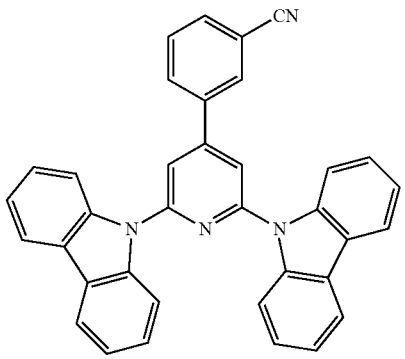

3

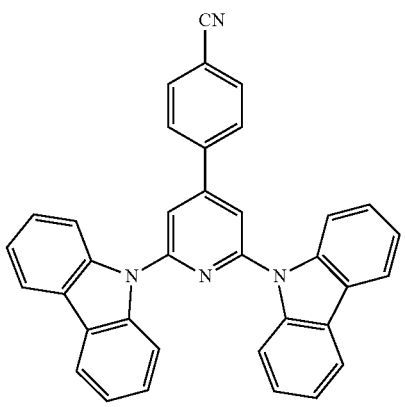

4

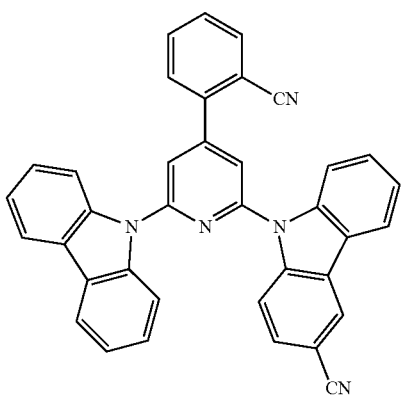

5

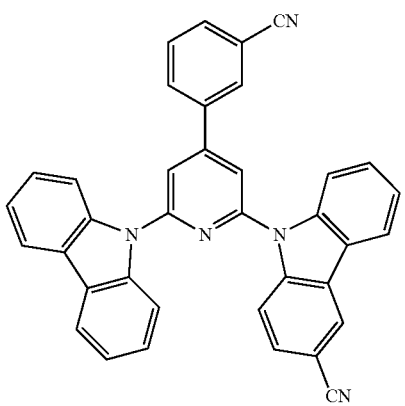

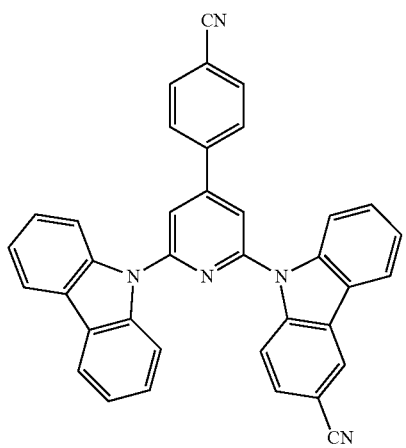
6
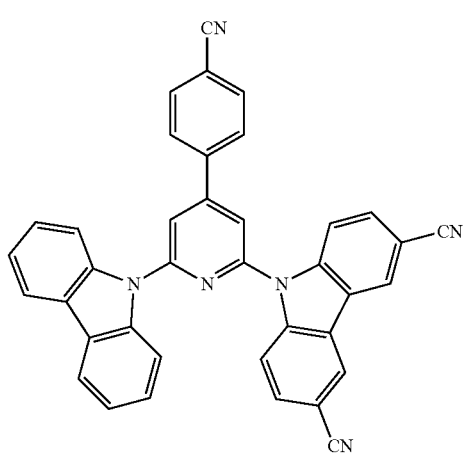
9
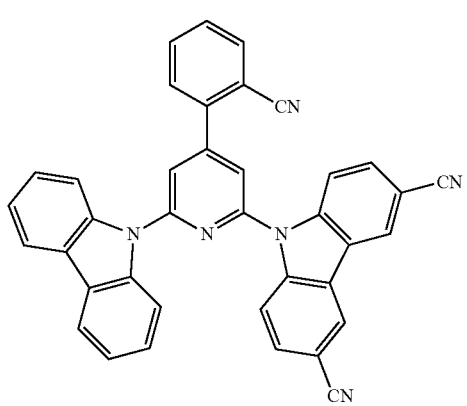
7
10
11
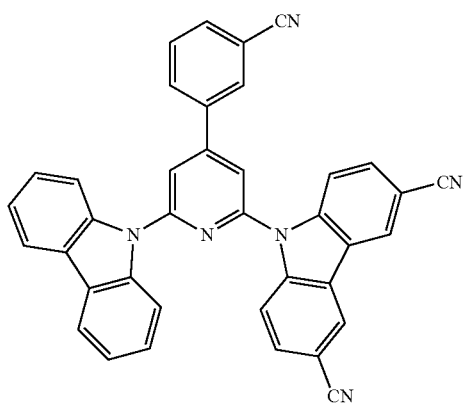
8
12

13
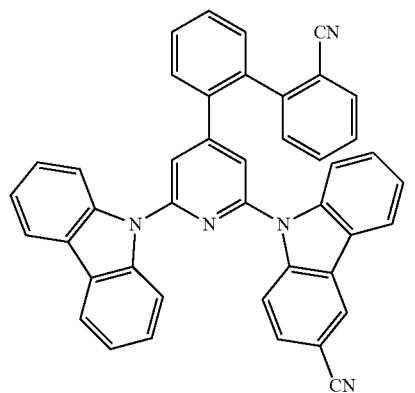
14
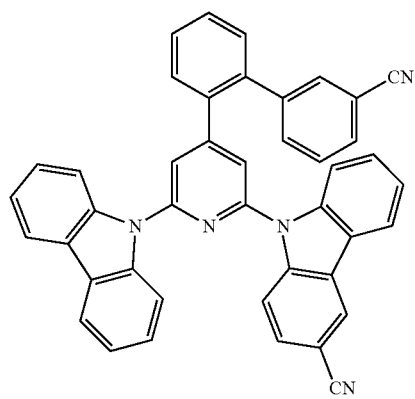
15
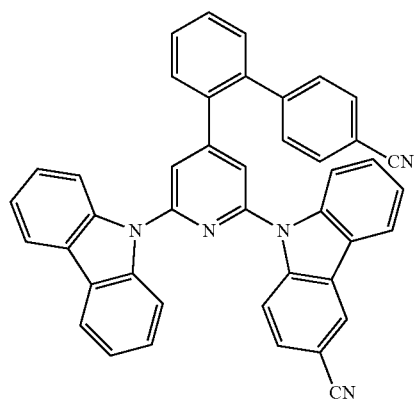
16
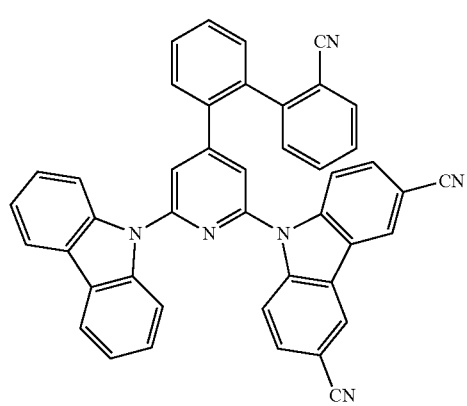
17
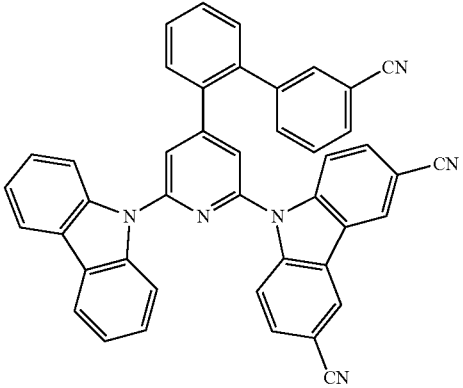
18
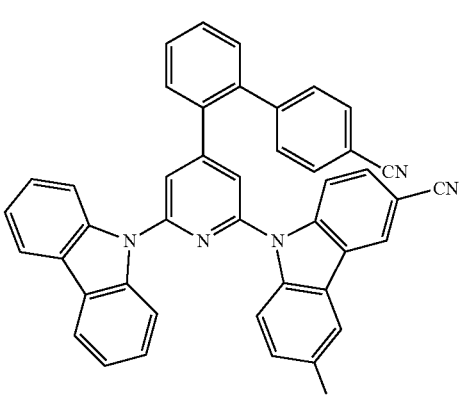
19
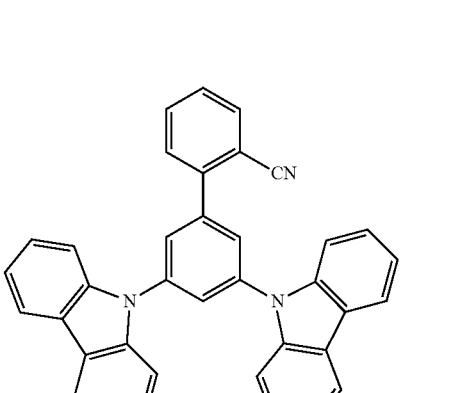
20

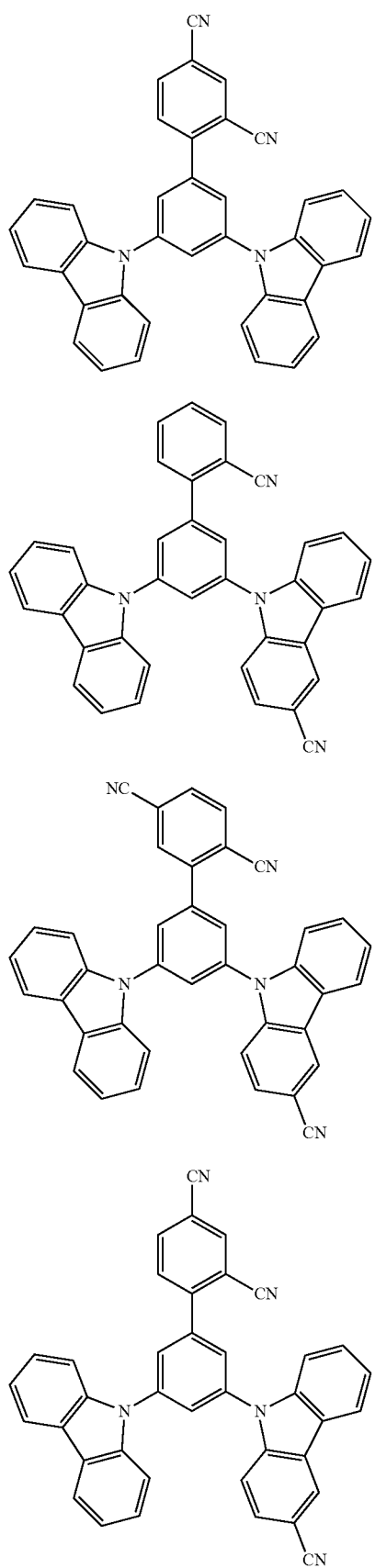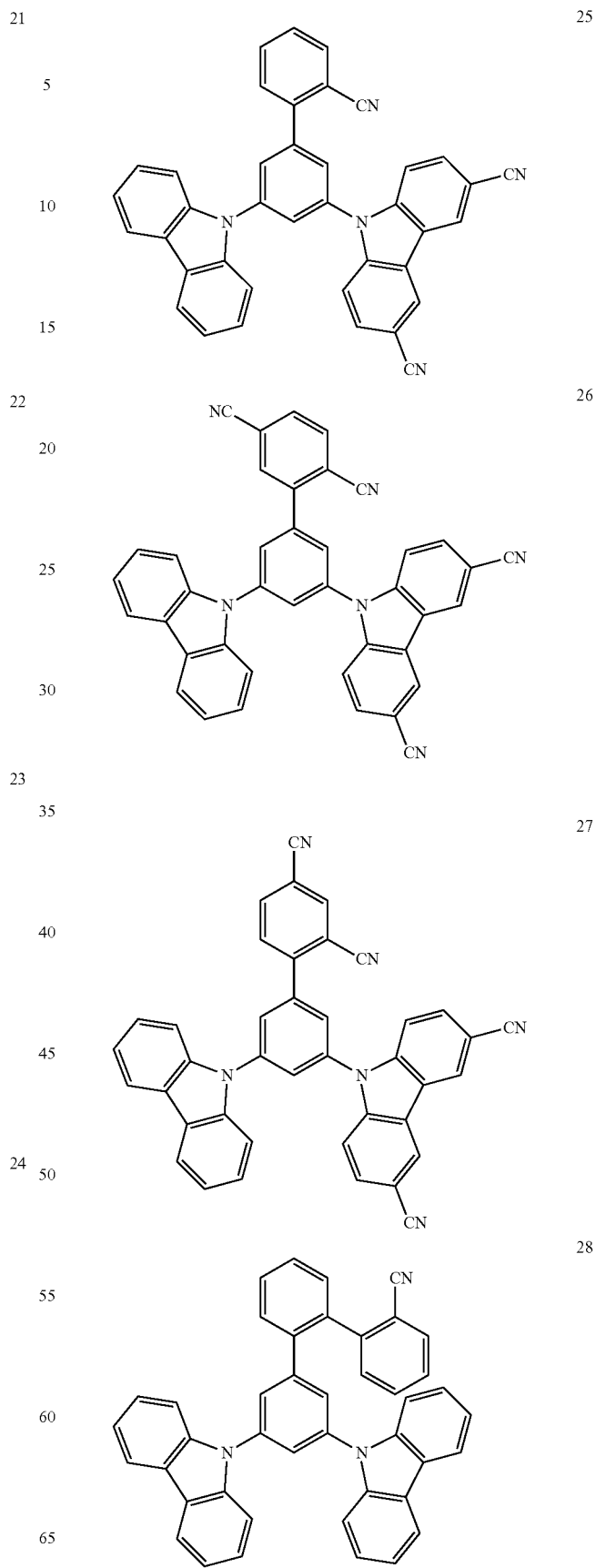

29
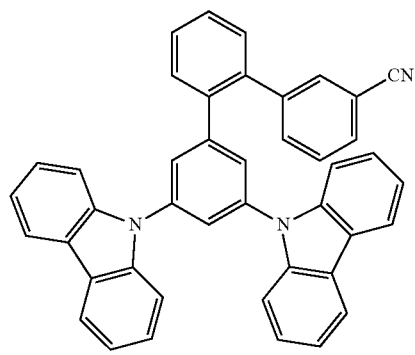
30
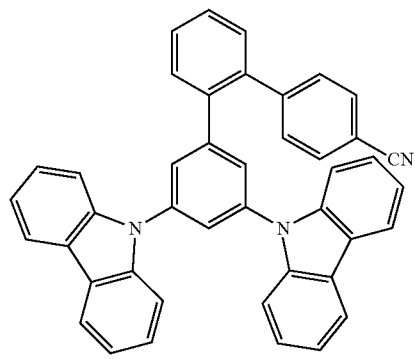
31
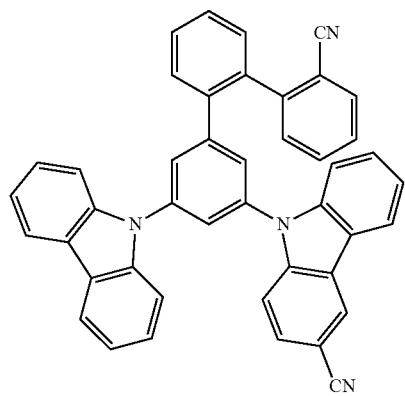
32
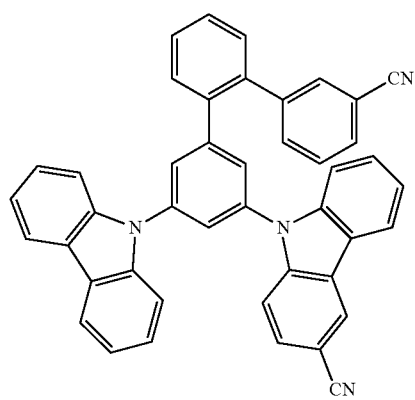
33
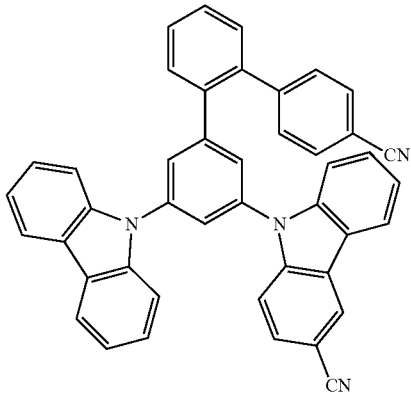
34
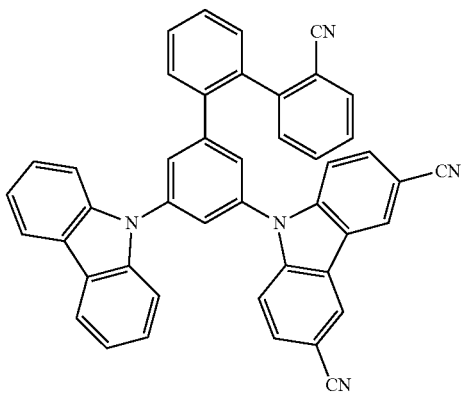
35
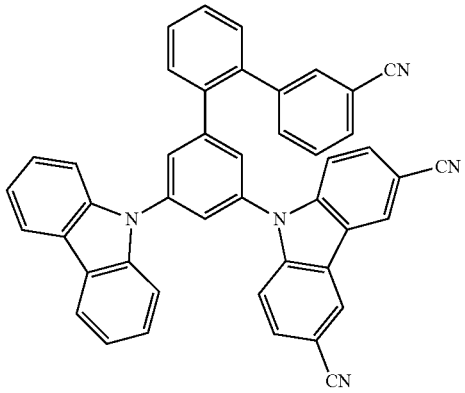
36
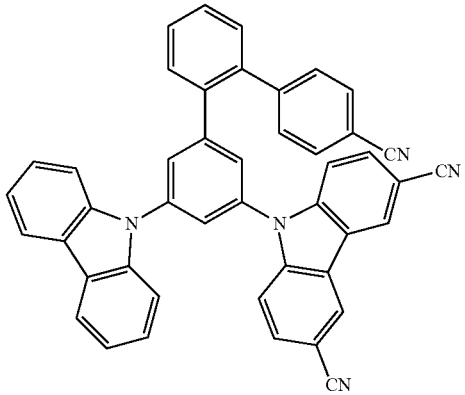

37
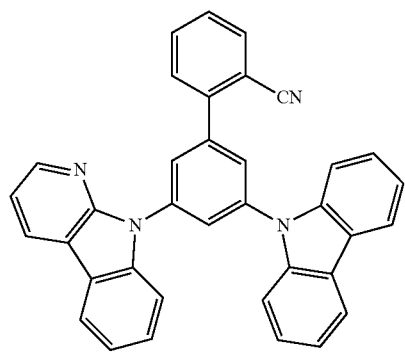
38
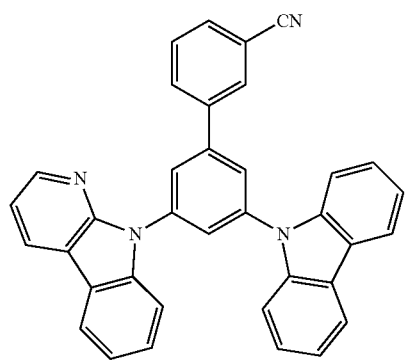
39
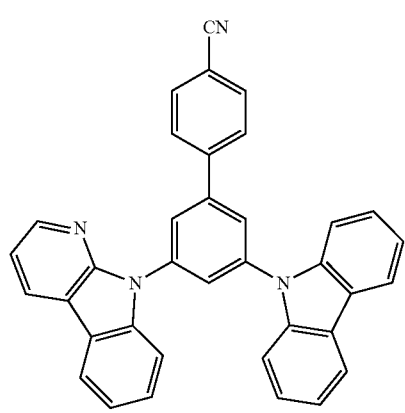
40
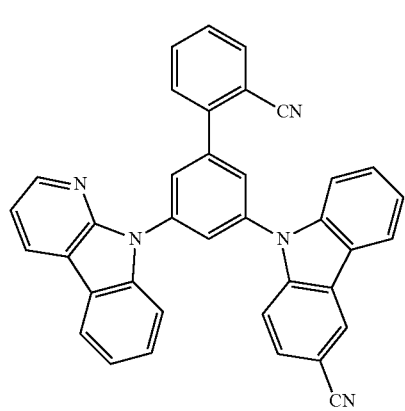
41
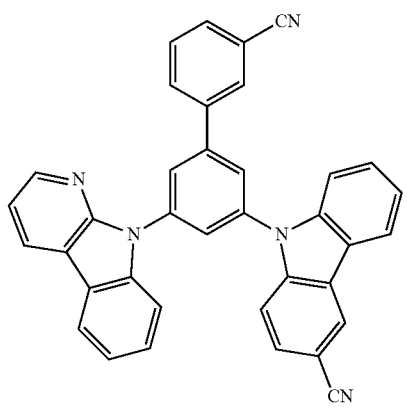
42
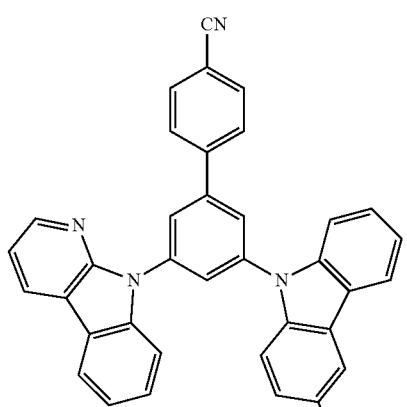
43
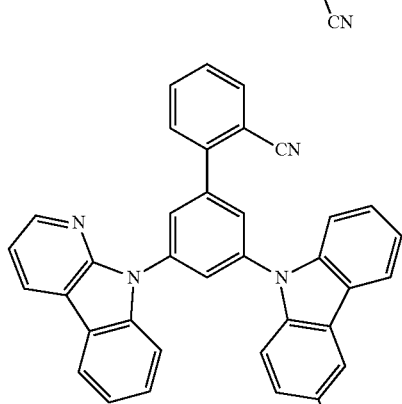
44
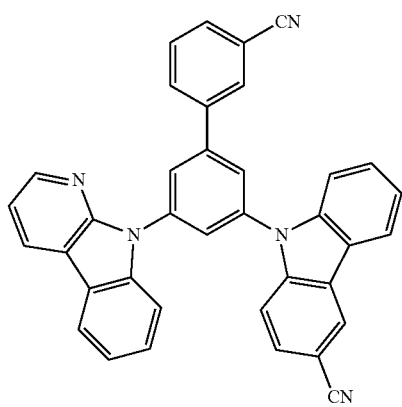

45
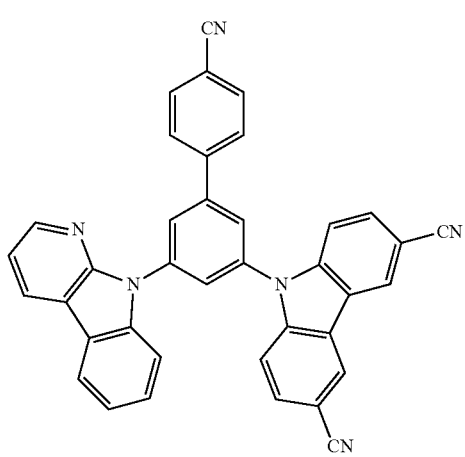
46
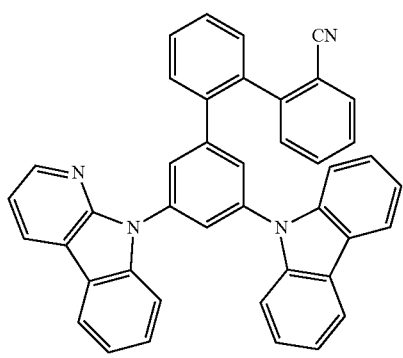
47
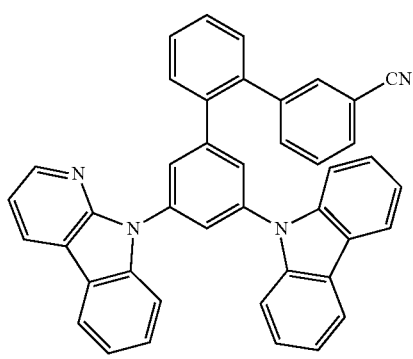
48
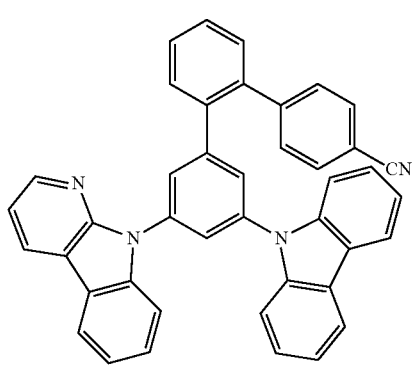
49
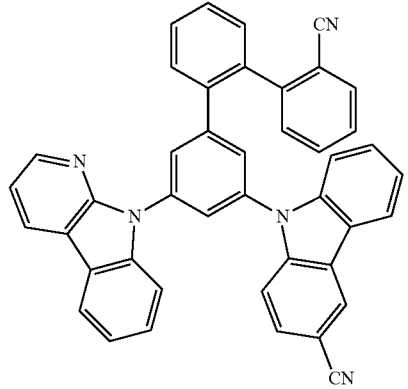
50
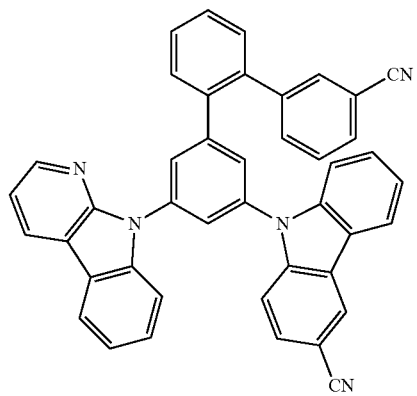
51
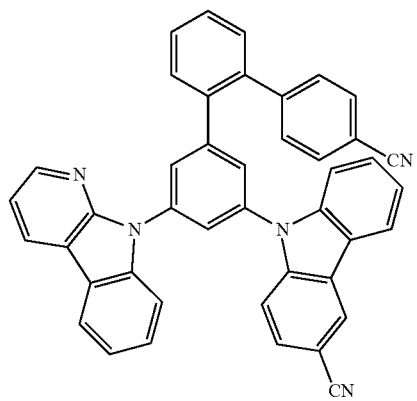
52
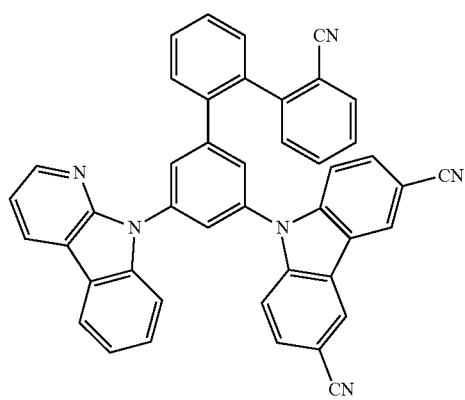

53
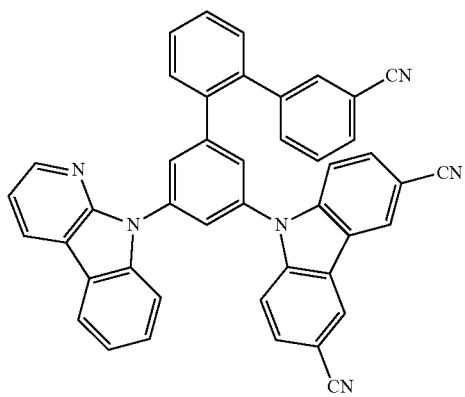
54
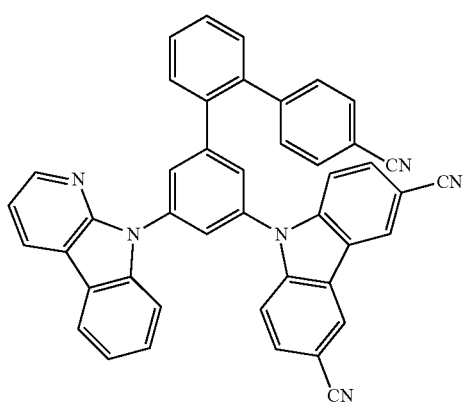
55
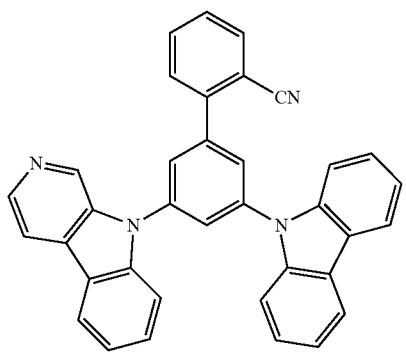
56
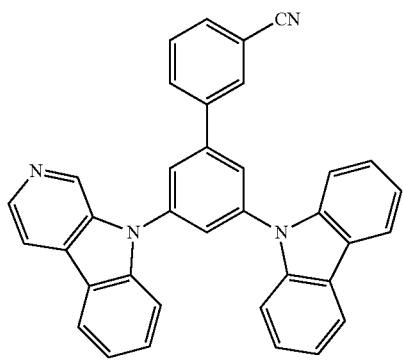
57
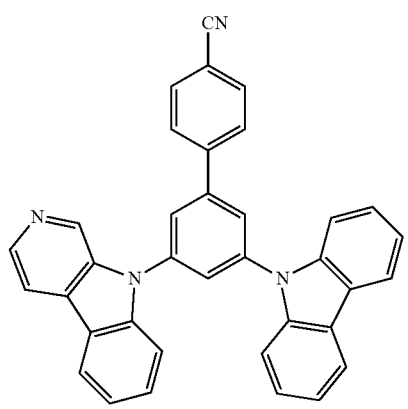
58
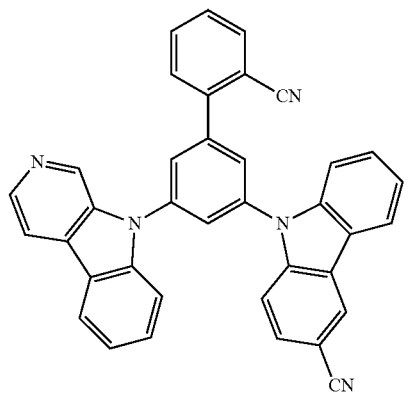
59
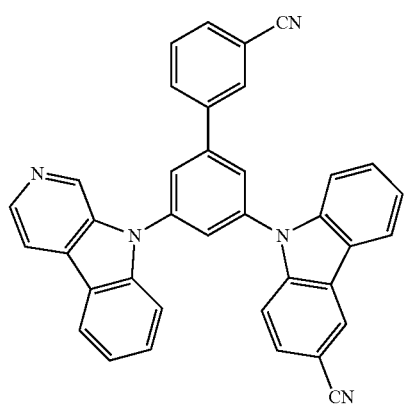
60
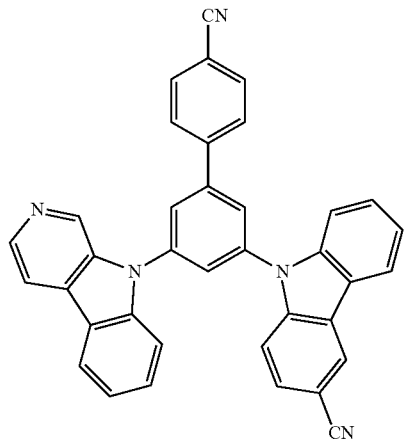

61
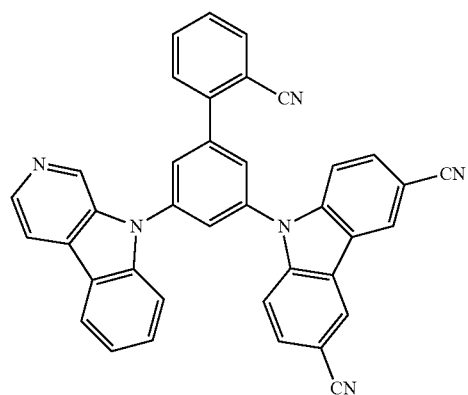
62
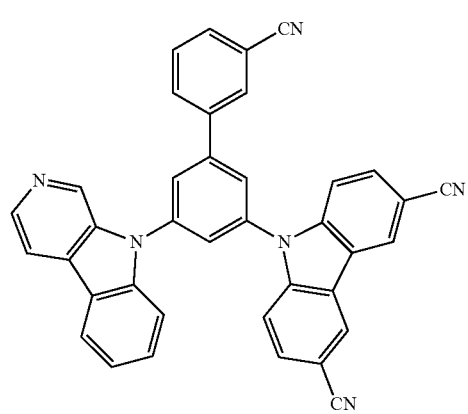
63
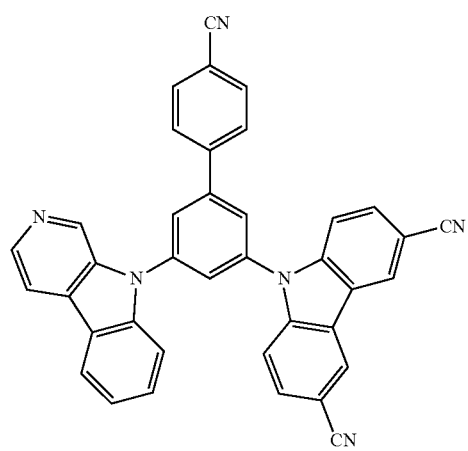
64
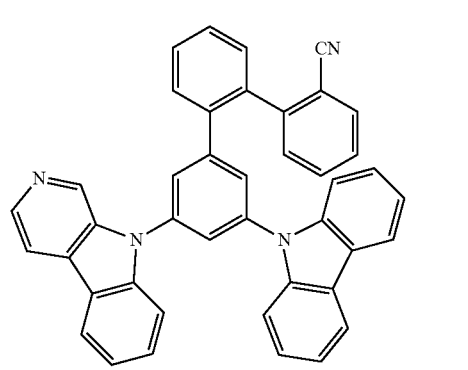
65
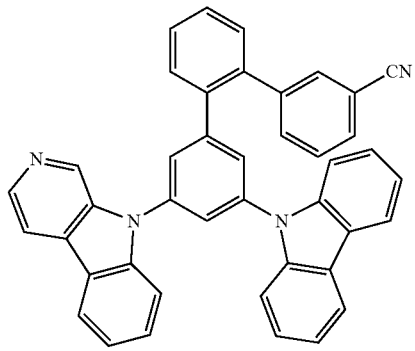
66
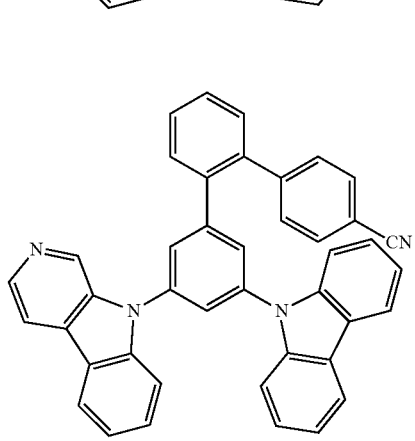
67
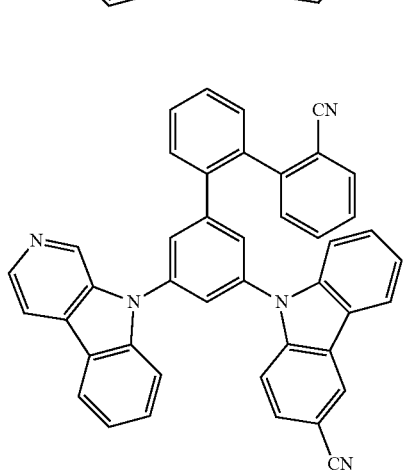
68
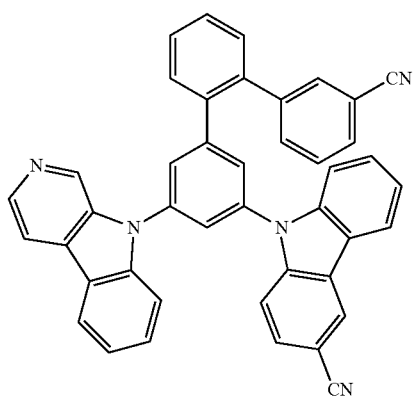

71
-continued
69
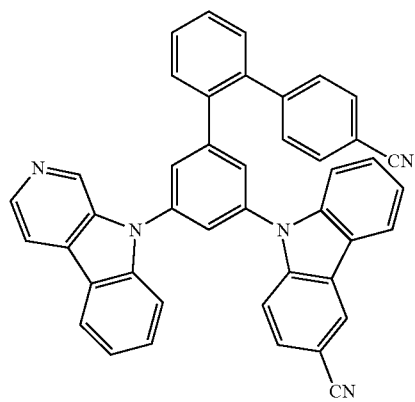
70
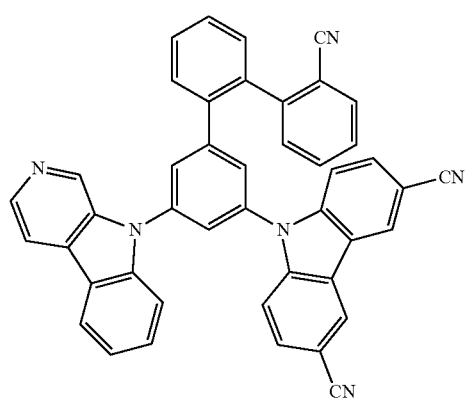
71
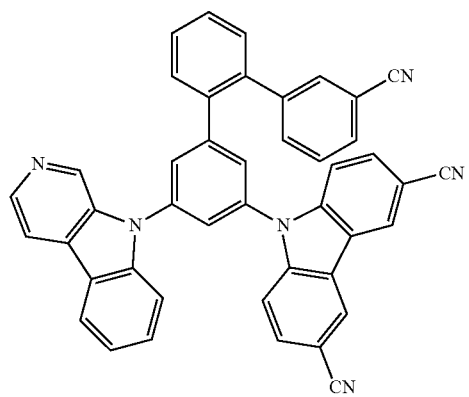
72
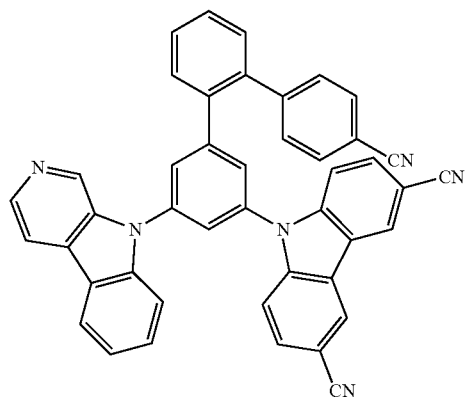
72
-continued
73
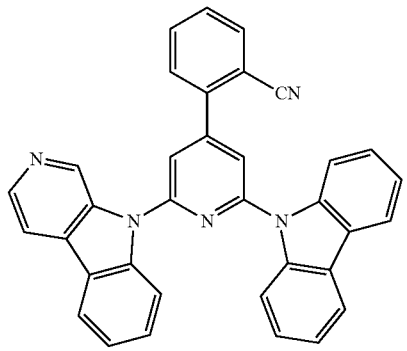
74
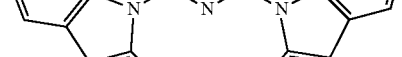
75
76
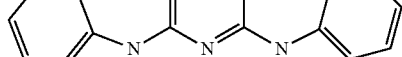

-continued
77
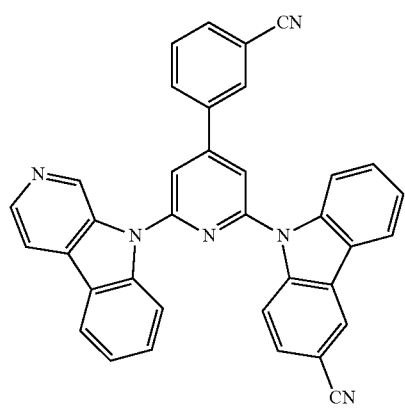
78
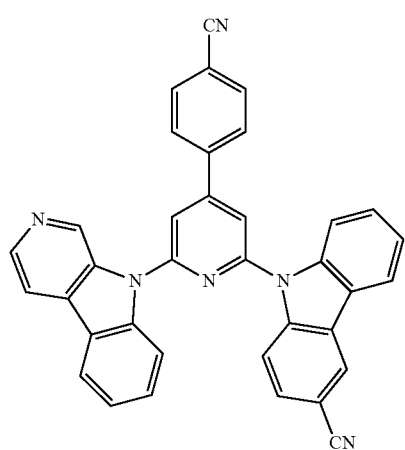
79
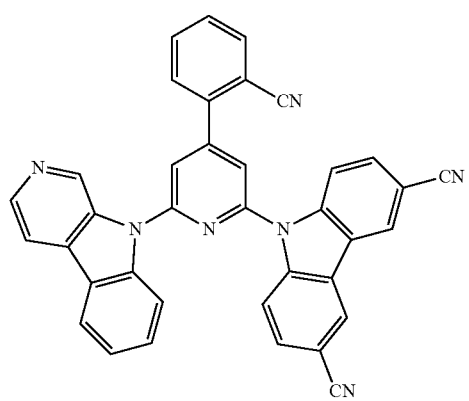
80
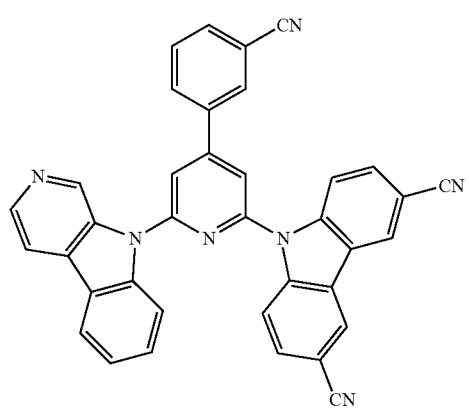
-continued
81
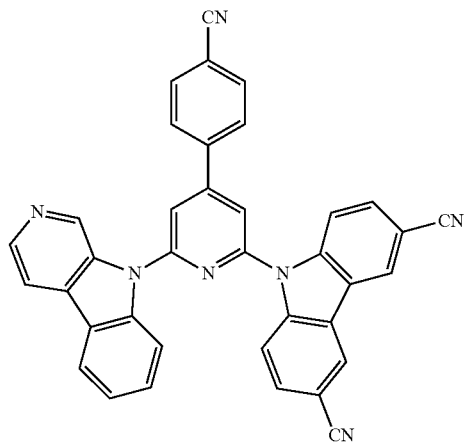
82
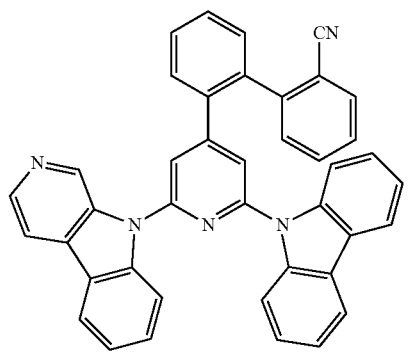
83
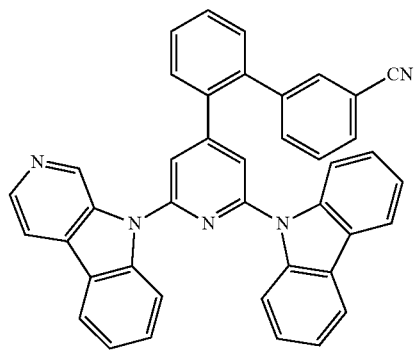
84
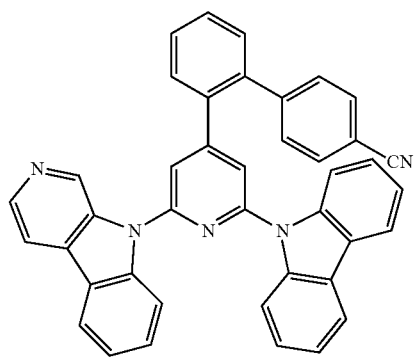

85
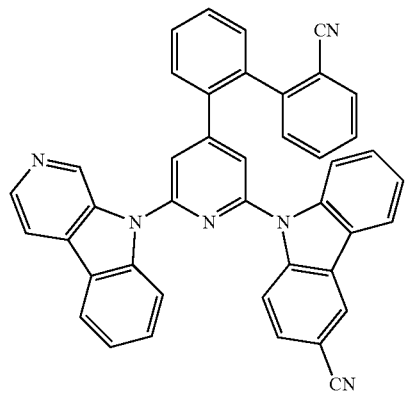
86
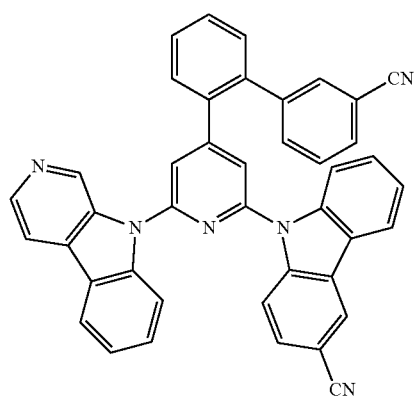
87
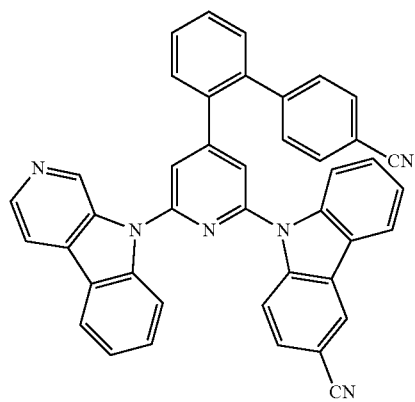
88
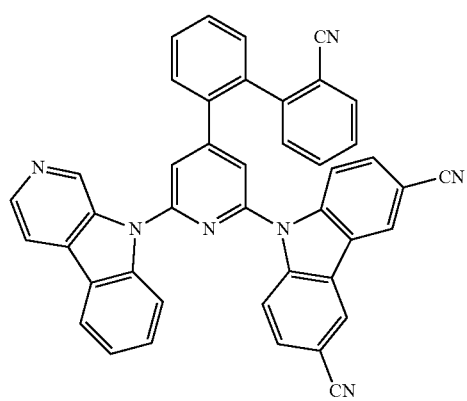
89
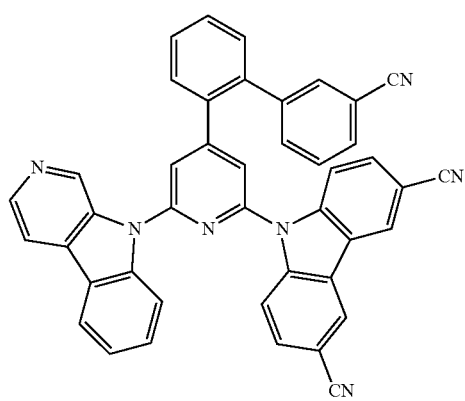
90
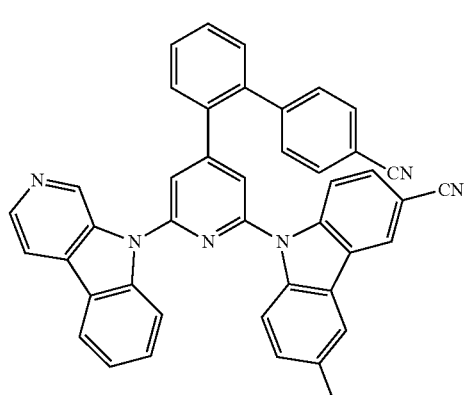
91
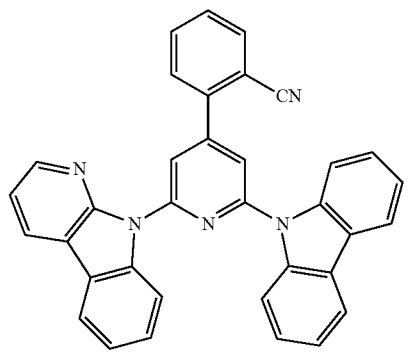
92
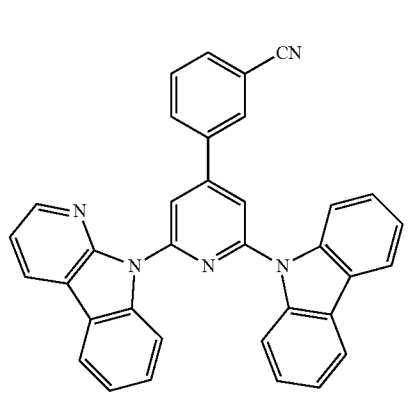

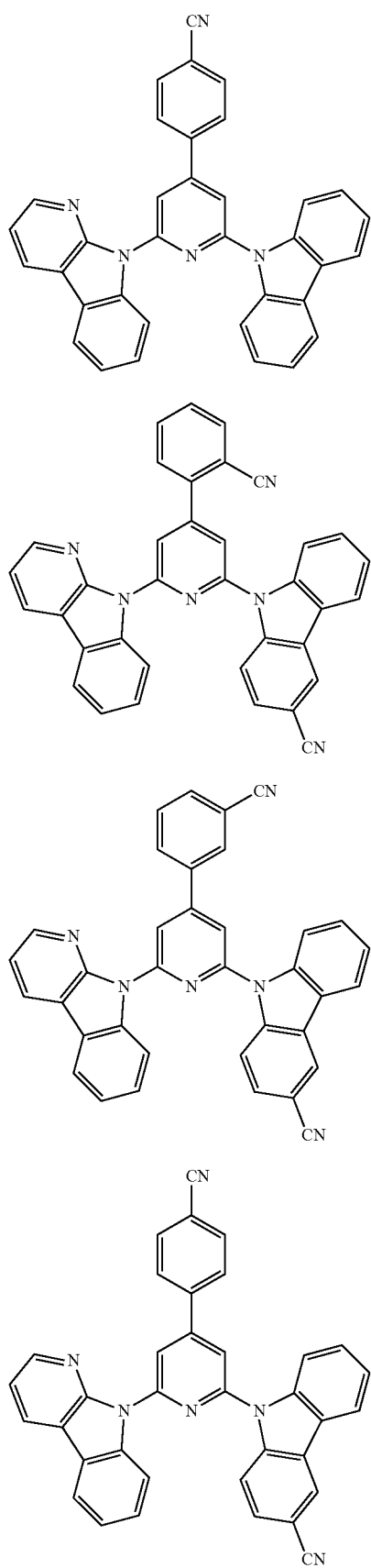
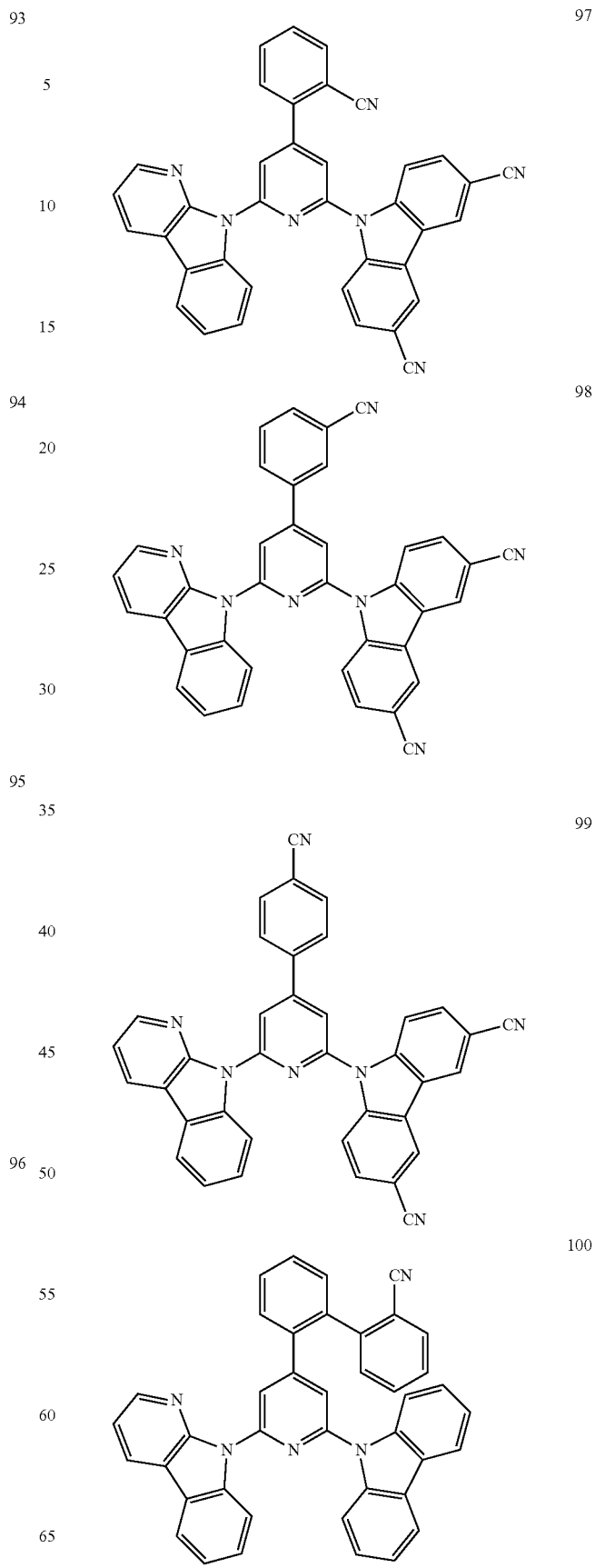

101
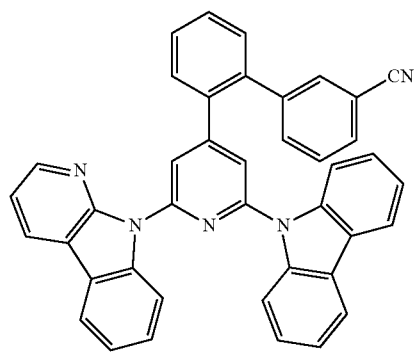
102
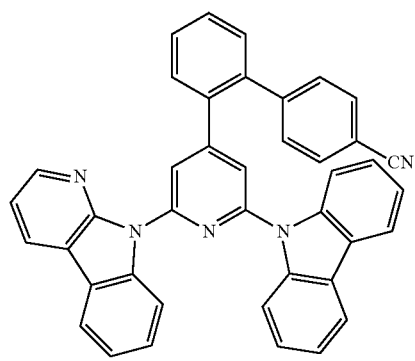
103
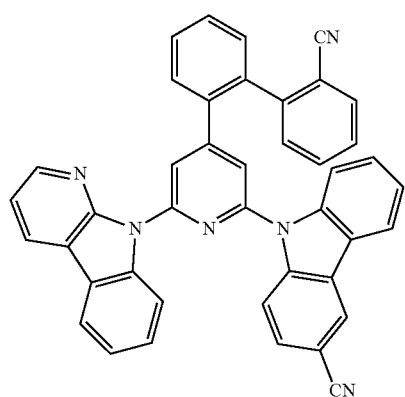
104
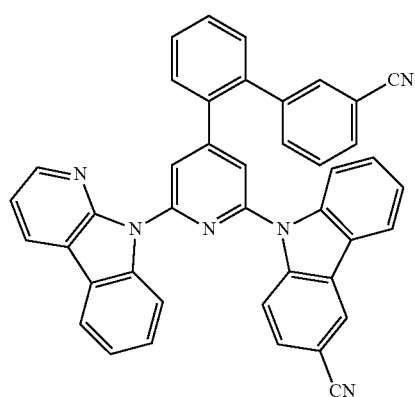
105
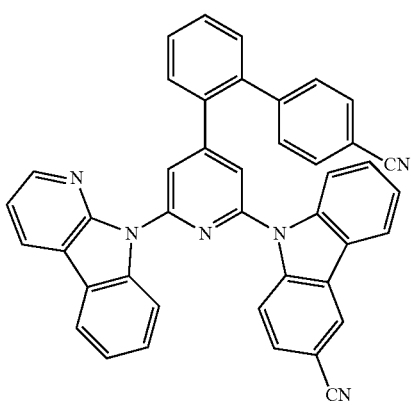
106
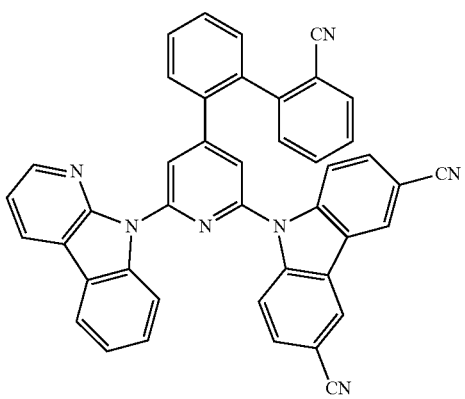
107
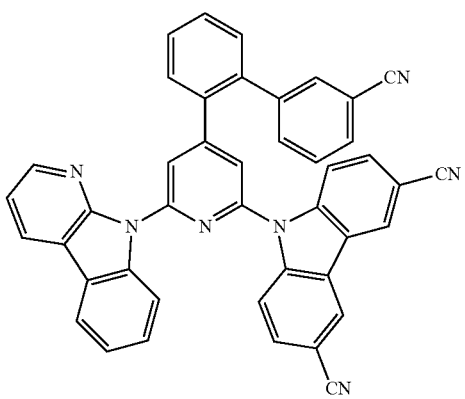
108
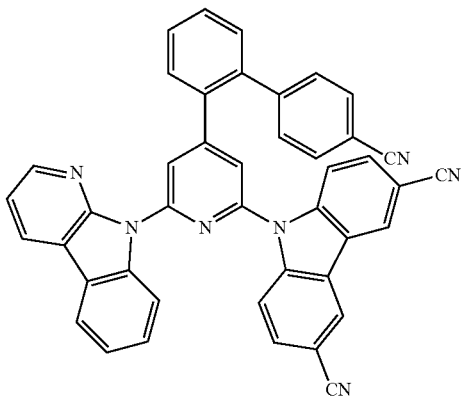

-continued
109
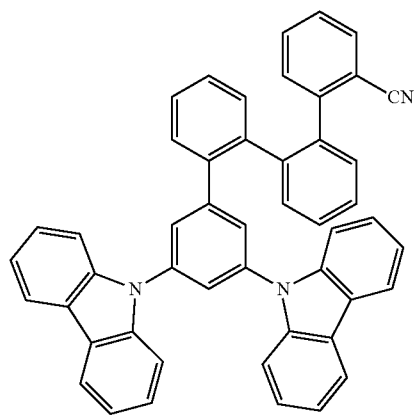
110
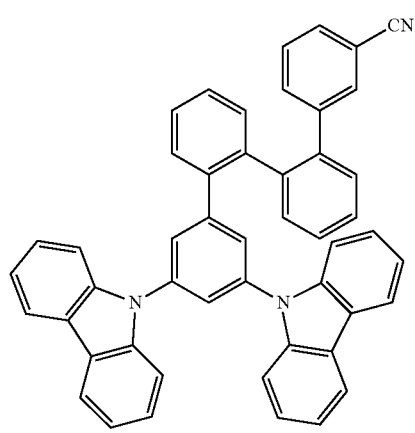
111
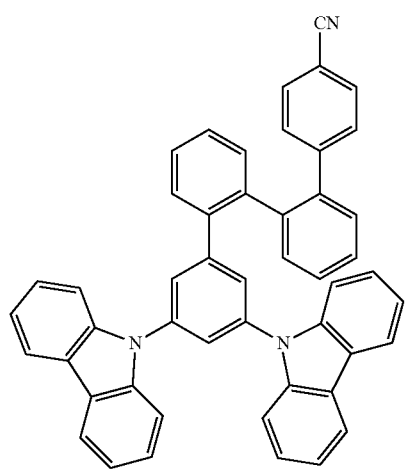
-continued
112
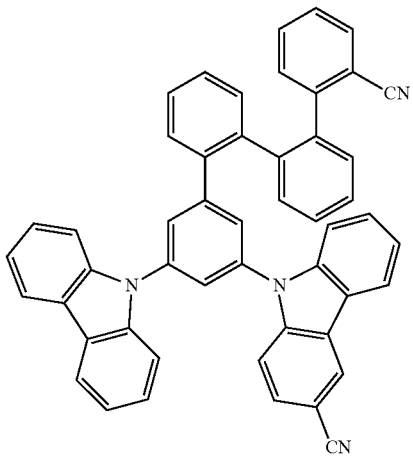
113
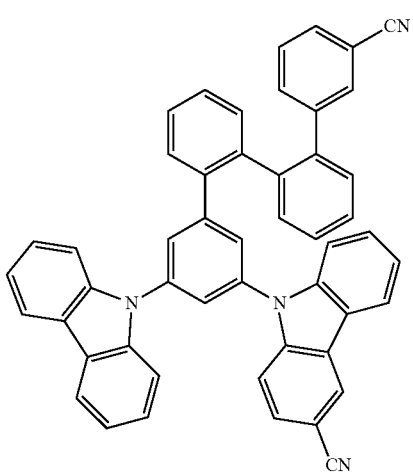
114
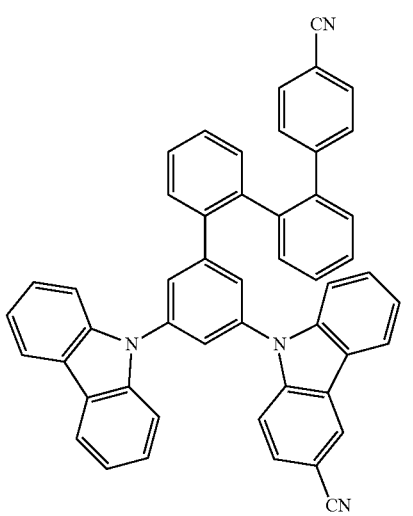

115
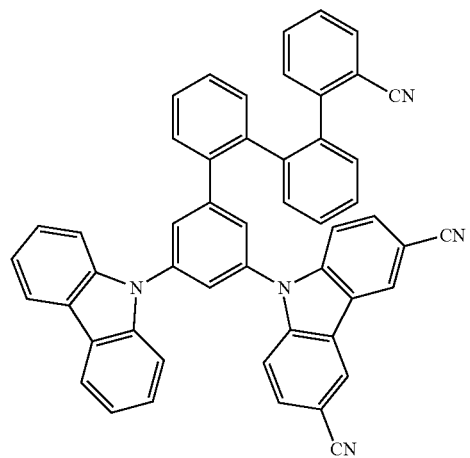
116
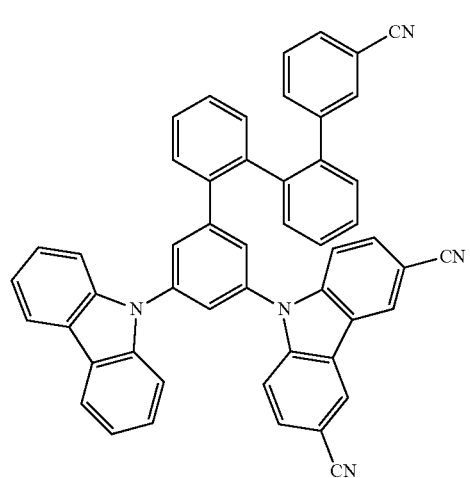
117
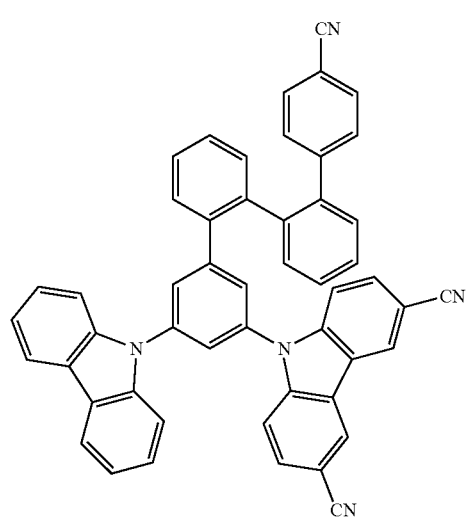
118
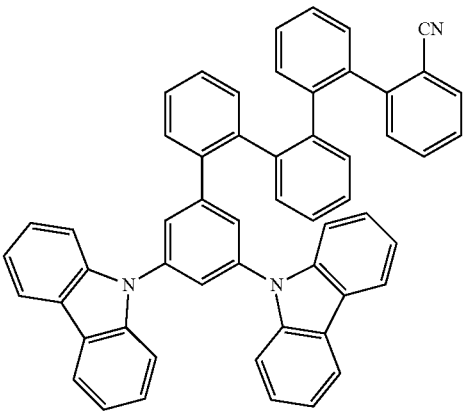
119
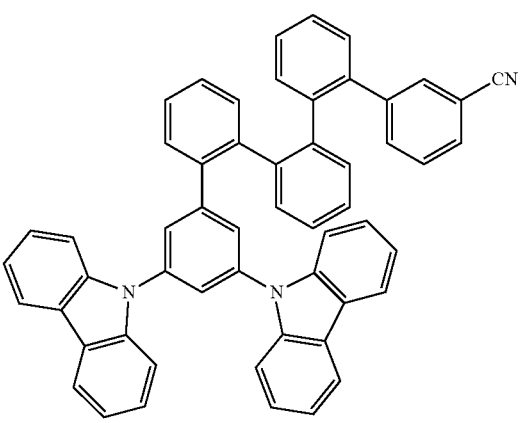
120
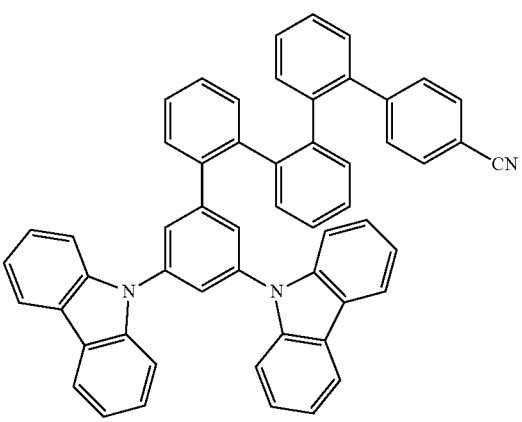

121
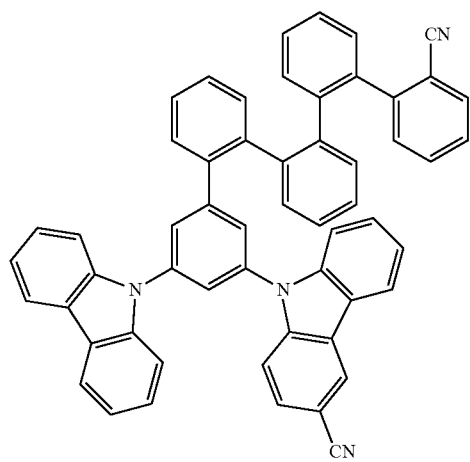
122
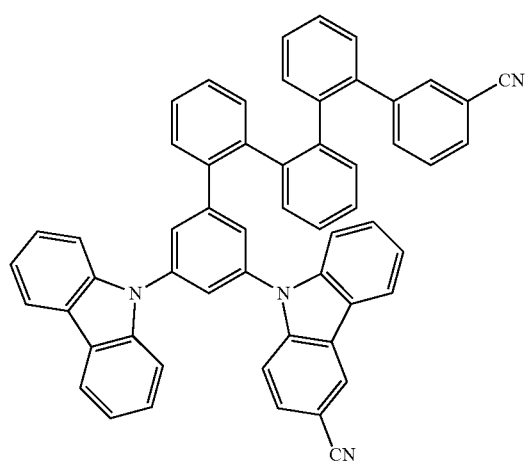
123
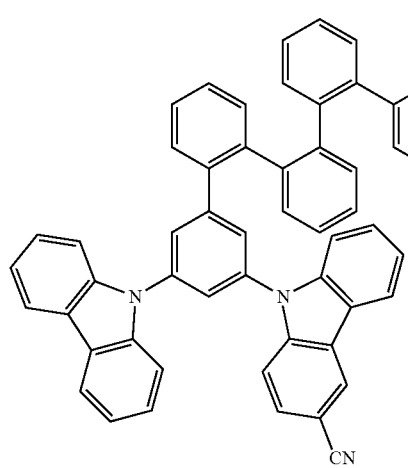
124
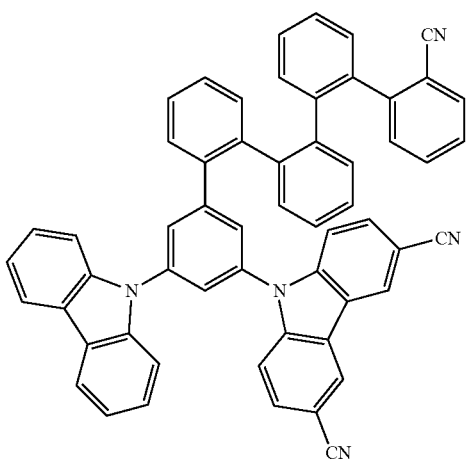
125
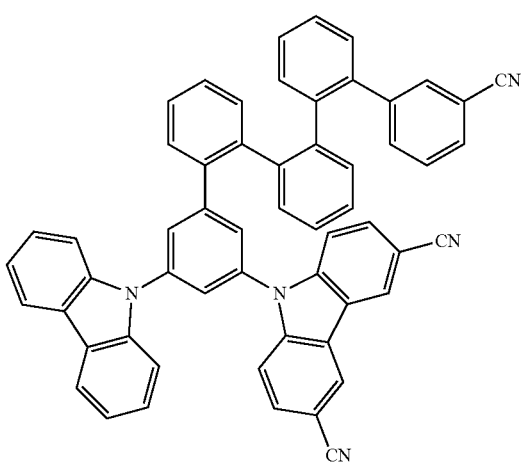
126
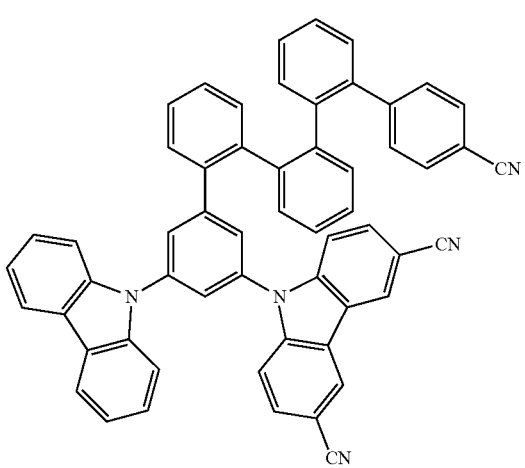

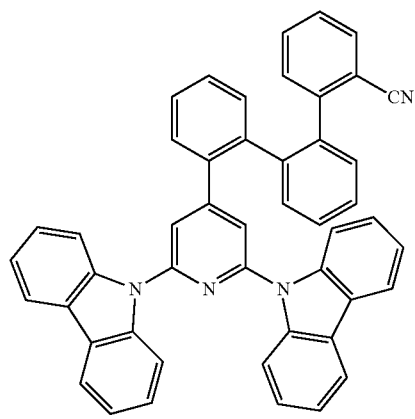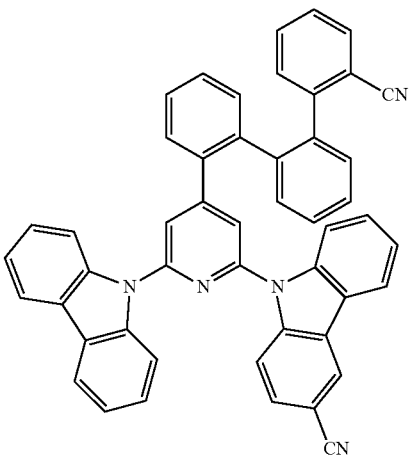

133
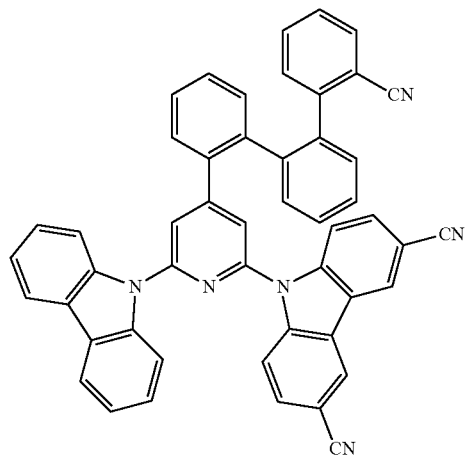
134
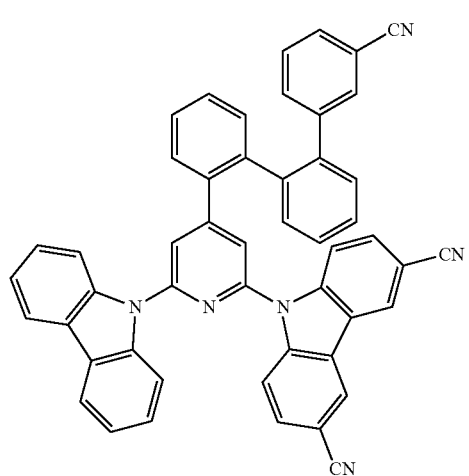
135
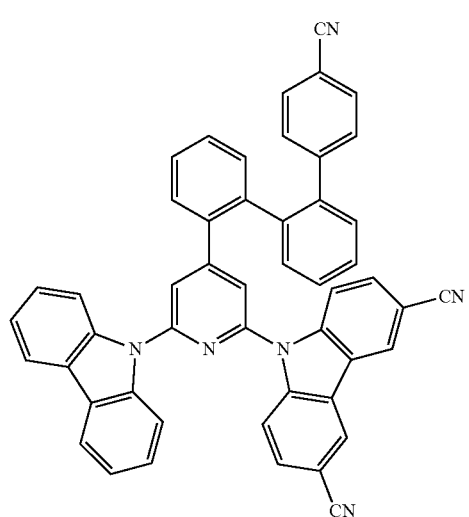
136
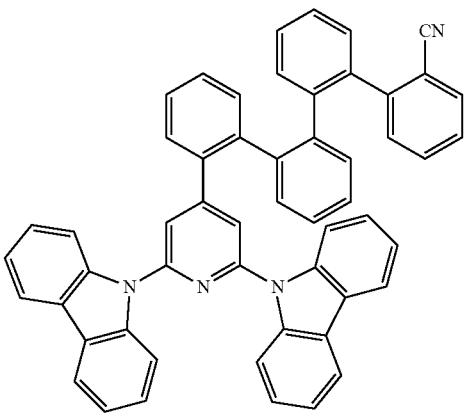
137
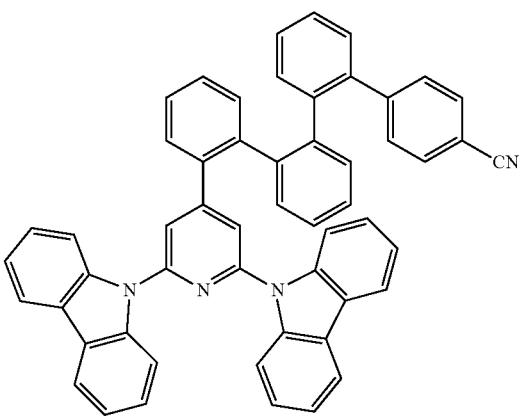
138

-continued
139
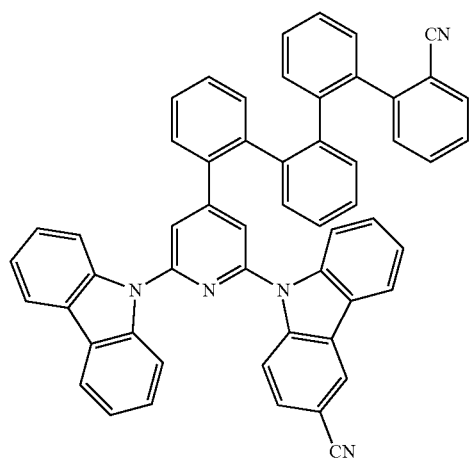
140
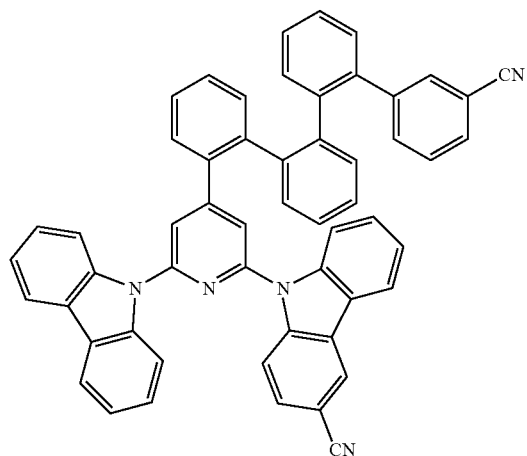
141
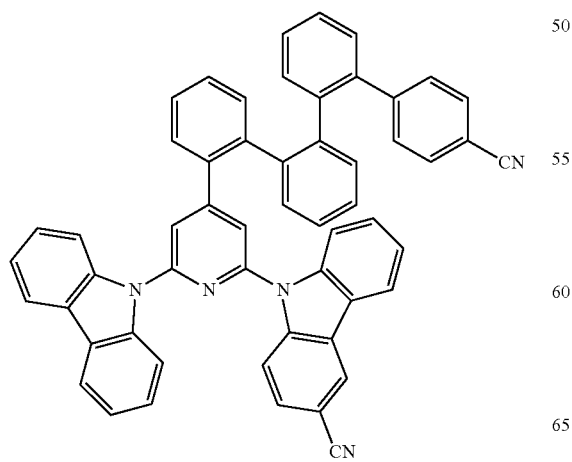
-continued
142
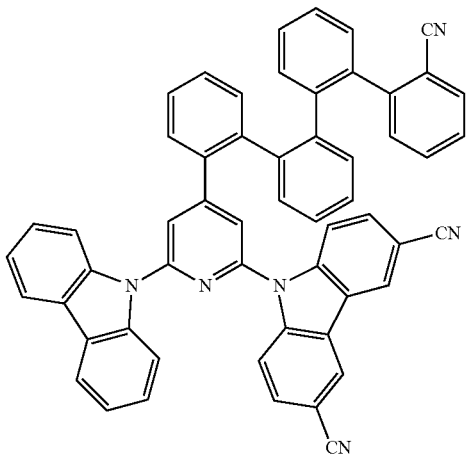
143
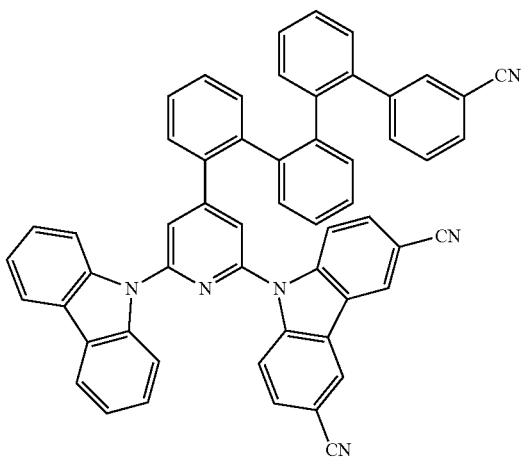
144
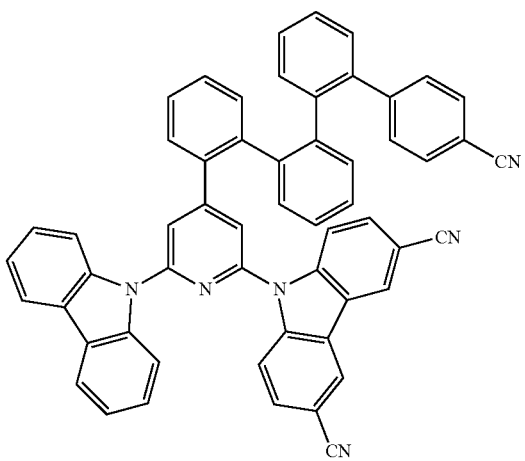

145
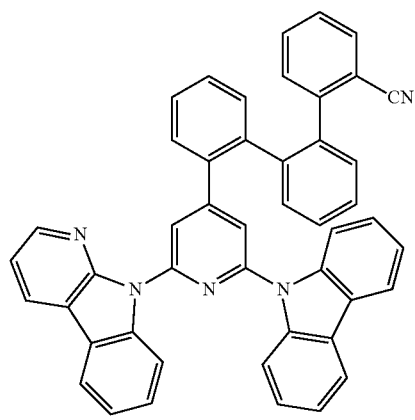
146
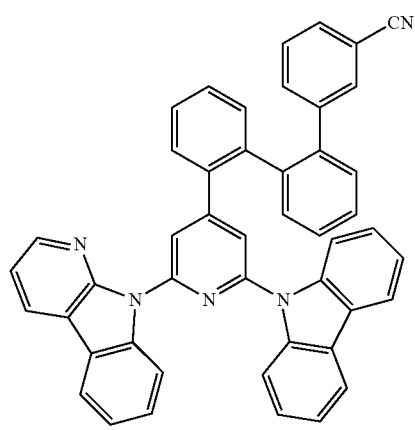
147
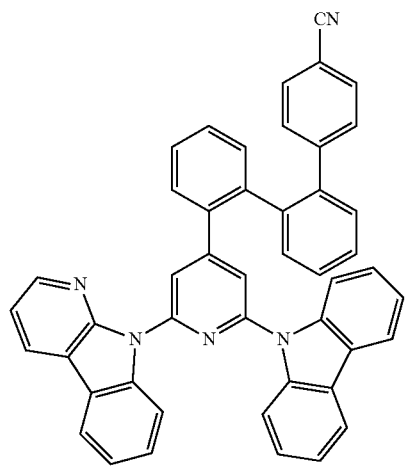
148
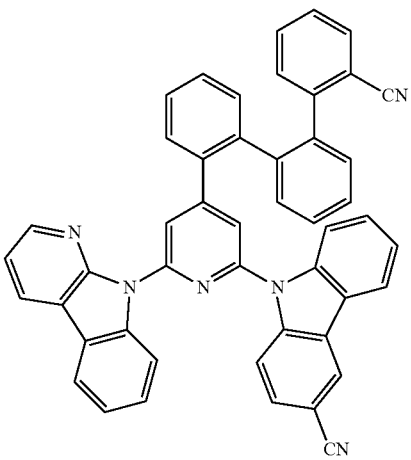
149
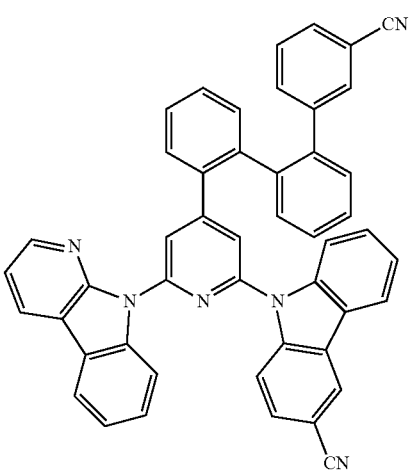
150
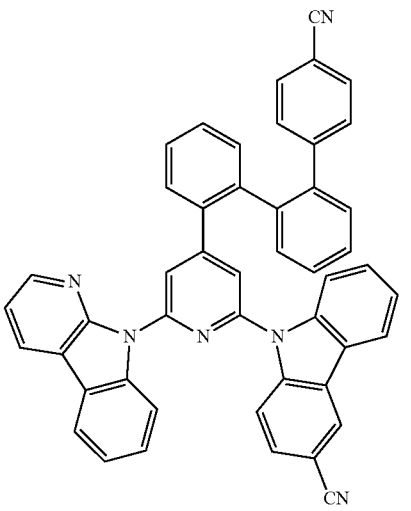

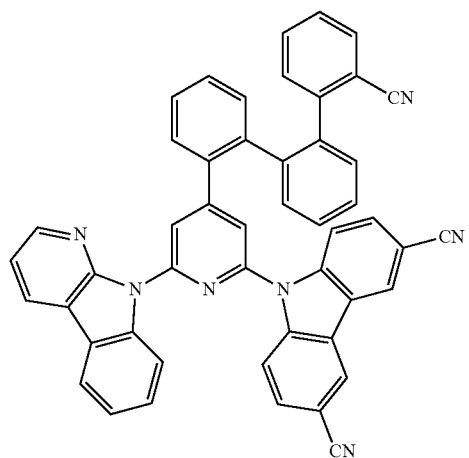
151
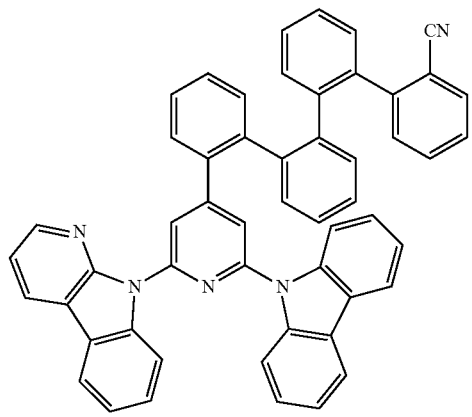
154
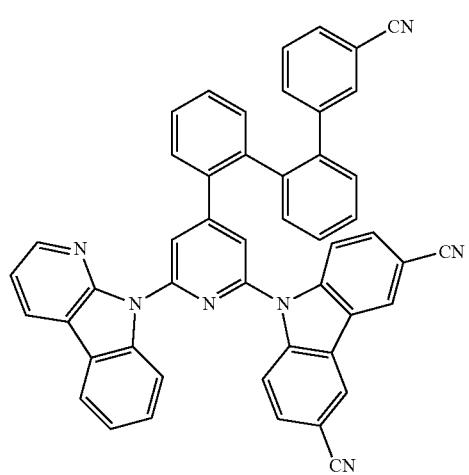
152
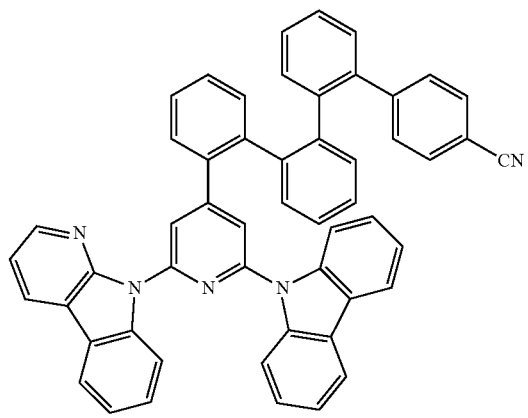
155
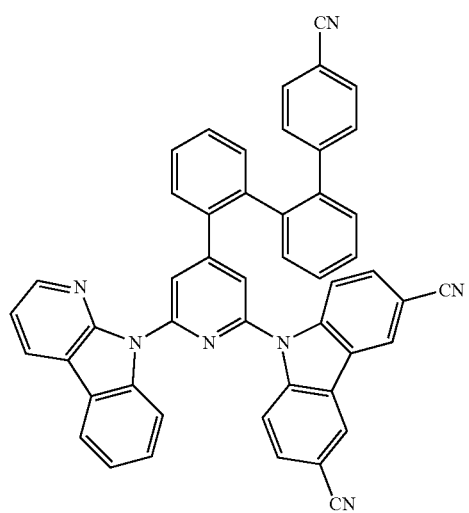
153
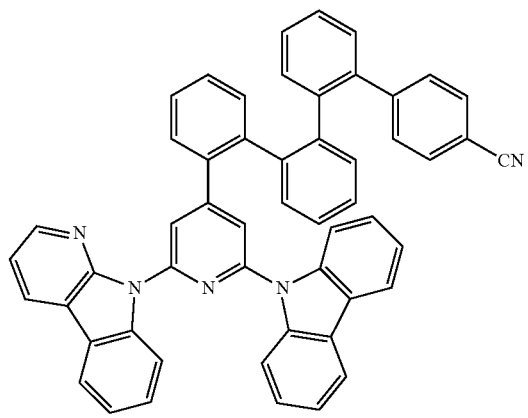
156

157 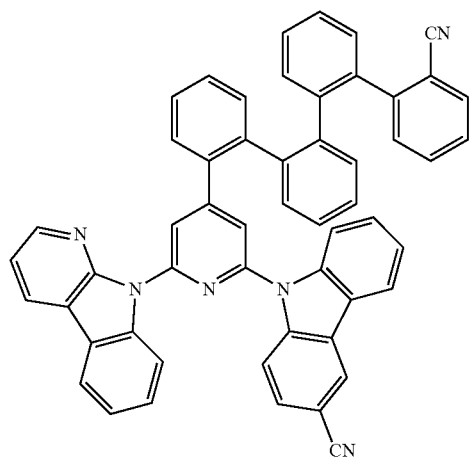
160 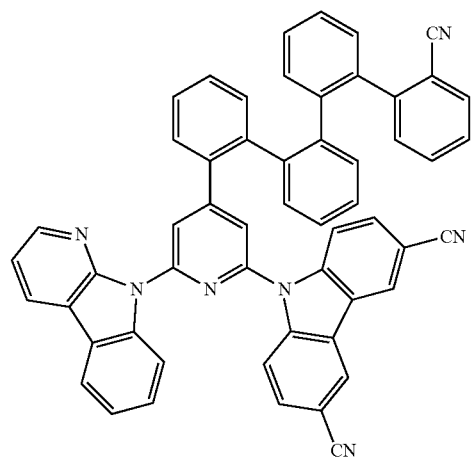
158 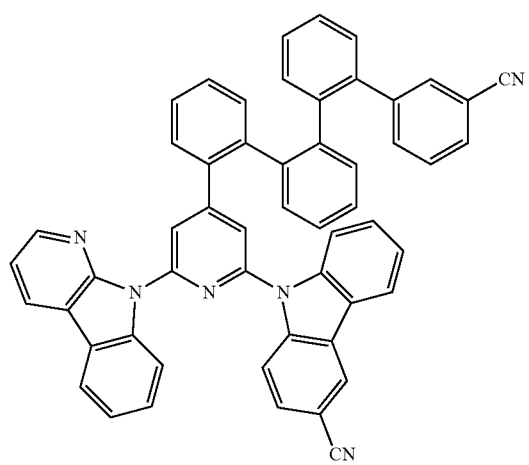
161 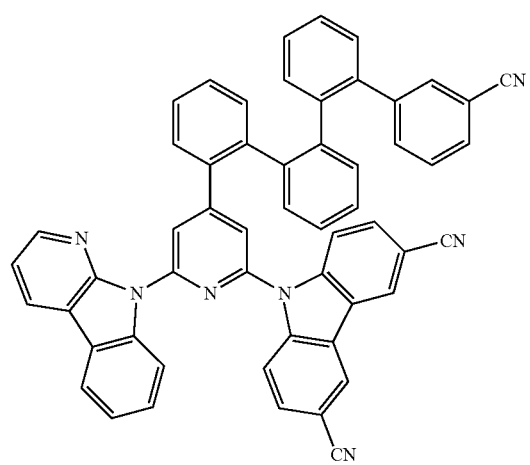
159 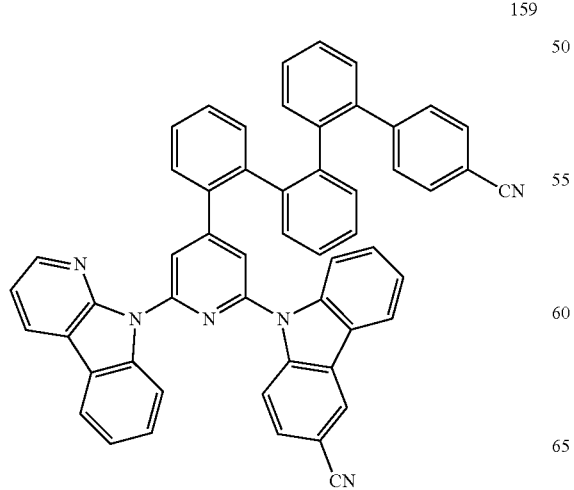
162 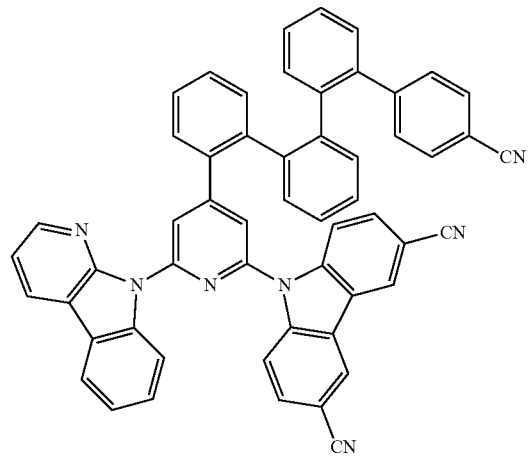

163
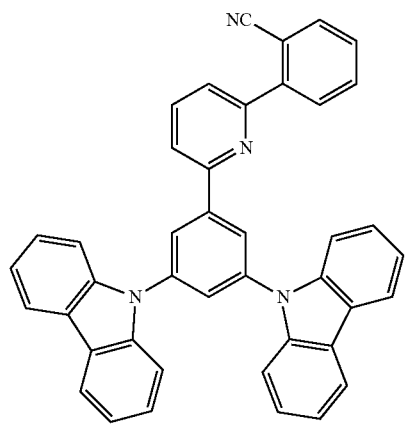
164
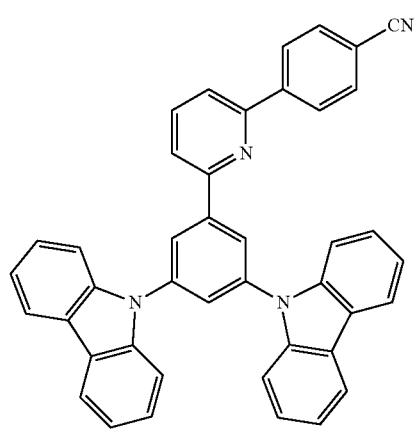
166
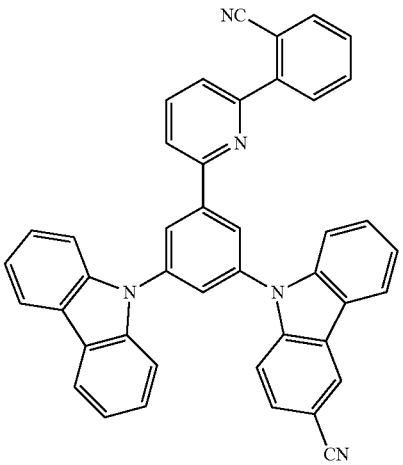
167
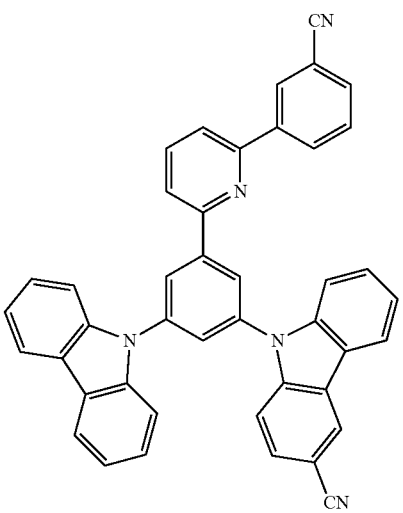
165
168
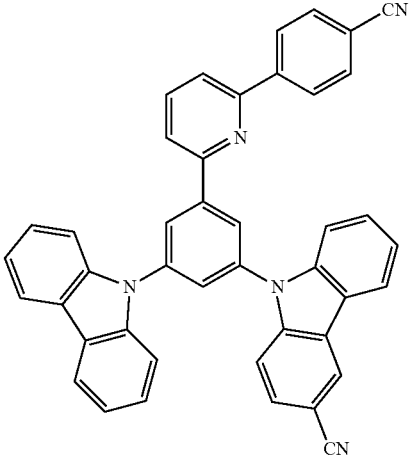

101
-continued
169
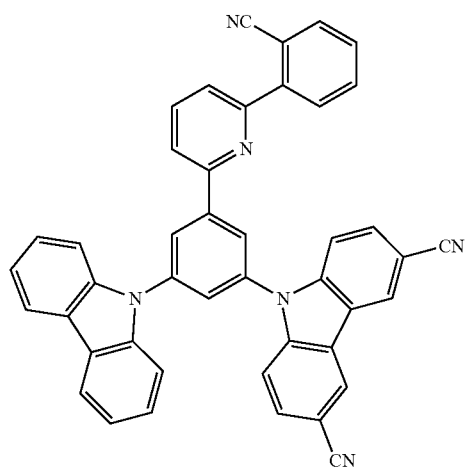
170
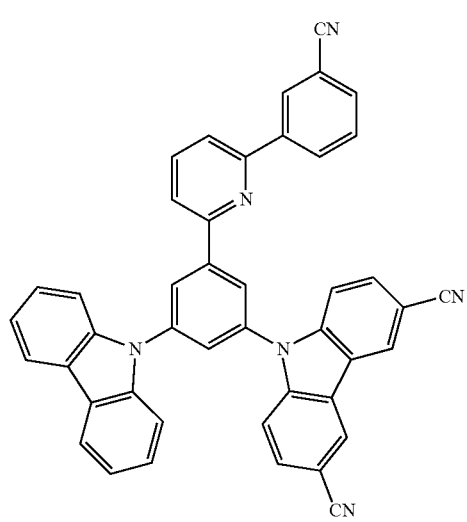
171
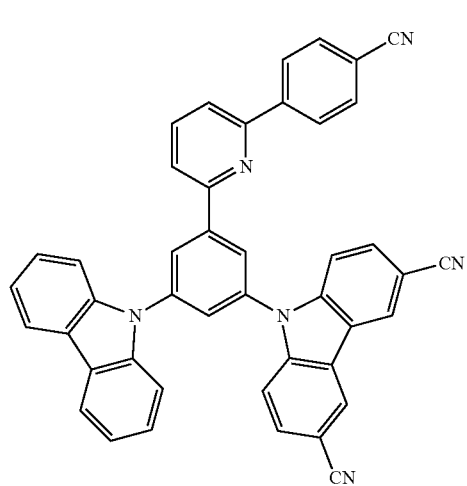
102
-continued
172
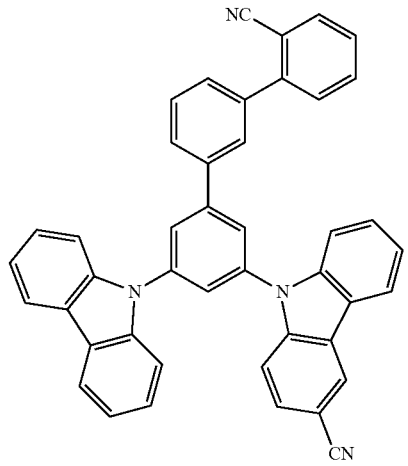
173
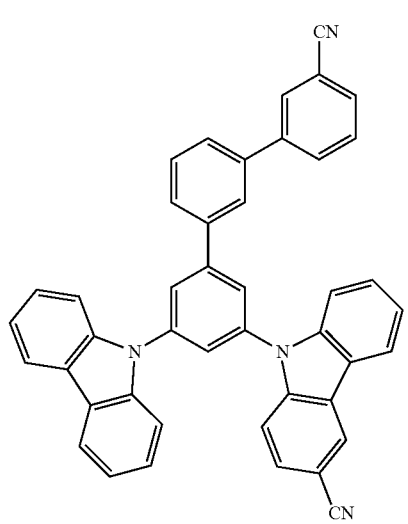
174
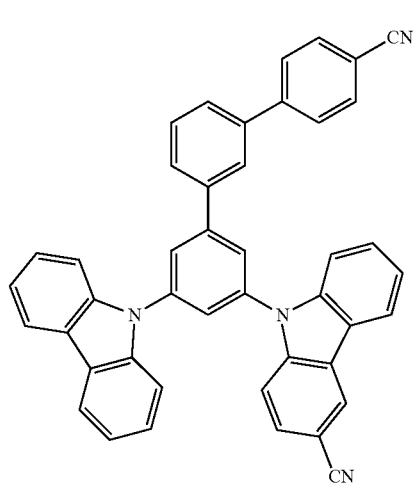

-continued
175
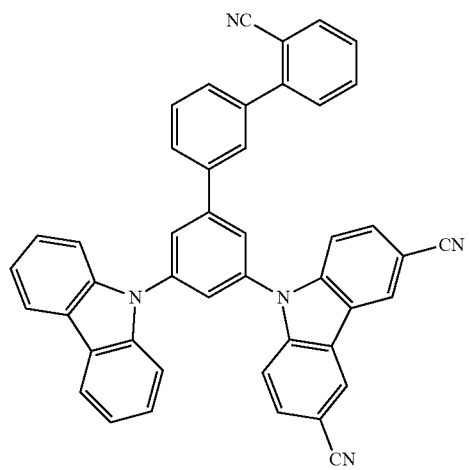
176
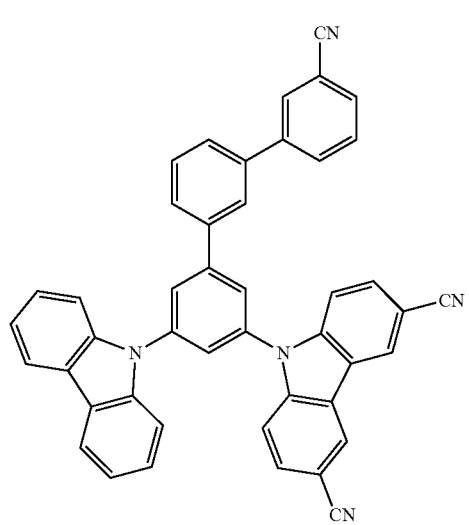
177
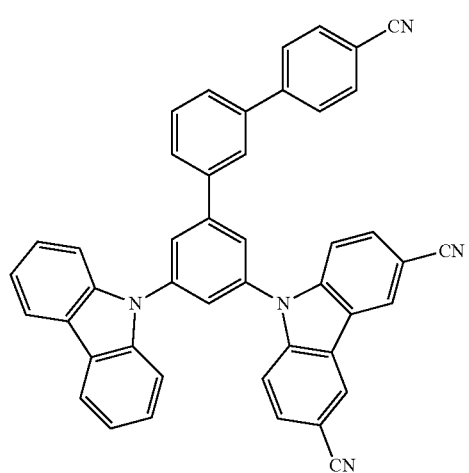
-continued
178
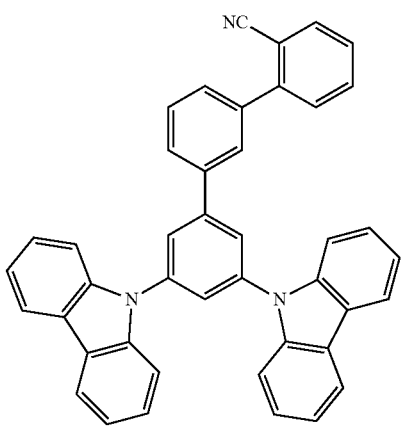
179
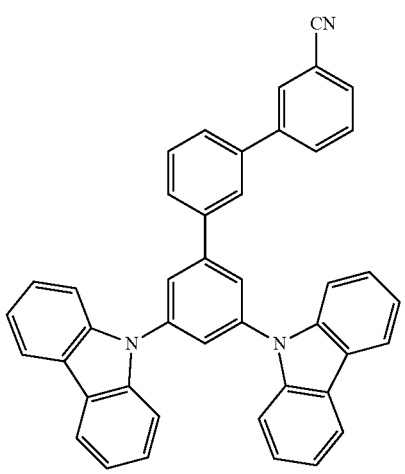
180
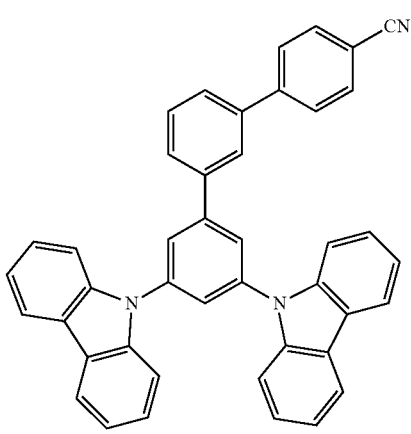

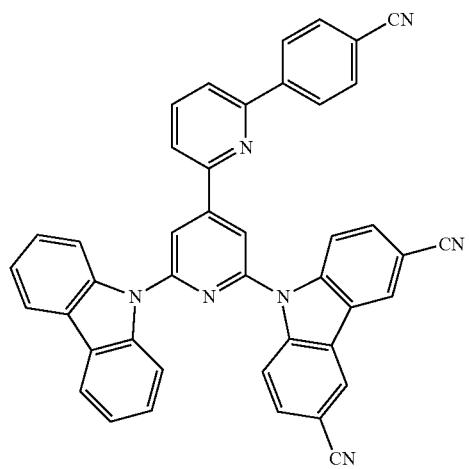
181
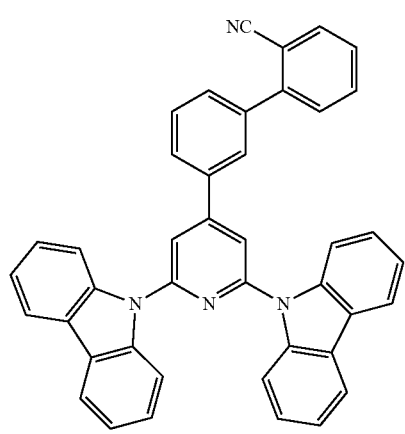
182
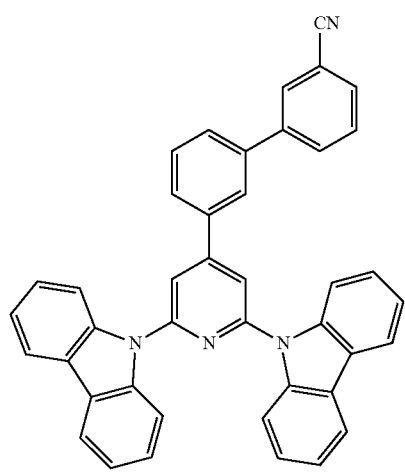
183
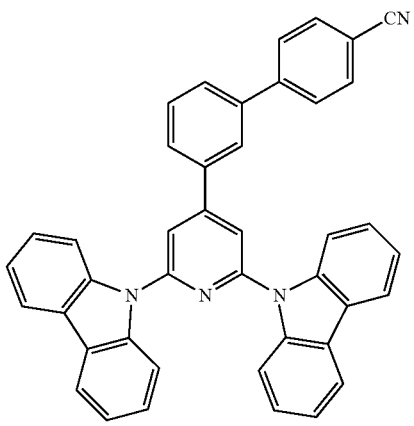
184
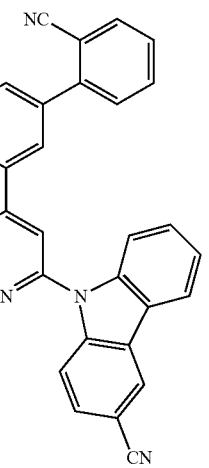
185
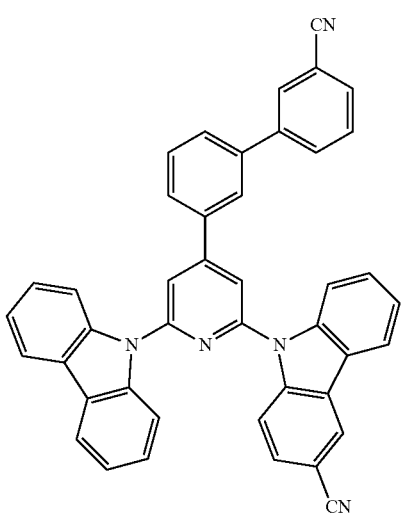
186

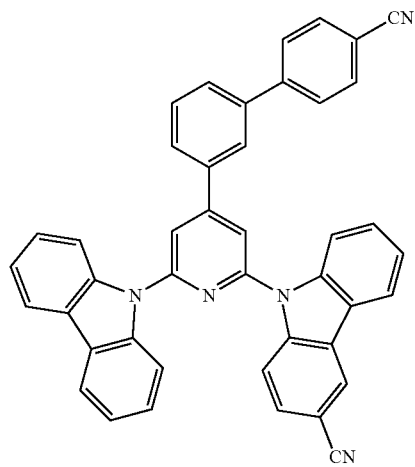
187
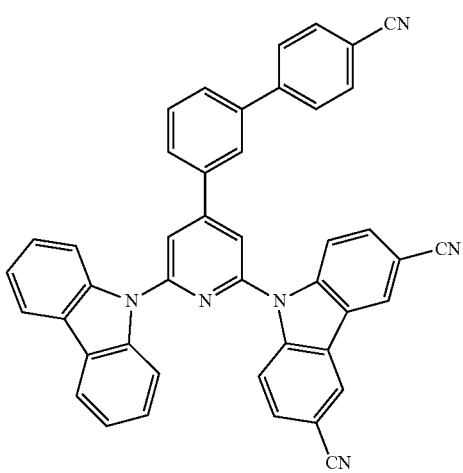
190
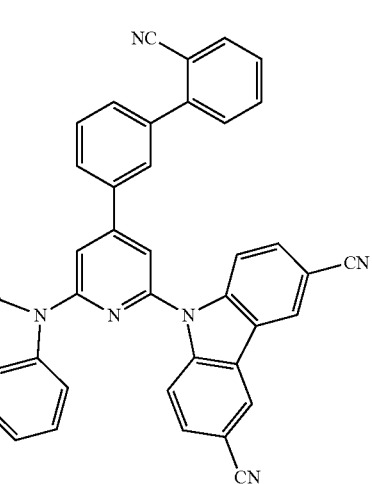
188
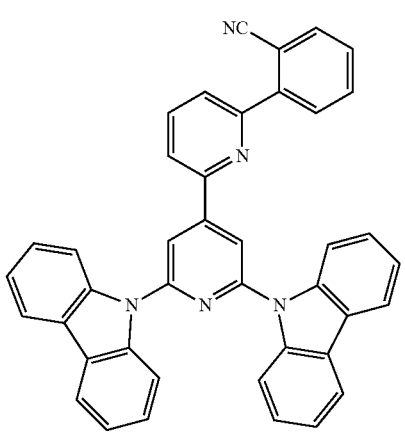
191
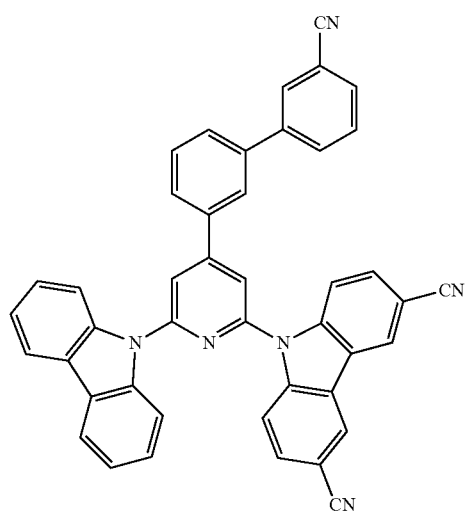
189
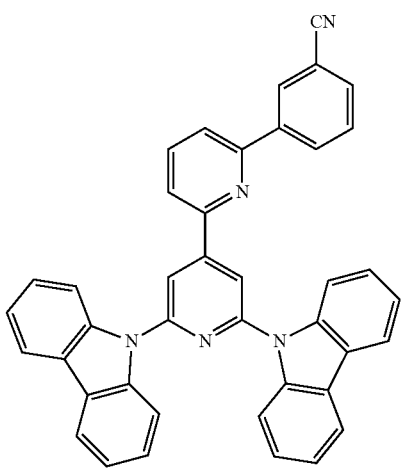
192

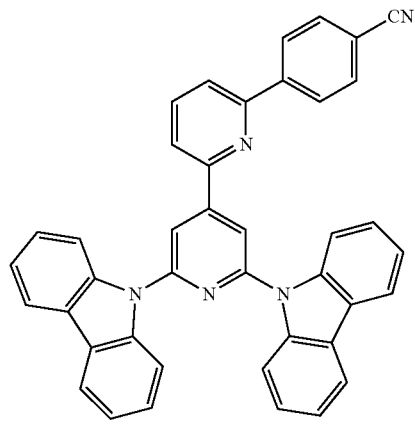
193
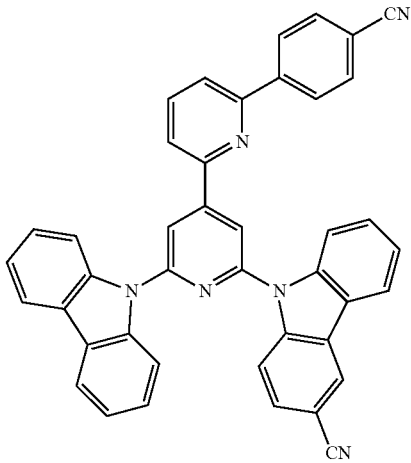
196
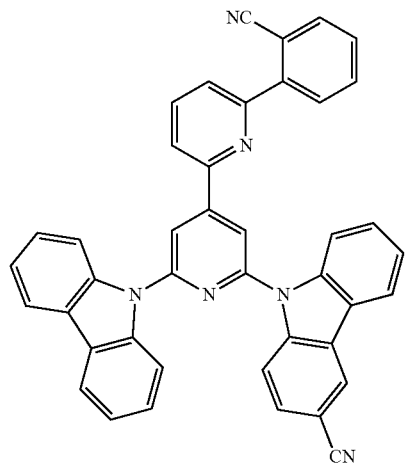
194
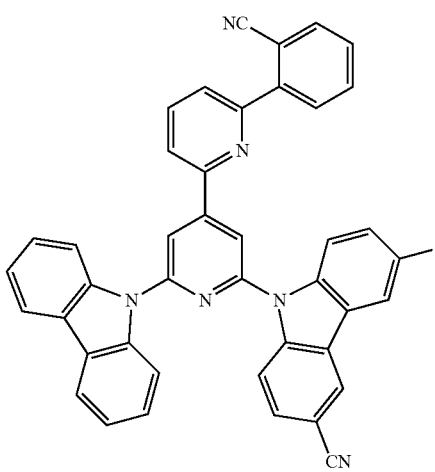
197
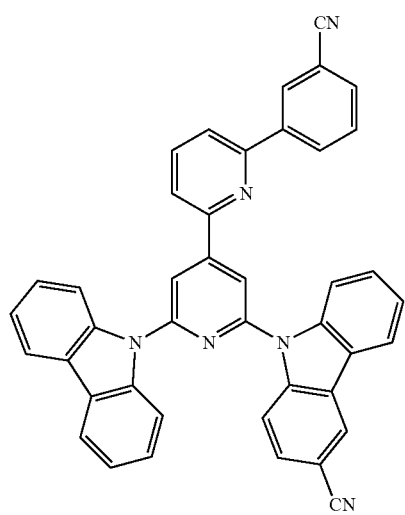
195
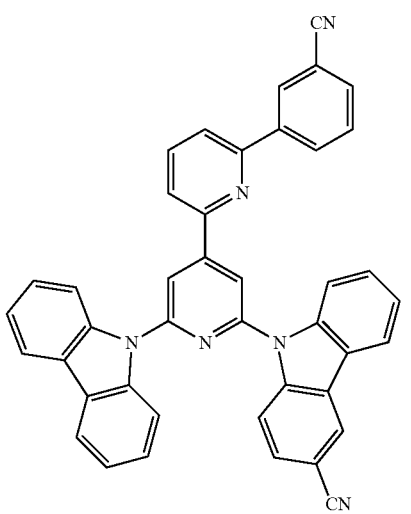
198

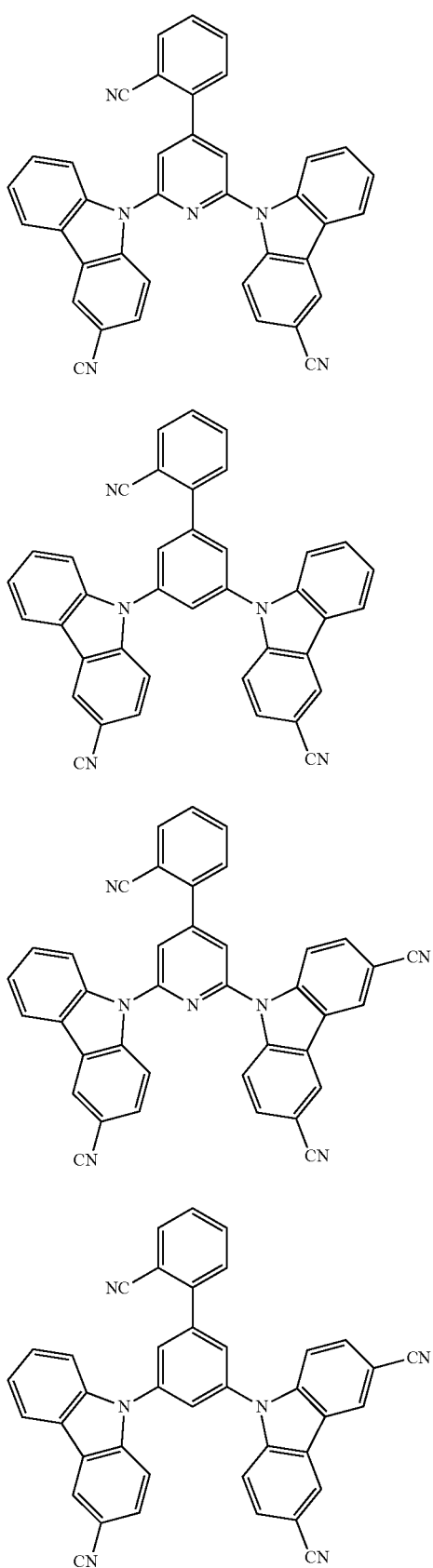

In the carbazole compound represented by Formula 1,
i) when each of $X_1$ to $X_8$ and $X_{11}$ to $X_{19}$ is not N, at least one selected from $R_{41}$ to $R_{43}$ may be a group represented by one of Formulae 2A(1), 2B, 2C and 2D, and ii) when at least one selected from $X_1$ to $X_8$ and $X_{11}$ to $X_{19}$ is N, at least one selected from $R_{41}$ to $R_{43}$ is a group represented by Formulae 2A(2), 2B, 2C, and 2D.

Herein, i) when each of $X_1$ to $X_8$ and $X_{11}$ to $X_{19}$ is not N, like Formula 2A(1), a cyano group may be substituted at an ortho-position (see Formula 2A(1)), ii) at least one of groups $R_{27}$ in the number of a2 in Formula 2B is a cyano group, iii) $R_{22}$ to $R_{26}$ in Formula 2B are not a cyano group, iv) $R_{22}$ to $R_{26}$ in Formula 2B are not a cyano group-substituted phenyl group, v) at least one selected from $R_{31}$ to $R_{35}$, groups $R_{36}$ in the number of a3 and groups $R_{37}$ in the number of a4 in Formula 2C may be a cyano group, and vi) $R_{31}$ to $R_{35}$, groups $R_{36}$ in the number of a3, groups $R_{37}$ in the number of a5 and groups $R_{38}$ in the number of a6 in Formula 2D is a cyano group. Accordingly, the carbazole compound represented by Formula 1 may have a highest occupied molecular orbital (HOMO) energy level, a lowest unoccupied molecular orbital (LUMO) energy level, $S_1$ energy level, and $T_1$ energy level which are suitable for use in an electric device, for example, an organic light-emitting device, and may have small $\Delta E_{st}$, allowing the manufactured electric device to have excellent optical stability. In addition, by varying the number of cyano groups, the carbazole compound represented by Formula 1 may readily induce a desired HOMO energy level or a desired LUMO energy level, and by varying the number of phenyl groups, mobility of holes and electrons of the carbazole compound may be readily adjusted.

The carbazole compound represented by Formula 1 may have a molecular weight of about 350 grams per mole (g/mol) to about 800 g/mol. Accordingly, the carbazole compound may have excellent heat stability. For example, the carbazole compound may have a decomposition temperature that is higher than a sublimation temperature at a vacuum degree of $10^{-8}$ torr to $10^{-3}$ torr. Accordingly, an organic light-emitting device using the carbazole compound may have a long lifespan.

For example, HOMO, LUMO, $T_1$ and $S_1$ energy levels of some of the compounds described above and Compounds A to E were subjected to simulation evaluation by using the Gaussian method. Evaluation Results are shown in Table 1 below:

TABLE 1

| | HOMO (eV) | LUMO (eV) | $T_1$ (eV) | $S_1$ (eV) |
|---|---|---|---|---|
| Compound 19 | −5.456 | −1.742 | 3.072 | 3.226 |
| Compound 163 | −5.31 | −1.76 | 2.919 | 3.062 |
| Compound 172 | −5.697 | −1.749 | 3.076 | 3.544 |
| Compound 173 | −5.739 | −1.736 | 3.061 | 3.513 |
| Compound 174 | −5.732 | −1.945 | 2.984 | 3.405 |
| Compound 31 | −5.622 | −1.754 | 3.117 | 3.377 |
| Compound 32 | −5.668 | −1.658 | 3.117 | 3.511 |
| Compound 33 | −5.659 | −1.878 | 3.101 | 3.307 |
| Compound 178 | −5.501 | −1.635 | 3.071 | 3.522 |
| Compound 179 | −5.560 | −1.613 | 3.056 | 3.528 |
| Compound 180 | −5.572 | −1.829 | 2.979 | 3.379 |
| Compound 28 | −5.465 | −1.601 | 3.16 | 3.377 |
| Compound 29 | −5.509 | −1.513 | 3.163 | 3.526 |
| Compound 30 | −5.498 | −1.727 | 3.094 | 3.301 |
| Compound A | −5.587 | −1.743 | 3.048 | 3.356 |
| Compound B | −5.64 | −1.991 | 2.902 | 3.154 |
| Compound C | −5.570 | −1.728 | 2.997 | 3.356 |
| <Compound D> | −5.604 | −1.987 | 2.996 | 3.264 |
| <Compound E> | −5.57 | −1.818 | 2.988 | 3.376 |

TABLE 1-continued

| | HOMO (eV) | LUMO (eV) | T₁ (eV) | S₁(eV) |

Compound A

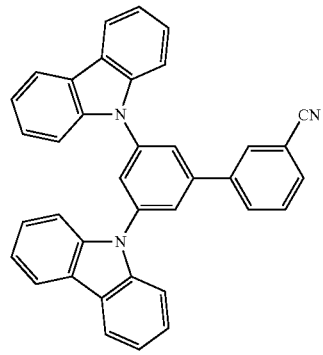 [SMILES: N#Cc1cccc(-c2cc(-n3c4ccccc4c4ccccc43)cc(-n3c4ccccc4c4ccccc43)c2)c1]

Compound B

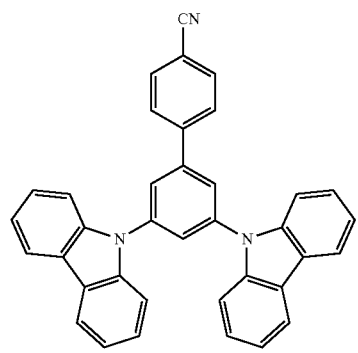 [SMILES: N#Cc1ccc(-c2cc(-n3c4ccccc4c4ccccc43)cc(-n3c4ccccc4c4ccccc43)c2)cc1]

Compound C

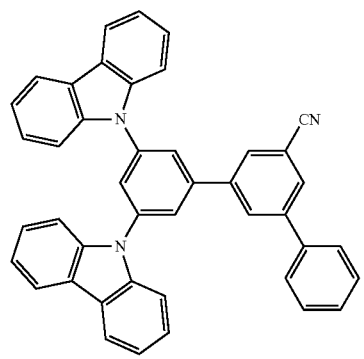 [SMILES: N#Cc1cc(-c2ccccc2)cc(-c2cc(-n3c4ccccc4c4ccccc43)cc(-n3c4ccccc4c4ccccc43)c2)c1]

Compound D

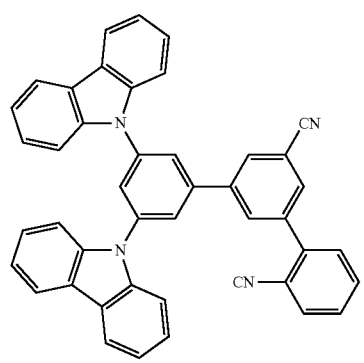

TABLE 1-continued

| | HOMO (eV) | LUMO (eV) | T₁ (eV) | S₁(eV) |

Compound E

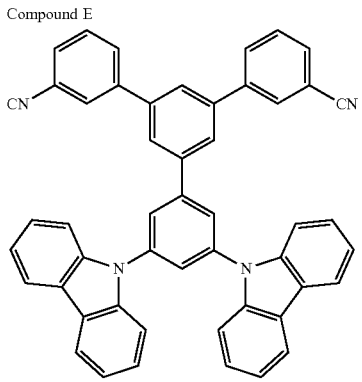

From Table 1, it was confirmed that the carbazole compound represented by Formula 1 has a HOMO energy level and a LUMO energy level, which are suitable for use as a material for an organic light-emitting device, and has high $T_1$. Also, it was confirmed that a desired HOMO energy level and a desired LUMO energy level are adjustable by controlling the number of cyano groups.

Synthesis methods of the carbazole compound represented by Formula 1 may be understood by one of ordinary skill in the art by referring to Synthesis Examples provided below.

The carbazole compound represented by Formula 1 is suitable for use in an organic layer of an organic light-emitting device, for example, for use as a host in an emission layer of the organic layer. Thus, another aspect provides an organic light-emitting device that includes:

a first electrode;

a second electrode; and an organic layer that is disposed between the first electrode and the second electrode, wherein the organic layer includes an emission layer and at least one carbazole compound represented by Formula 1.

The organic light-emitting device may have, due to the inclusion of an organic layer including the carbazole compound represented by Formula 1, a low driving voltage, a high efficiency, a high brightness, a high quantum emission efficiency, and a long lifespan.

The carbazole compound of Formula 1 may be used between a pair of electrodes of an organic light-emitting device. For example, the carbazole compound may be included in at least one selected from an emission layer, a hole transport region (including, for example, at least one selected from a hole injection layer, a hole transport layer, a buffer layer, and an electron blocking layer) that is disposed between the first electrode and the emission layer, and an electron transport region (including, for example, at least one selected from a hole blocking layer, an electron transport layer, and an electron injection layer) that is disposed between the emission layer and the second electrode. For example, the carbazole compound represented by Formula 1 may be included in the emission layer. In this regard, the carbazole compound may further include a dopant, and the carbazole compound included in the emission layer may act as a host. The emission layer may be a green emission layer emitting green light or a blue emission layer emitting blue light, and the dopant may be a phosphorescent dopant.

The expression that "(an organic layer) includes at least one carbazole compound" as used herein may include a case in which "(an organic layer) includes one carbazole compounds represented by Formula 1 and a case in which (an organic layer) includes two or more different carbazole compounds represented by Formula 1.

For example, the organic layer may include, as the carbazole compound, only Compound 1. In this regard, Compound 1 may be included in an emission layer of the organic light-emitting device. In some embodiments, the organic layer may include, as the carbazole compound, Compound 1 and Compound 2. In this regard, Compound 1 and Compound 2 may be included in either an identical layer (for example, Compound 1 and Compound 2 all may be included in an emission layer), or different layers.

The first electrode may be an anode, which is a hole injection electrode, and the second electrode may be a cathode, which is an electron injection electrode; or the first electrode may be a cathode, which is an electron injection electrode, or the second electrode may be an anode, which is a hole injection electrode.

For example, the first electrode may be an anode, and the second electrode may be a cathode, and the organic layer may include:

i) a hole transport region that is disposed between the first electrode and the emission layer, wherein the hole transport region includes at least one selected from a hole injection layer, a hole transport layer, and an electron blocking layer, and ii) an electron transport region that is disposed between the emission layer and the second electrode, wherein the electron transport region may include at least one selected from a hole blocking layer, an electron transport layer, and an electron injection layer.

The term "organic layer" as used herein refers to a single layer and/or a plurality of layers disposed between the first electrode and the second electrode of an organic light-emitting device. The "organic layer" may include, in addition to an organic compound, an organometallic complex including metal.

FIG. 1 is a schematic view of an organic light-emitting device 10 according to an embodiment. Hereinafter, the structure of an organic light-emitting device according to an embodiment, and a method of manufacturing an organic light-emitting device according to an embodiment will be described in connection with FIG. 1. The organic light-emitting device 10 includes a first electrode 11, an organic layer 15, and a second electrode 19, which are sequentially stacked.

In FIG. 1, a substrate may be additionally disposed under the first electrode 11 or above the second electrode 19. As the substrate, any substrate that is used in general organic light-emitting devices may be used. The substrate may be a glass substrate or transparent plastic substrate, each with excellent mechanical strength, thermal stability, transparency, surface smoothness, ease of handling, and waterproofness.

The first electrode 11 may be formed by depositing or sputtering a material for forming the first electrode on the substrate. The first electrode 11 may be an anode. The material for the first electrode 11 may be selected from materials with a high work function to allow holes be easily provided. The first electrode 11 may be a reflective electrode or a transmissive electrode. The material for the first electrode may be, for example, indium tin oxide (ITO), indium zinc oxide (IZO), tin oxide ($SnO_2$), and zinc oxide (ZnO). In some embodiments, magnesium (Mg), aluminum (Al), aluminum-lithium (Al—Li), calcium (Ca), magnesium-indium (Mg—In), or magnesium-silver (Mg—Ag) may be used as the material for the first electrode.

The first electrode 11 may have a single-layer structure or a multi-layer structure including two or more layers. For example, the first electrode 11 may have a three-layered structure of ITO/Ag/ITO, but the structure of the first electrode 11 is not limited thereto.

An organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In some embodiments, the hole transport region may have a structure of hole injection layer/hole transport layer or hole injection layer/hole transport layer/electron blocking layer, which are sequentially stacked in this stated order from the first electrode 11.

A hole injection layer hole injection layer may be formed on the first electrode 11 by using various methods, such as vacuum deposition, spin coating, casting, or Langmuir-Blodgett (LB).

When a hole injection layer is formed by vacuum deposition, the deposition conditions may vary depending on a material that is used to form the hole injection layer, and the structure and thermal characteristics of the hole injection layer. For example, the deposition conditions may include a deposition temperature of about 100 to about 500° C., a vacuum pressure of about $10^{-8}$ to about $10^{-3}$ torr, and a deposition rate of about 0.01 to about 100 Angstroms per second (Å/sec). However, the deposition conditions are not limited thereto.

When the hole injection layer is formed using spin coating, coating conditions may vary depending on the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, methylated NPB, TAPC, HMTPD, 4,4',4''-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (PANI/CSA), (polyaniline)/poly(4-styrenesulfonate) (Pani/PSS), a compound represented by Formula 201 below, and a compound represented by Formula 202 below:

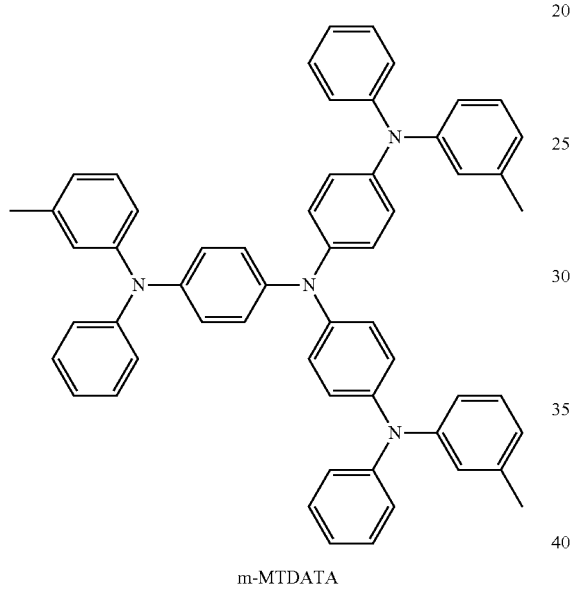

m-MTDATA

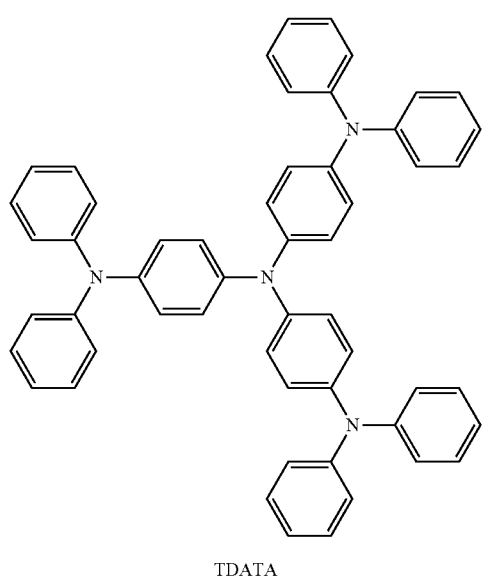

TDATA

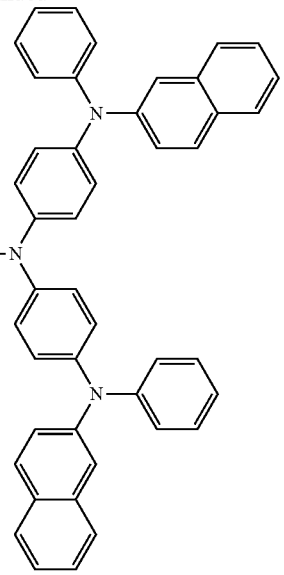

2-TNATA

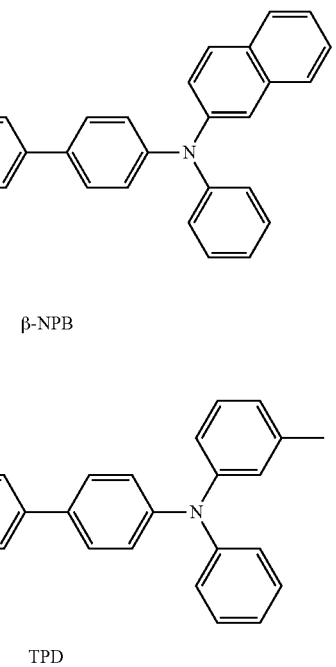

NPB

β-NPB

TPD

-continued

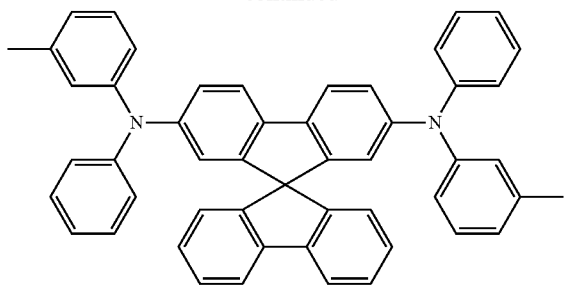

Spiro-TPD

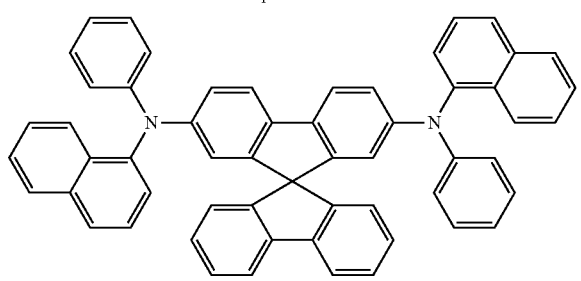

Spiro-NPB

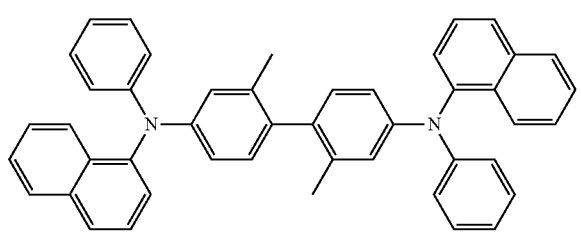

methylated-NPB

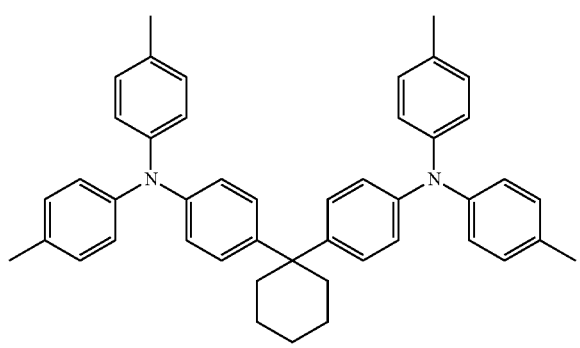

TAPC

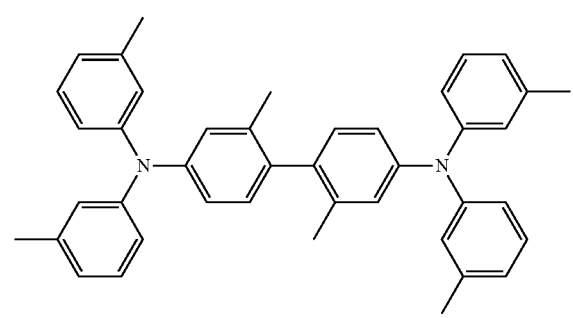

HMTPD

-continued

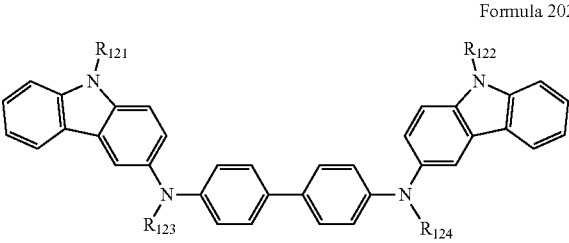

Formula 201

Formula 202

$Ar_{101}$ to $Ar_{102}$ in Formula 201 may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may be each independently an integer selected from 0 to 5, or 0, 1, or 2. For example, xa is 1 and xb is 0, but xa and xb are not limited thereto.

$R_{101}$ to $R_{108}$, $R_{111}$ to $R_{119}$ and $R_{121}$ to $R_{124}$ in Formulae 201 and 202 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, and so on), and a $C_1$-$C_{10}$ alkoxy group (for example, a methoxy group, an ethoxy group, a propoxy group, a butoxy group, a pentoxy group, and so on);

a $C_1$-$C_{10}$ alkyl group and a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but they are not limited thereto.

$R_{109}$ in Formula 201 may be selected from a phenyl group, a naphthyl group, an anthracenyl group, and a pyridinyl group; and a phenyl group, a naphthyl group, an anthracenyl group, and a pyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, or a $C_1$-$C_{20}$ alkoxy group.

According to an embodiment, the compound represented by Formula 201 may be represented by Formula 201A, but is not limited thereto:

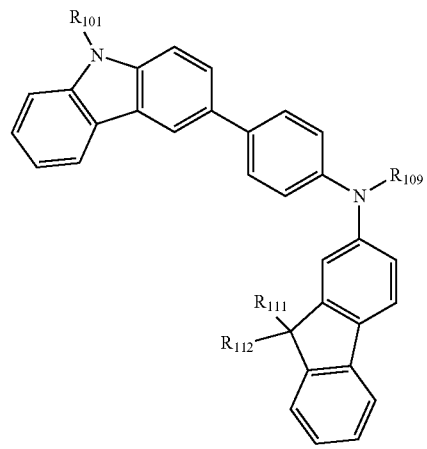

Formula 201A $R_{101}$, $R_{111}$, $R_{112}$, and $R_{109}$ in Formula 201A may be understood by referring to the description provided herein.

For example, the compound represented by Formula 201, and the compound represented by Formula 202 may include compounds HT1 to HT20 illustrated below, but are not limited thereto.

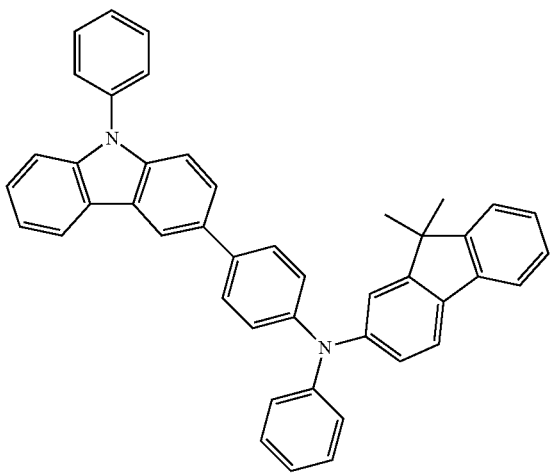

HT1

HT2
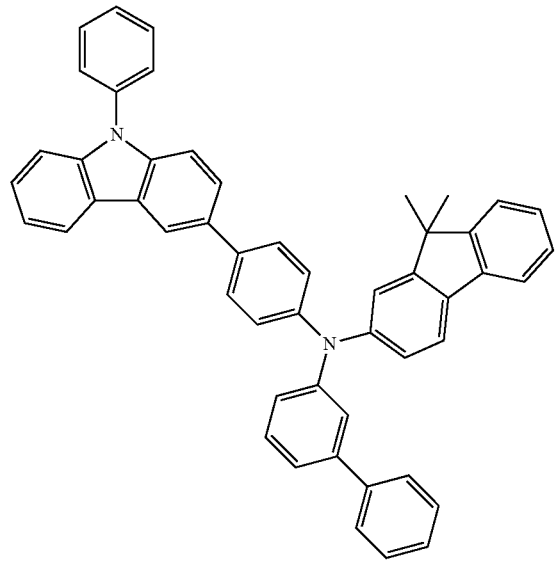
HT4
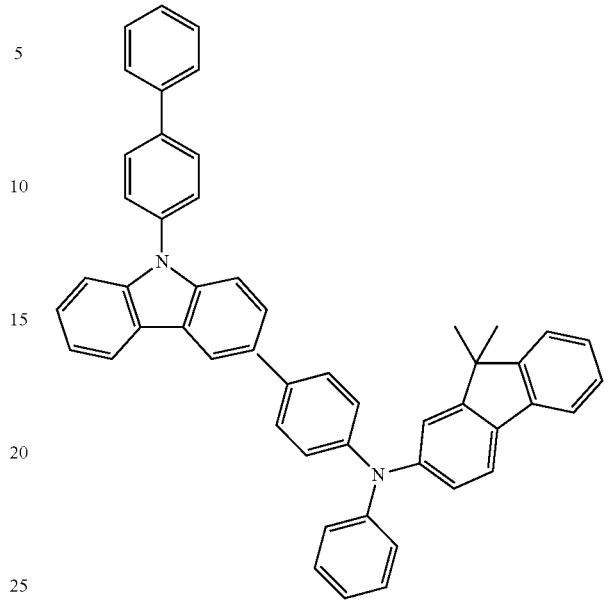
HT3
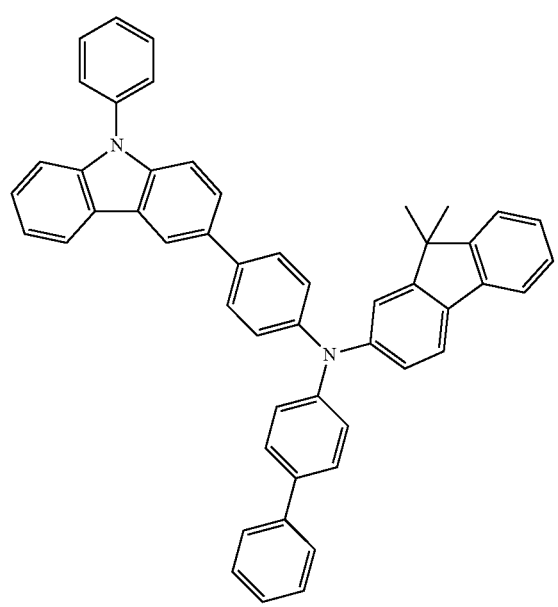
HT5
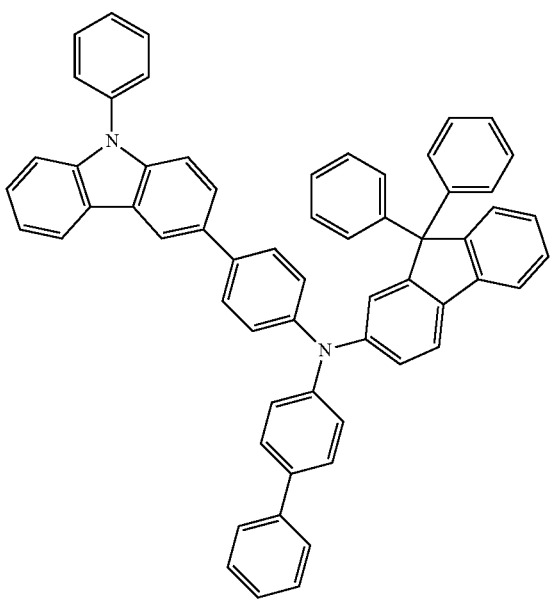

HT6
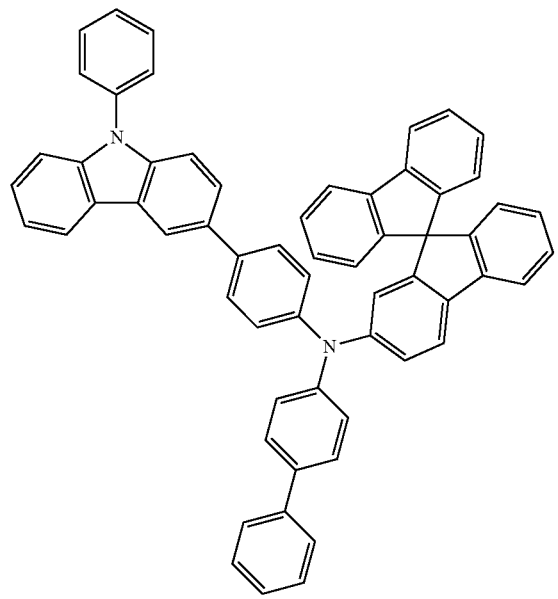
HT7
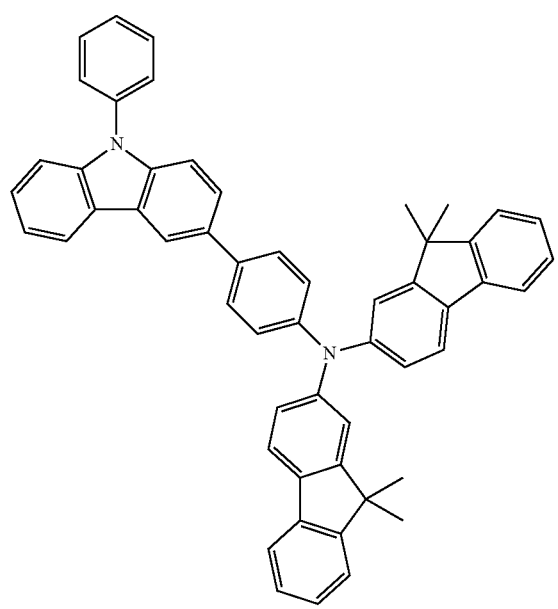
HT8
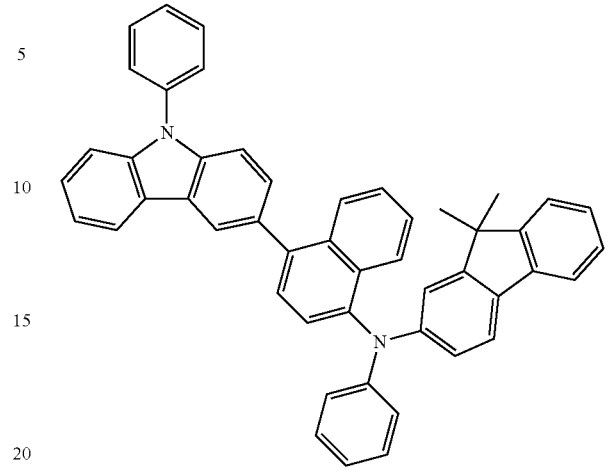
HT9
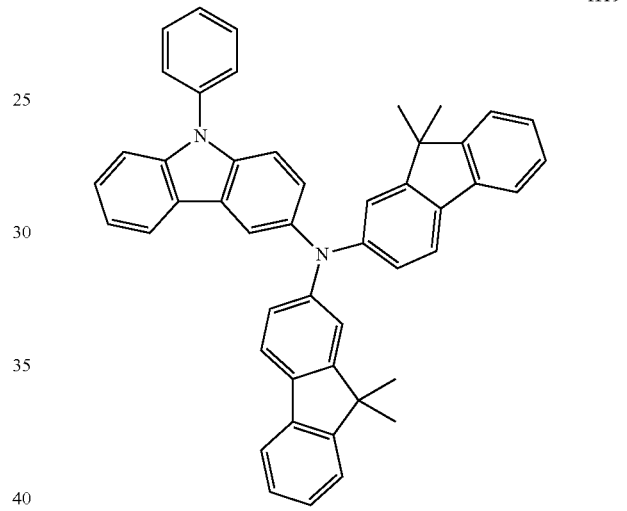
HT10
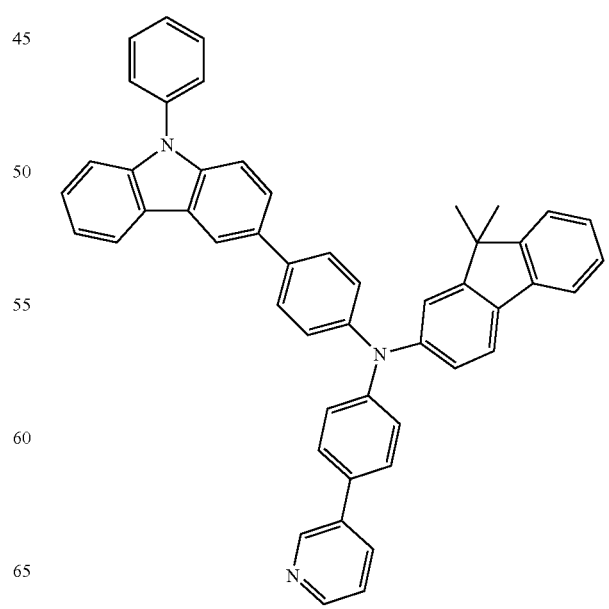

HT11
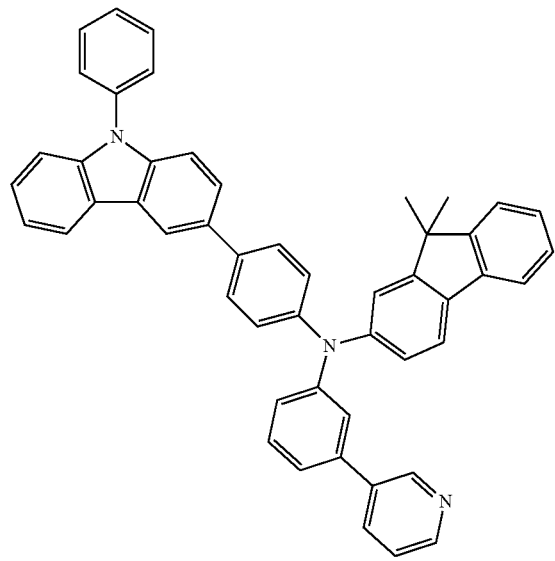
HT12
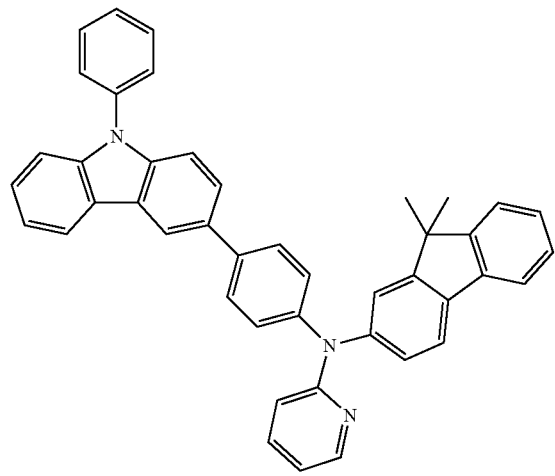
HT13
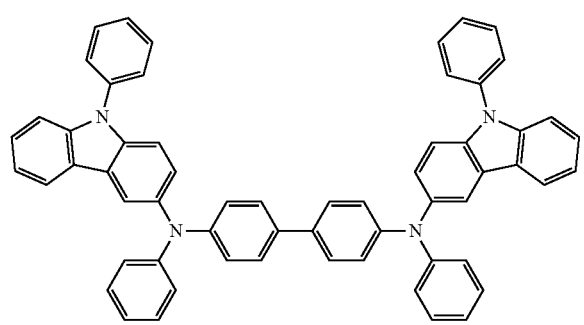
HT14
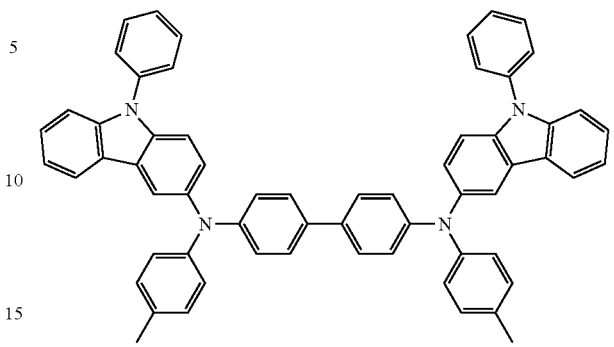
HT15
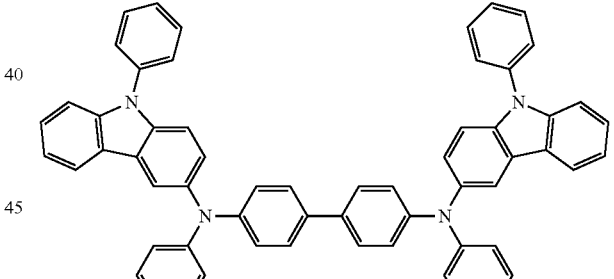
HT16
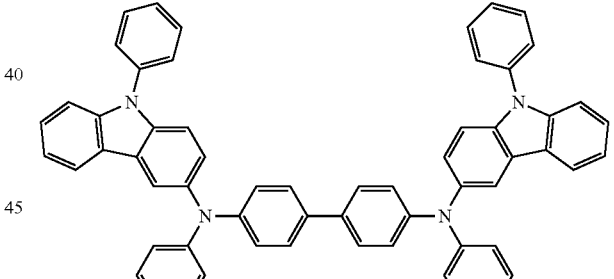
HT17
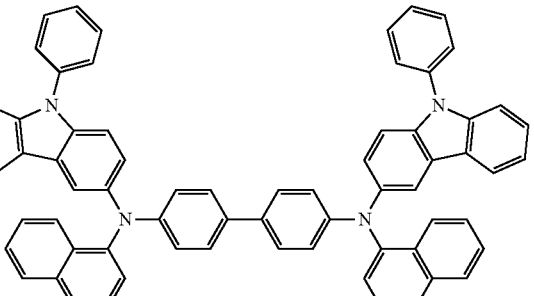

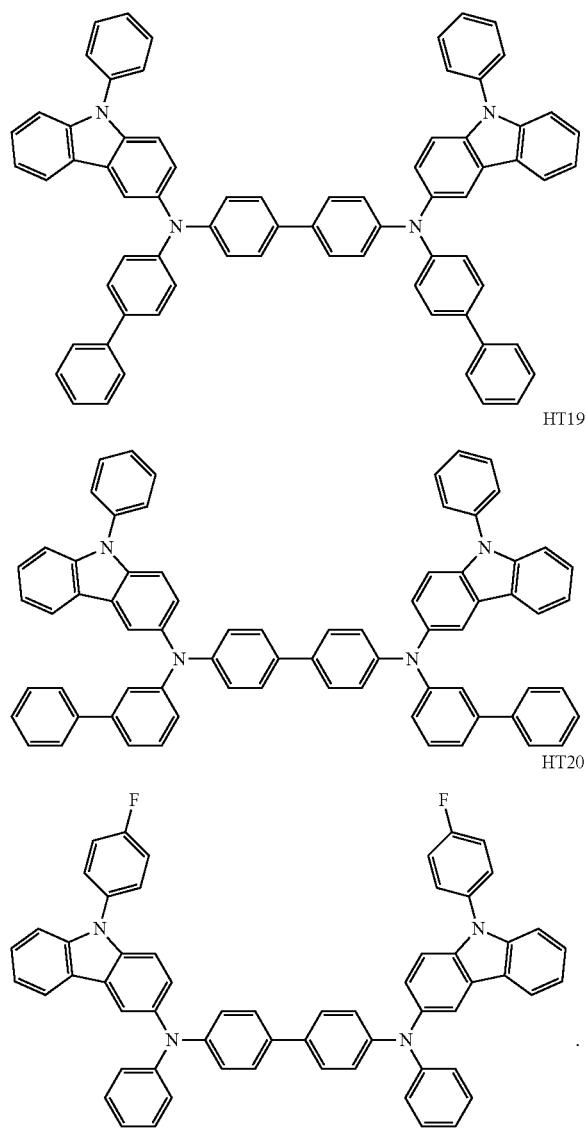

HT18

HT19

HT20

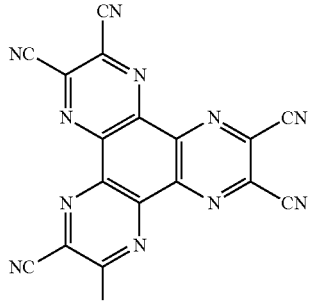

Compound HT-D1

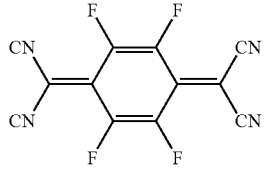

F4-TCNQ

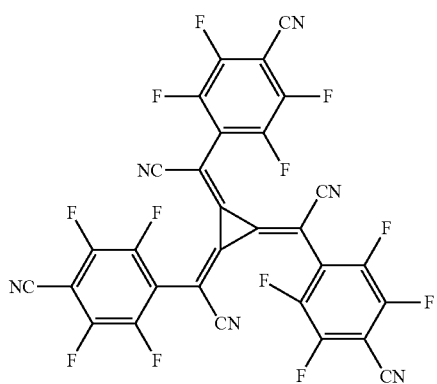

Compound HP-1

A thickness of the hole transport region may be in a range of about 100 Å to about 10,000 Å, for example, about 100 Å to about 1,000 Å. When the hole transport region includes a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenium oxide; and a cyano group-containing compound, such as Compound HT-D1 or HP-1, but are not limited thereto.

The hole transport region may include a buffer layer.

Also, the buffer layer may compensate for an optical resonance distance depending on a wavelength of light emitted from the emission layer. Thus, efficiency of a formed organic light-emitting device may be improved.

Then, an emission layer (EML) may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary according to the material that is used to form the emission layer.

The electron transport region may further include an electron blocking layer. The electron blocking layer may include, for example, mCP, but a material therefor is not limited thereto.

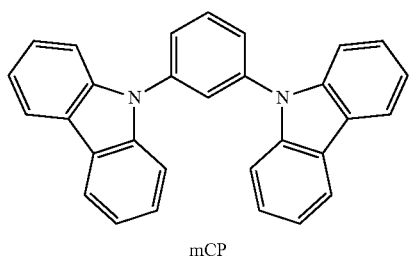 [SMILES: c1cc(-n2c3ccccc3c3ccccc32)cc(-n2c3ccccc3c3ccccc32)c1]

mCP

When the organic light-emitting device is a full color organic light-emitting device, the emission layer may be patterned into a red emission layer, a green emission layer, and a blue emission layer. In some embodiments, due to a stacking structure including a red emission layer, a green emission layer, and/or a blue emission layer, the emission layer may emit white light.

The emission layer may include the carbazole compound represented by Formula 1. The emission layer may include a dopant. The dopant may be at least one selected from a phosphorescent dopant and a fluorescent dopant.

For example, a host in the emission layer may include the carbazole compound represented by Formula 1.

A dopant in the emission layer may be a fluorescent dopant that emits light according to a fluorescent emission mechanism or a phosphorescent dopant that emits light according to a phosphorescent emission mechanism.

According to an embodiment, the dopant in the emission layer may be a phosphorescent dopant, and the phosphorescent dopant may include an organometallic compound represented by Formula 81 below:

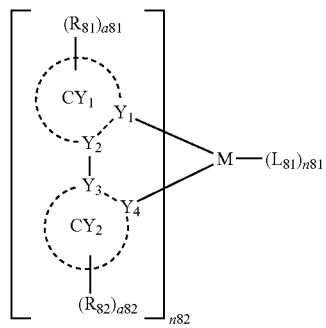

Formula 81 wherein in Formula 81,

M may be selected from iridium (Ir), platinum (Pt), osmium (Os), titanium (Ti), zirconium (Zr), hafnium (Hf), europium (Eu), terbium (Tb), and thulium (Tm);

$Y_1$ to $Y_4$ are each independently carbon (C) or nitrogen (N);

$Y_1$ and $Y_2$ are linked via a single bond or a double bond, and $Y_3$ and $Y_4$ are linked via a single bond or a double bond;

$CY_1$ and $CY_2$ are each independently selected from a benzene, a naphthalene, a fluorene, a spiro-fluorene, an indene, a pyrrole, a thiophene, a furan, an imidazole, a pyrazole, a thiazole, an isothiazole, an oxazole, an isoxazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzoxazole, an isobenzoxazole, a triazole, a tetrazole, an oxadiazole, a triazine, a dibenzofuran, and a dibenzothiophene, and $CY_1$ and $CY_2$ are further optionally linked to each other through an organic linking group;

$R_{81}$ and $R_{82}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic heterocondensed polycyclic group, —$N(Q_1)(Q_2)$, —$Si(Q_3)(Q_4)(Q_5)$, and —$B(Q_6)(Q_7)$;

a81 and a82 are each independently an integer selected from 1 to 5;

n81 is an integer selected from 0 to 4;

n82 is 1, 2, or 3; and $L_{81}$ is a monovalent organic ligand, a divalent organic ligand, or a trivalent organic ligand.

$R_{81}$ and $R_{82}$ may be understood by referring to the description provided herein in connection with $R_{41}$.

The phosphorescent dopant may include at least one selected from Compounds PD1 to PD78 and CIM02 below, but embodiments are not limited thereto:

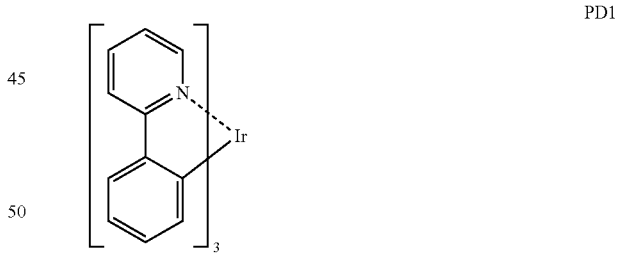

PD1

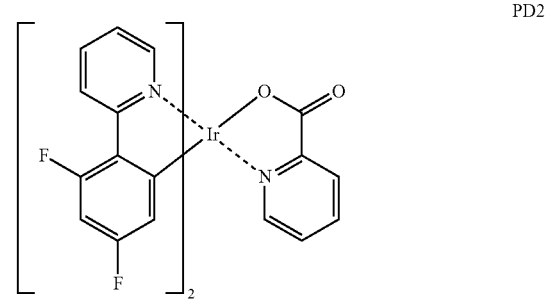

PD2

PD3 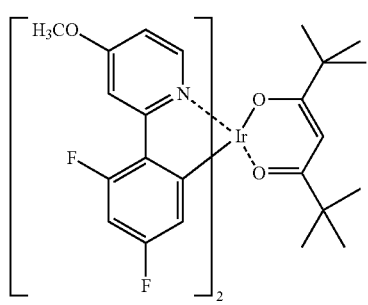
PD4 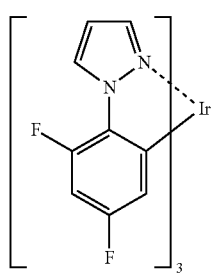
PD5 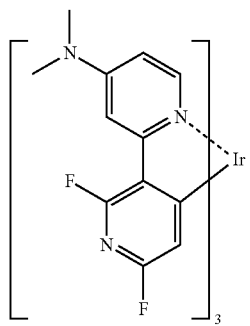
PD6 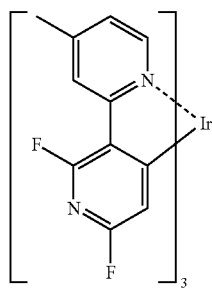
PD7 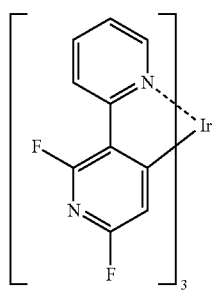
PD8 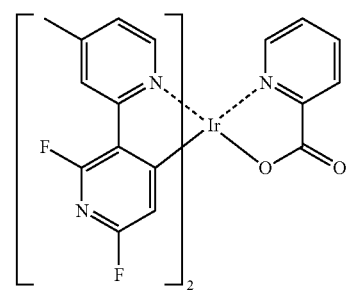
PD9 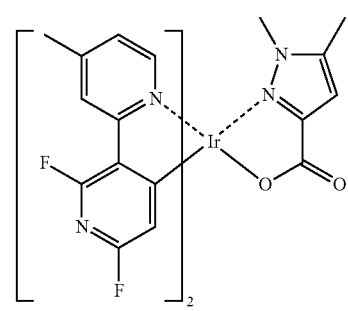
PD10 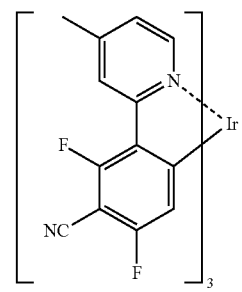
PD11 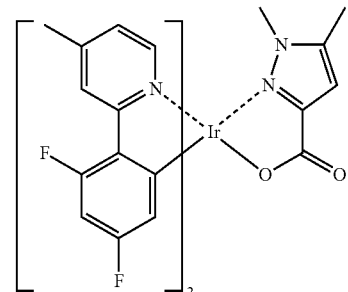
PD12 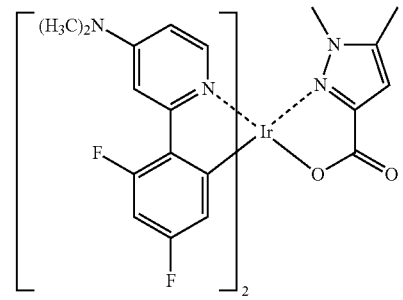

-continued
PD13
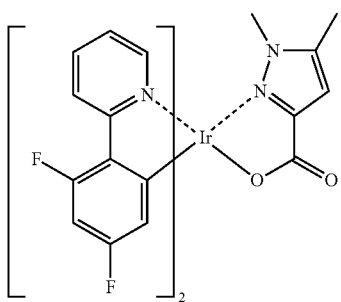
PD14
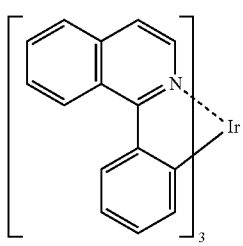
PD15
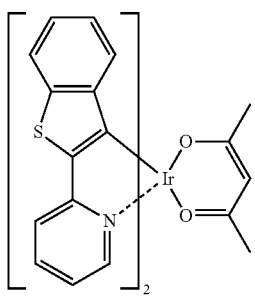
PD16
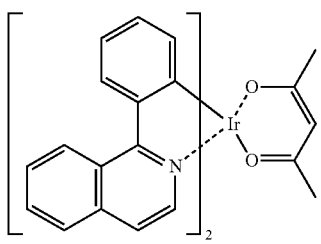
PD17
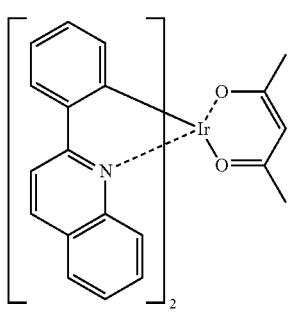
-continued
PD18
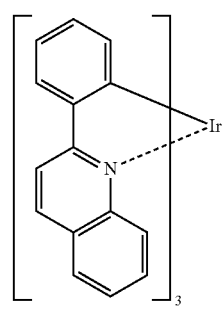
PD19
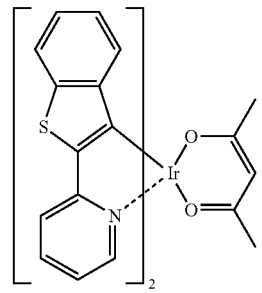
PD20
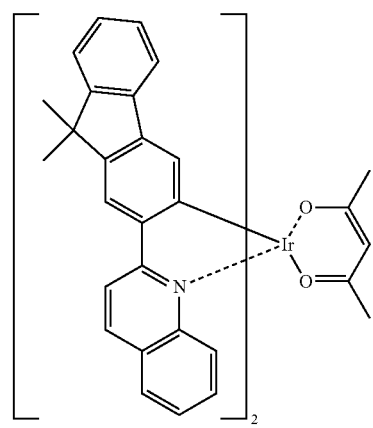
PD21
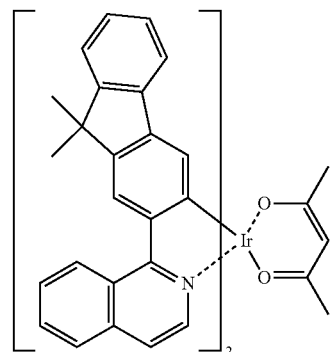
PD22
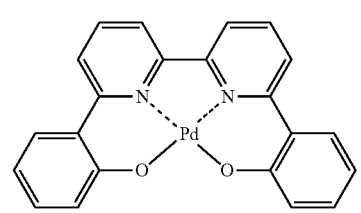

PD23
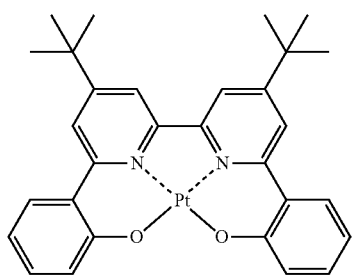
PD24
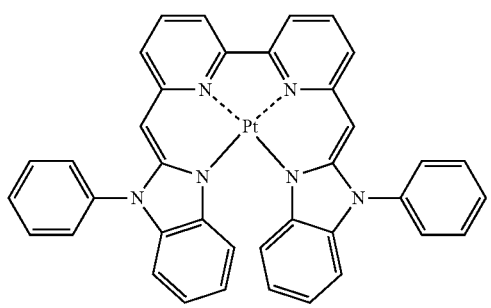
PD25
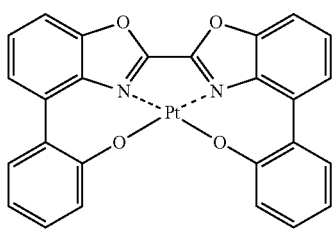
PD26
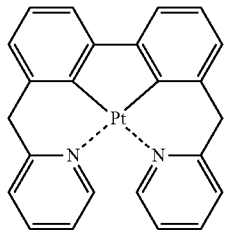
PD27
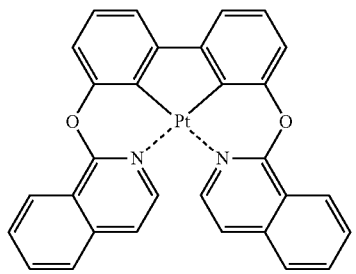
PD28
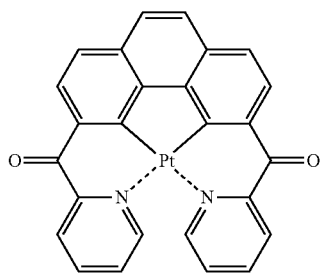
PD29
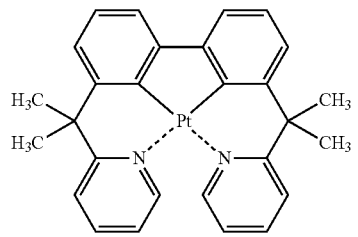
PD30
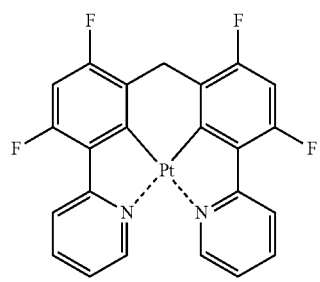
PD31
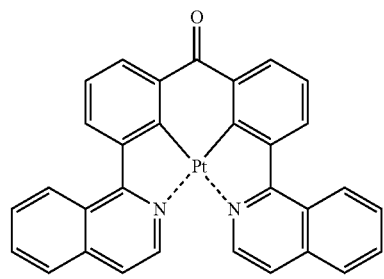
PD32
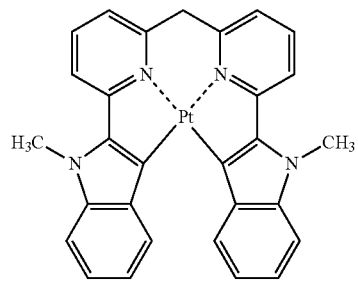
PD33
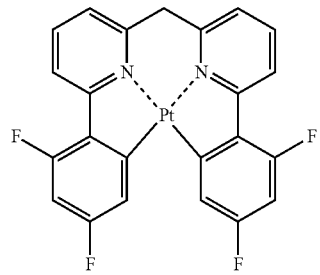
PD34
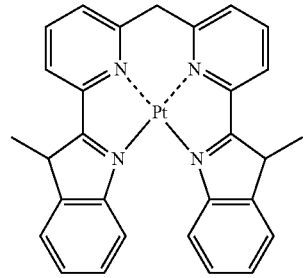

-continued
PD35 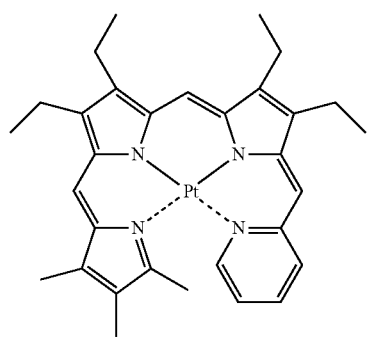
PD36 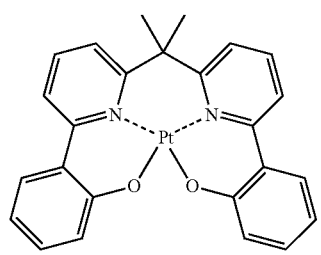
PD37 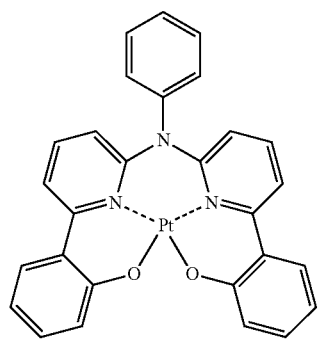
PD38 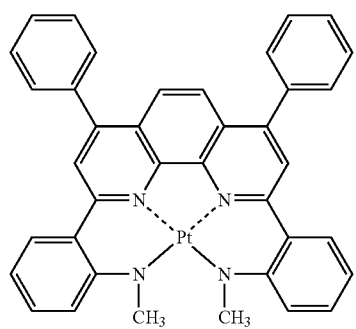
PD39 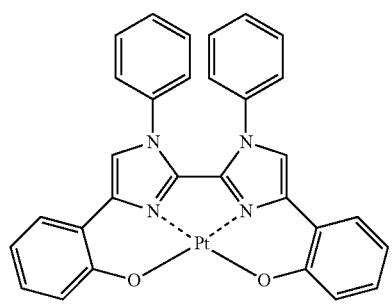
-continued
PD40 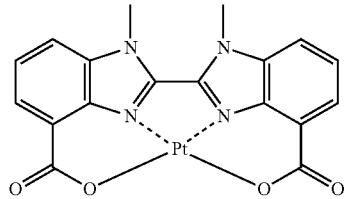
PD41 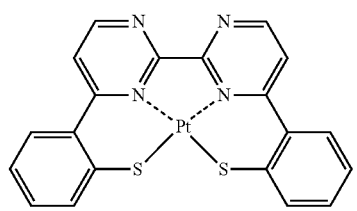
PD42 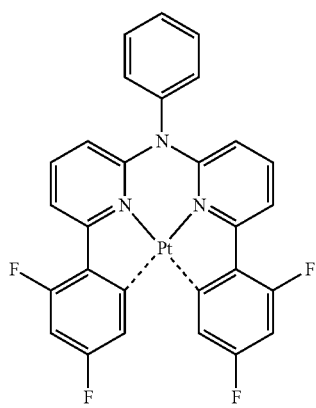
PD43 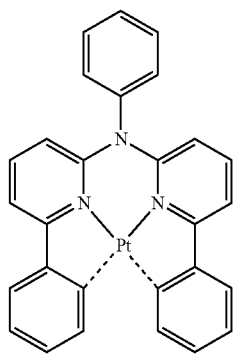
PD44 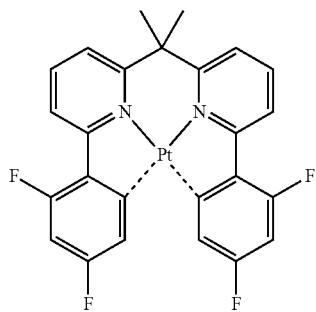

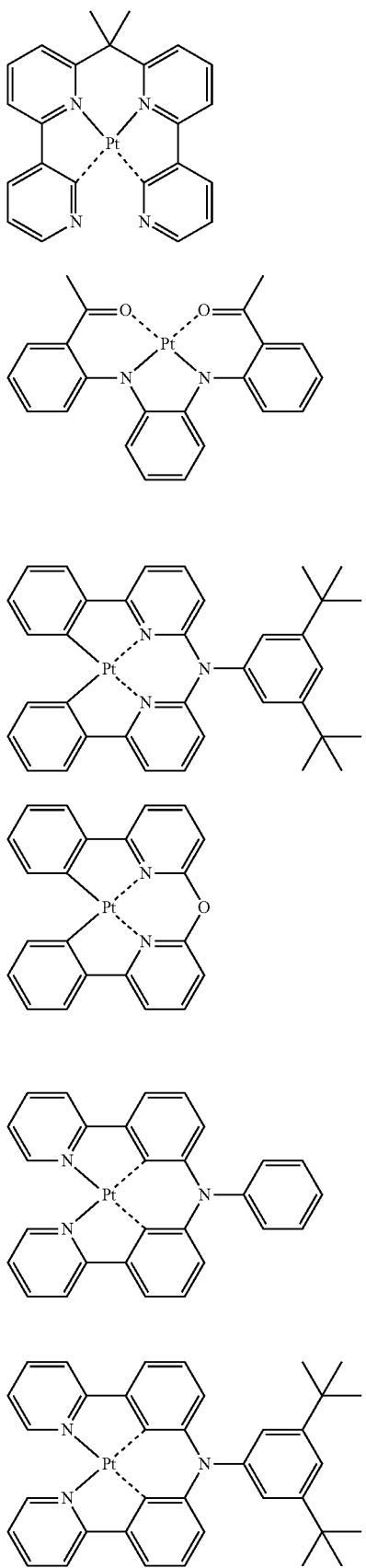
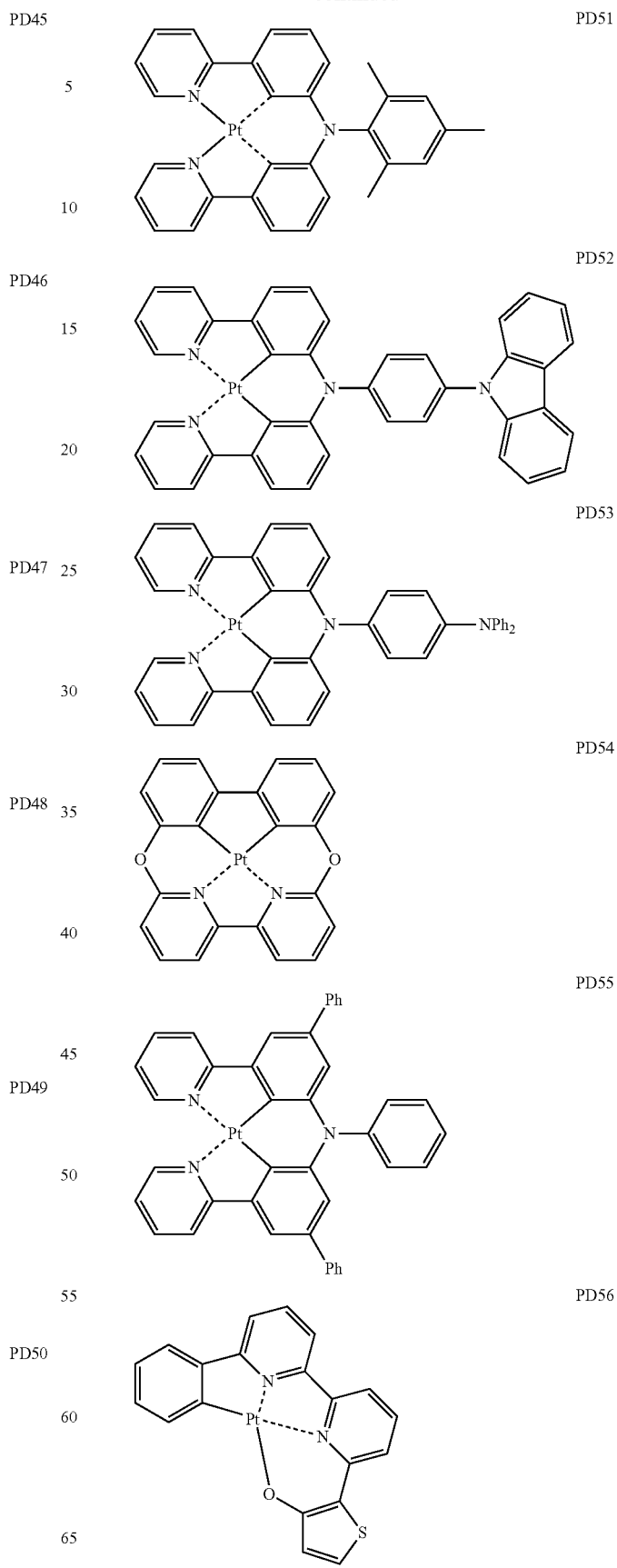

PD57
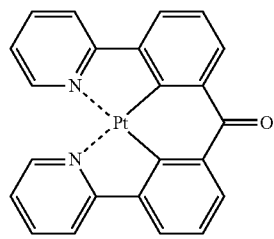
PD58
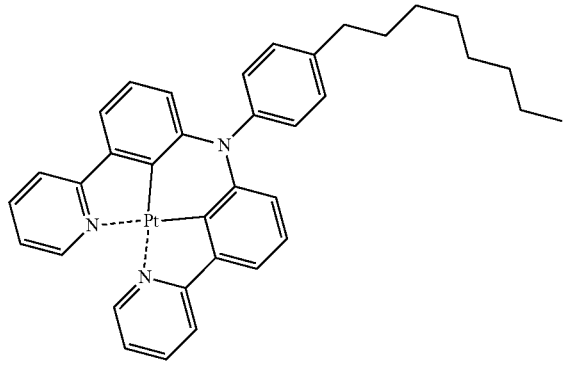
PD59
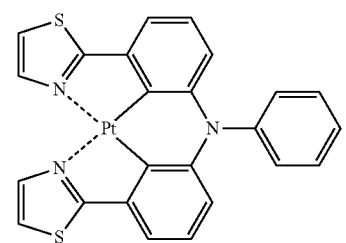
PD60
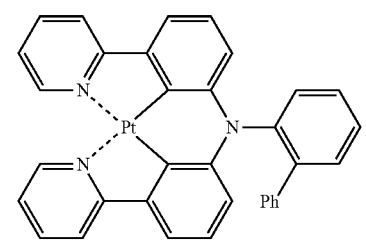
PD61
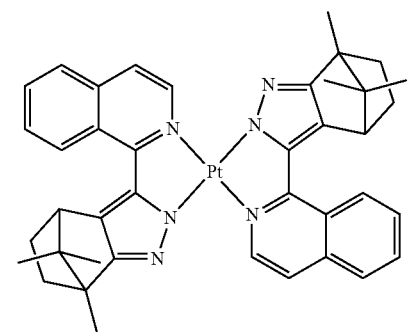
PD62
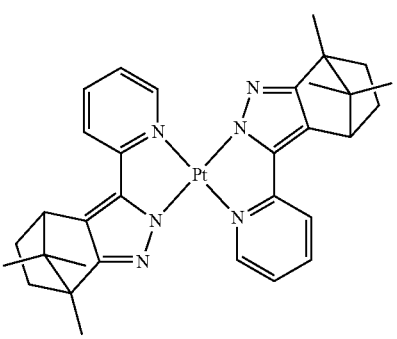
PD63
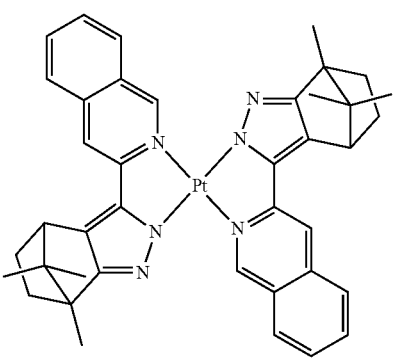
PD64
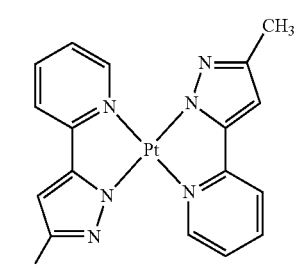
PD65
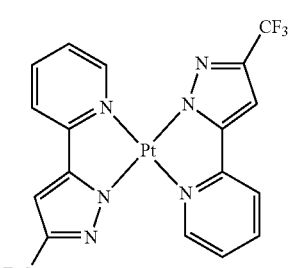
PD66
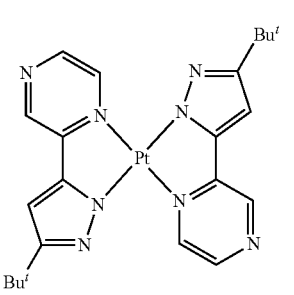

PD67 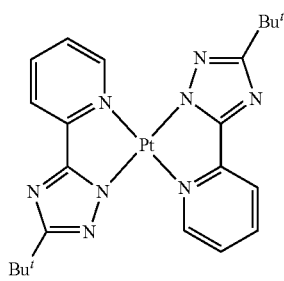
PD68 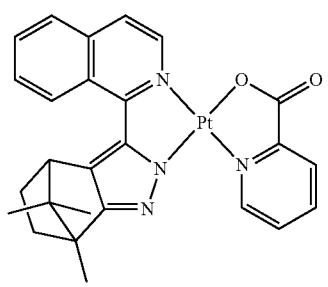
PD69 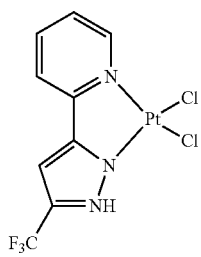
PD70 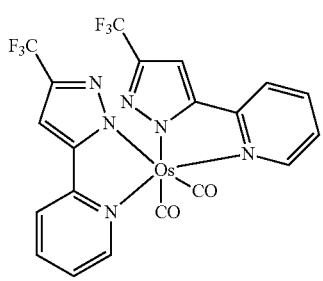
PD71 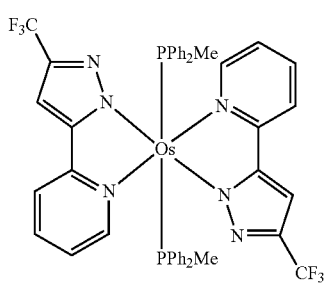
PD72 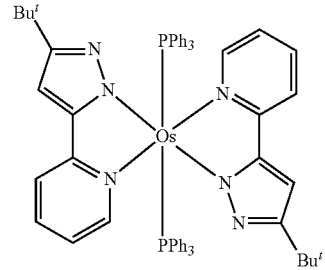
PD73 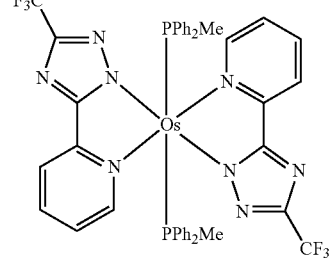
PD74 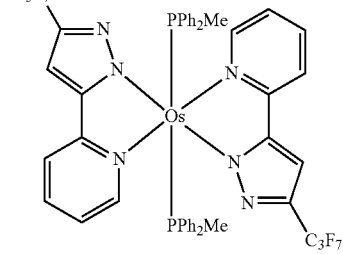
PD75 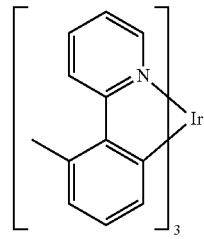
PD76 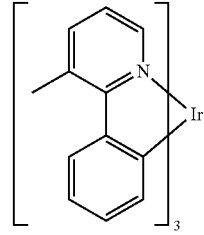
PD77 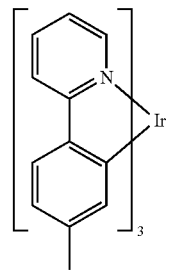

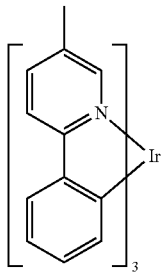

PD78

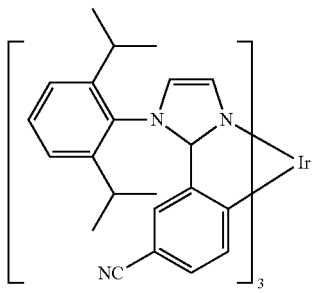

CIM02

In some embodiments, the phosphorescent dopant may include PtOEP:

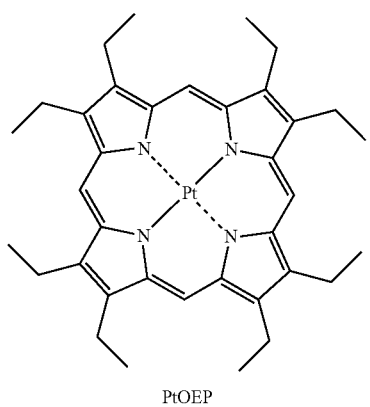

PtOEP

When the emission layer includes a host and a dopant, an amount of the dopant may be in a range of about 0.01 to about 20 parts by weight based on 100 parts by weight of the host, but is not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer.

For example, the electron transport region may have a structure of hole blocking layer/electron transport layer/electron injection layer or a structure of electron transport layer/electron injection layer, but the structure of the electron transport region is not limited thereto. The electron transport layer may have a single-layered structure or a multi-layer structure including two or more different materials.

Conditions for forming the hole blocking layer, the electron transport layer, and the electron injection layer which constitute the electron transport region may be understood by referring to the conditions for forming the hole injection layer.

When the electron transport layer includes a hole blocking layer, the hole blocking layer may include, for example, at least one selected from BCP, Bphen, and Compound PBH021, but embodiments are not limited thereto.

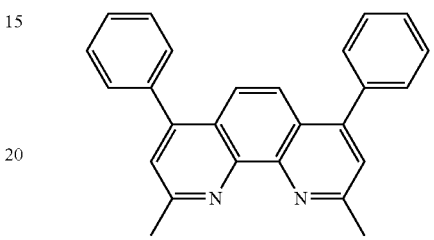

BCP

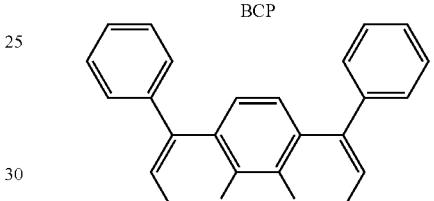

Bphen

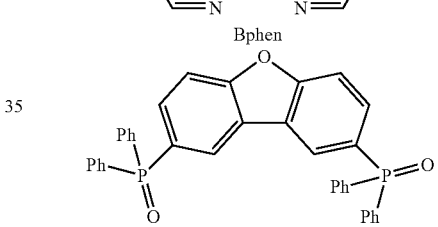

PBH021

A thickness of the hole blocking layer may be in a range of about 20 Å to about 1,000 Å, for example, about 30 Å to about 300 Å. When the thickness of the hole blocking layer is within these ranges, the hole blocking layer may have improved hole blocking ability without a substantial increase in driving voltage.

The electron transport layer may further include at least one selected from BCP, Bphen, Alq$_3$, Balq, TAZ, and NTAZ.

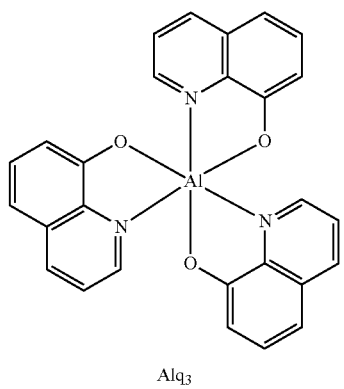

Alq$_3$

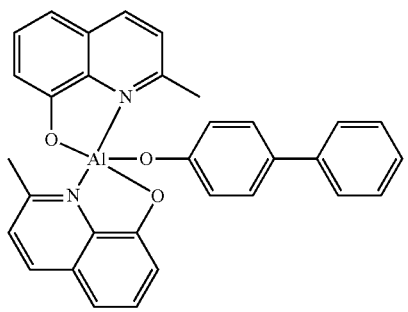

BAlq

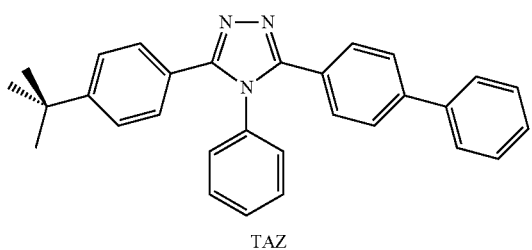

TAZ

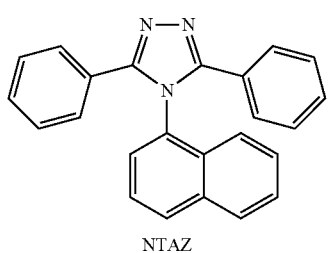

NTAZ

In some embodiments, the electron transport layer may include at least one selected from Compounds ET1, ET2, and ET3, but embodiments are not limited thereto:

ET1

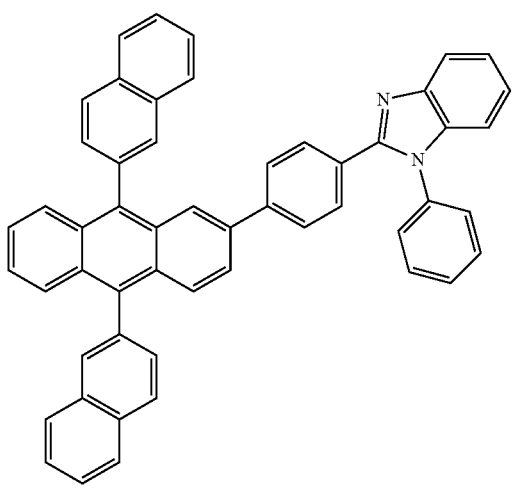

ET2

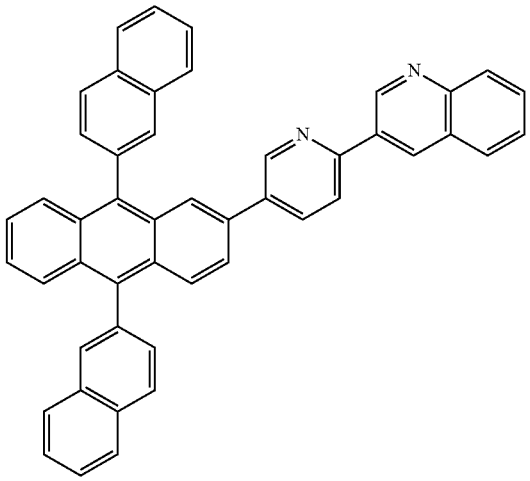

ET3

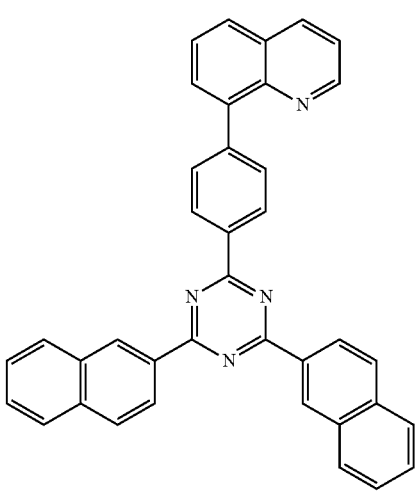

A thickness of the electron transport layer may be in a range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2.

ET-D1

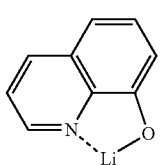

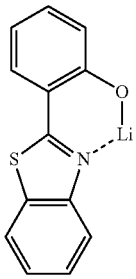
ET-D2

The electron transport region may include an electron injection layer (EIL) that allows electrons to be easily provided from a second electrode 19.

The electron injection layer may include at least one selected from, LiF, NaCl, CsF, Li$_2$O, BaO, and LiQ.

A thickness of the electron injection layer may be in a range of about 1 Å to about 100 Å, for example, about 3 Å to about 90 Å. When the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be selected from metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as a material for forming the second electrode 19. To manufacture a top emission type light-emitting device, a transmissive electrode formed using ITO or IZO may be used as the second electrode 19.

Hereinbefore, the organic light-emitting device has been described with reference to FIG. 1, but is not limited thereto.

A $C_1$-$C_{60}$ alkyl group as used herein refers to a linear or branched aliphatic hydrocarbon monovalent group having 1 to 60 carbon atoms. Detailed examples thereof are a methyl group, an ethyl group, a propyl group, an isobutyl group, a sec-butyl group, a tert-butyl group, a pentyl group, an iso-amyl group, and a hexyl group. A $C_1$-$C_{60}$ alkylene group as used herein refers to a divalent group having the same structure as the $C_1$-$C_{60}$ alkyl group.

A $C_1$-$C_{60}$ alkoxy group as used herein refers to a monovalent group represented by —OA$_{101}$ (wherein A$_{101}$ is the $C_1$-$C_{60}$ alkyl group). Detailed examples thereof are a methoxy group, an ethoxy group, and an isopropyloxy group.

A $C_2$-$C_{60}$ alkenyl group as used herein refers to a hydrocarbon group formed by substituting at least one carbon double bond in the middle or at the terminal of the $C_2$-$C_{60}$ alkyl group. Detailed examples thereof are an ethenyl group, a propenyl group, and a butenyl group. A $C_2$-$C_{60}$ alkenylene group as used herein refers to a divalent group having the same structure as the $C_2$-$C_{60}$ alkenyl group.

A $C_2$-$C_{60}$ alkynyl group as used herein refers to a hydrocarbon group formed by substituting at least one carbon trip bond in the middle or at the terminal of the $C_2$-$C_{60}$ alkyl group. Detailed examples thereof are an ethynyl group, and a propynyl group. A $C_2$-$C_{60}$ alkynylene group as used herein refers to a divalent group having the same structure as the $C_2$-$C_{60}$ alkynyl group.

A $C_3$-$C_{10}$ cycloalkyl group as used herein refers to a monovalent hydrocarbon monocyclic group having 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as the $C_3$-$C_{10}$ cycloalkyl group.

A $C_1$-$C_{10}$ heterocycloalkyl group as used herein refers to a monovalent monocyclic group having at least one hetero atom selected from N, O, P, and S as a ring-forming atom and 1 to 10 carbon atoms. Detailed examples thereof are a tetrahydrofuranyl group, and a tetrahydrothiophenyl group. A $C_1$-$C_{10}$ heterocycloalkylene group as used herein refers to a divalent group having the same structure as the $C_1$-$C_{10}$ heterocycloalkyl group.

A $C_3$-$C_{10}$ cycloalkenyl group as used herein refers to a monovalent monocyclic group that has 3 to 10 carbon atoms and at least one double bond in the ring thereof, and which is not aromatic. Detailed examples thereof are a cyclopentenyl group, a cyclohexenyl group, and a cycloheptenyl group. A $C_3$-$C_{10}$ cycloalkenylene group as used herein refers to a divalent group having the same structure as the $C_3$-$C_{10}$ cycloalkenyl group.

A $C_1$-$C_{10}$ heterocycloalkenyl group as used herein refers to a monovalent monocyclic group that has at least one hetero atom selected from N, O, P, and S as a ring-forming atom, 1 to 10 carbon atoms, and at least one double bond in its ring. Detailed examples of the $C_1$-$C_{10}$ heterocycloalkenyl group are a 2,3-dihydrofuranyl group and a 2,3-dihydrothiophenyl group. A $C_1$-$C_{10}$ heterocycloalkenylene group as used herein refers to a divalent group having the same structure as the $C_1$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group as used herein refers to a monovalent group having a carbocyclic aromatic system that has at least one hetero atom selected from N, O, P, and S as a ring-forming atom, and 1 to 60 carbon atoms. A $C_1$-$C_{60}$ heteroarylene group as used herein refers to a divalent group having a carbocyclic aromatic system that has at least one hetero atom selected from N, O, P, and S as a ring-forming atom, and 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

A $C_6$-$C_{60}$ aryloxy group as used herein indicates —OA$_{102}$ (wherein A$_{102}$ is the $C_6$-$C_{60}$ aryl group), and a $C_6$-$C_{60}$ arylthio group as used herein indicates —SA$_{103}$ (wherein A$_{103}$ is the $C_6$-$C_{60}$ aryl group).

A monovalent non-aromatic condensed polycyclic group as used herein refers to a monovalent group that has two or more rings condensed to each other, only carbon atoms (for example, the number of carbon atoms may be in a range of 8 to 60) as a ring forming atom, which is non-aromatic in the entire molecular structure. An example of the monovalent non-aromatic condensed polycyclic group is a fluorenyl group. A divalent non-aromatic condensed polycyclic group as used herein refers to a divalent group having the same structure as the monovalent non-aromatic condensed polycyclic group.

A monovalent non-aromatic condensed heteropolycyclic group as used herein refers to a monovalent group that has two or more rings condensed to each other, has a heteroatom selected from N, O, P, and S, other than carbon atoms (for example, the number of carbon atoms may be in a range of 1 to 60), as a ring forming atom, which is non-aromatic in the entire molecular structure. An example of the monovalent non-aromatic condensed heteropolycyclic group is a carbazolyl group. A divalent non-aromatic condensed heteropolycyclic group as used herein refers to a divalent group having the same structure as the monovalent non-aromatic condensed heteropolycyclic group.

At least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted a divalent non-aromatic condensed polycyclic group, substituted a divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group and —Si($Q_{31}$)($Q_{32}$)($Q_{33}$), and $Q_1$ to $Q_3$, $Q_{11}$ to $Q_{13}$, $Q_{21}$ to $Q_{23}$, and $Q_{31}$ to $Q_{33}$ may be each independently selected from a hydrogen, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group and a monovalent non-aromatic condensed heteropolycyclic group.

The "biphenyl group" as used therein refers to "a phenyl group substituted with a phenyl group."

Hereinafter, a compound and an organic light-emitting device according to embodiments are described in detail with reference to Synthesis Example and Examples. However, the organic light-emitting device is not limited thereto. The wording "B was used instead of A" used in describing Synthesis Examples means that an amount of A used was identical to an amount of B used, in terms of a molar equivalent.

EXAMPLE

Synthesis Example 1: Synthesis of Compound 19

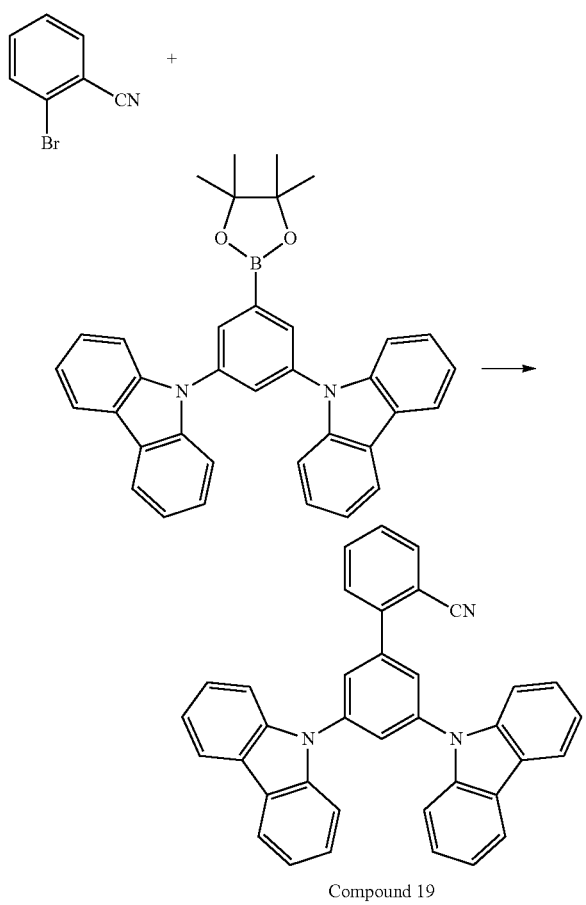

Compound 19

9 grams (g) (49.45 millimoles (mmol)) of 2-bromobenzonitrile, 31.7 g (59.33 mmol) of 9,9'-(5-(4,4,5,5-tetramethyl-1,3,2-dioxaborolan-2-yl)-1,3-phenylene)bis(9H-carbazole), 2.285 g (1.98 mmol) of tetrakis(triphenylphosphine)palladium [Pd(PPh$_3$)$_4$], and 20.5 g (148.34 mmol) of potassium carbonate were added to 300 milliliters (mL) of THF and 150 mL of distilled water in a round-bottomed flask, and the mixture was refluxed for 12 hours while heating. Once the reaction was complete, the reaction product was cooled to room temperature. THF was separated from distilled water and was added dropwise to 600 mL of methanol to force crystallization. The solid was filtered, and washed with water and methanol. The resultant solid was dried in a vacuum oven to obtain Compound 19 (22.68 g, the yield of 90%).

¹H NMR (400 MHz, CDCl₃): δ 8.18 (d, 4H), 7.96 (t, 1H), 7.89 (d, 3H), 7.72 (d, 6H), 7.58 (d, 1H), 7.49 (t, 4H), 7.34 (t, 4H)

MS (m/z, [M]⁺): 510.24

Synthesis Example 2: Synthesis of Compound 179

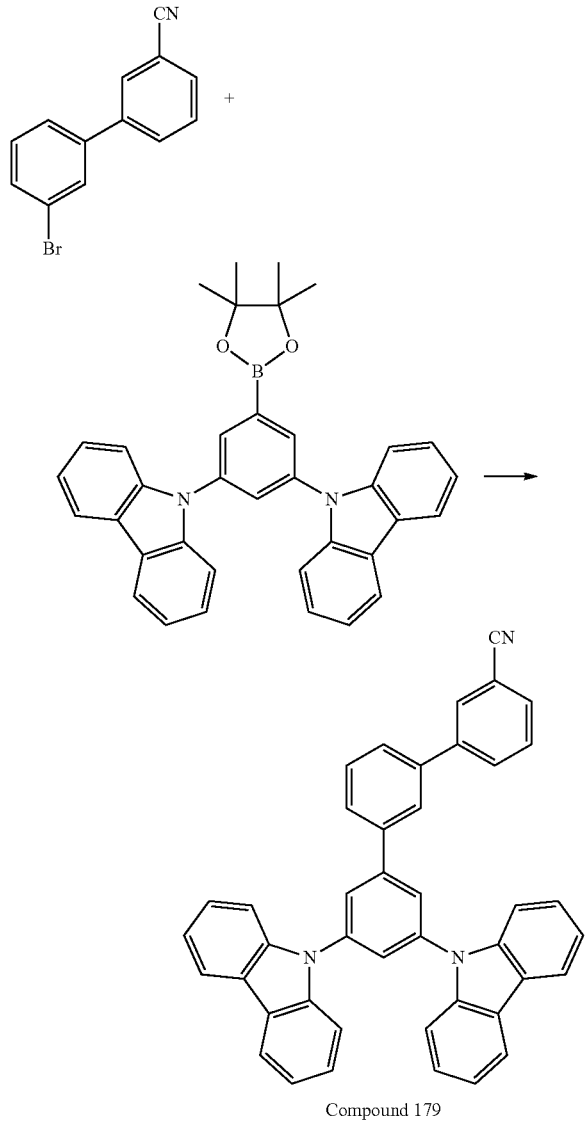

Compound 179

8 g (31 mmol) of 3'-bromo-[1,1'-biphenyl]-3-carbonitrile, 19.8 g (37.19 mmol) of 9,9'-(5-(4,4,5,5-tetramethyl-1,3,2-dioxaborolan-2-yl)-1,3-phenylene)bis(9H-carbazole), 1.433 g (1.24 mmol) of tetrakis(triphenylphosphine)palladium [Pd (PPh₃)₄], and 12.8 g (92.98 mmol) of potassium carbonate were added to 300 mL of THF and 150 mL of distilled water in a round-bottomed flask, and the mixture was refluxed for 12 hours while heating. Once the reaction was complete, the reaction product was cooled to room temperature. THF was separated from distilled water and added dropwise to 600 mL of methanol to force crystallization. The solid was filtered, and washed with water and methanol. The resultant solid obtained therefrom was dried in a vacuum oven to obtain Compound 179 (15.97 g, the yield of 88%).

¹H NMR (400 MHz, CDCl₃): δ 8.19 (d, 4H), 8.00 (d, 2H), 7.93 (s, 1H), 7.87 (s, 3H), 7.79 (m, 1H), 7.62 (d, 7H), 7.54 (d, 1H), 7.46 (t, 4H), 7.33 (d, 4H)

MS (m/z, [M]⁺): 585.30

Synthesis Example 3: Synthesis of Compound 28

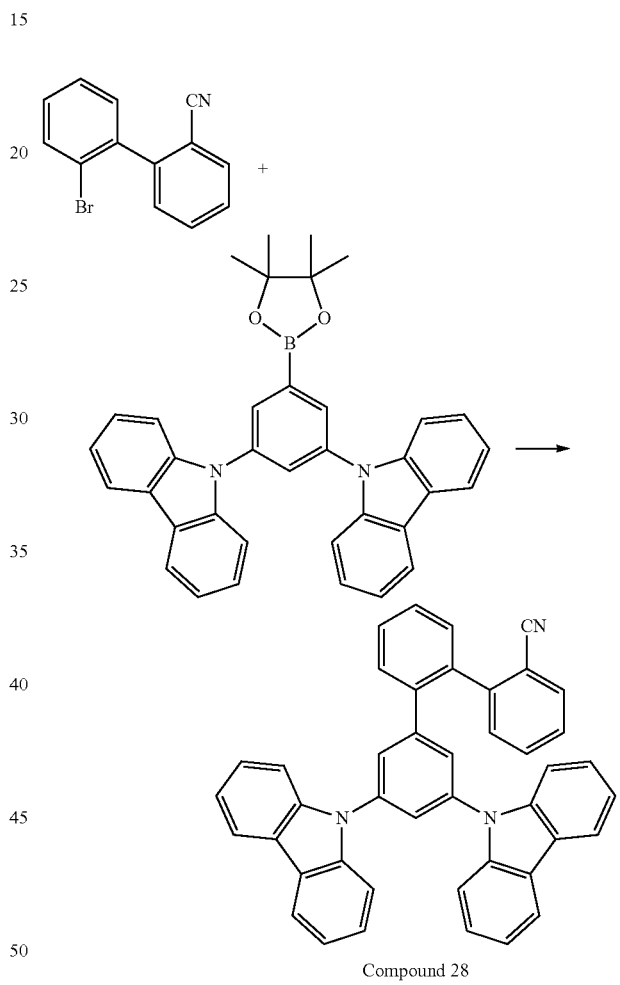

Compound 28

8 g (31 mmol) of 2'-bromo-[1,1'-biphenyl]-2-carbonitrile, 19.8 g (37.19 mmol) of 9,9'-(5-(4,4,5,5-tetramethyl-1,3,2-dioxaborolan-2-yl)-1,3-phenylene)bis(9H-carbazole), 1.433 g (1.24 mmol) of tetrakis(triphenylphosphine)palladium [Pd (PPh₃)₄], and 12.8 g (92.98 mmol) of potassium carbonate were added to 300 mL of THF and 150 mL of distilled water in a round-bottomed flask, and the mixture was refluxed for 12 hours while heating. Once the reaction was complete, the reaction product was cooled to room temperature and THF was separated from distilled water, and the THF separated therefrom was added dropwise to 600 mL of methanol and crystallized. Then, the solid was filtered, and washed with water and methanol. The resultant solid obtained therefrom was dried in a vacuum oven to obtain Compound 28 (14.52 g, the yield of 80%).

$^1$H NMR (400 MHz, CDCl$_3$): δ 8.12 (d, 4H), 7.84 (d, 1H), 7.54 (m, 10H), 7.38 (t, 4H), 7.28 (t, 8H)

MS (m/z, [M]$^+$): 585.32

Synthesis Example 4: Synthesis of Compound 30

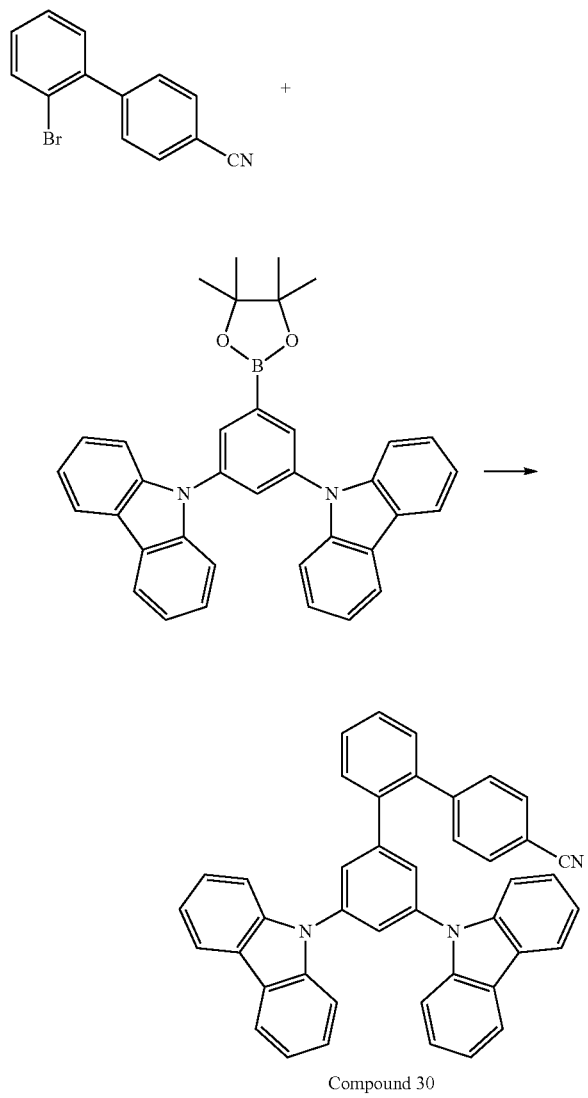

Compound 30

6 g (23.25 mmol) of 2'-bromo-[1,1'-biphenyl]-4-carbonitrile, 14.9 g (27.9 mmol) of 9,9'-(5-(4,4,5,5-tetramethyl-1,3,2-dioxaborolan-2-yl)-1,3-phenylene)bis(9H-carbazole), 1.074 g (0.93 mmol) of tetrakis(triphenylphosphine)palladium [Pd(PPh$_3$)$_4$], and 9.638 g (69.74 mmol) of potassium carbonate were added to 200 mL of THF and 100 mL of distilled water in a round-bottomed flask, and the mixture was refluxed for 12 hours while heating. Once the reaction was complete, the temperature was decreased to room temperature. THF was separated from distilled water and added dropwise to 600 mL of methanol to force crystallization. The solid was filtered, and washed with water and methanol. The resultant solid obtained therefrom was dried in a vacuum oven to obtain Compound 30 (11.16 g, the yield of 82%).

$^1$H NMR (400 MHz, CDCl$_3$): δ 8.14 (d, 4H), 7.80 (d, 2H), 7.72 (t, 1H), 7.63 (m, 1H), 7.50 (m, 11H), 7.31 (t, 4H), 7.21 (d, 4H)

MS (m/z, [M]$^+$): 585.32

Evaluation Example 1: Evaluation on HOMO, LUMO, and Triplets (T$_1$) Energy Levels HOMO, LUMO and T$_1$ energy levels of Compounds 19, 179, and 28 were evaluated according to the method indicated in Table 2. The results thereof are shown in Table 3.

TABLE 2

| | |
|---|---|
| HOMO energy level evaluation method | A potential (Volts, V) - current (Amperes, A) graph of each compound was obtained by using cyclic voltammetry (CV) (electrolyte: 0.1M Bu$_4$NClO$_4$/solvent: CH$_2$Cl$_2$/electrode: 3 electrode system (working electrode: GC, reference electrode: Ag/AgCl, auxiliary electrode: Pt)). From reduction onset of the graph, a HOMO energy level of the compound was calculated. |
| LUMO energy level evaluation method | Each compound was diluted at a concentration of 1 × 10$^{-5}$ M in CHCl$_3$, and an UV absorption spectrum thereof was measured at room temperature by using a Shimadzu UV-350 spectrometer. A LUMO energy level thereof was calculated by using an optical band gap (Eg) from an edge of the absorption spectrum. |
| T1 energy level evaluation method | A mixture (each compound was dissolved in an amount of 1 milligrams (mg) in 3 cubic centimeters (cc) of toluene) of toluene and each compound was loaded into a quartz cell. The resultant quartz cell was loaded into liquid nitrogen (77 Kelvins (K)), and a photoluminescence spectrum thereof was measured by using a device for measuring photoluminescence. The obtained spectrum was compared with a photoluminescence spectrum measured at room temperature, and the peaks observed only at low temperature were analyzed to calculate T1 energy levels. |

TABLE 3

| Compound No. | HOMO (eV) (calc.) | LUMO (eV) (calc.) | T1 energy level (eV) |
|---|---|---|---|
| 19 | −5.57 | −1.98 | 3.02 |
| 179 | −5.69 | −2.11 | 2.82 |
| 28 | −5.74 | −2.16 | 3.02 |

From Table 3, it is confirmed that the compounds above have electric characteristics that are suitable for use as a material for forming an organic light-emitting device.

Evaluation Example 2: Thermal Characteristics Evaluation

Each of Compounds 19, 179, and 28 was subjected to thermal analysis (N$_2$ atmosphere, temperature range: room temperature to 800° C. (10° C./min)-TGA, room temperature to 400° C.-DSC, Pan Type: Pt Pan in disposable Al Pan(TGA), disposable Al pan(DSC)) using thermogravimetric analysis (TGA) and differential scanning calorimetry (DSC), and obtained results are shown in Table 4 below. As shown in Table 4, it was confirmed that the synthesized compounds had excellent thermal stability.

TABLE 4

| Compound No. | Tg (° C.) |
|---|---|
| 19 | 105 |
| 179 | 117 |
| 28 | 123 |

Example 1

A glass substrate with a 1,500 Å-thick ITO (indium tin oxide) electrode (first electrode, anode) formed thereon was washed with distilled water in the presence of ultrasonic waves. When the washing with distilled water was completed, sonification washing was performed using a solvent, such as isopropyl alcohol, acetone, or methanol. The resultant substrate was dried, transferred to a plasma washer, washed with oxygen plasma for 5 minutes, and transferred to a vacuum depositing device.

Compound HT3 and Compound HP-1 were co-deposited on the ITO electrode on the glass substrate to form a hole injection layer having a thickness of 100 Å. Compound HT3 was deposited on the hole injection layer to form a hole transport layer having a thickness of 1,300 Å. mCP was deposited on the hole transport layer to form an electron blocking layer having a thickness of 150 Å, thereby completing the manufacture of a hole transport region.

Compound 19 (host) and CIM02 (dopant, 10 percent by weight (wt %)) were co-deposited on the hole transport region to form an emission layer having a thickness of 300 Å.

PBH021 was vacuum deposited on the emission layer to form a hole blocking layer having a thickness of 100 Å, Compound ET3 and Liq were vacuum deposited on the hole blocking layer to form an electron transport layer having a thickness of 250 Å. Then, Liq was deposited on the electron transport layer to form an electron injection layer having a thickness of 5 Å, and Al second electrode(cathode) having a thickness of 1,000 Å was formed on the electron injection layer, thereby completing the manufacture of an organic light-emitting device.

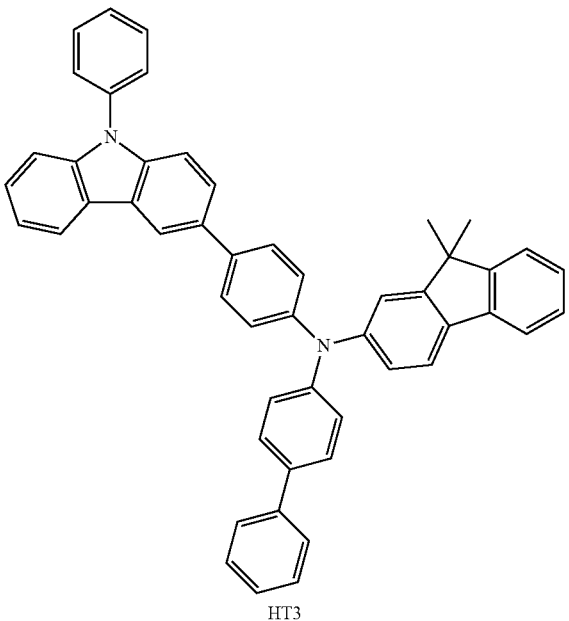

Compound HT3

HT3

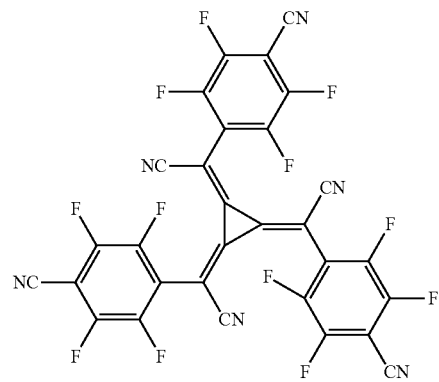

Compound HP-1

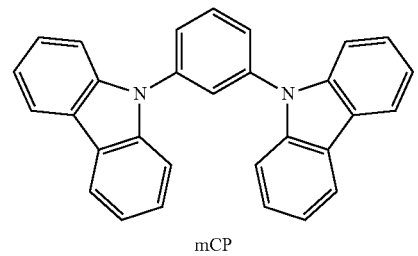

mCP

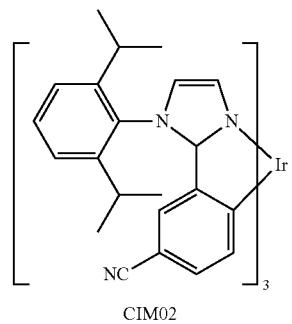

CIM02

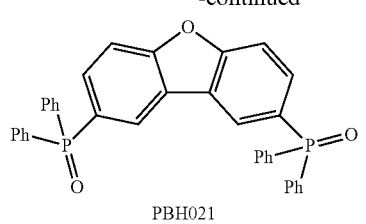

PBH021

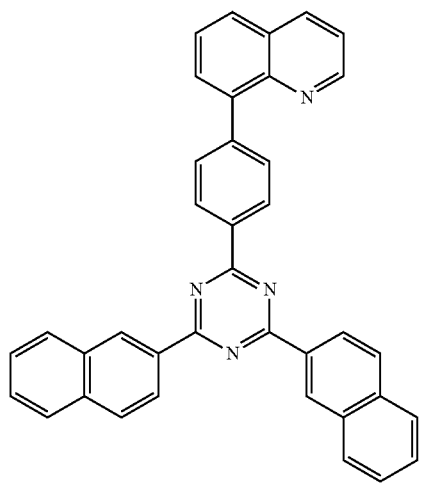

ET3

Examples 2 to 4 and Comparative Example 1

Organic light-emitting devices were manufactured in the same manner as in Example 1, except that in forming an emission layer, as a host, the compounds shown in Table 4 were used instead of Compound 19.

Evaluation Example 3: Evaluation on Characteristics of Organic Light-Emitting Devices The driving voltage, efficiency, electric power, quantum efficiency, and lifespan of the organic light-emitting devices of Examples 1 to 6 and Comparative Example 1 were measured by using a current-voltage meter (Keithley 2400) and a luminance meter (Minolta Cs-1000A), and results thereof are shown in Table 5. $T_{95}$ (at 500 candelas per square meter (cd/m$^2$)) in Table 5 indicates an amount of time that lapsed when 100% of the initial luminance was decreased to 95%.

TABLE 5

| Host | | Driving Voltage Voltage (V) | Efficiency (cd/A) | Electric power (lm/W) | Quantum efficiency (%) | $T_{95}$ (hr) |
|---|---|---|---|---|---|---|
| Example 1 | Compound 19 | 4.99 | 35.85 | 22.01 | 21.2 | 6.4 |
| Example 2 | Compound 179 | 4.62 | 36.94 | 24.98 | 20 | 2.4 |
| Example 3 | Compound 28 | 4.93 | 32.01 | 20.40 | 17.8 | 2.0 |
| Example 4 | Compound 30 | 4.72 | 32.09 | 21.36 | 18.1 | 1.9 |
| Comparative Example 1 | Compound A | 4.77 | 34.66 | 22.80 | 17.5 | 1.4 |

TABLE 5-continued

| Host | Driving Voltage Voltage (V) | Efficiency (cd/A) | Electric power (lm/W) | Quantum efficiency (%) | $T_{95}$ (hr) |
|---|---|---|---|---|---|

19

179

28

30

TABLE 5-continued

| Host | Driving Voltage Voltage (V) | Effi- ciency (cd/A) | Electric power (lm/W) | Quan- tum effi- ciency (%) | $T_{95}$ (hr) |
|---|---|---|---|---|---|
| Compound A | | | | | |

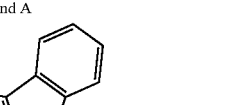

From Table 5, it was confirmed that the organic light-emitting devices of Examples 1 to 4 have a lower driving voltage, a higher efficiency, a higher electric power, a high quantum luminescent efficiency, and a longer lifespan than the organic light-emitting device of Comparative Example 1.

The carbazole compound according to embodiments has excellent electric characteristics and thermal stability. Accordingly, an organic light-emitting device including the carbazole compound may have a low driving voltage, high efficiency, high electric power, high quantum efficiency, and a long lifespan.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the FIGURES, it will be understood by those of ordinary skill in the art that various changes in form and details may be made therein without departing from the spirit and scope as defined by the following claims.

What is claimed is:
1. A carbazole compound represented by Formula 1:

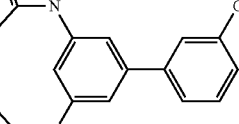

Formula 1

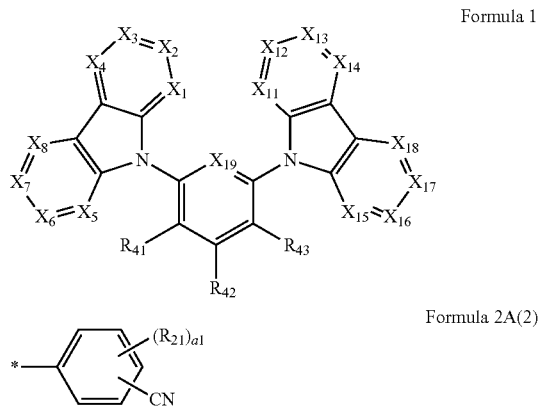

Formula 2A(2)

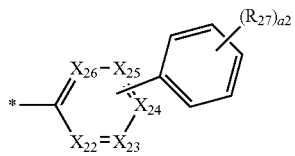

Formula 2B

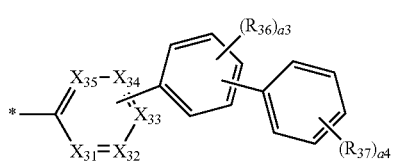

Formula 2C

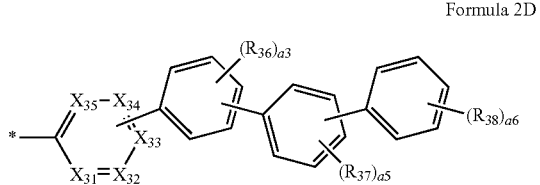

Formula 2D wherein in the Formulae 1, 2A(2), 2B, 2C, and 2D,
$X_1$ is N or $C(R_1)$, $X_2$ is N or $C(R_2)$, $X_3$ is N or $C(R_3)$, $X_4$ is N or $C(R_4)$, $X_5$ is N or $C(R_5)$, $X_6$ is N or $C(R_6)$, $X_7$ is N or $C(R_7)$, $X_8$ is N or $C(R_8)$, $X_{11}$ is N or $C(R_{11})$, $X_{12}$ is N or $C(R_{12})$, $X_{13}$ is N or $C(R_{13})$, $X_{14}$ is N or $C(R_{14})$, $X_{15}$ is N or $C(R_5)$, $X_{16}$ is N or $C(R_{16})$, $X_{17}$ is N or $C(R_7)$, $X_{18}$ is N or $C(R_8)$, $X_{19}$ is $C(R_{19})$ wherein $R_{19}$ is a hydrogen, $X_{22}$ is N, C or $C(R_{22})$, $X_{23}$ is N, C or $C(R_{23})$, $X_{24}$ is N, C or $C(R_{24})$, $X_{25}$ is N, C or $C(R_{25})$, $X_{26}$ is N, C or $C(R_{26})$, $X_{31}$ is N, C or $C(R_{31})$, $X_{32}$ is N, C or $C(R_{32})$, $X_{33}$ is N, C or $C(R_{33})$, $X_{34}$ is N, C or $C(R_{34})$, and $X_{35}$ is N, C or $C(R_{35})$,
provided that at least one selected from $X_1$ to $X_8$ and $X_{11}$ to $X_{18}$ is N,
provided that when $X_{22}$ is C, $X_{22}$ is connected to a carbon of a phenyl group of Formula 2B, when $X_{23}$ is C, $X_{23}$ is connected to a carbon of a phenyl group of Formula 2B, when $X_{24}$ is C, $X_{24}$ is connected to a carbon of a phenyl group of Formula 2B, when $X_{25}$ is C, $X_{25}$ is connected to a carbon of a phenyl group of Formula 2B, when $X_{26}$ is C, $X_{26}$ is connected to a carbon of a phenyl group of Formula 2B, when $X_{31}$ is C, $X_{31}$ is connected to a carbon of a phenyl group of Formulae 2C and 2D, when $X_{32}$ is C, $X_{32}$ is connected to a carbon of a phenyl group of Formulae 2C and 2D, when $X_{33}$ is C, $X_{33}$ is connected to a carbon of a phenyl group of Formulae 2C and 2D, when $X_{34}$ is C, $X_{34}$ is connected to a carbon of a phenyl group of Formulae 2C and 2D, when $X_{35}$ is C, $X_{35}$ is connected to a carbon of a phenyl group of Formulae 2C and 2D, one selected from $X_{22}$ to $X_{26}$ in Formula 2B is C, and one selected from $X_{31}$ to $X_{35}$ in Formulae 2C and 2D is C,
$R_1$ to $R_8$, $R_{11}$ to $R_{18}$, $R_{21}$ to $R_{27}$, and $R_{31}$ to $R_{38}$ are each independently selected from
a hydrogen, a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;
a $C_1$-$C_{20}$ alkyl group and a $C_1$-$C_{20}$ alkoxy group, each substituted with at least one selected from a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof and a phosphoric acid group or a salt thereof;

a phenyl group, a pyridinyl group, a fluorenyl group, a dibenzofuranyl group, and a dibenzothiophenyl group;

a phenyl group, a pyridinyl group, a fluorenyl group, a dibenzofuranyl group and a dibenzothiophenyl group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group, and —Si($Q_1$)($Q_2$)($Q_3$); and —Si($Q_{11}$)($Q_{12}$)($Q_{13}$), a1, a3, and a5 are each independently an integer selected from 1 to 4, and a2, a4 and a6 are each independently an integer selected from 1 to 5, each of $R_{22}$ to $R_{26}$ is not a cyano group, at least one of groups $R_{27}$ in the number of a2 in Formula 2B is a cyano group, at least one selected from $R_{31}$ to $R_{35}$, groups $R_{36}$ in the number of a3 and groups $R_{37}$ in the number of a4 in Formula 2C is a cyano group, and at least one selected from $R_{31}$ to $R_{35}$, groups $R_{36}$ in the number of a3, groups $R_{37}$ in the number of a5, and groups $R_{38}$ in the number of a6 in Formula 2D is a cyano group, $R_{41}$ to $R_{43}$ are each independently selected from groups represented by Formulae 2A(2), 2B, 2C, and 2D;

a hydrogen, a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof and a phosphoric acid group or a salt thereof;

a phenyl group, a pyridinyl group, a fluorenyl group, a dibenzofuranyl group, and a dibenzothiophenyl group;

a phenyl group, a pyridinyl group, a fluorenyl group, a dibenzofuranyl group and a dibenzothiophenyl group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group, and —Si($Q_{21}$)($Q_{22}$)($Q_{23}$); and —Si($Q_{31}$)($Q_{32}$)($Q_{33}$), at least one selected from $R_{41}$ to $R_{43}$ is a group represented by one of Formulae 2A(2), 2B, 2C, and 2D, and $Q_1$ to $Q_3$, $Q_{11}$ to $Q_{13}$, $Q_{21}$ to $Q_{23}$ and $Q_{31}$ to $Q_{33}$ are each independently selected from a hydrogen, a $C_1$-$C_{20}$ alkyl group, a $C_1$-$C_{20}$ alkoxy group, a phenyl group, a naphthyl group, a pyridinyl group, a fluorenyl group, a dibenzofuranyl group, and a dibenzothiophenyl group.

2. The carbazole compound of claim 1, wherein $R_1$ to $R_8$, $R_{11}$ to $R_{18}$, $R_{21}$ to $R_{27}$, and $R_{31}$ to $R_{38}$ are each independently selected from a hydrogen, a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a $C_1$-$C_{10}$ alkyl group and a $C_1$-$C_{10}$ alkoxy group, each substituted with at least one selected from a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof and a phosphoric acid group or a salt thereof;

a phenyl group and a pyridinyl group;

a phenyl group and a pyridinyl group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a pyridinyl group, and —Si($Q_1$)($Q_2$)($Q_3$); and —Si($Q_{11}$)($Q_{12}$)($Q_{13}$), a1 to a6 are each independently an integer selected from 1 to 3, $Q_1$ to $Q_3$ and $Q_{11}$ to $Q_{13}$ are each independently selected from a $C_1$-$C_{10}$ alkyl group, a $C_1$-$C_{10}$ alkoxy group, a phenyl group, a naphthyl group and a pyridinyl group, $R_{22}$ to $R_{26}$ are not a cyano group, and at least one of groups $R_{27}$ in the number of a2 in Formula 2B is a cyano group, at least one selected from $R_{31}$ to $R_{35}$, groups $R_{36}$ in the number of a3 and groups $R_{37}$ in the number of a4 in Formula 2C is a cyano group, and at least one selected from $R_{31}$ to $R_{35}$, groups $R_{36}$ in the number of a3, groups $R_{37}$ in the number of a5, and groups $R_{38}$ in the number of a6 in Formula 2D is a cyano group.

3. The carbazole compound of claim 1, wherein $R_{41}$ to $R_{43}$ are each independently selected from groups represented by Formulae 2A(2), 2B, 2C, and 2D;

a hydrogen, a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a $C_1$-$C_{10}$ alkyl group and a $C_1$-$C_{10}$ alkoxy group, each substituted with at least one selected from a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof and a phosphoric acid group or a salt thereof;

a phenyl group and a pyridinyl group;

a phenyl group and a pyridinyl group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a pyridinyl group, and —Si($Q_{21}$)($Q_{22}$)($Q_{23}$); and —Si($Q_{31}$)($Q_{32}$)($Q_{33}$), at least one selected from $R_{41}$ to $R_{43}$ is a group represented by one of Formulae 2A(2), 2B, 2C, and 2D, $Q_{21}$ to $Q_{23}$ and $Q_{31}$ to $Q_{33}$ are each independently selected from a $C_1$-$C_{10}$ alkyl group, a $C_1$-$C_{10}$ alkoxy group, a phenyl group, a naphthyl group and a pyridinyl group.

4. The carbazole compound of claim 1, wherein $R_{42}$ in Formula 1 is represented by one of Formulae 2A(2), 2B, 2C, and 2D.

5. The carbazole compound of claim 1, wherein at least one selected from $X_3$, $X_7$, $X_{13}$, and $X_{17}$ in Formula 1 is C(CN).

6. The carbazole compound of claim 1, wherein the carbazole compound is represented by one of Formulae 1A to 1F:

Formula 1A

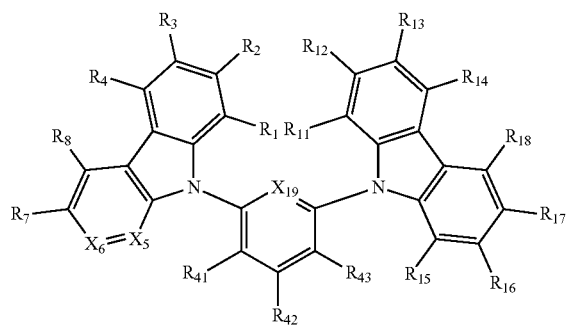

Formula 1B

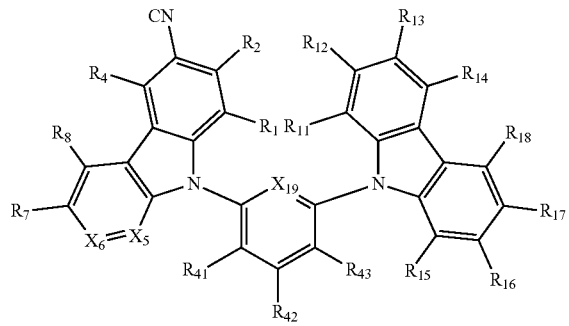

Formula 1C

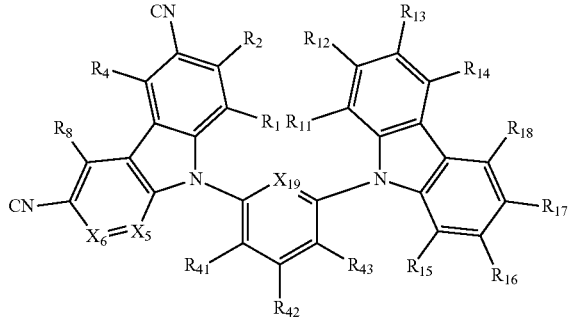

Formula 1D

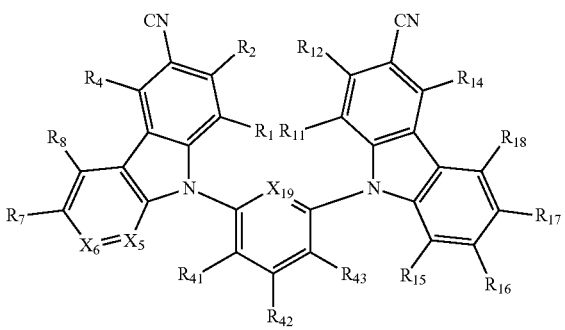

Formula 1E

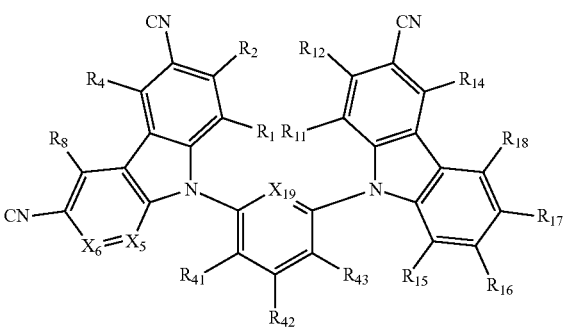

Formula 1F

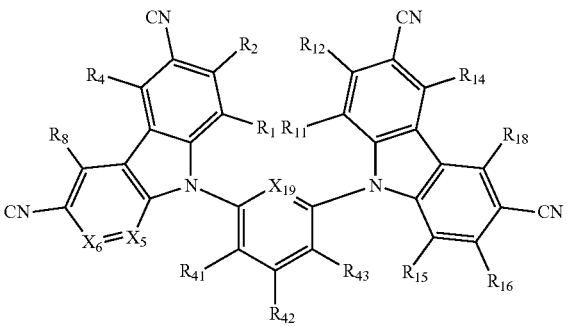

wherein in Formulae 1A to 2F, $X_5$ is N or C($R_5$), and $X_6$ is N or C($R_6$) wherein at least one of $X_5$ and $X_6$ is N, $R_1$ to $R_8$ and $R_{11}$ to $R_{18}$ are each independently selected from a hydrogen, a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a $C_1$-$C_{10}$ alkyl group and a $C_1$-$C_{10}$ alkoxy group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof and a phosphoric acid group or a salt thereof;

a phenyl group and a pyridinyl group;

a phenyl group and a pyridinyl group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a pyridinyl group, and —Si($Q_1$)($Q_2$)($Q_3$); and —Si($Q_{11}$)($Q_{12}$)($Q_{13}$), $Q_1$ to $Q_3$ and $Q_{11}$ to $Q_{13}$ are each independently selected from a hydrogen, a $C_1$-$C_{10}$ alkyl group, a $C_1$-$C_{10}$ alkoxy group, a phenyl group, a naphthyl group, a pyridinyl group, a fluorenyl group, a dibenzofuranyl group, and a dibenzothiophenyl group, and $X_{19}$, $R_{41}$, $R_{42}$, and $R_{43}$ are the same as in claim 1.

7. The carbazole compound of claim 1, wherein in Formulae 2A(2), 2B, 2C, and 2D, $R_{21}$ to $R_{27}$ and $R_{31}$ to $R_{38}$ are each independently selected from a hydrogen, a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, and —Si($Q_{11}$)($Q_{12}$)($Q_{13}$), and a1 to a6 are each independently 1 or 2.

8. The carbazole compound of claim 1, wherein the group represented by Formula 2A(2) comprises a group represented by one of Formulae 2A-1 to 2A-7:

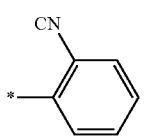

Formula 2A-1

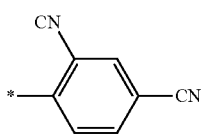

Formula 2A-2

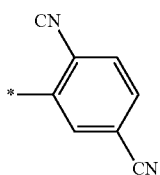

Formula 2A-3

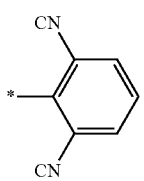

Formula 2A-4

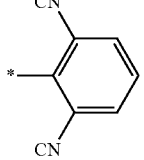

-continued

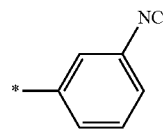

Formula 2A-5

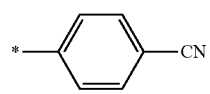

Formula 2A-6

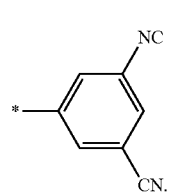

Formula 2A-7

9. The carbazole compound of claim 1, wherein the group represented by Formula 2B comprises a group represented by one of Formulae 2B-1 to 2B-7:

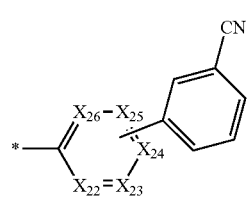

Formula 2B-1

Formula 2B-2

Formula 2B-3

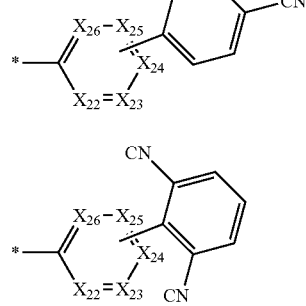

Formula 2B-4

Formula 2B-5

-continued
Formula 2B-6
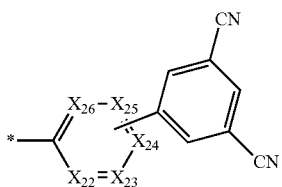
Formula 2B-7
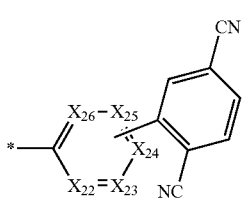
wherein $X_{22}$ to $X_{26}$ in Formulae 2B-1 to 2B-7 are the same as in claim 1.
10. The carbazole compound of claim 1, wherein the group represented by Formula 2B comprises a group represented by one of Formulae 2B(1) to 2B(13):
Formula 2B(1)
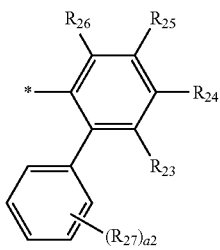
Formula 2B(2)
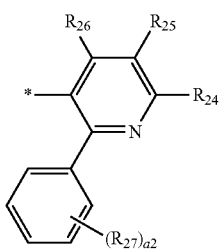
Formula 2B(3)
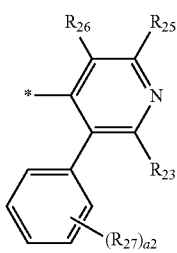
Formula 2B(4)
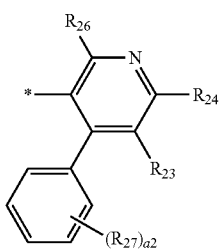
-continued
Formula 2B(5)
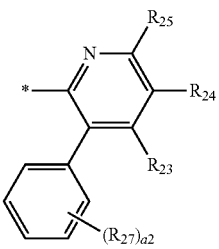
Formula 2B(6)
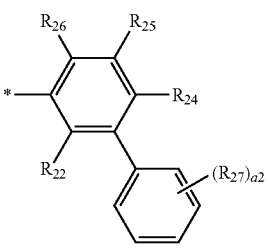
Formula 2B(7)
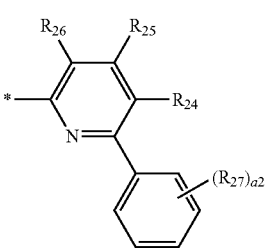
Formula 2B(8)
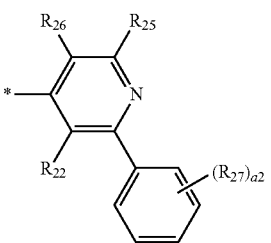
Formula 2B(9)
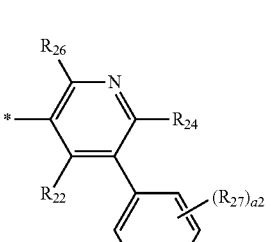
Formula 2B(10)
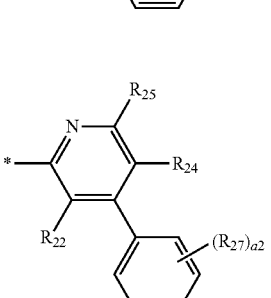

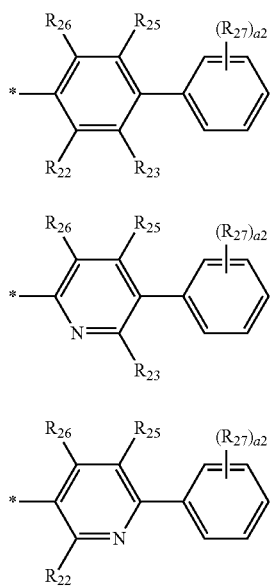
Formula 2B(11)
Formula 2B(12)
Formula 2B(13)
wherein $R_{22}$ to $R_{27}$ and a2 in Formulae 2B(1) to 2B(13) are the same as in claim 1.
11. The carbazole compound of claim 1, wherein
the group represented by Formula 2B comprises a group represented by one of Formulae 2B(1)-1 to 2B(13)-1, 2B(1)-2 to 2B(13)-2, 2B(1)-3 to 2B(13)-3, 2B(1)-4 to 2B(13)-4, 2B(1)-5 to 2B(13)-5, 2B(1)-6 to 2B(13)-6, and 2B(1)-7 to 2B(13)-7:
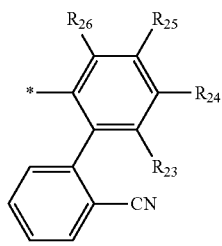
Formula 2B(1)-1
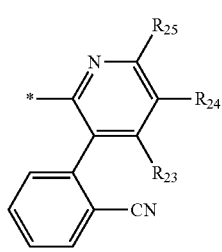
Formula 2B(2)-1
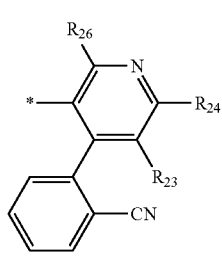
Formula 2B(3)-1
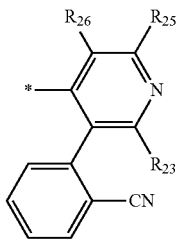
Formula 2B(4)-1
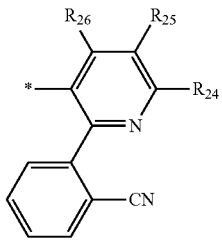
Formula 2B(5)-1
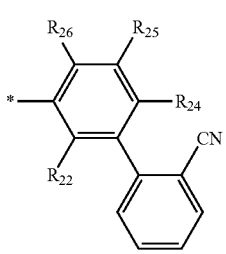
Formula 2B(6)-1
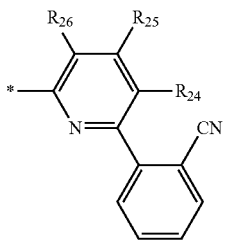
Formula 2B(7)-1
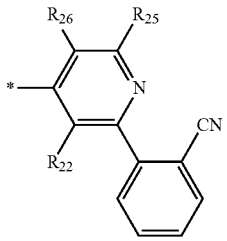
Formula 2B(8)-1
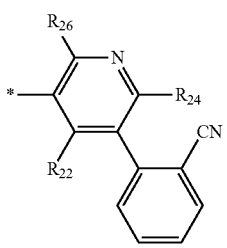
Formula 2B(9)-1

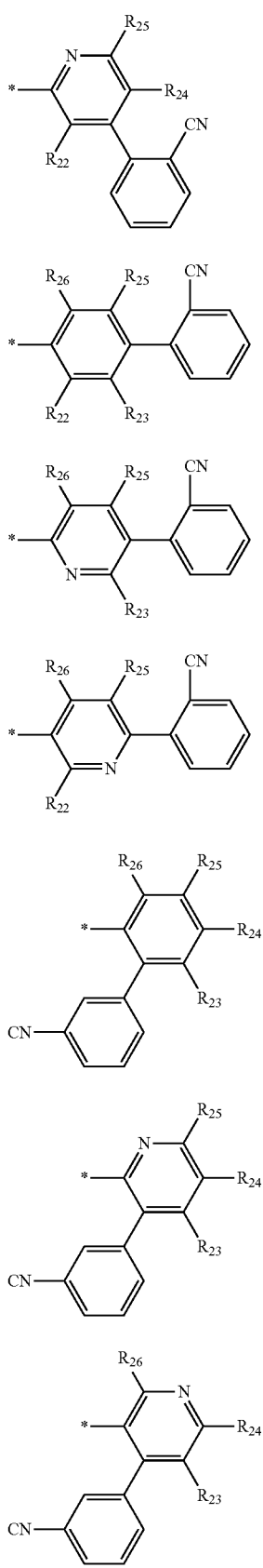
Formula 2B(10)-1
Formula 2B(11)-1
Formula 2B(12)-1
Formula 2B(13)-1
Formula 2B(1)-2
Formula 2B(2)-2
Formula 2B(3)-2
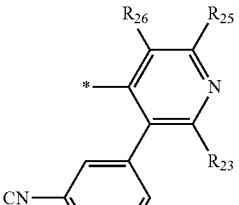
Formula 2B(4)-2
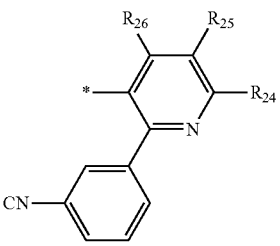
Formula 2B(5)-2
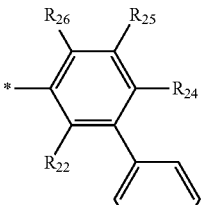
Formula 2B(6)-2
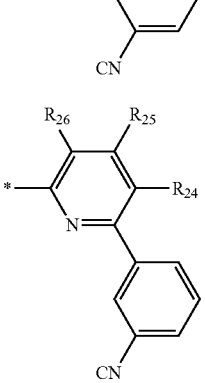
Formula 2B(7)-2
Formula 2B(8)-2
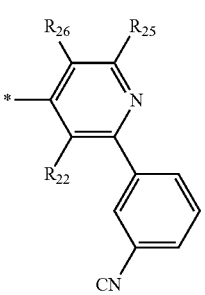
Formula 2B(9)-2
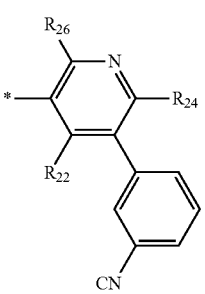

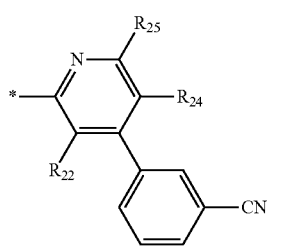
Formula 2B(10)-2
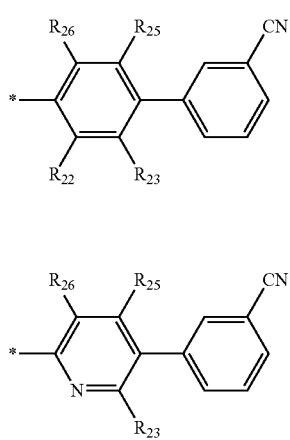
Formula 2B(11)-2
Formula 2B(12)-2
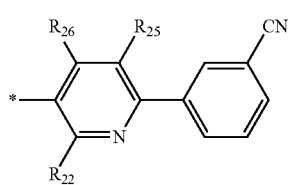
Formula 2B(13)-2
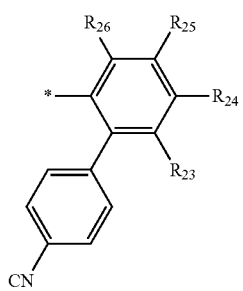
Formula 2B(1)-3
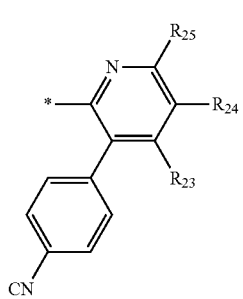
Formula 2B(2)-3
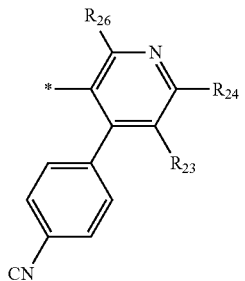
Formula 2B(3)-3
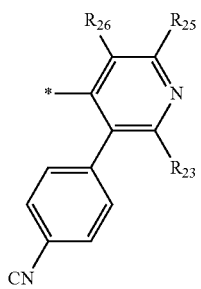
Formula 2B(4)-3
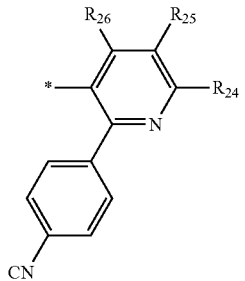
Formula 2B(5)-3
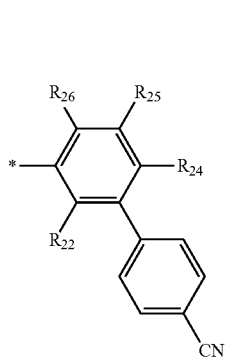
Formula 2B(6)-3
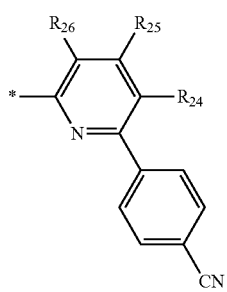
Formula 2B(7)-3

-continued
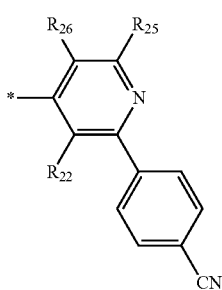
Formula 2B(8)-3
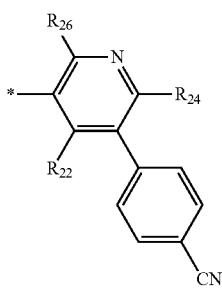
Formula 2B(9)-3
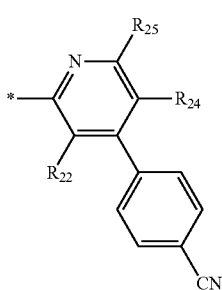
Formula 2B(10)-3
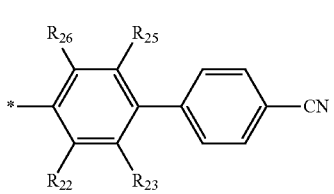
Formula 2B(11)-3
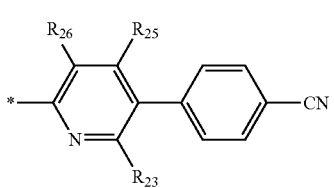
Formula 2B(12)-3
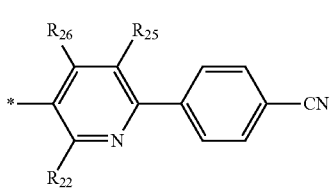
Formula 2B(13)-3
-continued
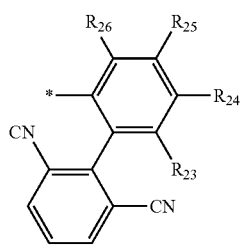
Formula 2B(1)-4
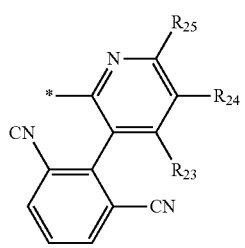
Formula 2B(2)-4
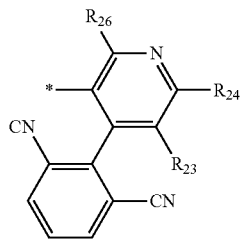
Formula 2B(3)-4
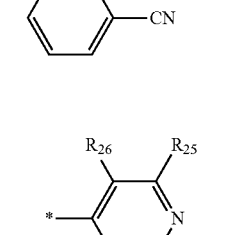
Formula 2B(4)-4
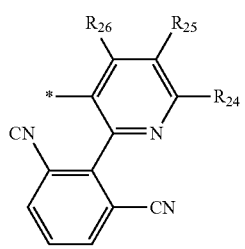
Formula 2B(5)-4
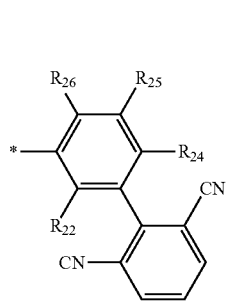
Formula 2B(6)-4

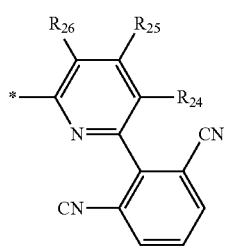 Formula 2B(7)-4
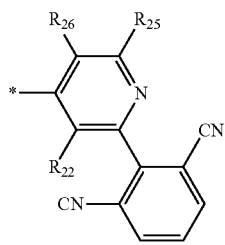 Formula 2B(8)-4
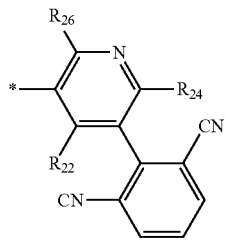 Formula 2B(9)-4
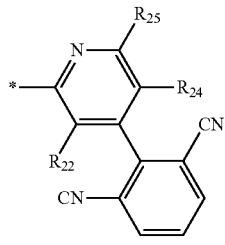 Formula 2B(10)-4
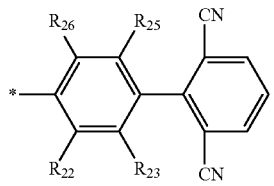 Formula 2B(11)-4
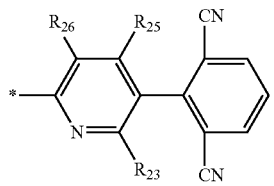 Formula 2B(12)-4
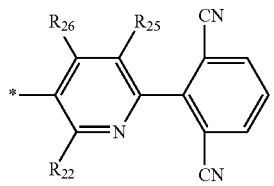 Formula 2B(13)-4
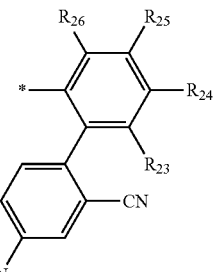 Formula 2B(1)-5
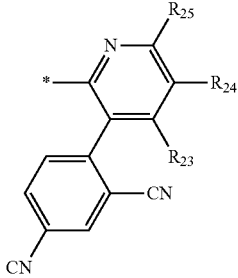 Formula 2B(2)-5
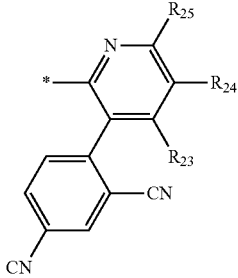 Formula 2B(3)-5
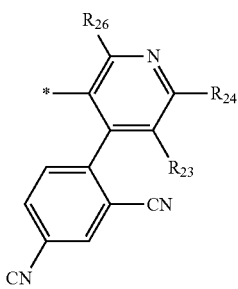 Formula 2B(4)-5
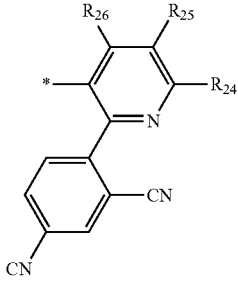 Formula 2B(5)-5

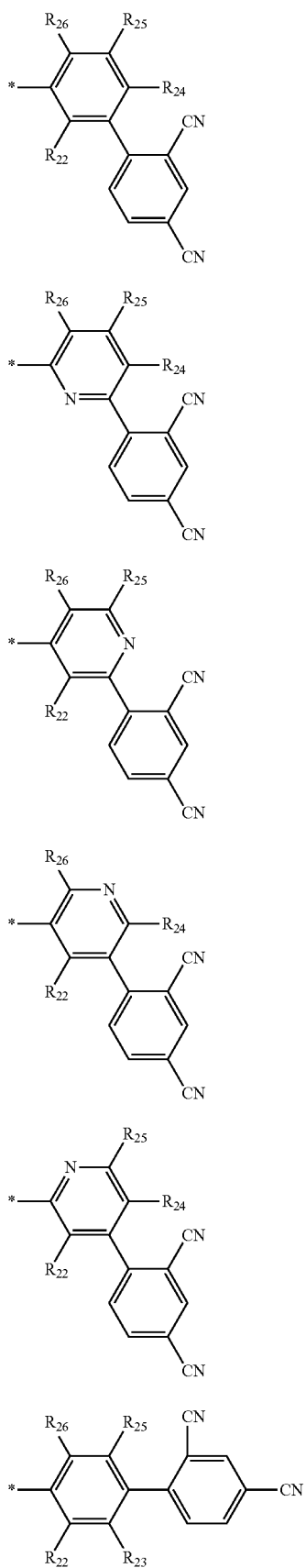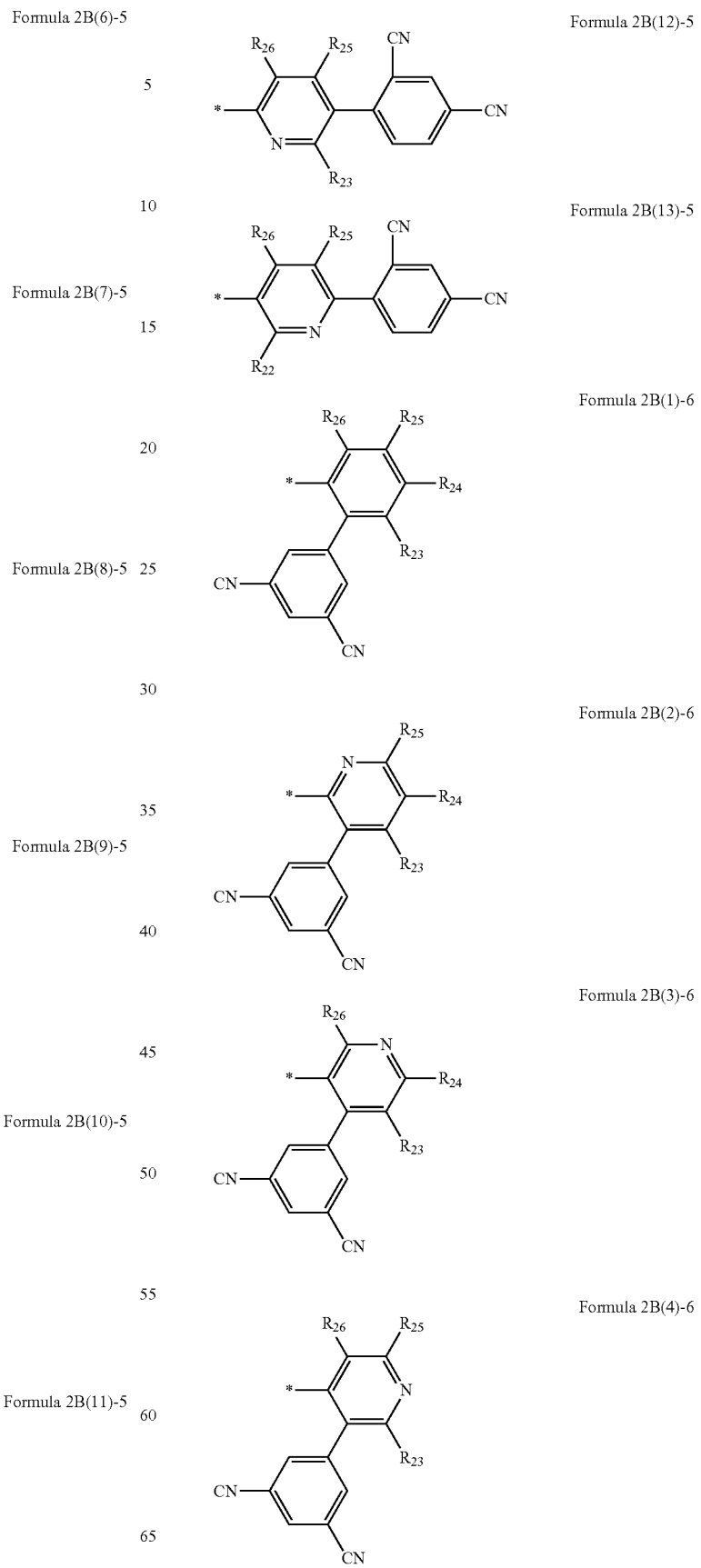

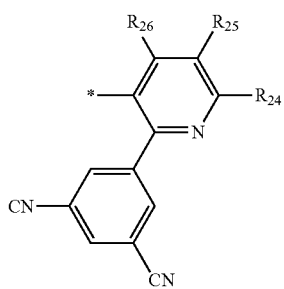
Formula 2B(5)-6
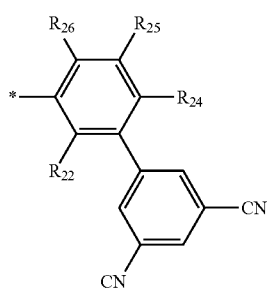
Formula 2B(6)-6
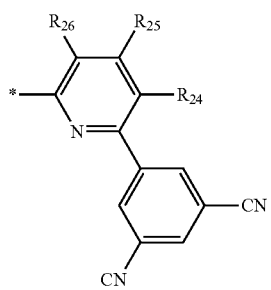
Formula 2B(7)-6
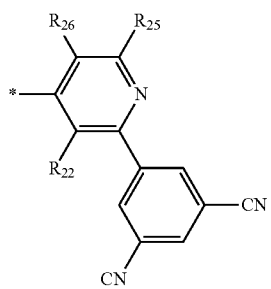
Formula 2B(8)-6
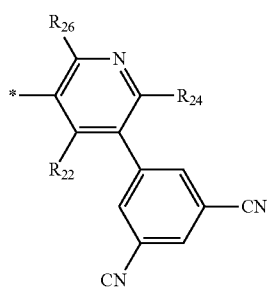
Formula 2B(9)-6
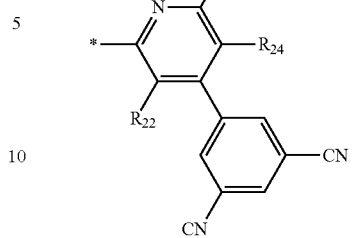
Formula 2B(10)-6
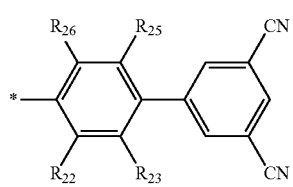
Formula 2B(11)-6
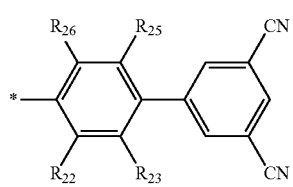
Formula 2B(12)-6
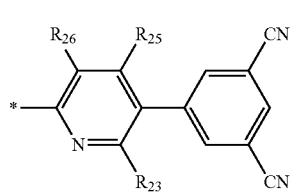
Formula 2B(13)-6
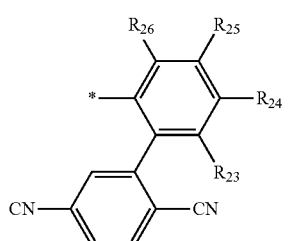
Formula 2B(1)-7
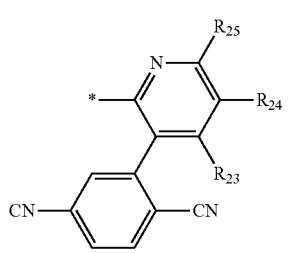
Formula 2B(2)-7
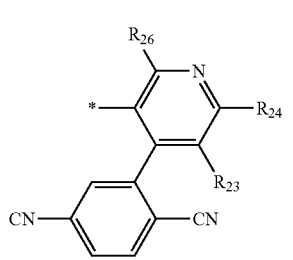
Formula 2B(3)-7

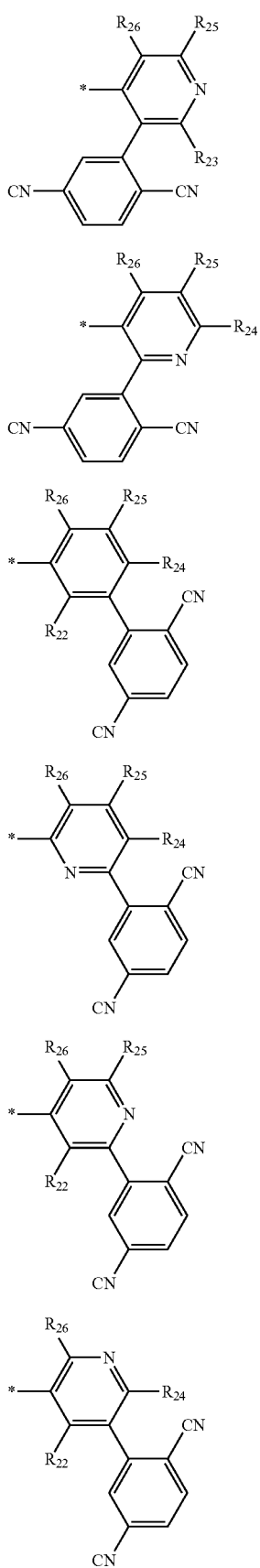
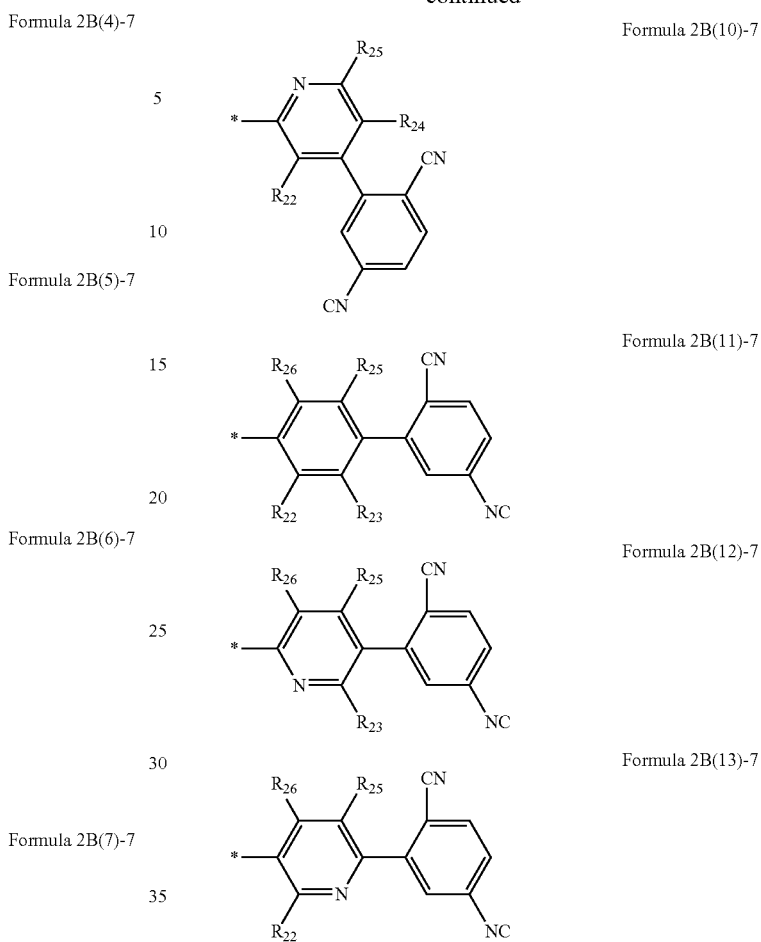
wherein $R_{22}$ to $R_{26}$ in Formulae 2B(1)-1 to 2B(13)-1, 2B(1)-2 to 2B(13)-2, 2B(1)-3 to 2B(13)-3, 2B(1)-4 to 2B(13)-4, 2B(1)-5 to 2B(13)-5, 2B(1)-6 to 2B(13)-6, and 2B(1)-7 to 2B(13)-7 are the same as in claim 1.
12. The carbazole compound of claim 1, wherein the group represented by Formula 2C comprises a group represented by one of Formulae 2C-1 to 2C-9, and 2C-1(1) to 2C-9(1):
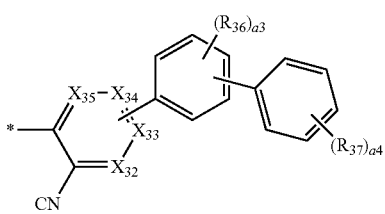
Formula 2C-1
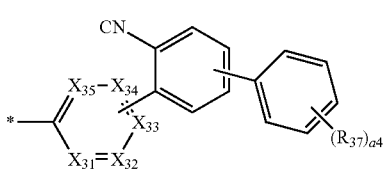
Formula 2C-2

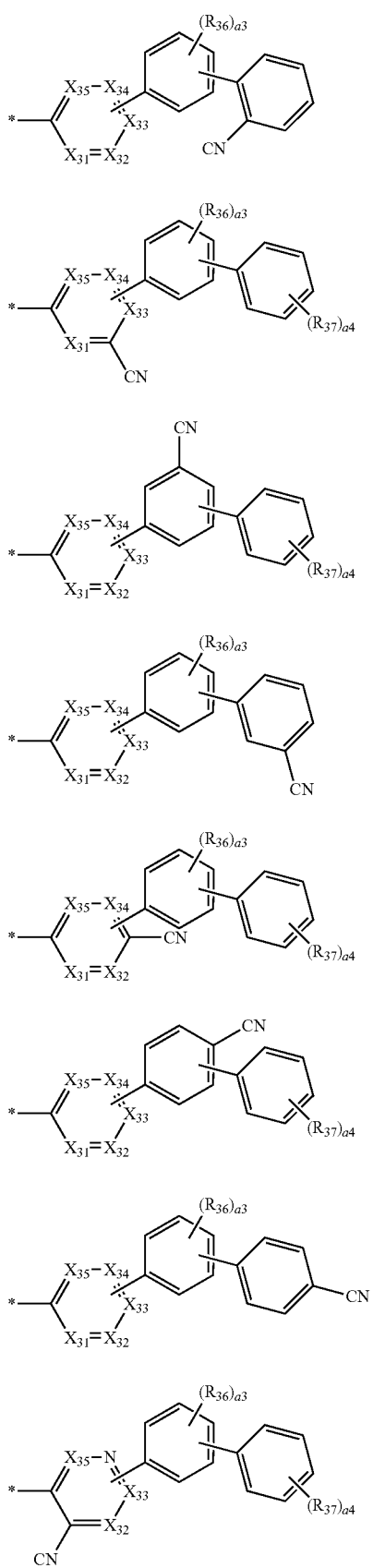
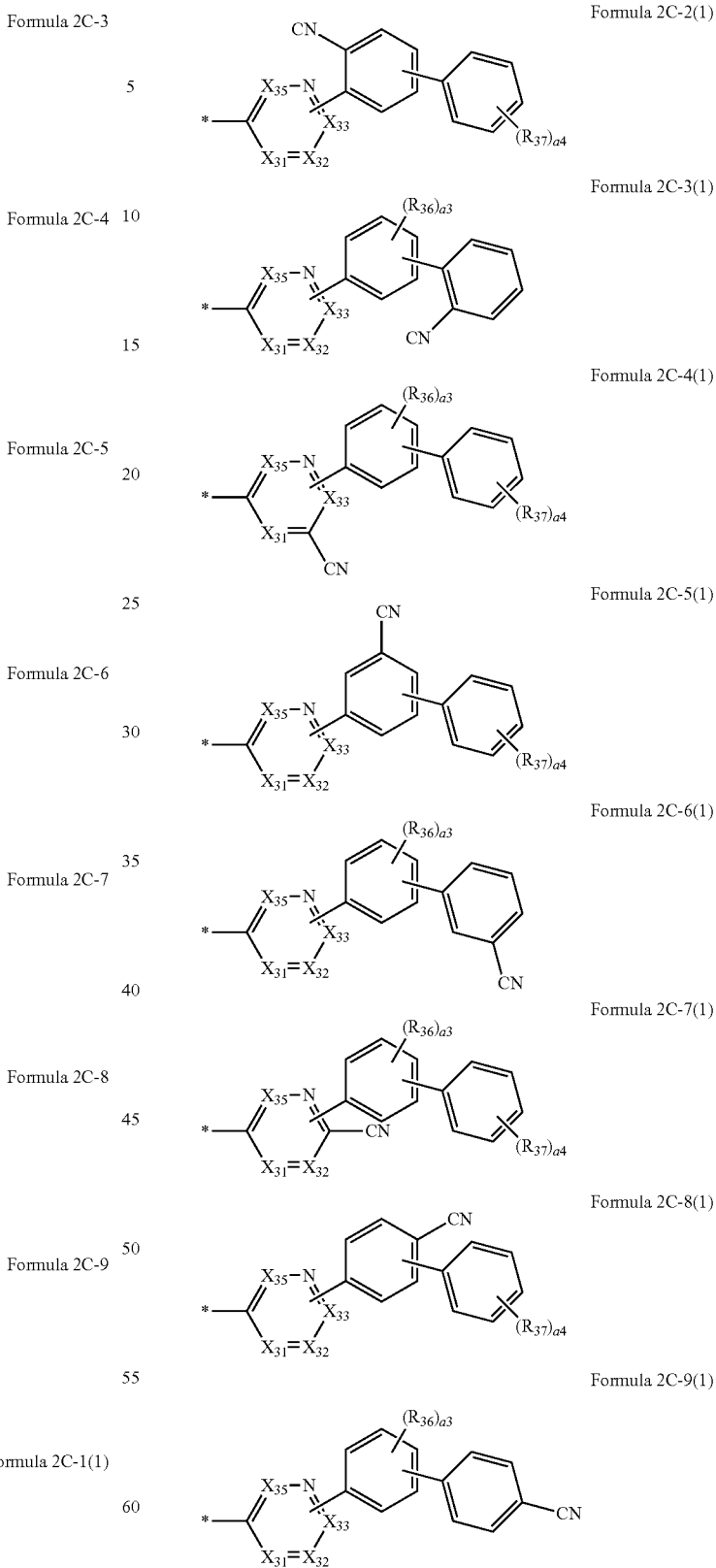
wherein $X_{31}$ to $X_{35}$, $R_{36}$, $R_{37}$, a3, and a4 in Formulae 2C-1 to 2C-9, and 2C-1(1) to 2C-9(1) are the same as in claim 1.

13. The carbazole compound of claim 1, wherein the group represented by Formula 2C comprises a group represented by one of Formulae 2C(1) to 2C(9):

Formula 2C(1)
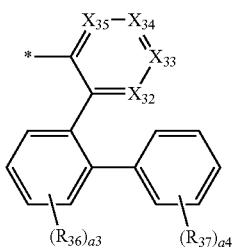

Formula 2C(2)
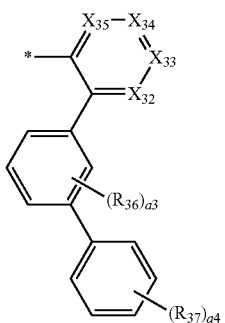

Formula 2C(3)
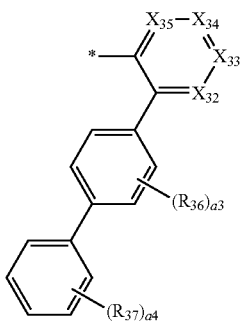

Formula 2C(4)
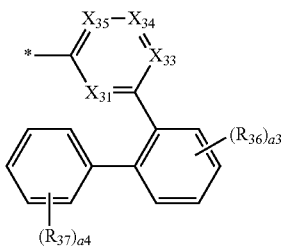

Formula 2C(5)
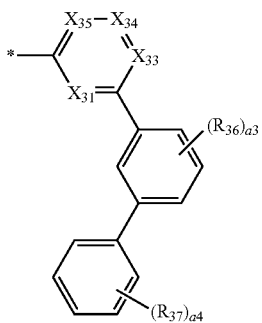

-continued

Formula 2C(6)
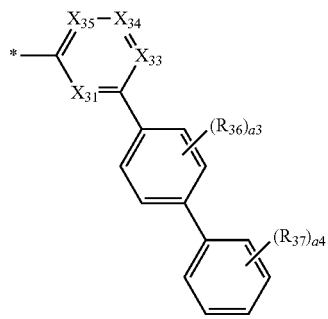

Formula 2C(7)
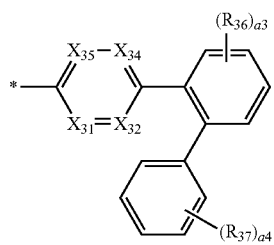

Formula 2C(8)
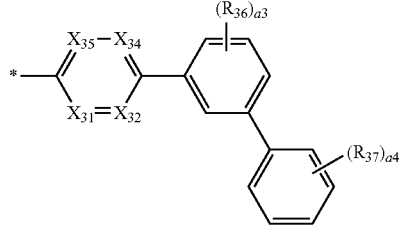

Formula 2C(9)
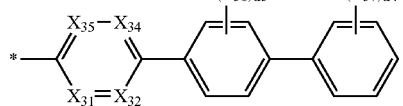

wherein $X_{31}$ to $X_{35}$, $R_{36}$, $R_{37}$, a3, and a4 in Formulae 2C(1) to 2C(9) are the same as in claim 1.

14. The carbazole compound of claim 1, wherein the group represented by Formula 2D comprises a group represented by one of Formulae 2D-1 to 2D-12 and 2D-1(1) to 2D-12(1):

Formula 2D-1
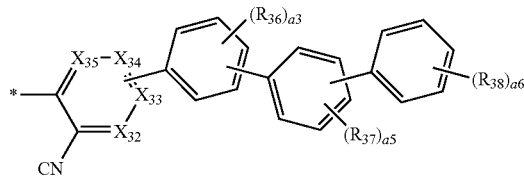

Formula 2D-2
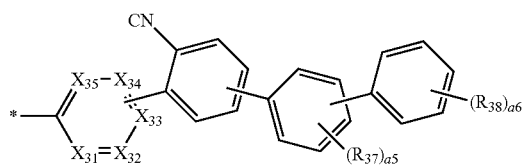

-continued
Formula 2D-3
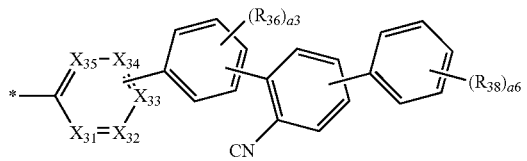
Formula 2D-4
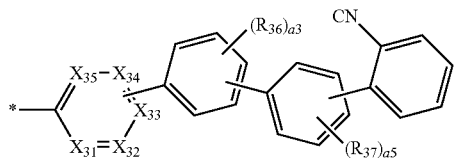
Formula 2D-5
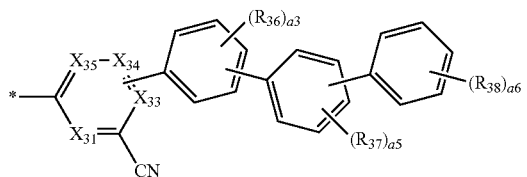
Formula 2D-6
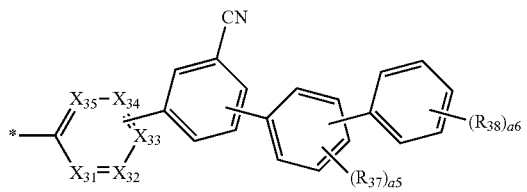
Formula 2D-7
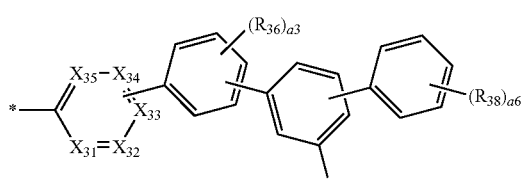
Formula 2D-8
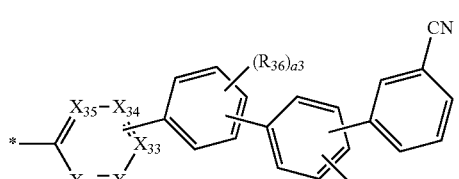
Formula 2D-9
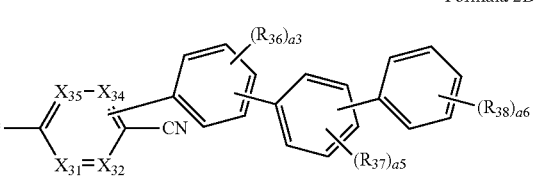
Formula 2D-10
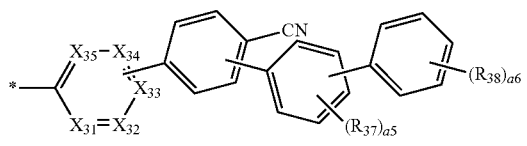
-continued
Formula 2D-11
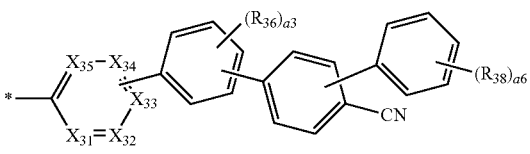
Formula 2D-12
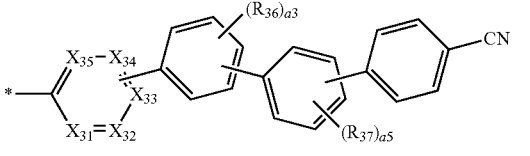
Formula 2D-1(1)
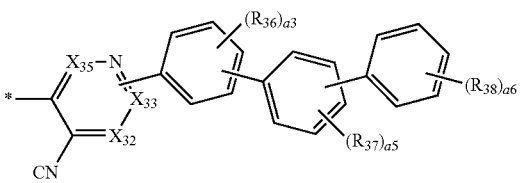
Formula 2D-2(1)
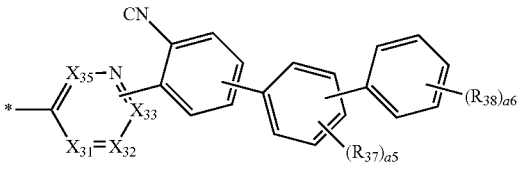
Formula 2D-3(1)
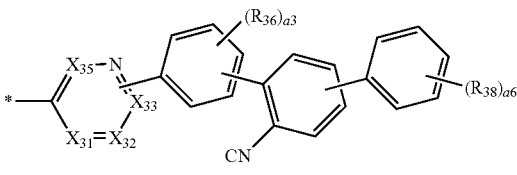
Formula 2D-4(1)
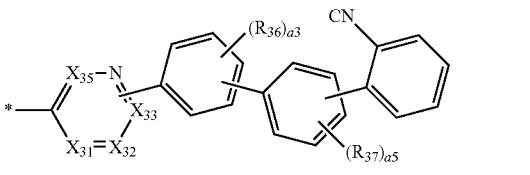
Formula 2D-5(1)
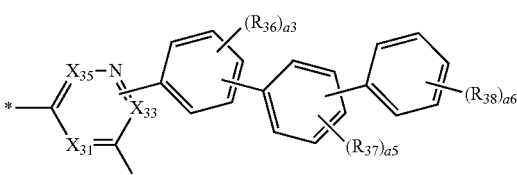
Formula 2D-6(1)
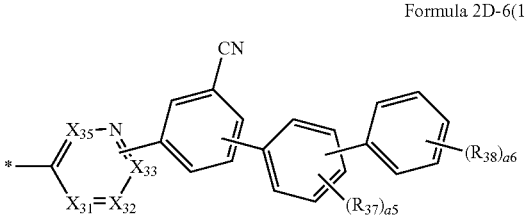

-continued
Formula 2D-7(1)
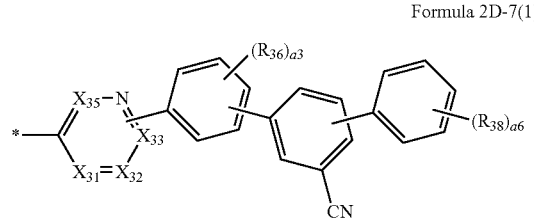
Formula 2D-8(1)
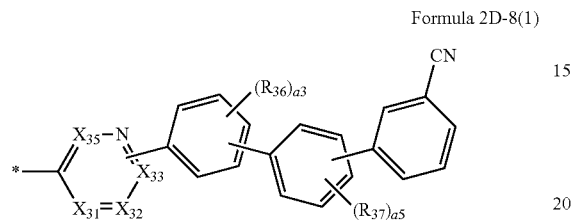
Formula 2D-9(1)
Formula 2D-10(1)
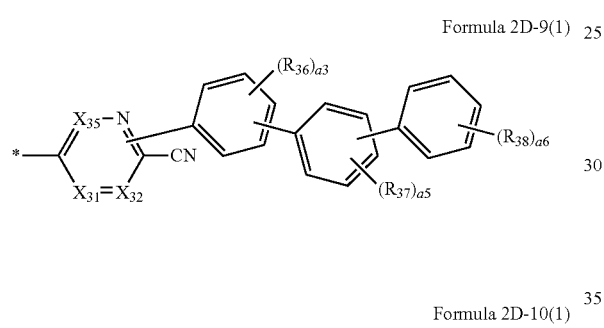
Formula 2D-11(1)
Formula 2D-12(1)
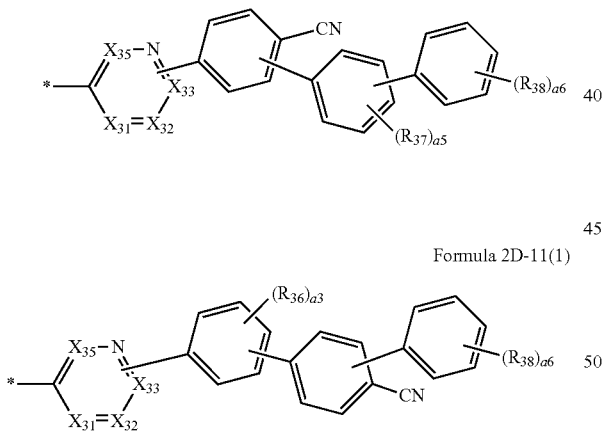
wherein $X_{31}$ to $X_{35}$, $R_{36}$, $R_{37}$, $R_{38}$, a3, a5, and a6 in Formulae 2D-1 to 2D-12 and 2D-1(1) to 2D-12(1) are the same as in claim 1.
15. The carbazole compound of claim 1, wherein the group represented by Formula 2D comprises a group represented by one of Formulae 2D(1) to 2D(27):
Formula 2D(1)
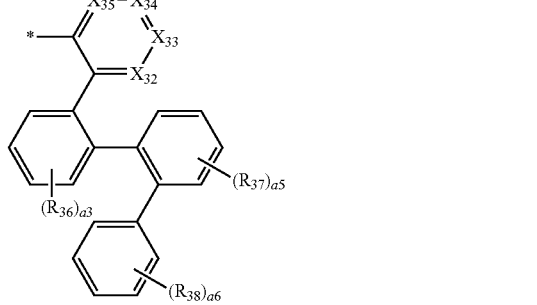
Formula 2D(2)
Formula 2D(3)
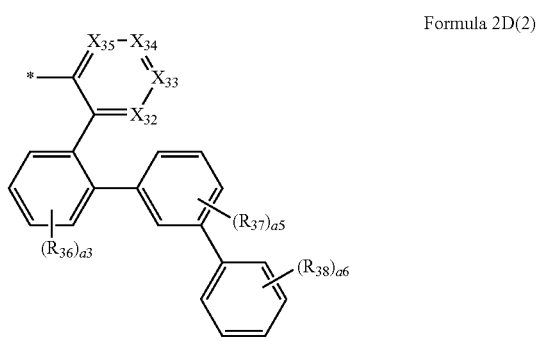
Formula 2D(4)
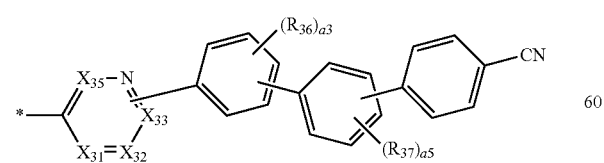

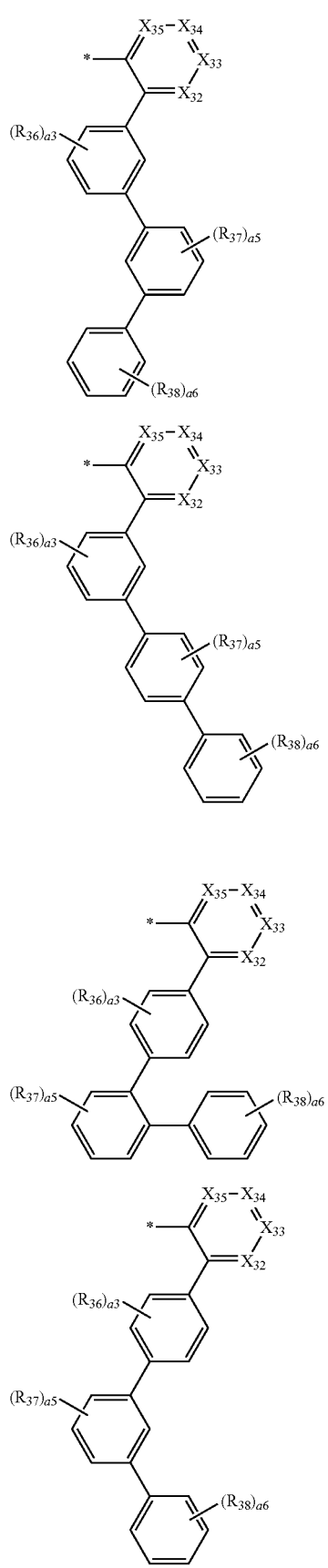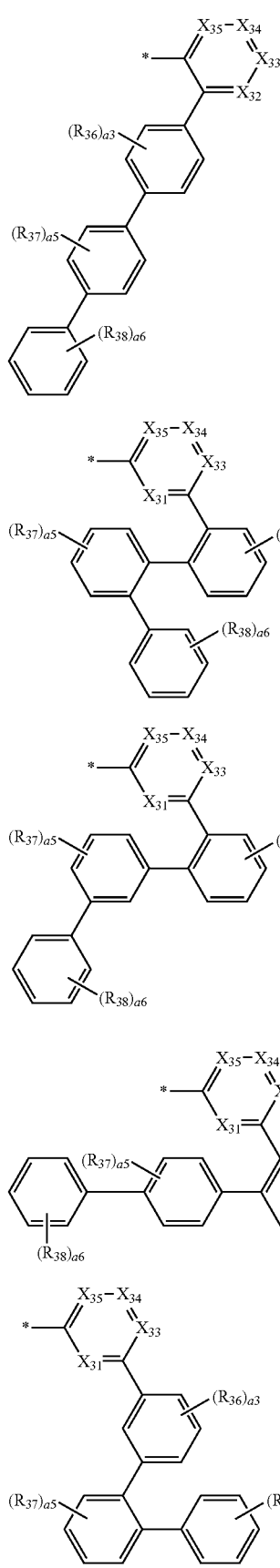

Formula 2D(14)
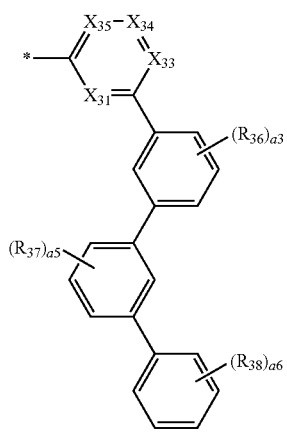
Formula 2D(15)
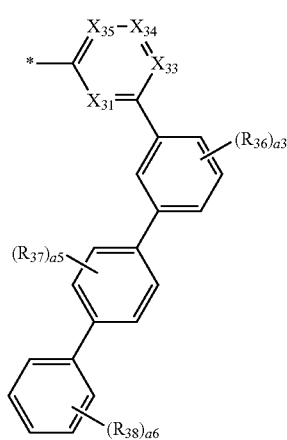
Formula 2D(16)
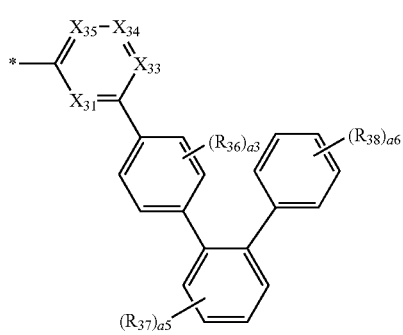
Formula 2D(17)
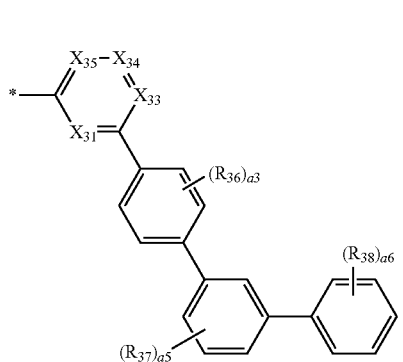
Formula 2D(18)
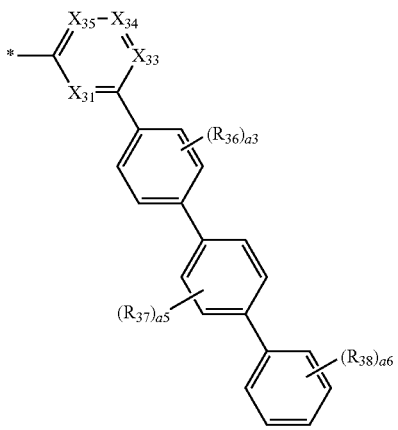
Formula 2D(19)
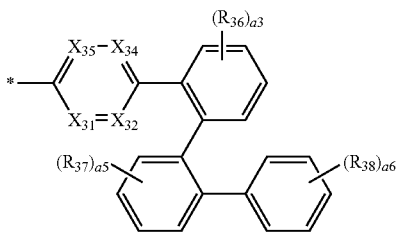
Formula 2D(20)
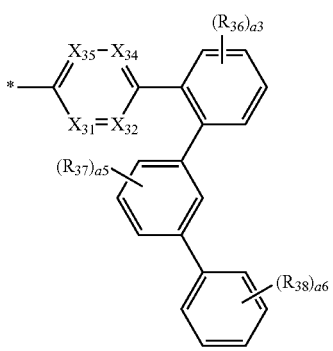
Formula 2D(21)
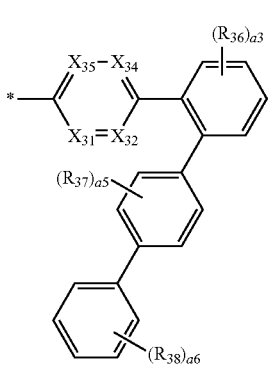

-continued
Formula 2D(22)
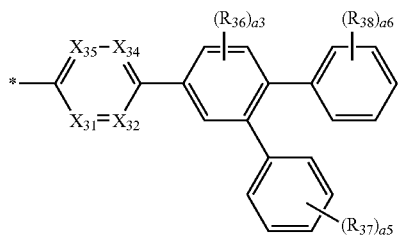
Formula 2D(23)
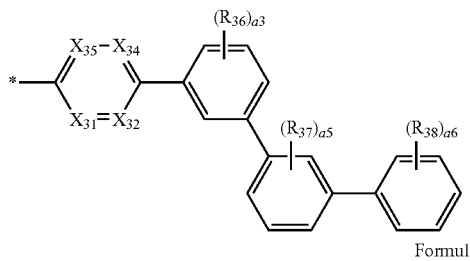
Formula 2D(24)
Formula 2D(25)
Formula 2D(26)
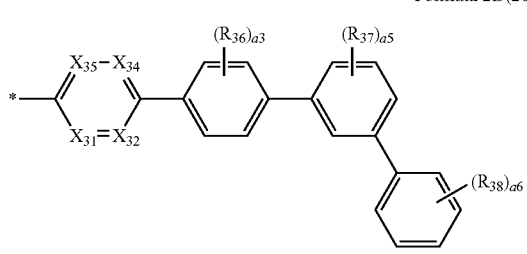
Formula 2D(27)
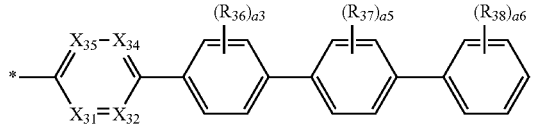
descriptions of $X_{31}$ to $X_{35}$, $R_{36}$, $R_{37}$, $R_{38}$, a3, a5, and a6 in Formulae 2D(1) to 2D(27) are the same as recited in claim 1.
16. The carbazole compound of claim 1, wherein $R_{42}$ in Formula 1 is represented by one of Formulae 2A-1 to 2A-7, 3B-1 to 3B-12, 3C-1 to 3C-6, and 3D-1 to 3D-6:
Formula 2A-1
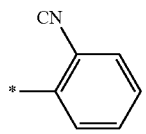
Formula 2A-2
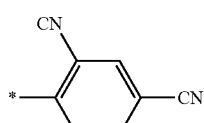
Formula 2A-3
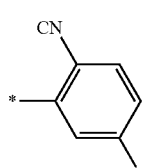
Formula 2A-4
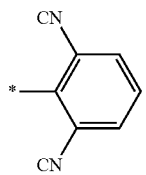
Formula 2A-5
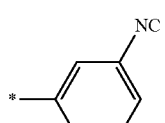
Formula 2A-6
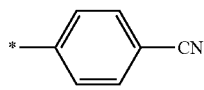
Formula 2A-7
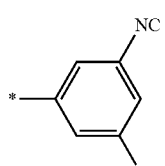
Formula 3B-1
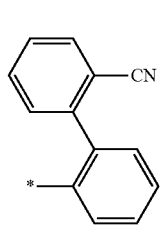

-continued
Formula 3B-2
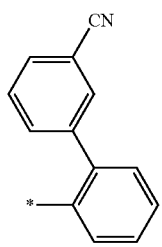
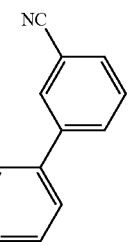
Formula 3B-8
Formula 3B-3
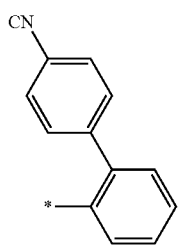
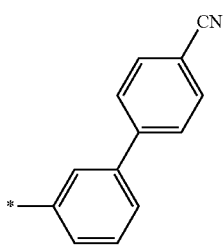
Formula 3B-9
Formula 3B-4
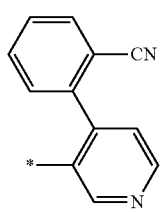
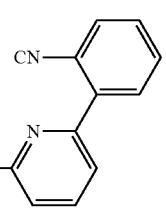
Formula 3B-10
Formula 3B-5
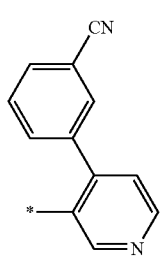
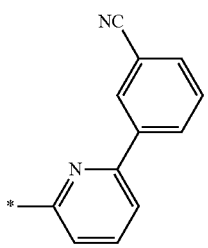
Formula 3B-11
Formula 3B-6
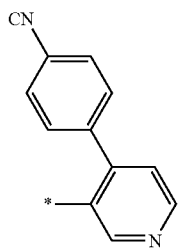
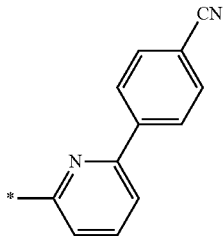
Formula 3B-12
Formula 3B-7
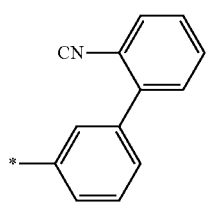
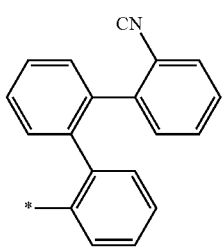
Formula 3C-1

-continued
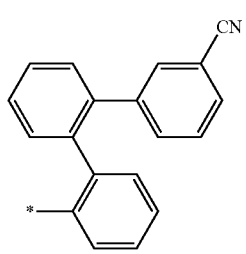
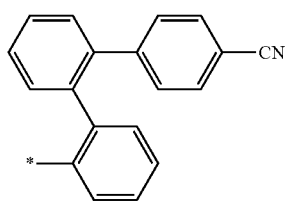
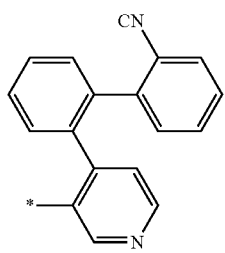
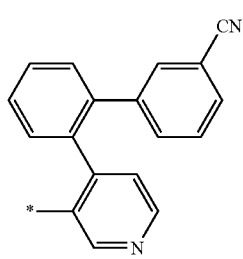
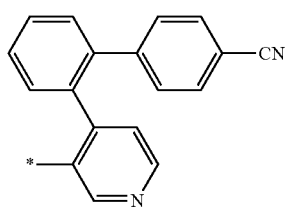
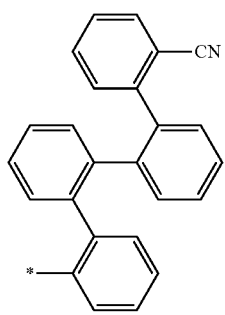
-continued
Formula 3C-2
Formula 3C-3
Formula 3C-4
Formula 3C-5
Formula 3C-6
Formula 3D-1
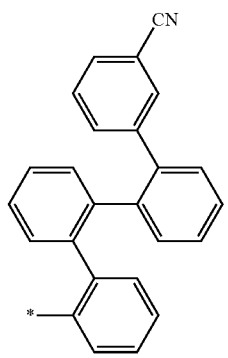
Formula 3D-2
Formula 3D-3
Formula 3D-4
Formula 3D-5

Formula 3D-6
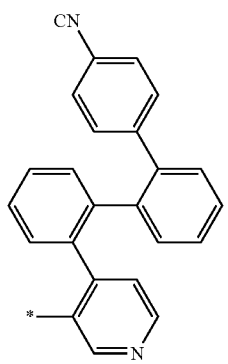
17. A carbazole compound selected from Compounds 10 to 18, 37 to 72, 79 to 90, 97 to 108, 127 to 171, and 181 to 202:
10
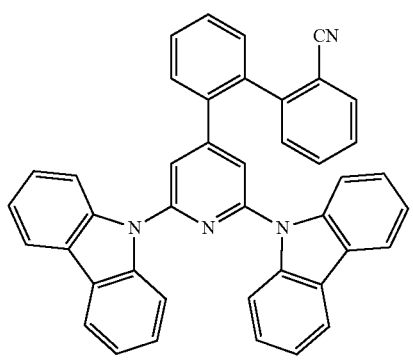
11
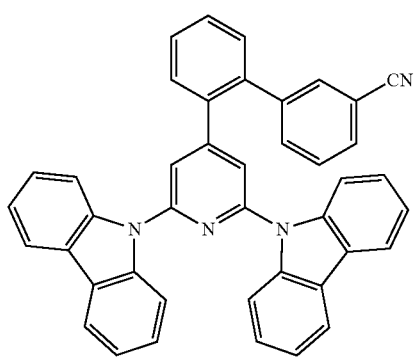
12
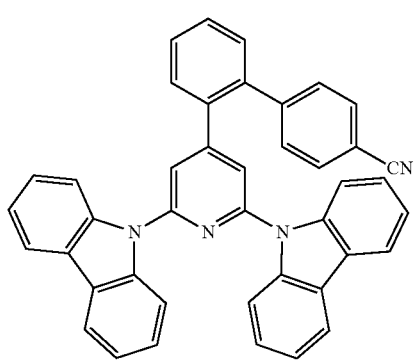
13
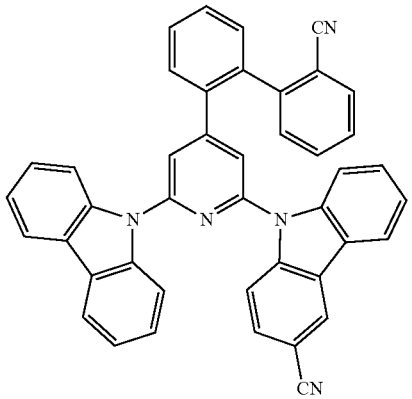
14
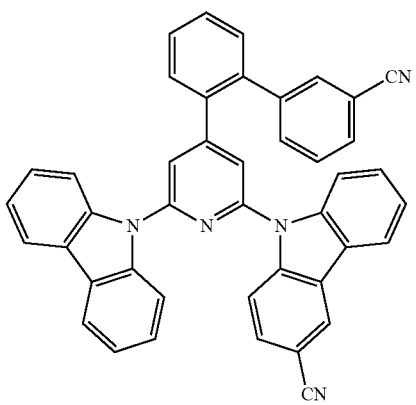
15
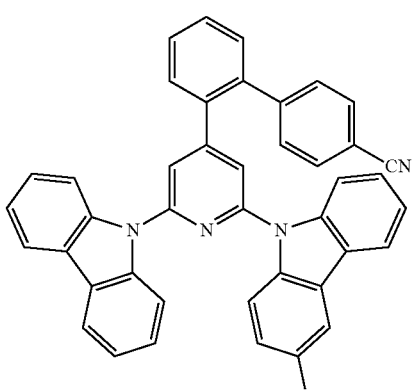 [SMILES: N#Cc1ccc(-c2ccccc2-c2cc(-n3c4ccccc4c4ccccc43)cc(-n3c4ccccc4c4ccccc43)c2)cc1]
16
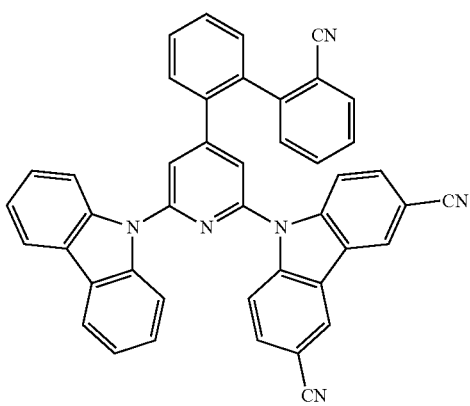

17
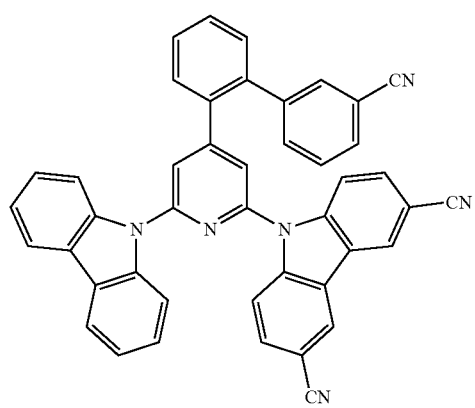
18
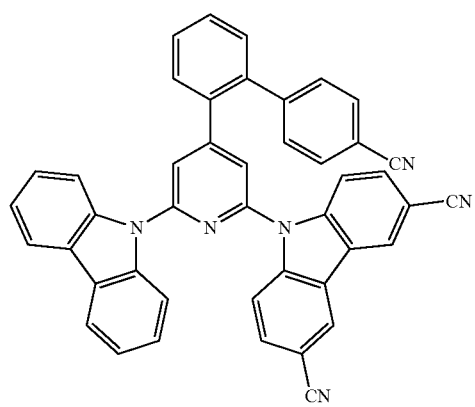
37
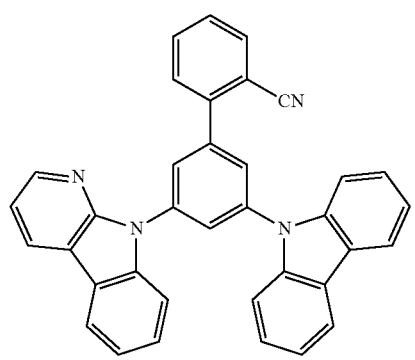
38
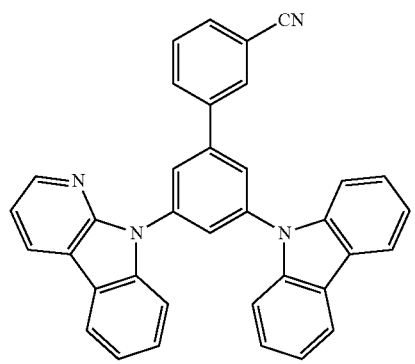
39
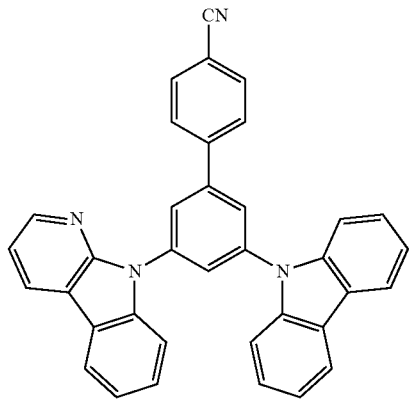
40
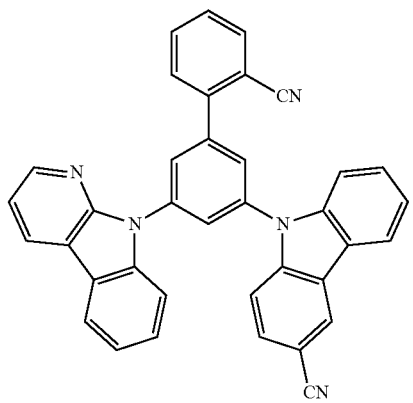
41
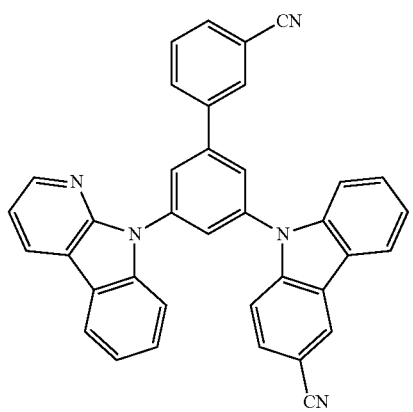
42
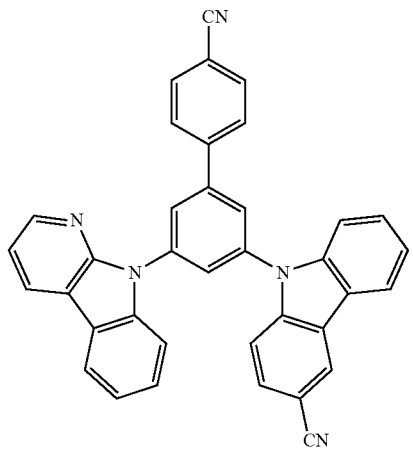

43
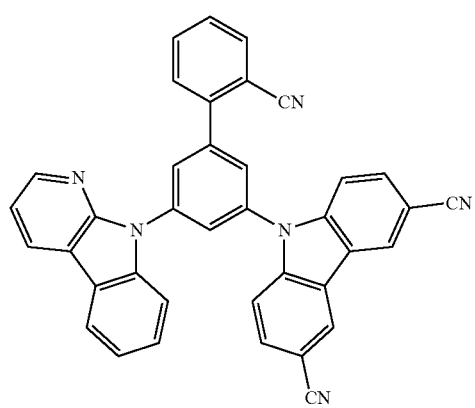
44
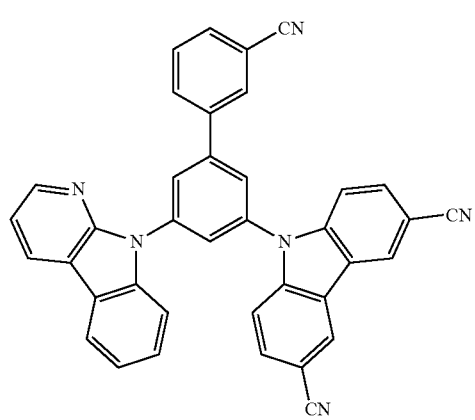
45
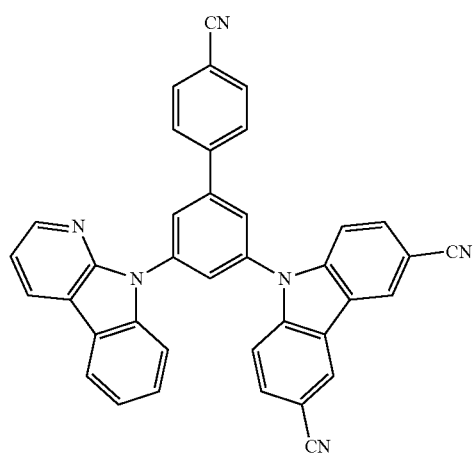
46
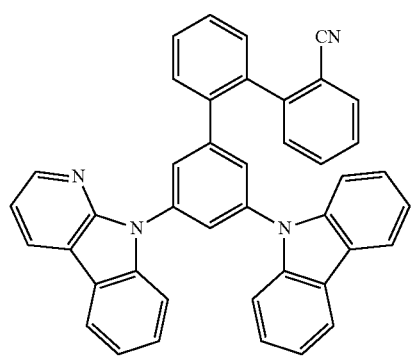
47
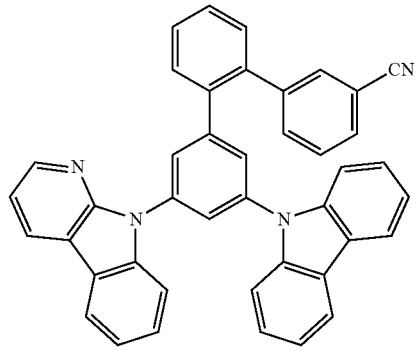
48
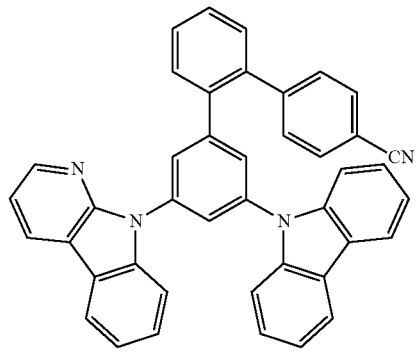
49
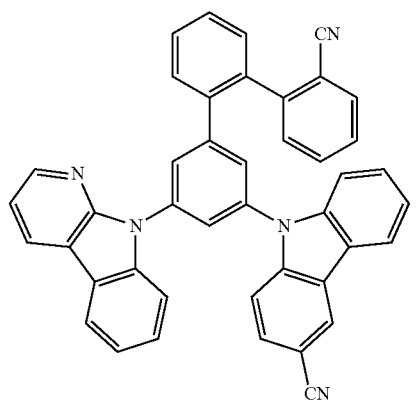
50
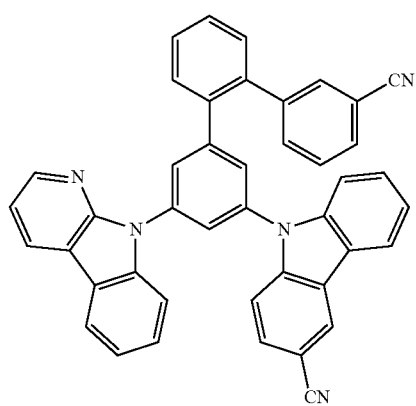

51
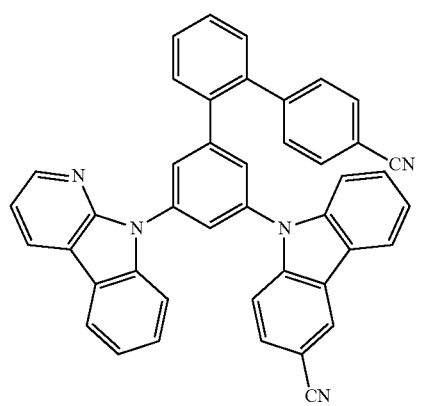
52
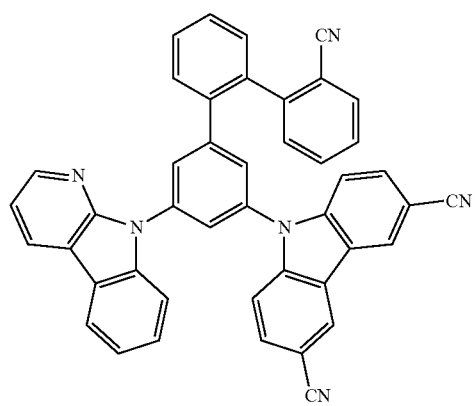
53
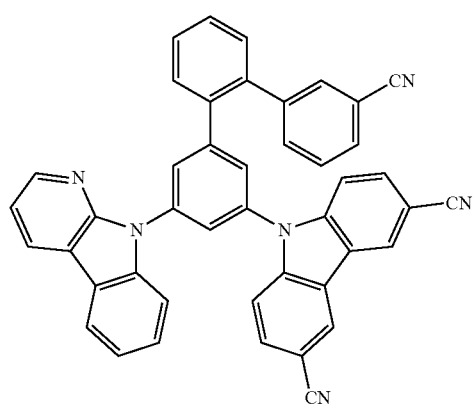
54
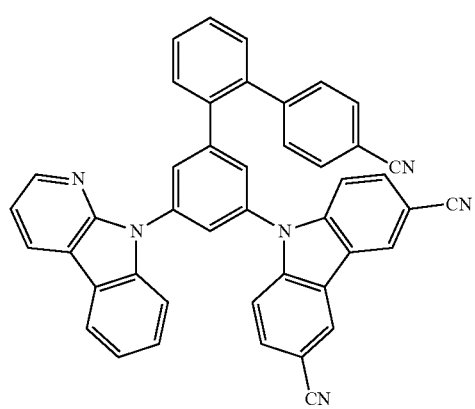
55
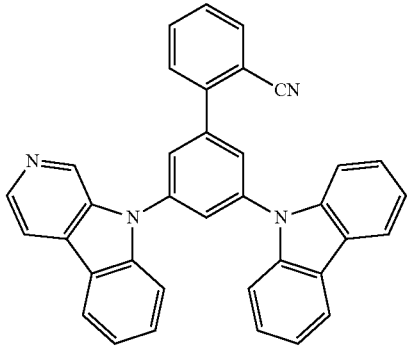
56
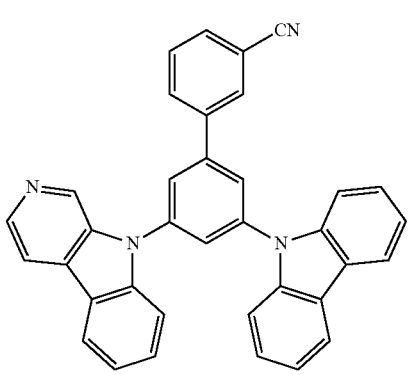
57
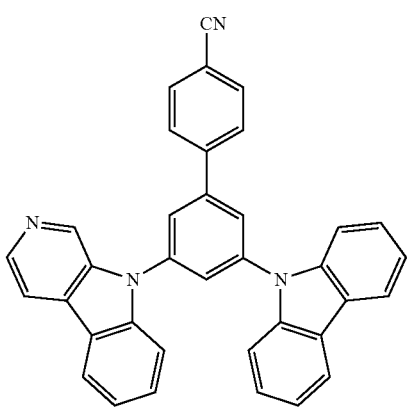
58
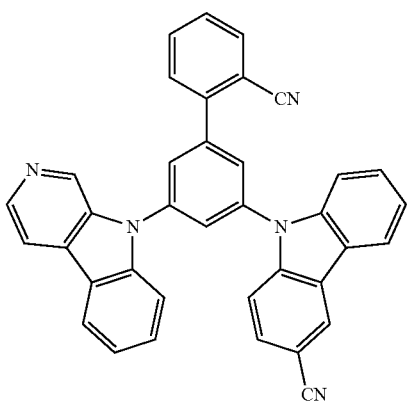

215
-continued
59
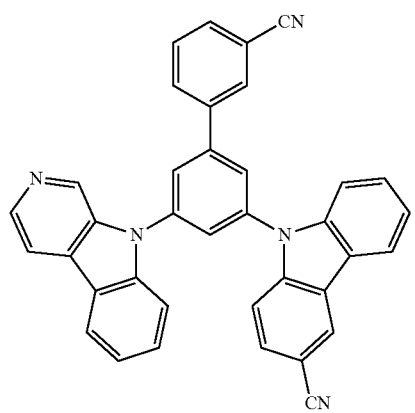
60
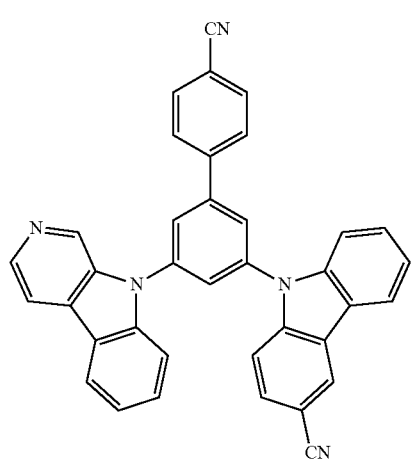
61
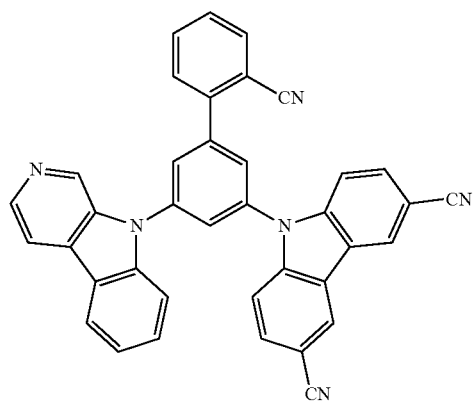
216
-continued
62
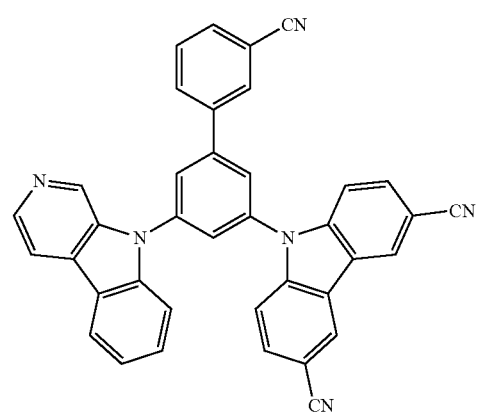
63
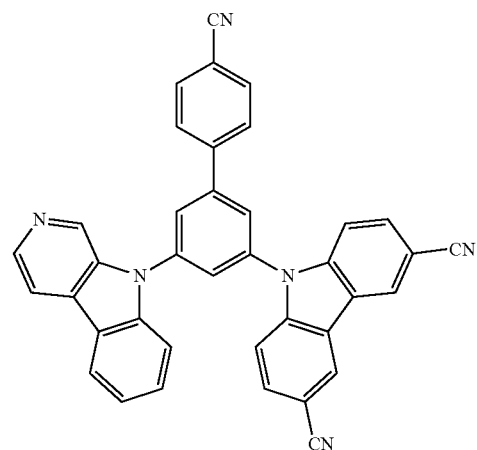
64
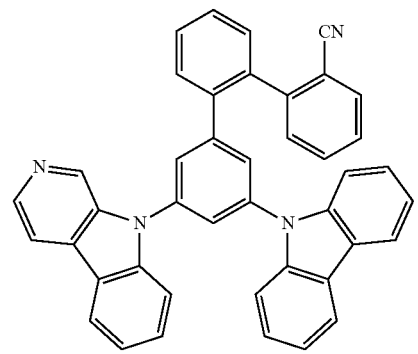
65
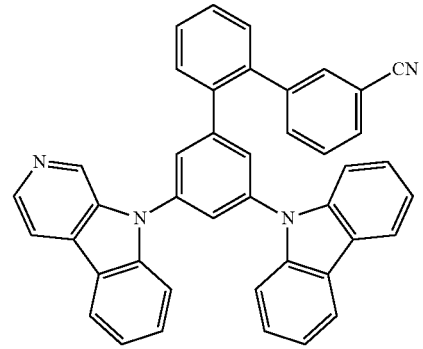

217
-continued
66
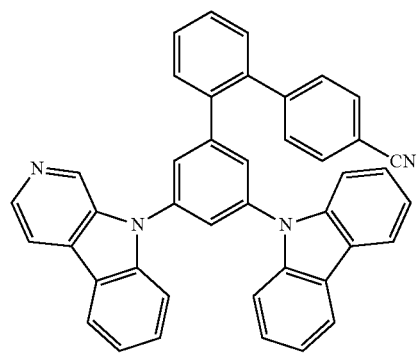
67
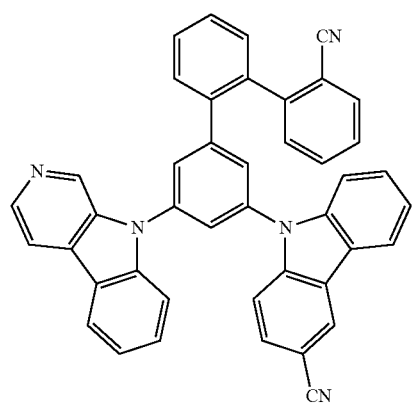
68
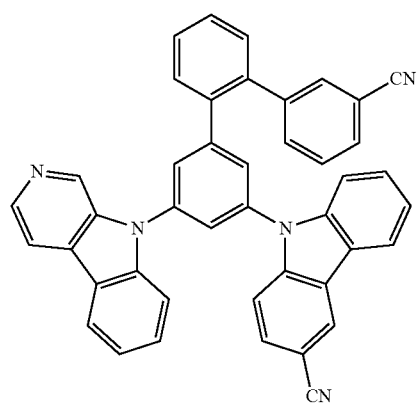
69
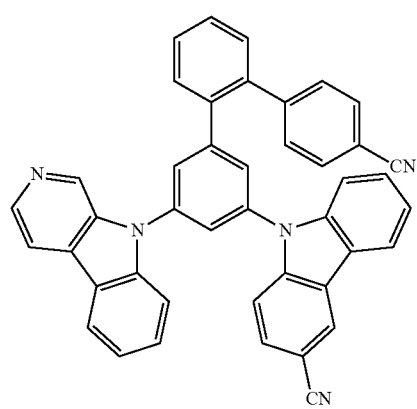
218
-continued
70
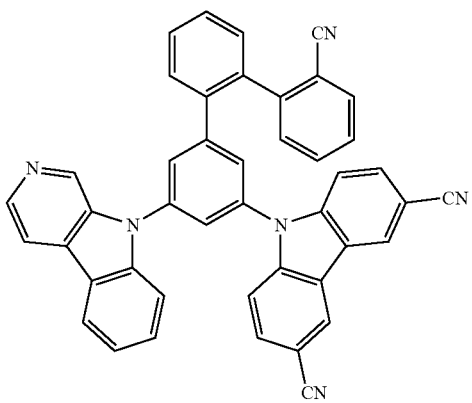
71
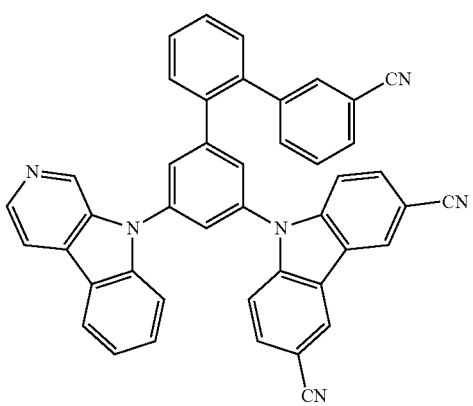
72
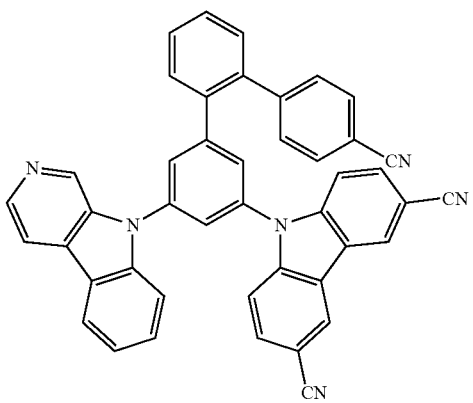
79

80
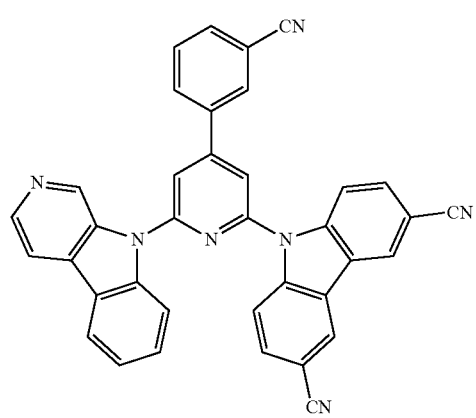
81
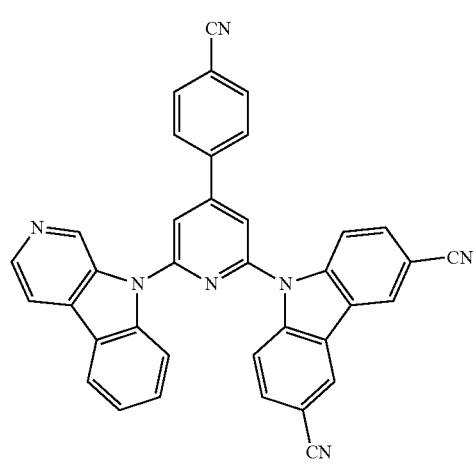
82
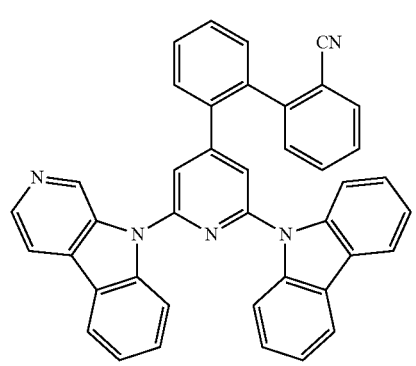
83
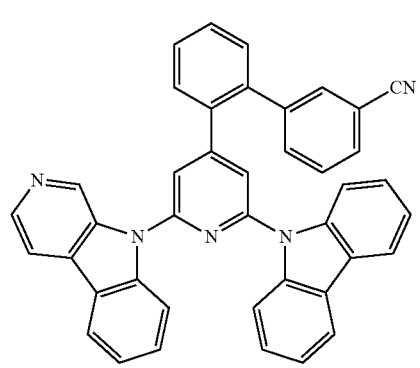
84
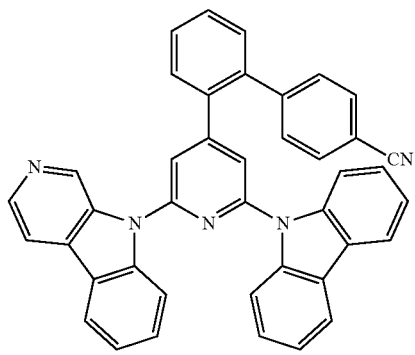
85
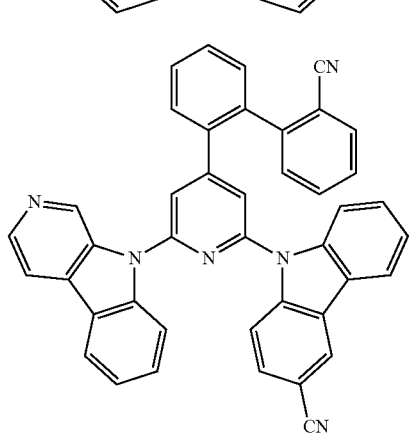
86
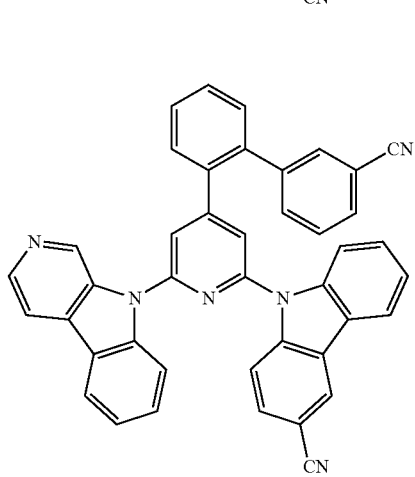
87
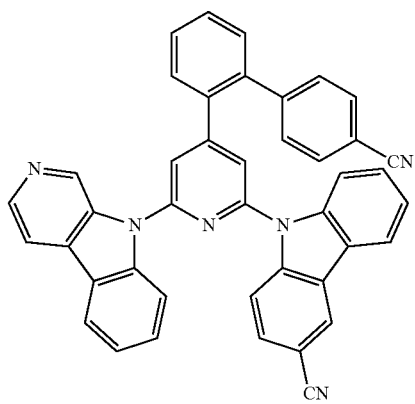

88
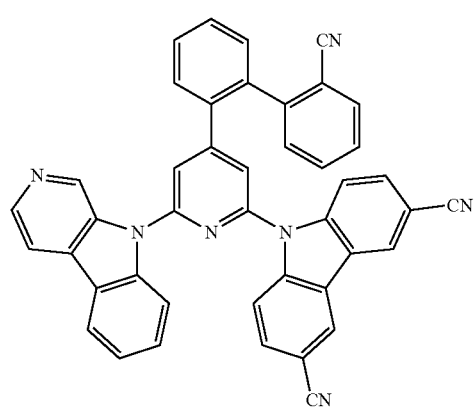
89
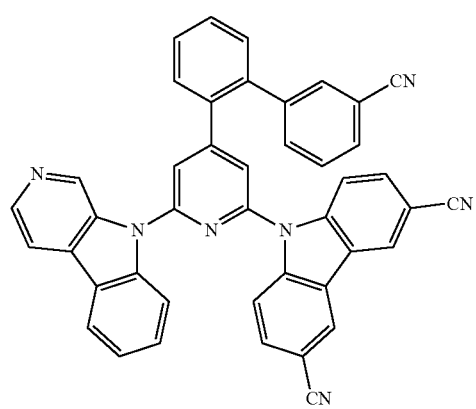
90
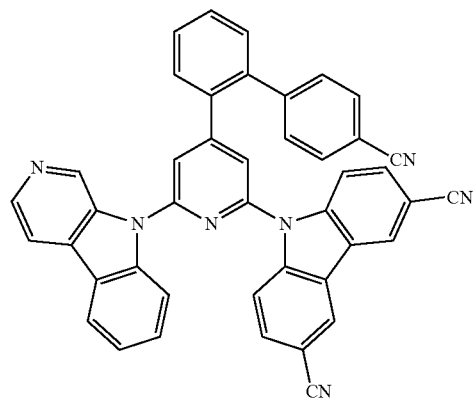
97
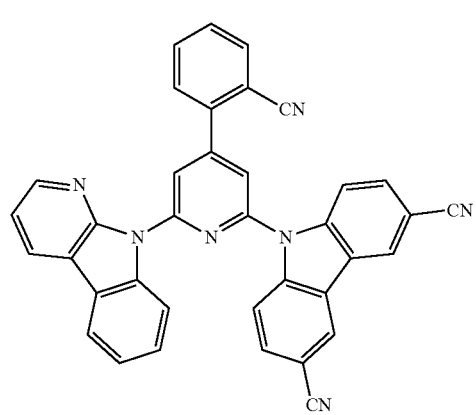
98
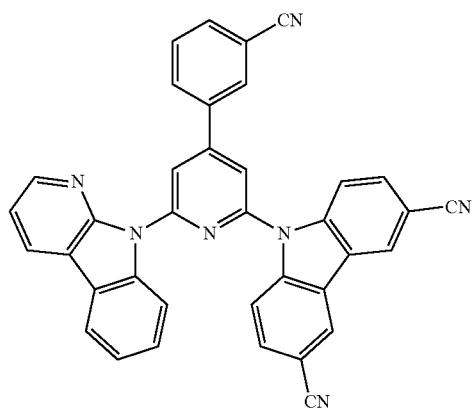
99
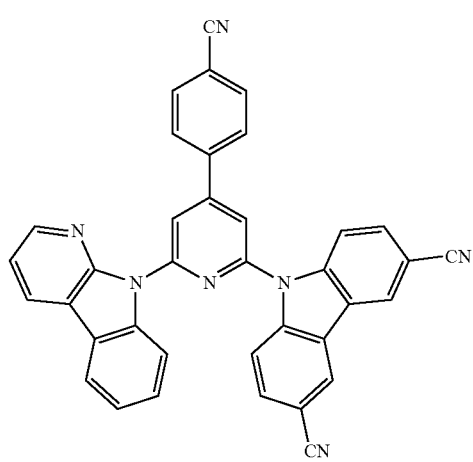
100
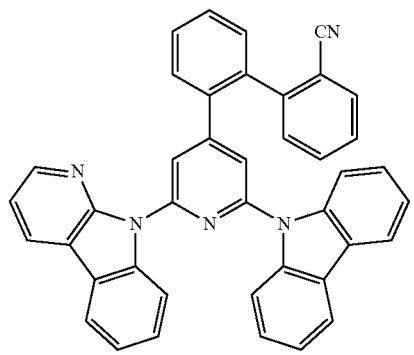
101
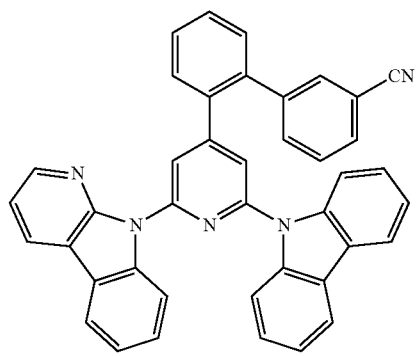

-continued
102
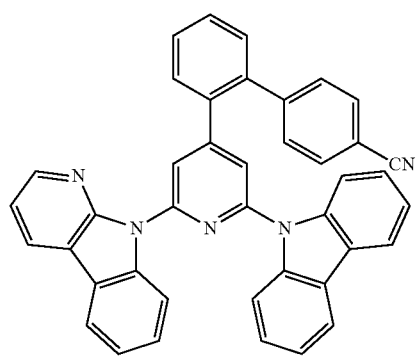
103
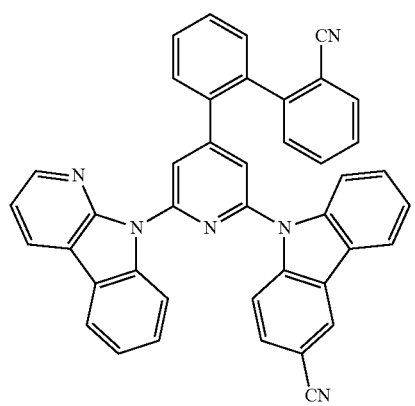
104
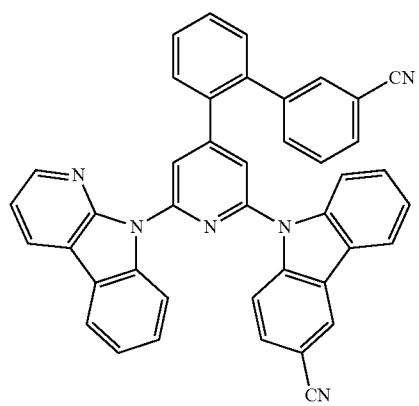
105
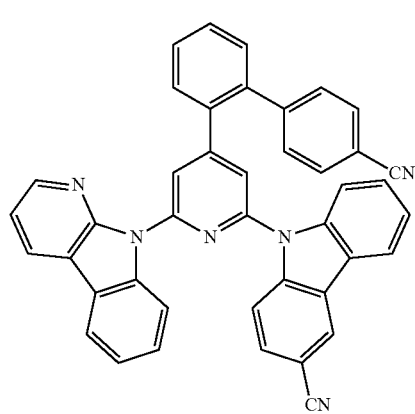
-continued
106
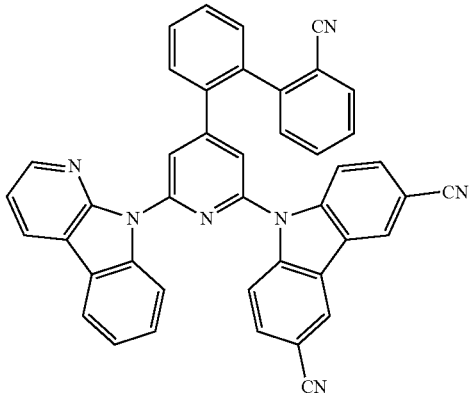
107
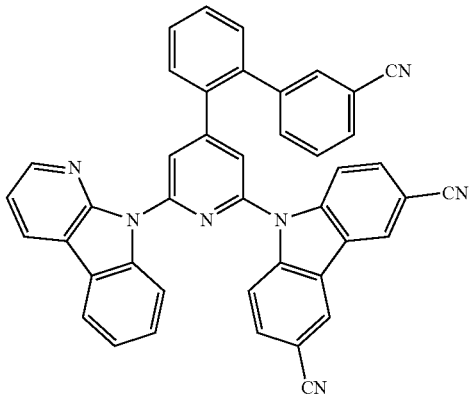
108
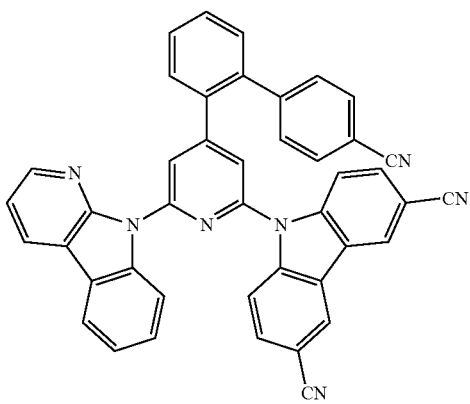
127
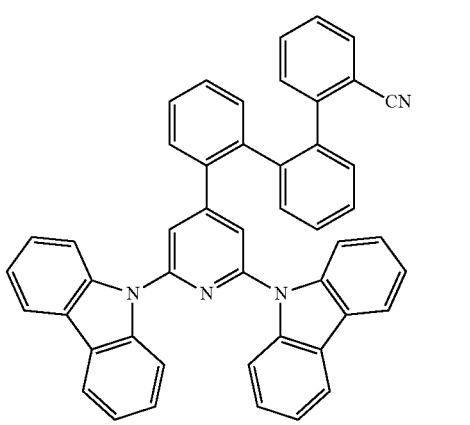

-continued
128
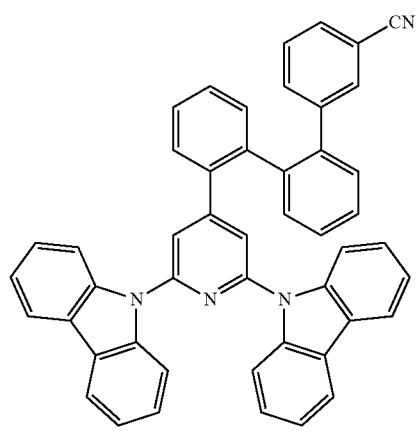
129
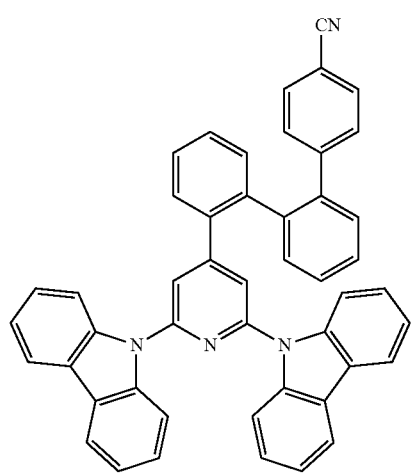
130
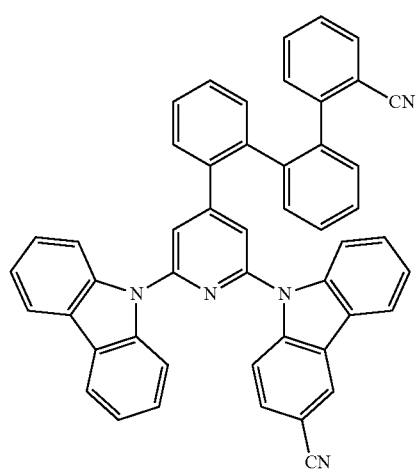
-continued
131
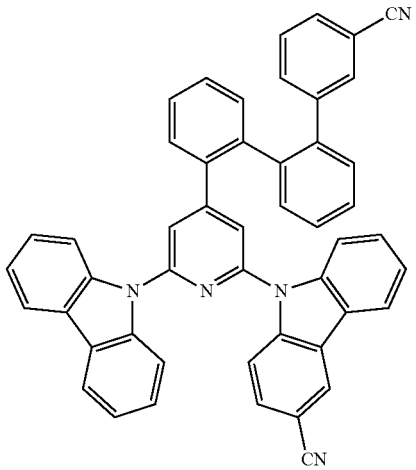
132
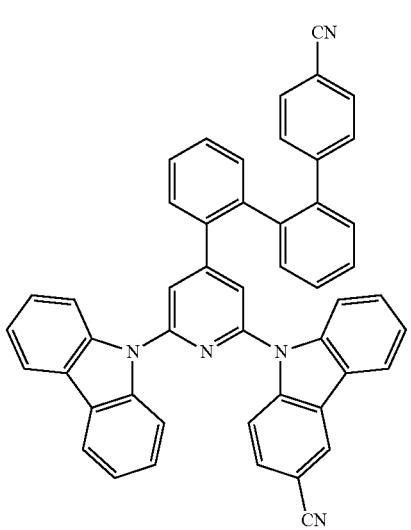
133
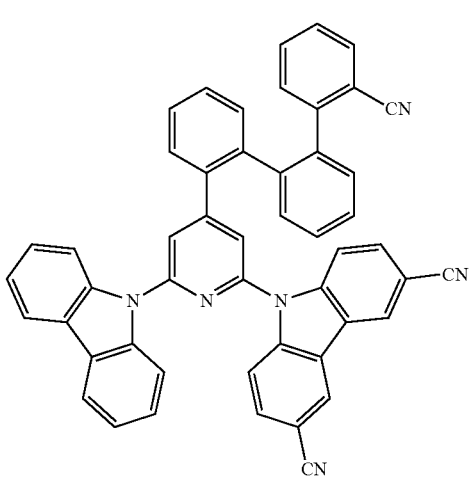

-continued
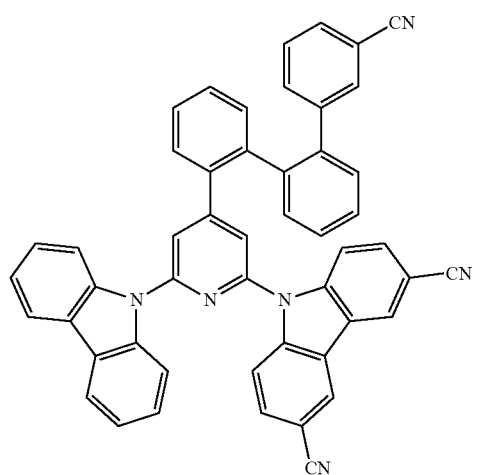
134
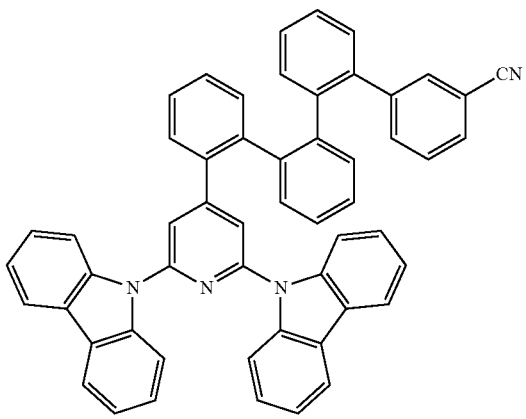
137
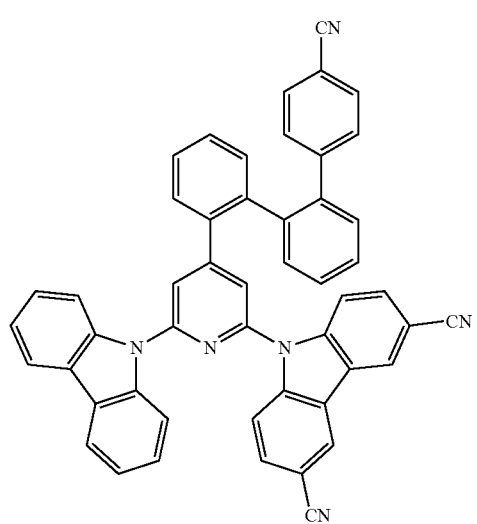
135
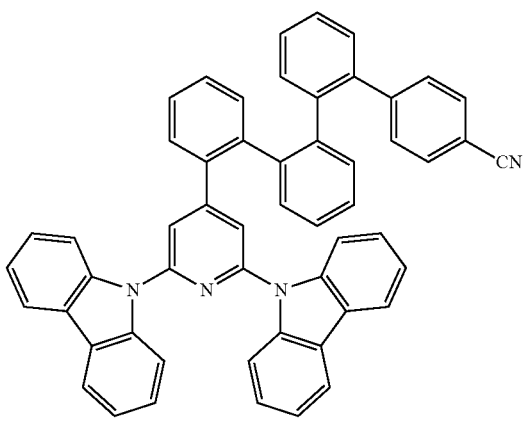
138
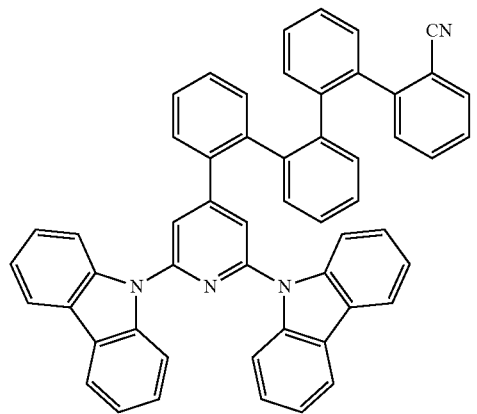
136
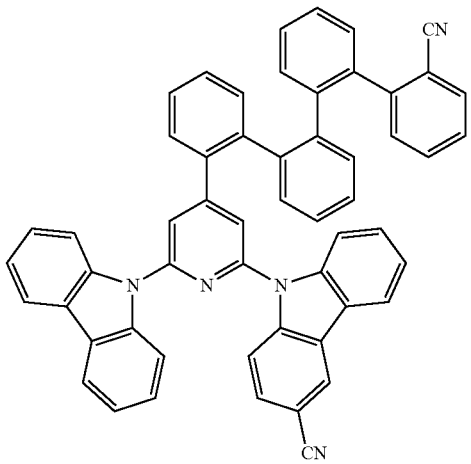
139

-continued
140
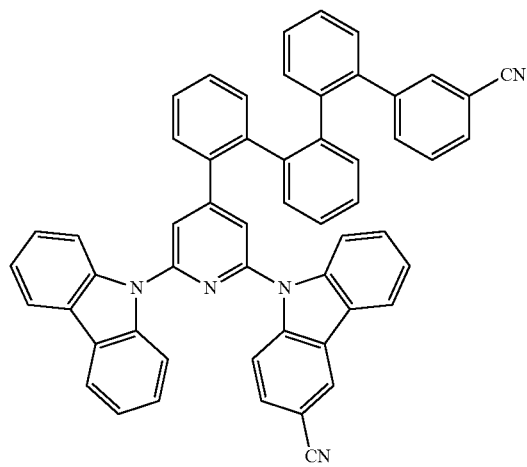
141
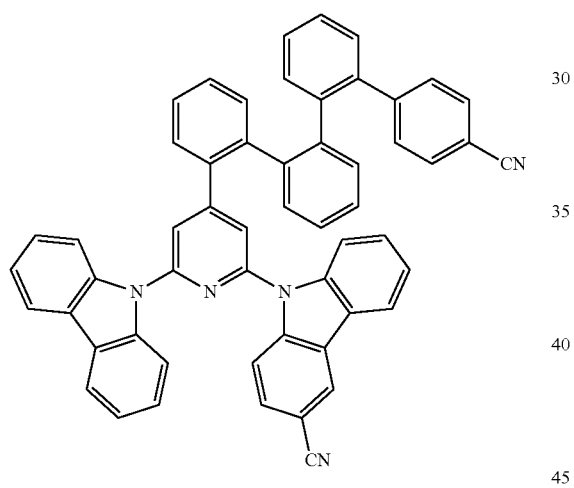
142
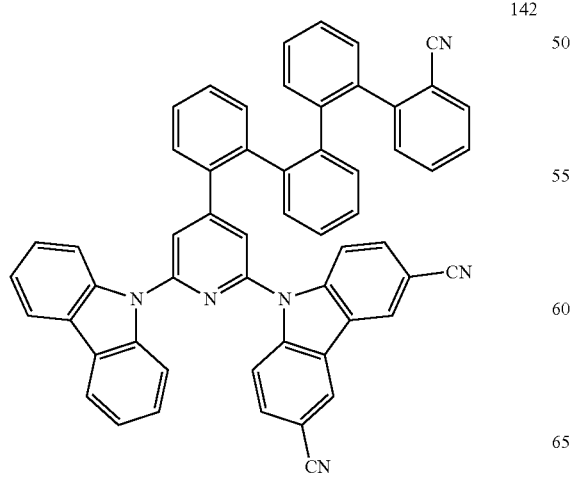
-continued
143
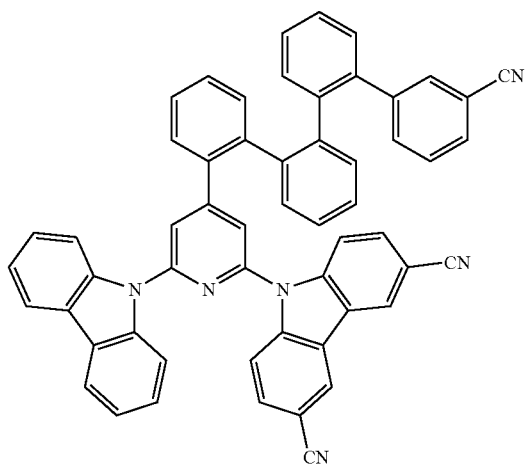
144
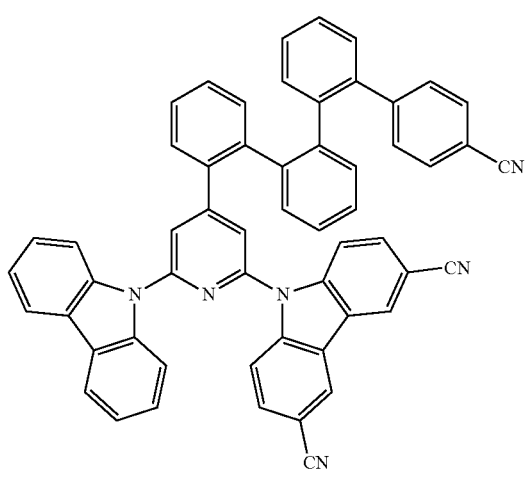
145
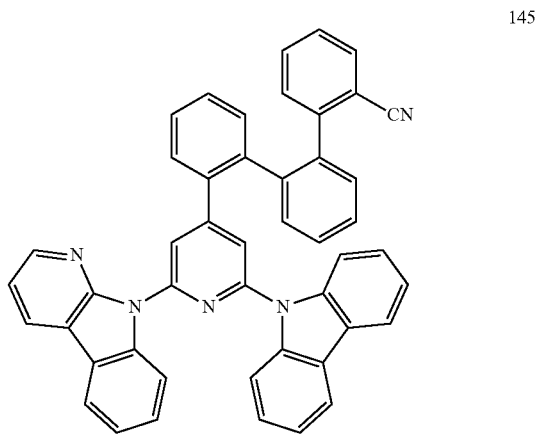 [SMILES: N#Cc1ccccc1-c1ccccc1-c1ccccc1-c1cc(-n2c3ccccc3c3ccccc32)nc(-n2c3ccccc3c3ccccc32)c1]

-continued
146
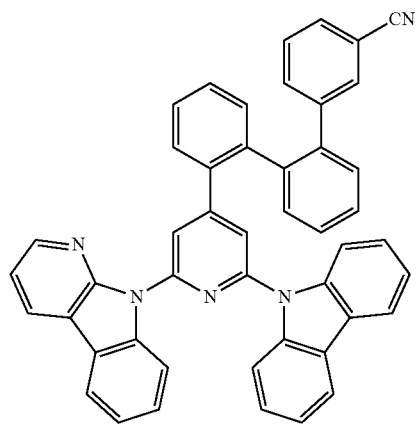
147
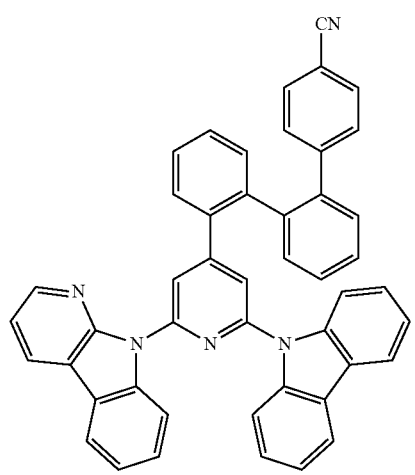
148
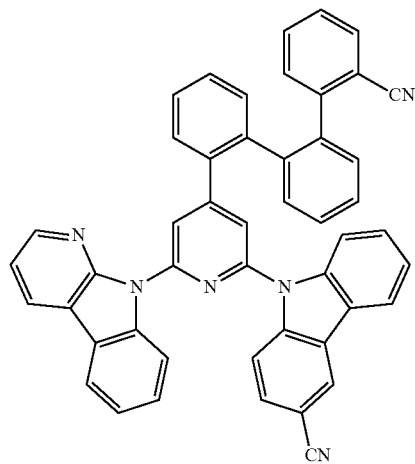
-continued
149
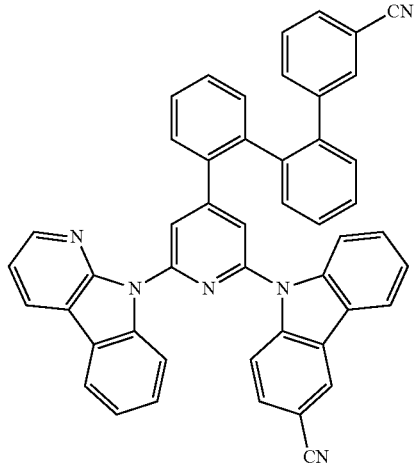
150
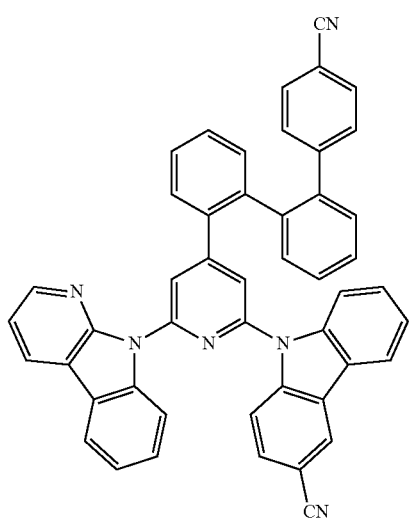
151
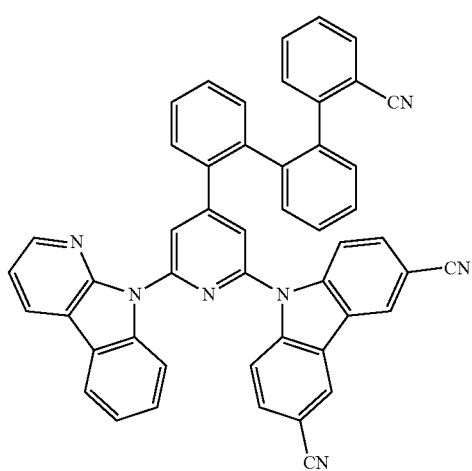

152
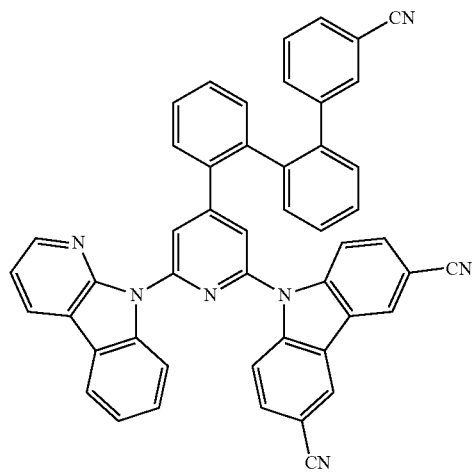
153
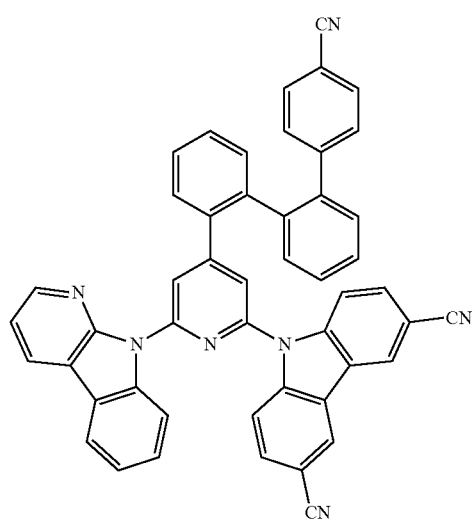
154
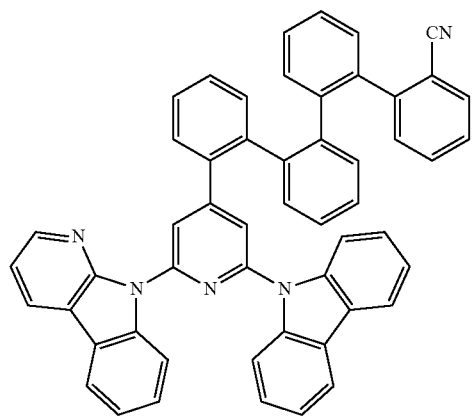
155
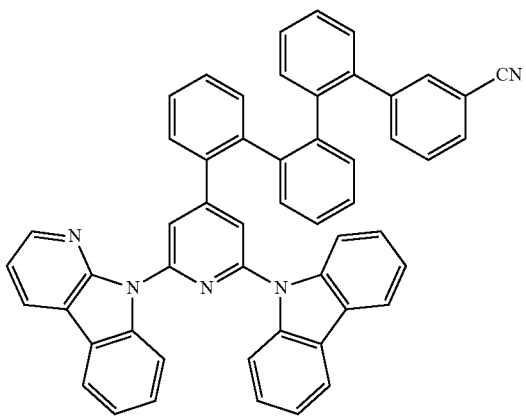
156
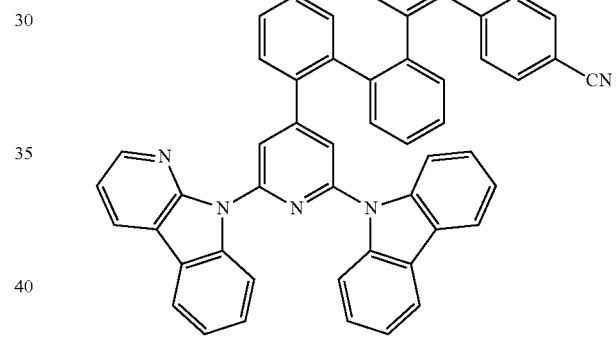
157
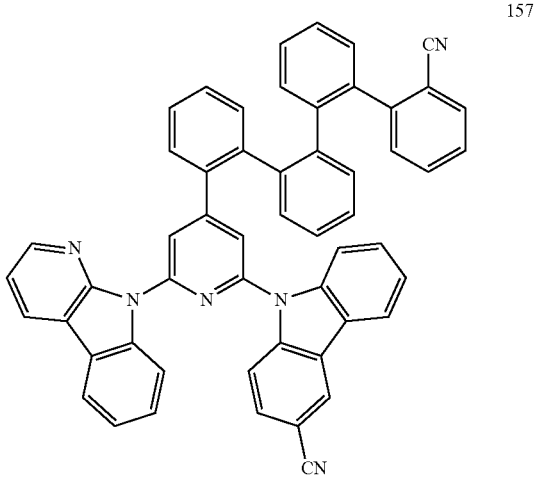

158
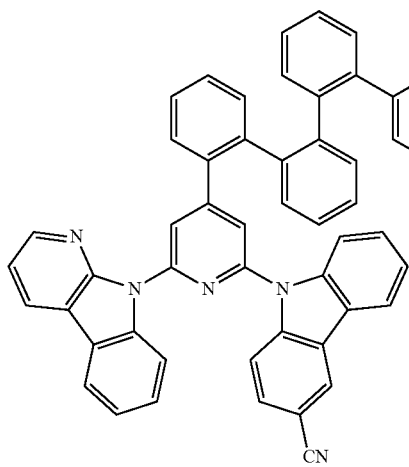
159
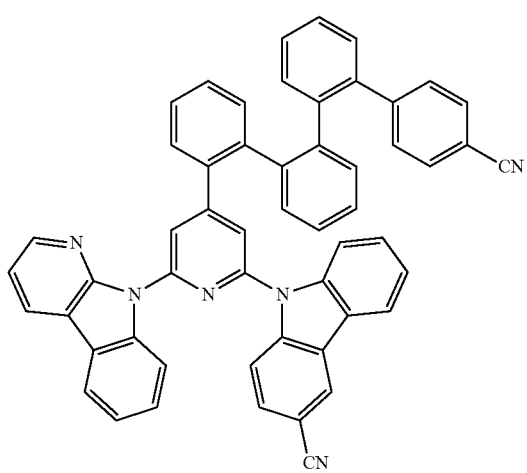
160
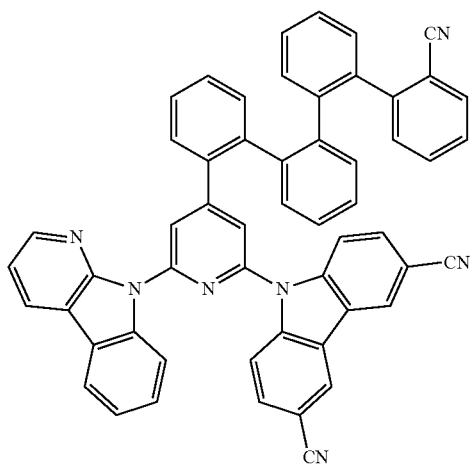
161
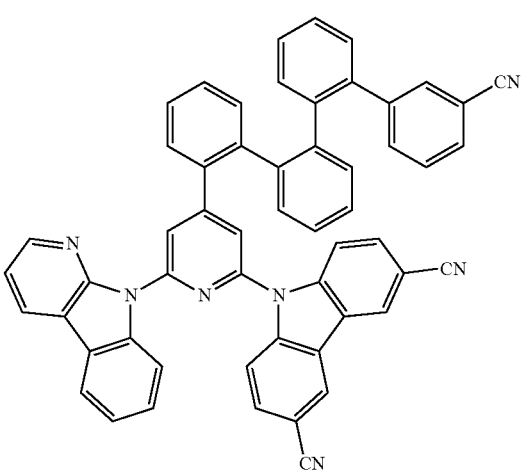
162
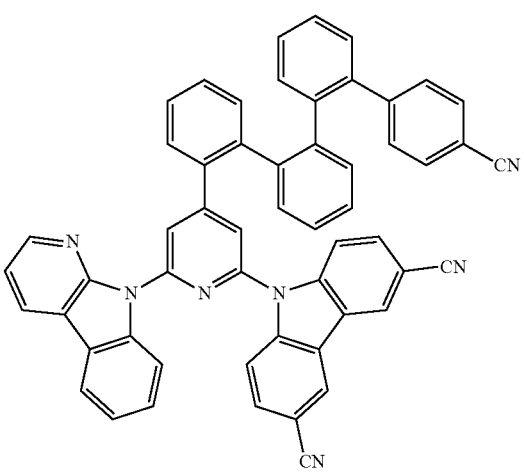
163
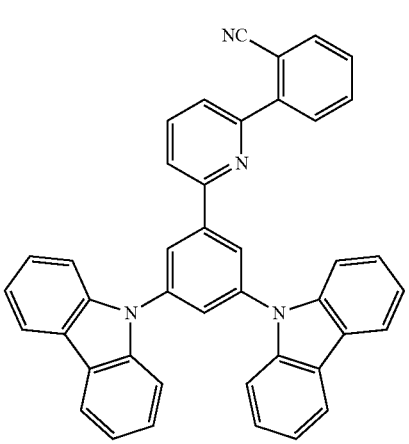

-continued
164
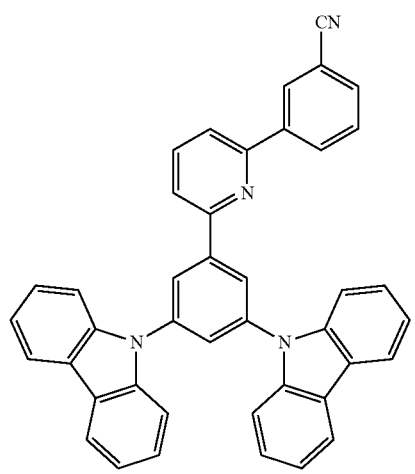
165
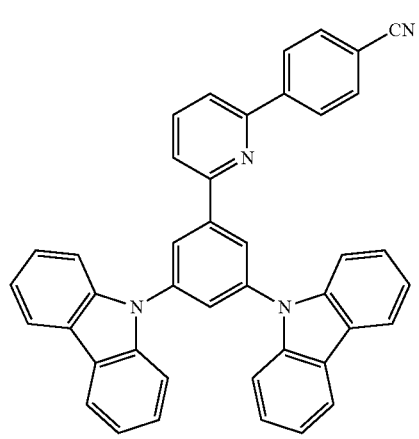
166
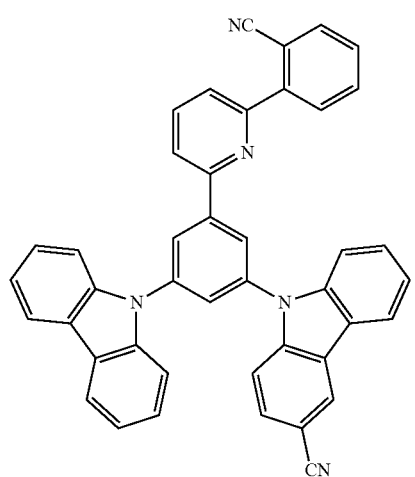
-continued
167
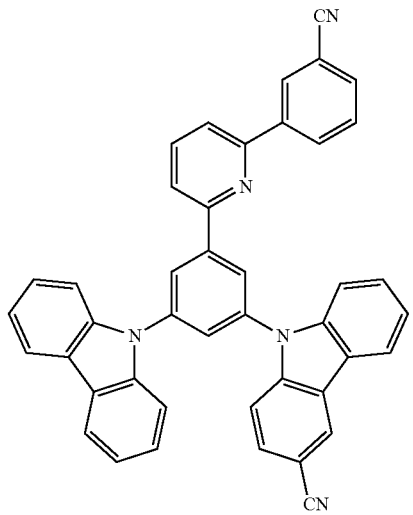
168
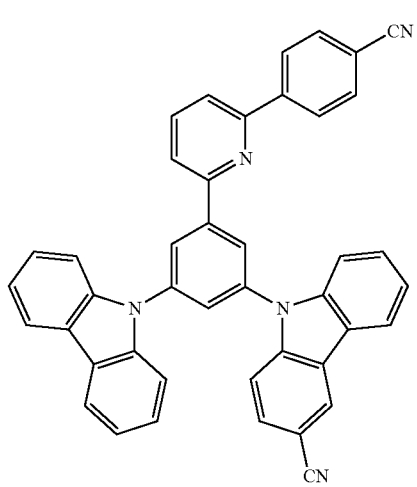
169
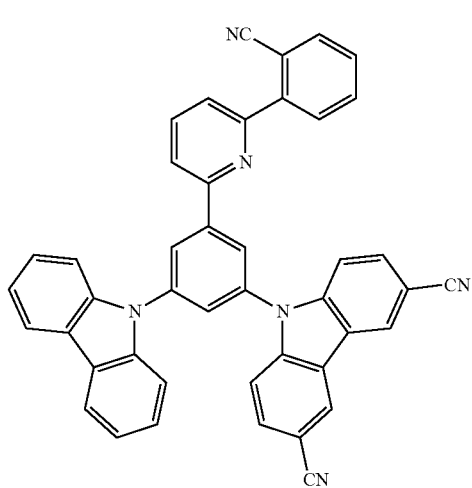

170
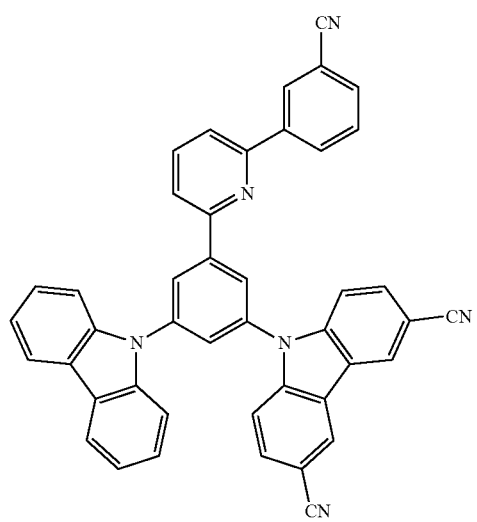
171
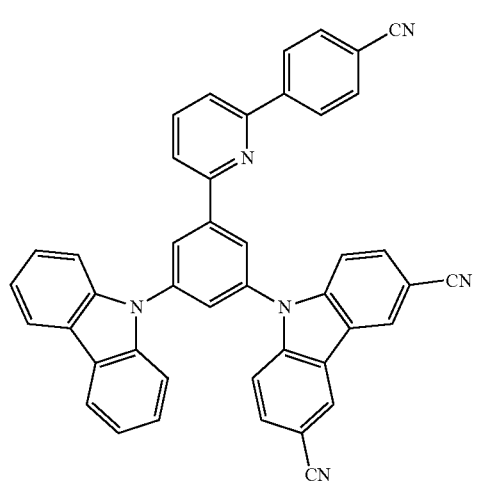
181
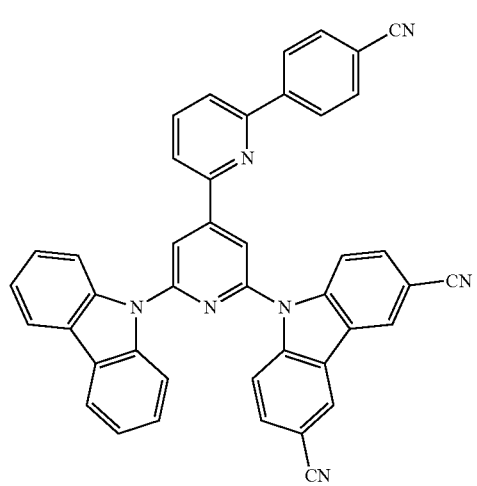
182
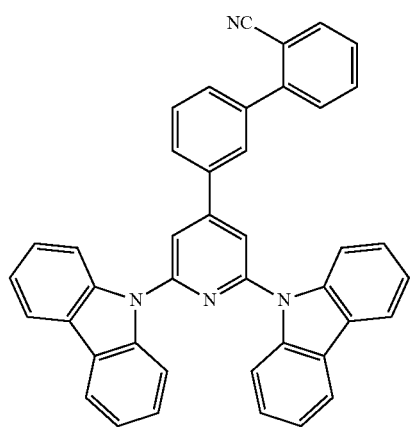
183
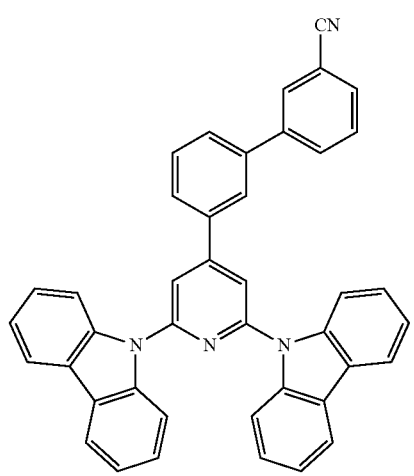
184
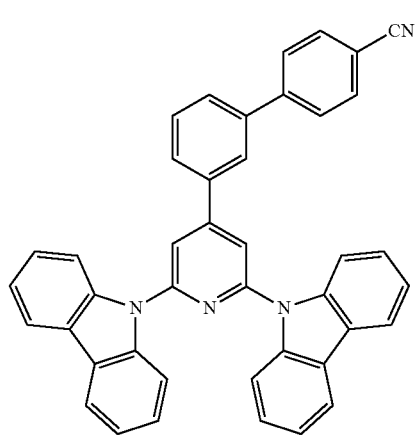

185
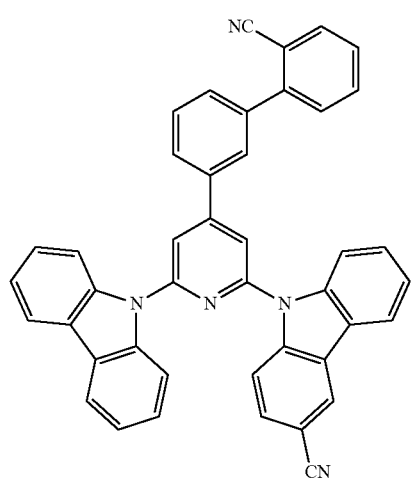
186
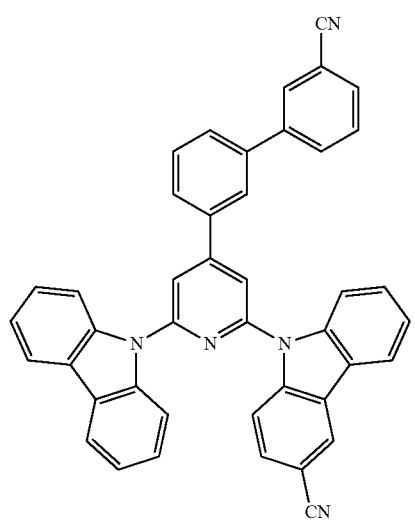
187
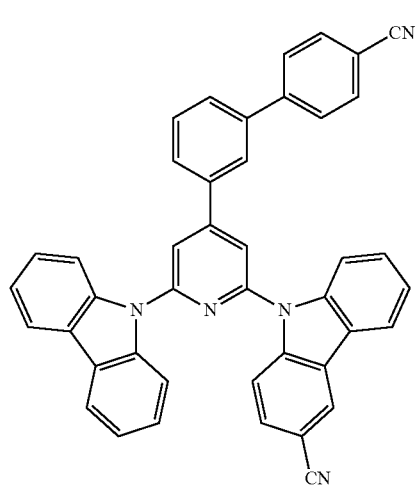
188
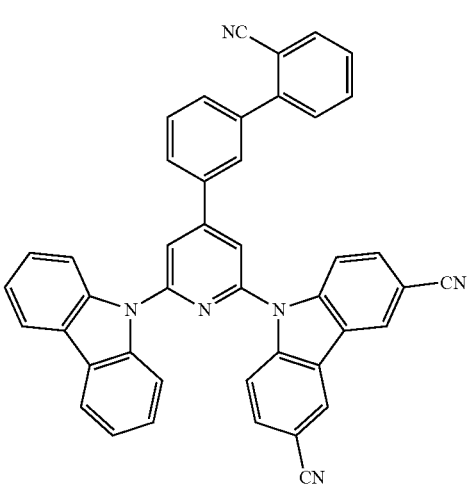
189
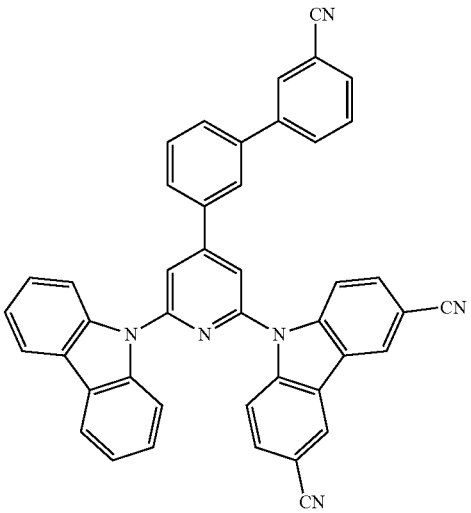
190
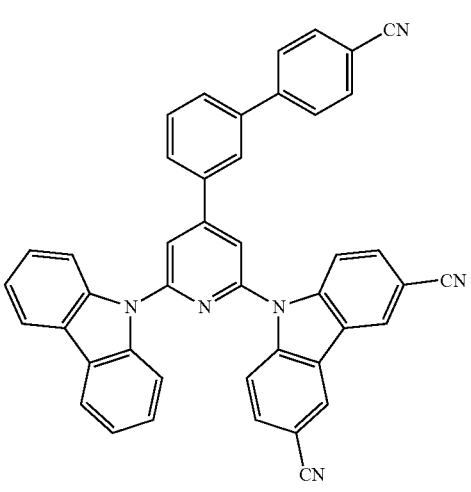

243
-continued
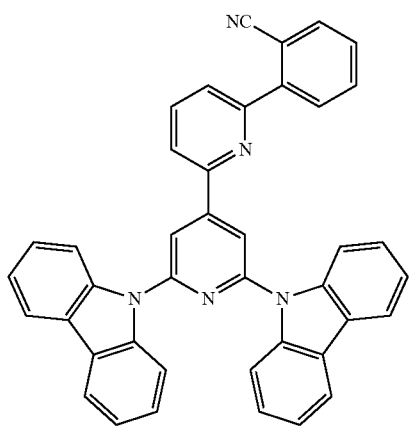
191
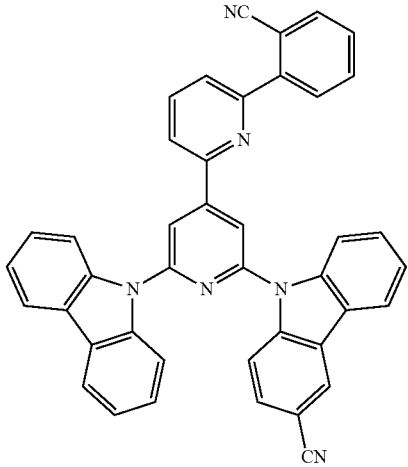
194
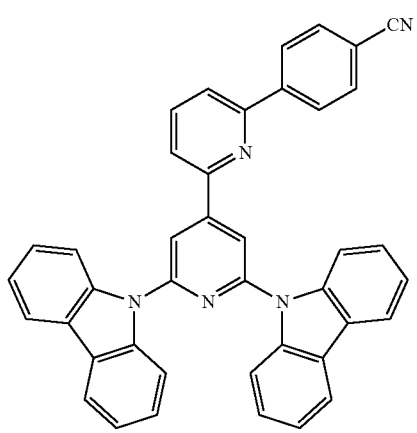
192
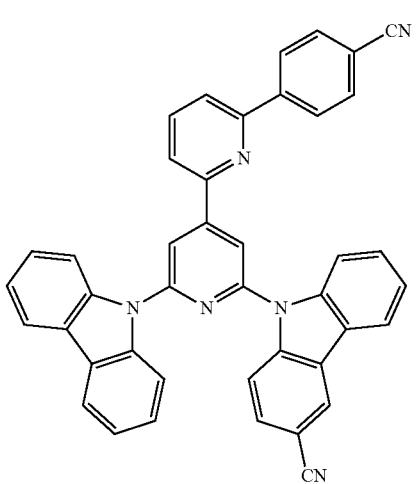
195
193
244
-continued
196

197 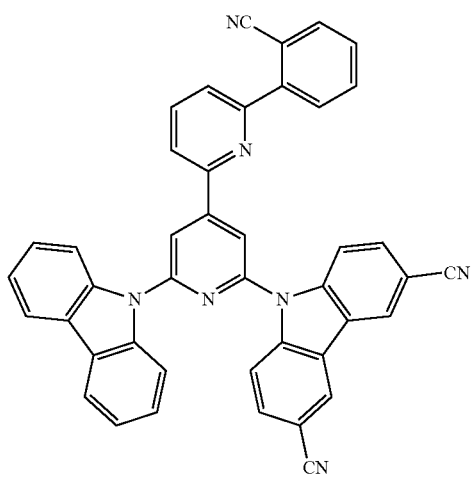

198 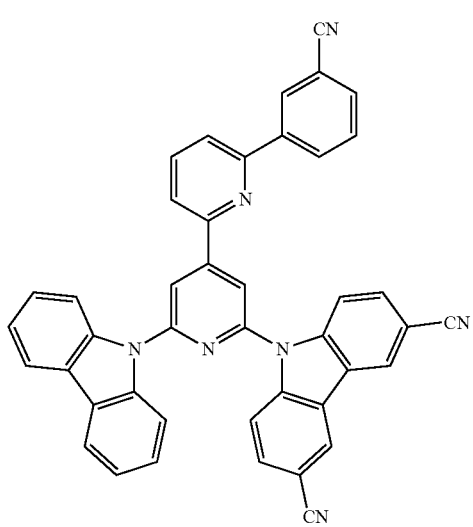

199 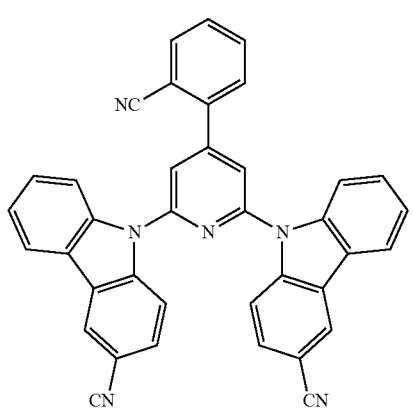

200 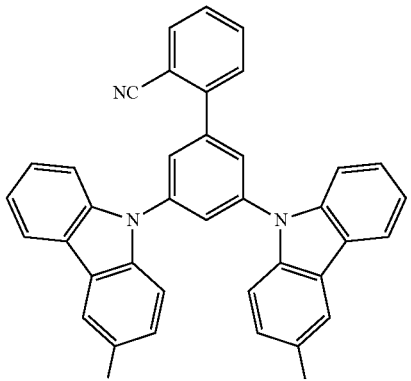

201 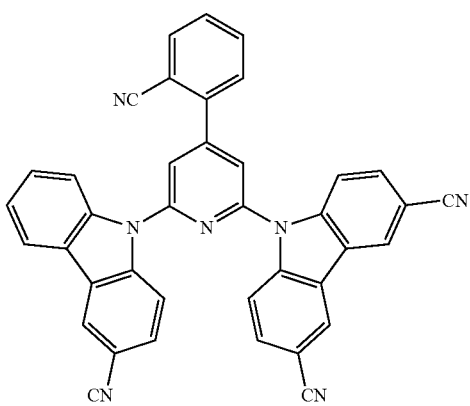

202 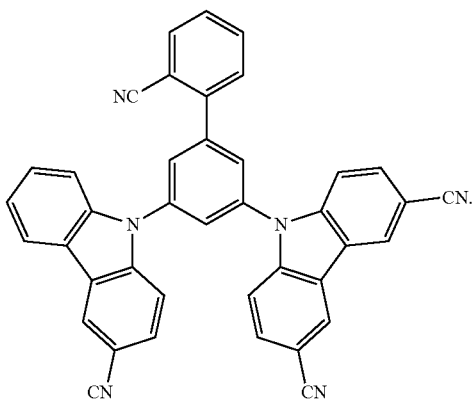

18. An organic light-emitting device comprising:
 a first electrode;
 a second electrode; and
 an organic layer disposed between the first electrode and the second electrode,
 wherein the organic layer comprises an emission layer and at least one carbazole compound of claim 1.

19. The organic light-emitting device of claim 18, wherein the emission layer comprises the at least one carbazole compound represented by Formula 1.

20. The organic light-emitting device of claim 18, wherein the emission layer comprises the at least one carbazole compound represented by Formula 1 and a phosphorescent dopant.

* * * * *